US012516115B2

(12) United States Patent
Kakiuchi et al.

(10) Patent No.: US 12,516,115 B2
(45) Date of Patent: Jan. 6, 2026

(54) COMPOSITION FOR PROPHYLAXIS OR TREATMENT OF IL-8 RELATED DISEASES

(71) Applicants: Chugai Seiyaku Kabushiki Kaisha, Tokyo (JP); Jichi Medical University, Tokyo (JP); National Institutes of Biomedical Innovation, Health and Nutrition, Osaka (JP)

(72) Inventors: Ayako Kakiuchi, Kanagawa (JP); Atsuhiko Kato, Shizuoka (JP); Shuji Hayashi, Shizuoka (JP); Izumi Yanagisawa, Kanagawa (JP); Ryo Konno, Saitama (JP); Sachiho Netsu, Saitama (JP); Tadashi Sankai, Ibaraki (JP)

(73) Assignees: CHUGAI SEIYAKU KABUSHIKI KAISHA, Tokyo (JP); JICHI MEDICAL UNIVERSITY, Tokyo (JP); NATIONAL INSTITUTES OF BIOMEDICAL INNOVATION, HEALTH AND NUTRITION, Osaka (JP)

( * ) Notice: Subject to any disclaimer, the term of this patent is extended or adjusted under 35 U.S.C. 154(b) by 4 days.

(21) Appl. No.: 18/450,863

(22) Filed: Aug. 16, 2023

(65) Prior Publication Data

US 2024/0083996 A1 Mar. 14, 2024

Related U.S. Application Data

(62) Division of application No. 17/333,256, filed on May 28, 2021, now Pat. No. 11,780,912, which is a division of application No. 16/323,142, filed as application No. PCT/JP2017/028346 on Aug. 4, 2017, now Pat. No. 11,053,308.

(30) Foreign Application Priority Data

Aug. 5, 2016 (JP) ................................ 2016-154174

(51) Int. Cl.

| | |
|---|---|
| ***A61K 39/395*** | (2006.01) |
| ***A61K 45/00*** | (2006.01) |
| ***A61P 1/16*** | (2006.01) |
| ***A61P 11/00*** | (2006.01) |
| ***A61P 13/12*** | (2006.01) |
| ***A61P 15/00*** | (2006.01) |
| ***A61P 15/08*** | (2006.01) |
| ***A61P 17/06*** | (2006.01) |
| ***A61P 29/00*** | (2006.01) |
| ***A61P 43/00*** | (2006.01) |
| ***C07K 16/24*** | (2006.01) |
| ***C07K 16/28*** | (2006.01) |
| *A61K 39/00* | (2006.01) |

(52) U.S. Cl.

CPC .......... *C07K 16/244* (2013.01); *A61K 39/395* (2013.01); *A61K 45/00* (2013.01); *A61P 1/16* (2018.01); *A61P 11/00* (2018.01); *A61P 13/12* (2018.01); *A61P 15/00* (2018.01); *A61P 15/08* (2018.01); *A61P 17/06* (2018.01); *A61P 29/00* (2018.01); *A61P 43/00* (2018.01); *C07K 16/2866* (2013.01); *A61K 2039/505* (2013.01); *A61K 2039/507* (2013.01); *C07K 16/24* (2013.01); *C07K 2317/24* (2013.01); *C07K 2317/31* (2013.01); *C07K 2317/52* (2013.01); *C07K 2317/56* (2013.01); *C07K 2317/565* (2013.01); *C07K 2317/567* (2013.01); *C07K 2317/92* (2013.01); *C07K 2317/94* (2013.01)

(58) Field of Classification Search

CPC .................................................... A61K 39/395

See application file for complete search history.

(56) References Cited

U.S. PATENT DOCUMENTS

| | | | |
|---|---|---|---|
| 4,676,980 | A | 6/1987 | Segal et al. |
| 4,689,299 | A | 8/1987 | Insel et al. |
| 4,737,456 | A | 4/1988 | Weng et al. |
| 4,801,687 | A | 1/1989 | Ngo |
| 4,816,567 | A | 3/1989 | Cabilly et al. |
| 5,202,253 | A | 4/1993 | Esmon et al. |
| 5,208,020 | A | 5/1993 | Chari et al. |
| 5,322,678 | A | 6/1994 | Morgan, Jr. et al. |
| 5,416,064 | A | 5/1995 | Chari et al. |
| 5,500,362 | A | 3/1996 | Robinson et al. |
| 5,501,854 | A | 3/1996 | Raso |
| 5,571,894 | A | 11/1996 | Wels et al. |
| 5,585,089 | A | 12/1996 | Queen et al. |
| 5,587,458 | A | 12/1996 | King et al. |
| 5,624,821 | A | 4/1997 | Winter et al. |

(Continued)

FOREIGN PATENT DOCUMENTS

| | | | |
|---|---|---|---|
| AU | 2010206050 | A1 | 8/2010 |
| AU | 2011244851 | A1 | 11/2011 |

(Continued)

OTHER PUBLICATIONS

Accession P01871 (downloaded from https://rest.uniprot.org/unisave/P01871?format=txt&versions=1 on Sep. 19, 2023; published Mar. 20, 1987).

(Continued)

*Primary Examiner* — Prema M Mertz

(74) *Attorney, Agent, or Firm* — Nixon & Vanderhye P.C.

(57) ABSTRACT

For example, therapeutic methods and the like for novel IL-8-related diseases using an IL-8 signal inhibitor are provided. Alternatively, for example, therapeutic methods and the like for known or novel IL-8-related diseases using a novel anti-IL-8 antibody are provided.

16 Claims, 29 Drawing Sheets

Specification includes a Sequence Listing.

(56) References Cited

U.S. PATENT DOCUMENTS

| | | | |
|---|---|---|---|
| 5,635,483 | A | 6/1997 | Pettit et al. |
| 5,639,641 | A | 6/1997 | Pedersen et al. |
| 5,648,237 | A | 7/1997 | Carter |
| 5,648,260 | A | 7/1997 | Winter et al. |
| 5,712,374 | A | 1/1998 | Kuntsmann et al. |
| 5,714,586 | A | 2/1998 | Kunstmann et al. |
| 5,731,168 | A | 3/1998 | Carter et al. |
| 5,739,116 | A | 4/1998 | Hamann et al. |
| 5,750,373 | A | 5/1998 | Garrard et al. |
| 5,767,285 | A | 6/1998 | Hamann et al. |
| 5,770,429 | A | 6/1998 | Lonberg et al. |
| 5,770,701 | A | 6/1998 | Mcgahren et al. |
| 5,770,710 | A | 6/1998 | Mcgahren et al. |
| 5,773,001 | A | 6/1998 | Hamann et al. |
| 5,780,588 | A | 7/1998 | Pettit et al. |
| 5,789,199 | A | 8/1998 | Joly et al. |
| 5,795,965 | A | 8/1998 | Tsuchiya et al. |
| 5,821,337 | A | 10/1998 | Carter et al. |
| 5,827,733 | A | 10/1998 | Lee et al. |
| 5,830,478 | A | 11/1998 | Raso et al. |
| 5,840,523 | A | 11/1998 | Simmons et al. |
| 5,869,046 | A | 2/1999 | Presta et al. |
| 5,877,296 | A | 3/1999 | Hamann et al. |
| 5,935,935 | A | 8/1999 | Connelly et al. |
| 5,959,177 | A | 9/1999 | Hein et al. |
| 5,990,286 | A | 11/1999 | Khawli et al. |
| 5,994,524 | A | 11/1999 | Matsushima et al. |
| 6,024,956 | A | 2/2000 | Matsushima et al. |
| 6,025,158 | A | 2/2000 | Gonzalez et al. |
| 6,040,498 | A | 3/2000 | Stomp et al. |
| 6,075,181 | A | 6/2000 | Kucherlapati et al. |
| 6,096,506 | A | 8/2000 | Lee et al. |
| 6,150,584 | A | 11/2000 | Kucherlapati et al. |
| 6,165,745 | A | 12/2000 | Ward et al. |
| 6,171,586 | B1 | 1/2001 | Lam et al. |
| 6,194,551 | B1 | 2/2001 | Idusogie et al. |
| 6,245,894 | B1 | 6/2001 | Matsushima et al. |
| 6,248,516 | B1 | 6/2001 | Winter et al. |
| 6,267,958 | B1 | 7/2001 | Andya et al. |
| 6,329,511 | B1 | 12/2001 | Vasquez et al. |
| 6,355,245 | B1 | 3/2002 | Evans et al. |
| 6,417,429 | B1 | 7/2002 | Hein et al. |
| 6,420,548 | B1 | 7/2002 | Vezina et al. |
| 6,458,355 | B1 | 10/2002 | Hsei et al. |
| 6,485,943 | B2 | 11/2002 | Stevens et al. |
| 6,602,684 | B1 | 8/2003 | Umana et al. |
| 6,630,579 | B2 | 10/2003 | Chari et al. |
| 6,677,436 | B1 | 1/2004 | Sato et al. |
| 6,737,056 | B1 | 5/2004 | Presta |
| 6,821,505 | B2 | 11/2004 | Ward |
| 6,884,879 | B1 | 4/2005 | Baca et al. |
| 6,913,747 | B1 | 7/2005 | Co et al. |
| 6,946,292 | B2 | 9/2005 | Kanda et al. |
| 6,982,321 | B2 | 1/2006 | Winter |
| 7,041,870 | B2 | 5/2006 | Tomizuka et al. |
| 7,052,873 | B2 | 5/2006 | Tsuchiya |
| 7,064,191 | B2 | 6/2006 | Shinkawa et al. |
| 7,087,409 | B2 | 8/2006 | Barbas, III et al. |
| 7,125,978 | B1 | 10/2006 | Vezina et al. |
| 7,138,501 | B2 | 11/2006 | Ruben et al. |
| 7,189,826 | B2 | 3/2007 | Rodman |
| 7,247,302 | B1 | 7/2007 | Rosok et al. |
| 7,261,893 | B2 | 8/2007 | Veldman et al. |
| 7,276,585 | B2 | 10/2007 | Lazar et al. |
| 7,282,568 | B2 | 10/2007 | Teeling et al. |
| 7,317,091 | B2 | 1/2008 | Lazar et al. |
| 7,320,789 | B2 | 1/2008 | Dunham et al. |
| 7,332,581 | B2 | 2/2008 | Presta |
| 7,358,054 | B2 | 4/2008 | Lyne et al. |
| 7,361,740 | B2 | 4/2008 | Hinton et al. |
| 7,365,166 | B2 | 4/2008 | Baca et al. |
| 7,371,826 | B2 | 5/2008 | Presta |
| 7,432,356 | B2 | 10/2008 | Fung et al. |
| 7,498,298 | B2 | 3/2009 | Doronina et al. |
| 7,521,541 | B2 | 4/2009 | Eigenbrot et al. |
| 7,527,791 | B2 | 5/2009 | Adams et al. |
| 7,572,456 | B2 | 8/2009 | Johnson et al. |
| 7,615,213 | B2 | 11/2009 | Kasaian et al. |
| 7,632,499 | B2 | 12/2009 | Davies et al. |
| 7,632,924 | B2 | 12/2009 | Cho et al. |
| 7,662,925 | B2 | 2/2010 | Lazar et al. |
| 7,667,004 | B2 | 2/2010 | Zhong et al. |
| 7,670,600 | B2 | 3/2010 | Dall'Acqua et al. |
| 7,691,568 | B2 | 4/2010 | Niwa et al. |
| 7,731,961 | B1 | 6/2010 | Aghajanian et al. |
| 7,749,753 | B2 | 7/2010 | Kanda et al. |
| 7,785,791 | B2 | 8/2010 | Presta |
| 7,785,903 | B2 | 8/2010 | Bond et al. |
| 7,786,270 | B2 | 8/2010 | Johnson et al. |
| 7,807,159 | B2 | 10/2010 | Chin et al. |
| 7,820,800 | B2 | 10/2010 | Rossi et al. |
| 7,871,607 | B2 | 1/2011 | Bookbinder et al. |
| 7,888,486 | B2 | 2/2011 | Walsh et al. |
| 7,955,590 | B2 | 6/2011 | Gillies et al. |
| 7,960,512 | B2 | 6/2011 | Stavenhagen et al. |
| 7,985,840 | B2 | 7/2011 | Fuh et al. |
| 8,054,268 | B2 | 11/2011 | Chen et al. |
| 8,062,635 | B2 | 11/2011 | Hattori et al. |
| 8,063,187 | B2 | 11/2011 | Chu et al. |
| 8,101,720 | B2 | 1/2012 | Lazar et al. |
| 8,147,829 | B2 | 4/2012 | Hariharan et al. |
| 8,188,231 | B2 | 5/2012 | Lazar et al. |
| 8,193,318 | B2 | 6/2012 | Koenig et al. |
| 8,323,962 | B2 | 12/2012 | Dall'Acqua et al. |
| 8,329,186 | B2 | 12/2012 | Kim et al. |
| 8,388,955 | B2 | 3/2013 | Lazar et al. |
| 8,410,328 | B2 | 4/2013 | Chung et al. |
| 8,414,893 | B2 | 4/2013 | Biere-Citron et al. |
| 8,415,459 | B2 | 4/2013 | Lavallie et al. |
| 8,486,895 | B2 | 7/2013 | Weaver et al. |
| 8,497,355 | B2 | 7/2013 | Igawa et al. |
| 8,551,485 | B2 | 10/2013 | Bernett et al. |
| 8,562,991 | B2 | 10/2013 | Igawa et al. |
| 8,568,992 | B2 | 10/2013 | Walker et al. |
| 8,604,174 | B2 | 12/2013 | Babcook et al. |
| 8,609,097 | B2 | 12/2013 | Bohrmann et al. |
| 8,637,641 | B2 | 1/2014 | Dahiyat et al. |
| 8,652,466 | B2 | 2/2014 | Stavenhagen et al. |
| 8,679,490 | B2 | 3/2014 | Dennis et al. |
| 8,685,725 | B2 | 4/2014 | Beliard et al. |
| 8,734,798 | B2 | 5/2014 | Finney et al. |
| 8,735,545 | B2 | 5/2014 | Lazar et al. |
| 8,753,629 | B2 | 6/2014 | Lazar et al. |
| 8,778,345 | B2 | 7/2014 | Zhang et al. |
| 8,791,323 | B2 | 7/2014 | Murphy et al. |
| 8,802,820 | B2 | 8/2014 | Chamberlain et al. |
| 8,802,823 | B2 | 8/2014 | Lazar et al. |
| 8,883,158 | B2 | 11/2014 | Diefenbach-Streiber et al. |
| 8,999,340 | B2 | 4/2015 | Magro |
| 8,999,343 | B2 | 4/2015 | Han et al. |
| 9,029,515 | B2 | 5/2015 | Pons et al. |
| 9,051,373 | B2 | 6/2015 | Lazar et al. |
| 9,079,949 | B1 | 7/2015 | Andrien, Jr. et al. |
| 9,096,651 | B2 | 8/2015 | Igawa et al. |
| 9,107,861 | B1 | 8/2015 | Andrien, Jr. et al. |
| 9,133,269 | B2 | 9/2015 | McConnell et al. |
| 9,206,251 | B2 | 12/2015 | Andrien, Jr. et al. |
| 9,255,154 | B2 | 2/2016 | Feldhaus et al. |
| 9,296,820 | B2 | 3/2016 | Umana et al. |
| 9,315,577 | B2 | 4/2016 | Foltz et al. |
| 9,447,190 | B2 | 9/2016 | Flanagan et al. |
| 9,481,725 | B2 | 11/2016 | Dutzar et al. |
| 9,605,061 | B2 | 3/2017 | Lazar et al. |
| 9,670,269 | B2 | 6/2017 | Igawa et al. |
| 9,688,762 | B2 | 6/2017 | Igawa et al. |
| 9,701,759 | B2 | 7/2017 | Desjarlais et al. |
| 9,765,135 | B2 | 9/2017 | Ruike et al. |
| 9,828,429 | B2 | 11/2017 | Igawa et al. |
| 9,868,948 | B2 | 1/2018 | Igawa et al. |
| 9,890,218 | B2 | 2/2018 | Mimoto et al. |
| 9,890,377 | B2 | 2/2018 | Igawa et al. |
| 9,969,800 | B2 | 5/2018 | Igawa et al. |
| 10,000,560 | B2 | 6/2018 | Ruike et al. |
| 10,023,630 | B2 | 7/2018 | Ruike et al. |

(56) References Cited

U.S. PATENT DOCUMENTS

| | | | |
|---|---|---|---|
| 10,233,252 | B2 | 3/2019 | Shusta et al. |
| 10,253,100 | B2 | 4/2019 | Igawa et al. |
| 10,385,122 | B2 | 8/2019 | Ruike et al. |
| 10,472,623 | B2 | 11/2019 | Igawa et al. |
| 10,519,229 | B2 | 12/2019 | Igawa et al. |
| 10,604,561 | B2 | 3/2020 | Sampei et al. |
| 10,618,965 | B2 | 4/2020 | Igawa et al. |
| 10,738,111 | B2 | 8/2020 | Ruike et al. |
| 10,919,953 | B2 | 2/2021 | Katada et al. |
| 11,046,784 | B2 | 6/2021 | Igawa et al. |
| 11,053,308 | B2 | 7/2021 | Kakiuchi et al. |
| 11,236,168 | B2 | 2/2022 | Igawa et al. |
| 11,248,053 | B2 | 2/2022 | Igawa et al. |
| 11,267,868 | B2 | 3/2022 | Mimoto et al. |
| 11,597,760 | B2 | 3/2023 | Ruike et al. |
| 11,891,434 | B2 | 2/2024 | Igawa et al. |
| 12,116,414 | B2 | 10/2024 | Igawa et al. |
| 12,122,840 | B2 | 10/2024 | Igawa et al. |
| 12,187,786 | B2 | 1/2025 | Sampei et al. |
| 2001/0036923 | A1 | 11/2001 | Chari et al. |
| 2002/0082396 | A1 | 6/2002 | Matsushima et al. |
| 2002/0098193 | A1 | 7/2002 | Ward |
| 2002/0137897 | A1 | 9/2002 | Stevens et al. |
| 2002/0142374 | A1 | 10/2002 | Gallo et al. |
| 2002/0164328 | A1 | 11/2002 | Shinkawa et al. |
| 2002/0164339 | A1 | 11/2002 | do Couto et al. |
| 2002/0199213 | A1 | 12/2002 | Tomizuka et al. |
| 2003/0059937 | A1 | 3/2003 | Ruben et al. |
| 2003/0077283 | A1 | 4/2003 | Ye |
| 2003/0103970 | A1 | 6/2003 | Tsuchiya |
| 2003/0115614 | A1 | 6/2003 | Kanda et al. |
| 2003/0129187 | A1 | 7/2003 | Fung et al. |
| 2003/0138422 | A1 | 7/2003 | Aghajanian et al. |
| 2003/0144486 | A1 | 7/2003 | Rodman |
| 2003/0157108 | A1 | 8/2003 | Presta |
| 2003/0166871 | A1 | 9/2003 | Barbas, III et al. |
| 2003/0224397 | A1 | 12/2003 | Lowman et al. |
| 2004/0001822 | A1 | 1/2004 | Levanon et al. |
| 2004/0001839 | A1 | 1/2004 | Levanon et al. |
| 2004/0002450 | A1 | 1/2004 | Lazarovits et al. |
| 2004/0081651 | A1 | 4/2004 | Karpusas et al. |
| 2004/0093621 | A1 | 5/2004 | Shitara et al. |
| 2004/0109865 | A1 | 6/2004 | Niwa et al. |
| 2004/0110226 | A1 | 6/2004 | Lazar et al. |
| 2004/0110282 | A1 | 6/2004 | Kanda et al. |
| 2004/0110704 | A1 | 6/2004 | Yamane et al. |
| 2004/0127688 | A1 | 7/2004 | Winter |
| 2004/0132101 | A1 | 7/2004 | Lazar et al. |
| 2004/0132140 | A1 | 7/2004 | Satoh et al. |
| 2004/0133357 | A1 | 7/2004 | Zhong et al. |
| 2004/0142382 | A1 | 7/2004 | Veldman et al. |
| 2004/0208873 | A1 | 10/2004 | Teeling et al. |
| 2004/0236080 | A1 | 11/2004 | Aburatani et al. |
| 2005/0014934 | A1 | 1/2005 | Hinton et al. |
| 2005/0032114 | A1 | 2/2005 | Hinton et al. |
| 2005/0054832 | A1 | 3/2005 | Lazar et al. |
| 2005/0064514 | A1 | 3/2005 | Stavenhagen et al. |
| 2005/0079574 | A1 | 4/2005 | Bond |
| 2005/0095243 | A1 | 5/2005 | Chan et al. |
| 2005/0119455 | A1 | 6/2005 | Fuh et al. |
| 2005/0123546 | A1 | 6/2005 | Umana et al. |
| 2005/0233382 | A1 | 10/2005 | Presta |
| 2005/0238649 | A1 | 10/2005 | Doronina et al. |
| 2005/0244403 | A1 | 11/2005 | Lazar et al. |
| 2005/0260186 | A1 | 11/2005 | Bookbinder et al. |
| 2005/0260213 | A1 | 11/2005 | Koenig et al. |
| 2005/0260711 | A1 | 11/2005 | Datta et al. |
| 2005/0261229 | A1 | 11/2005 | Gillies et al. |
| 2005/0266000 | A1 | 12/2005 | Bond et al. |
| 2005/0276802 | A1 | 12/2005 | Adams et al. |
| 2006/0014156 | A1 | 1/2006 | Rabbani et al. |
| 2006/0019342 | A1 | 1/2006 | Dall'Acqua et al. |
| 2006/0024298 | A1 | 2/2006 | Lazar et al. |
| 2006/0025576 | A1 | 2/2006 | Miller et al. |
| 2006/0057149 | A1 | 3/2006 | Johnson et al. |
| 2006/0063228 | A1 | 3/2006 | Kasaian et al. |
| 2006/0104968 | A1 | 5/2006 | Bookbinder et al. |
| 2006/0141456 | A1 | 6/2006 | Edwards et al. |
| 2006/0153860 | A1 | 7/2006 | Cho et al. |
| 2006/0194291 | A1 | 8/2006 | Presta |
| 2006/0198840 | A1 | 9/2006 | Dall'Acqua et al. |
| 2006/0263354 | A1 | 11/2006 | Chin et al. |
| 2007/0003546 | A1 | 1/2007 | Lazar et al. |
| 2007/0009523 | A1 | 1/2007 | Presta |
| 2007/0036785 | A1 | 2/2007 | Kishimoto et al. |
| 2007/0037734 | A1 | 2/2007 | Rossi et al. |
| 2007/0041978 | A1 | 2/2007 | Hattori et al. |
| 2007/0059312 | A1 | 3/2007 | Baca et al. |
| 2007/0061900 | A1 | 3/2007 | Murphy et al. |
| 2007/0087000 | A1 | 4/2007 | Walsh et al. |
| 2007/0092940 | A1 | 4/2007 | Eigenbrot et al. |
| 2007/0117126 | A1 | 5/2007 | Sidhu et al. |
| 2007/0135620 | A1 | 6/2007 | Chamberlain et al. |
| 2007/0148164 | A1 | 6/2007 | Farrington et al. |
| 2007/0160598 | A1 | 7/2007 | Dennis et al. |
| 2007/0190056 | A1 | 8/2007 | Kambadur et al. |
| 2007/0231329 | A1 | 10/2007 | Lazar et al. |
| 2007/0237764 | A1 | 10/2007 | Birtalan et al. |
| 2007/0248602 | A1 | 10/2007 | Lazar et al. |
| 2007/0269371 | A1 | 11/2007 | Krummen et al. |
| 2007/0292936 | A1 | 12/2007 | Barthelemy et al. |
| 2008/0044417 | A1 | 2/2008 | Johnson et al. |
| 2008/0050370 | A1 | 2/2008 | Glaser et al. |
| 2008/0069820 | A1 | 3/2008 | Fuh et al. |
| 2008/0138349 | A1 | 6/2008 | Stavenhagen et al. |
| 2008/0166756 | A1 | 7/2008 | Tsuchiya et al. |
| 2008/0181890 | A1 | 7/2008 | Lazar et al. |
| 2008/0199471 | A1 | 8/2008 | Bernett et al. |
| 2008/0206867 | A1 | 8/2008 | Desjarlais et al. |
| 2008/0274506 | A1 | 11/2008 | Presta |
| 2009/0002360 | A1 | 1/2009 | Chen et al. |
| 2009/0035836 | A1 | 2/2009 | Datta et al. |
| 2009/0041770 | A1 | 2/2009 | Chamberlain et al. |
| 2009/0053211 | A9 | 2/2009 | Lazar et al. |
| 2009/0053240 | A1 | 2/2009 | Lazar et al. |
| 2009/0076251 | A1 | 3/2009 | Koenig et al. |
| 2009/0130110 | A1 | 5/2009 | Babcook et al. |
| 2009/0131638 | A1 | 5/2009 | Davies et al. |
| 2009/0136485 | A1 | 5/2009 | Chu et al. |
| 2009/0148436 | A1 | 6/2009 | Lavallie et al. |
| 2009/0263392 | A1 | 10/2009 | Igawa et al. |
| 2009/0324589 | A1 | 12/2009 | Igawa et al. |
| 2010/0098710 | A1 | 4/2010 | Hariharan et al. |
| 2010/0098730 | A1 | 4/2010 | Lowman et al. |
| 2010/0099147 | A1 | 4/2010 | Hariharan et al. |
| 2010/0129365 | A1 | 5/2010 | Kim et al. |
| 2010/0166748 | A1 | 7/2010 | Guild et al. |
| 2010/0184959 | A1 | 7/2010 | Guler-Gane et al. |
| 2010/0216187 | A1 | 8/2010 | Lasters et al. |
| 2010/0239577 | A1 | 9/2010 | Igawa et al. |
| 2010/0249482 | A1 | 9/2010 | Chung et al. |
| 2010/0292443 | A1 | 11/2010 | Sabbadini et al. |
| 2010/0298542 | A1 | 11/2010 | Igawa et al. |
| 2011/0021755 | A1 | 1/2011 | Lazar et al. |
| 2011/0027276 | A1 | 2/2011 | Bernett et al. |
| 2011/0044986 | A1 | 2/2011 | Biere-Citron et al. |
| 2011/0059093 | A1 | 3/2011 | Bohrmann et al. |
| 2011/0076275 | A1 | 3/2011 | Igawa et al. |
| 2011/0098450 | A1 | 4/2011 | Igawa et al. |
| 2011/0105724 | A1 | 5/2011 | Clegg et al. |
| 2011/0111406 | A1 | 5/2011 | Igawa et al. |
| 2011/0135662 | A1 | 6/2011 | Finney et al. |
| 2011/0150888 | A1 | 6/2011 | Foltz et al. |
| 2011/0223658 | A1 | 9/2011 | Beliard et al. |
| 2011/0229489 | A1 | 9/2011 | Pons et al. |
| 2011/0245473 | A1 | 10/2011 | Igawa et al. |
| 2011/0311454 | A1 | 12/2011 | Dall'Acqua et al. |
| 2012/0028304 | A1 | 2/2012 | Dahiyat et al. |
| 2012/0093818 | A1 | 4/2012 | Jackson et al. |
| 2012/0189639 | A1 | 7/2012 | Schebye et al. |
| 2012/0301488 | A1 | 11/2012 | Zhang et al. |
| 2013/0011866 | A1 | 1/2013 | Igawa et al. |
| 2013/0022624 | A1 | 1/2013 | Weaver et al. |
| 2013/0064820 | A1 | 3/2013 | Magro |

(56) References Cited

U.S. PATENT DOCUMENTS

| | | | |
|---|---|---|---|
| 2013/0064836 | A1 | 3/2013 | Diefenbach-Streiber et al. |
| 2013/0085074 | A1 | 4/2013 | Walker et al. |
| 2013/0085265 | A1 | 4/2013 | Jackson et al. |
| 2013/0131319 | A1 | 5/2013 | Igawa et al. |
| 2013/0142788 | A1 | 6/2013 | Ashman et al. |
| 2013/0209457 | A1 | 8/2013 | Lazar et al. |
| 2013/0209489 | A1 | 8/2013 | Han et al. |
| 2013/0247234 | A1 | 9/2013 | Mcwhirter et al. |
| 2013/0259876 | A1 | 10/2013 | Murphy et al. |
| 2013/0302315 | A1 | 11/2013 | Lazar et al. |
| 2013/0302399 | A1 | 11/2013 | Feldhaus et al. |
| 2013/0303396 | A1 | 11/2013 | Igawa et al. |
| 2013/0336963 | A1 | 12/2013 | Igawa et al. |
| 2014/0044730 | A1 | 2/2014 | Yancopoulos et al. |
| 2014/0056878 | A1 | 2/2014 | Mcconnell et al. |
| 2014/0073768 | A1 | 3/2014 | Lazar et al. |
| 2014/0082760 | A1 | 3/2014 | Mcwhirter et al. |
| 2014/0093496 | A1 | 4/2014 | Mimoto et al. |
| 2014/0105889 | A1 | 4/2014 | Igawa et al. |
| 2014/0127209 | A1 | 5/2014 | Grabstein et al. |
| 2014/0199294 | A1 | 7/2014 | Mimoto et al. |
| 2014/0227292 | A1 | 8/2014 | Flanagan et al. |
| 2014/0234340 | A1 | 8/2014 | Igawa et al. |
| 2014/0235482 | A1 | 8/2014 | Georgiou et al. |
| 2014/0249297 | A1 | 9/2014 | Lazar et al. |
| 2014/0271459 | A1 | 9/2014 | Dutzar et al. |
| 2014/0294833 | A1 | 10/2014 | Desjarlais et al. |
| 2014/0335089 | A1 | 11/2014 | Igawa et al. |
| 2014/0356371 | A1 | 12/2014 | Swergold et al. |
| 2014/0363426 | A1 | 12/2014 | Moore et al. |
| 2014/0363428 | A1 | 12/2014 | Igawa et al. |
| 2015/0050269 | A1 | 2/2015 | Igawa et al. |
| 2015/0056182 | A1 | 2/2015 | Igawa et al. |
| 2015/0079088 | A1 | 3/2015 | Lowman et al. |
| 2015/0166636 | A1 | 6/2015 | Igawa et al. |
| 2015/0166654 | A1 | 6/2015 | Igawa et al. |
| 2015/0203577 | A1 | 7/2015 | Igawa et al. |
| 2015/0210763 | A1 | 7/2015 | Kuramochi et al. |
| 2015/0239966 | A1 | 8/2015 | Baciu et al. |
| 2015/0247849 | A1 | 9/2015 | Tamburini |
| 2015/0252107 | A1 | 9/2015 | Stevis et al. |
| 2015/0284465 | A1 | 10/2015 | Igawa et al. |
| 2015/0299296 | A1 | 10/2015 | Katada et al. |
| 2015/0299305 | A1 | 10/2015 | Andrien, Jr. et al. |
| 2015/0299313 | A1 | 10/2015 | Igawa et al. |
| 2015/0315278 | A1 | 11/2015 | Igawa et al. |
| 2015/0344570 | A1 | 12/2015 | Igawa et al. |
| 2015/0353630 | A1 | 12/2015 | Igawa et al. |
| 2016/0039912 | A1 | 2/2016 | Mimoto et al. |
| 2016/0046693 | A1 | 2/2016 | Igawa et al. |
| 2016/0068562 | A1 | 3/2016 | Cheng et al. |
| 2016/0068592 | A1 | 3/2016 | Chung et al. |
| 2016/0176954 | A1 | 6/2016 | Ruike et al. |
| 2016/0200807 | A1 | 7/2016 | Ruike et al. |
| 2016/0229908 | A1 | 8/2016 | Igawa et al. |
| 2016/0244526 | A1 | 8/2016 | Igawa et al. |
| 2017/0002080 | A1 | 1/2017 | Igawa et al. |
| 2017/0022270 | A1 | 1/2017 | Igawa et al. |
| 2017/0174778 | A1 | 6/2017 | Shusta et al. |
| 2017/0181987 | A1 | 6/2017 | Svensson et al. |
| 2018/0002415 | A1 | 1/2018 | Ruike et al. |
| 2018/0016327 | A1 | 1/2018 | Murata et al. |
| 2018/0142027 | A1 | 5/2018 | Igawa et al. |
| 2018/0258161 | A1 | 9/2018 | Igawa et al. |
| 2018/0258163 | A1 | 9/2018 | Igawa et al. |
| 2018/0282718 | A1 | 10/2018 | Igawa et al. |
| 2018/0282719 | A1 | 10/2018 | Igawa et al. |
| 2018/0319876 | A1 | 11/2018 | Ruike et al. |
| 2018/0319877 | A1 | 11/2018 | Ruike et al. |
| 2019/0002548 | A1 | 1/2019 | Ruike et al. |
| 2019/0062413 | A1 | 2/2019 | Ruike et al. |
| 2019/0112393 | A1 | 4/2019 | Igawa et al. |
| 2019/0169286 | A1 | 6/2019 | Kakiuchi et al. |
| 2019/0218277 | A1 | 7/2019 | Sampei et al. |
| 2019/0218309 | A1 | 7/2019 | Igawa et al. |
| 2019/0315840 | A1 | 10/2019 | Sampei et al. |
| 2019/0367599 | A1 | 12/2019 | Shinomiya et al. |
| 2020/0031913 | A1 | 1/2020 | Ruike et al. |
| 2020/0048627 | A1 | 2/2020 | Igawa et al. |
| 2020/0172610 | A1 | 6/2020 | Igawa et al. |
| 2020/0317768 | A1 | 10/2020 | Ruike et al. |
| 2020/0407432 | A1 | 12/2020 | Shinomiya et al. |
| 2021/0017256 | A1 | 1/2021 | Fink et al. |
| 2021/0095008 | A1 | 4/2021 | Sampei et al. |
| 2021/0301004 | A1 | 9/2021 | Shinomiya et al. |
| 2021/0301011 | A1 | 9/2021 | Kakiuchi et al. |
| 2021/0324109 | A1 | 10/2021 | Igawa et al. |
| 2022/0089715 | A1 | 3/2022 | Igawa et al. |
| 2022/0213140 | A1 | 7/2022 | Wakabayashi et al. |
| 2022/0275076 | A1 | 9/2022 | Ruike et al. |
| 2022/0389105 | A1 | 12/2022 | Igawa et al. |
| 2022/0389118 | A1 | 12/2022 | Igawa et al. |
| 2022/0411483 | A1 | 12/2022 | Mimoto et al. |
| 2023/0140797 | A1 | 5/2023 | Igawa et al. |
| 2023/0174655 | A1 | 6/2023 | Mimoto et al. |
| 2023/0203144 | A1 | 6/2023 | Murata et al. |
| 2024/0018219 | A1 | 1/2024 | Sampei et al. |
| 2024/0158482 | A1 | 5/2024 | Igawa et al. |
| 2024/0190948 | A1 | 6/2024 | Fink et al. |
| 2024/0190976 | A1 | 6/2024 | Igawa et al. |
| 2024/0239906 | A1 | 7/2024 | Igawa et al. |
| 2025/0076311 | A1 | 3/2025 | Ruike et al. |

FOREIGN PATENT DOCUMENTS

| | | | |
|---|---|---|---|
| AU | 2012222252 | A1 | 10/2013 |
| AU | 2014250434 | A | 10/2015 |
| AU | 2015227424 | A1 | 10/2015 |
| AU | 2012222252 | B2 | 8/2016 |
| CA | 2647846 | A1 | 10/2007 |
| CA | 2911000 | A1 | 10/2007 |
| CA | 2700986 | A1 | 4/2009 |
| CA | 2827923 | A1 | 8/2012 |
| CA | 2899589 | A1 | 8/2014 |
| CA | 2963760 | A1 | 6/2016 |
| CA | 3019904 | A1 | 12/2017 |
| CN | 1156460 | A | 8/1997 |
| CN | 1274289 | A | 11/2000 |
| CN | 1763097 | A | 4/2006 |
| CN | 1958615 | A | 5/2007 |
| CN | 101001873 | A | 7/2007 |
| CN | 101014619 | A | 8/2007 |
| CN | 101230102 | A | 7/2008 |
| CN | 101277976 | A | 10/2008 |
| CN | 101282992 | A | 10/2008 |
| CN | 100455598 | C | 1/2009 |
| CN | 101479381 | A | 7/2009 |
| CN | 101511871 | A | 8/2009 |
| CN | 101874042 | A | 10/2010 |
| CN | 101014619 | B | 11/2010 |
| CN | 101932593 | A | 12/2010 |
| CN | 101970492 | A | 2/2011 |
| CN | 1763097 | B | 4/2011 |
| CN | 102056946 | A | 5/2011 |
| CN | 102149729 | A | 8/2011 |
| CN | 102325793 | A | 1/2012 |
| CN | 102369291 | A | 3/2012 |
| CN | 101277976 | B | 4/2012 |
| CN | 101511871 | B | 7/2012 |
| CN | 102633880 | A | 8/2012 |
| CN | 101282992 | B | 2/2013 |
| CN | 102918057 | A | 2/2013 |
| CN | 101001873 | B | 3/2013 |
| CN | 102993304 | A | 3/2013 |
| CN | 103097415 | A | 5/2013 |
| CN | 103221426 | A | 7/2013 |
| CN | 103492565 | A | 1/2014 |
| CN | 101932593 | B | 8/2014 |
| CN | 102149729 | B | 8/2014 |
| CN | 103975060 | A | 8/2014 |
| CN | 102633880 | B | 2/2015 |
| CN | 101479381 | B | 4/2015 |
| CN | 104640879 | A | 5/2015 |
| CN | 103221426 | B | 1/2016 |

(56) References Cited

FOREIGN PATENT DOCUMENTS

| | | | |
|---|---|---|---|
| CN | 107108726 | A | 8/2017 |
| CN | 101874042 | B | 9/2018 |
| CN | 104640879 | B | 12/2018 |
| EA | 004317 | B1 | 2/2004 |
| EA | 200801027 | A1 | 10/2008 |
| EA | 015589 | B1 | 10/2011 |
| EA | 201100300 | A1 | 12/2011 |
| EA | 027575 | B1 | 8/2017 |
| EP | 0182495 | A1 | 5/1986 |
| EP | 0329185 | A2 | 8/1989 |
| EP | 0404097 | A2 | 12/1990 |
| EP | 0425235 | A2 | 5/1991 |
| EP | 0329185 | B1 | 4/1994 |
| EP | 0404097 | B1 | 9/1996 |
| EP | 0425235 | B1 | 9/1996 |
| EP | 0770628 | A1 | 5/1997 |
| EP | 0783893 | A1 | 7/1997 |
| EP | 1069185 | A1 | 1/2001 |
| EP | 1509770 | A1 | 3/2005 |
| EP | 1601697 | A1 | 12/2005 |
| EP | 0770628 | B1 | 9/2006 |
| EP | 1752471 | A1 | 2/2007 |
| EP | 1772465 | A1 | 4/2007 |
| EP | 1773391 | A2 | 4/2007 |
| EP | 1601697 | B1 | 5/2007 |
| EP | 1870459 | A1 | 12/2007 |
| EP | 1752471 | B1 | 11/2008 |
| EP | 1992692 | A1 | 11/2008 |
| EP | 2006381 | A1 | 12/2008 |
| EP | 2009101 | A1 | 12/2008 |
| EP | 1772465 | B1 | 2/2009 |
| EP | 2196541 | A1 | 6/2010 |
| EP | 2202245 | A1 | 6/2010 |
| EP | 2275443 | A1 | 1/2011 |
| EP | 1069185 | B1 | 6/2011 |
| EP | 2368911 | A1 | 9/2011 |
| EP | 2409990 | A1 | 1/2012 |
| EP | 2431393 | A1 | 3/2012 |
| EP | 0783893 | B1 | 4/2012 |
| EP | 2471813 | A1 | 7/2012 |
| EP | 1992692 | B1 | 1/2013 |
| EP | 2647706 | A1 | 10/2013 |
| EP | 2679681 | A1 | 1/2014 |
| EP | 2698431 | A1 | 2/2014 |
| EP | 2708558 | A2 | 3/2014 |
| EP | 1509770 | B1 | 7/2014 |
| EP | 2760890 | A2 | 8/2014 |
| EP | 2762166 | A1 | 8/2014 |
| EP | 2762493 | A1 | 8/2014 |
| EP | 2762564 | A1 | 8/2014 |
| EP | 2765192 | A1 | 8/2014 |
| EP | 2471813 | B1 | 12/2014 |
| EP | 2818183 | A1 | 12/2014 |
| EP | 2853898 | A1 | 4/2015 |
| EP | 2889377 | A1 | 7/2015 |
| EP | 2940043 | A1 | 11/2015 |
| EP | 2275443 | B1 | 12/2015 |
| EP | 2975055 | A1 | 1/2016 |
| EP | 2982689 | A1 | 2/2016 |
| EP | 1870459 | B1 | 6/2016 |
| EP | 3042912 | A1 | 7/2016 |
| EP | 2202245 | B1 | 8/2016 |
| EP | 2853898 | B1 | 1/2017 |
| EP | 3240804 | A1 | 11/2017 |
| EP | 2431393 | B1 | 5/2018 |
| EP | 2818183 | B1 | 4/2020 |
| JP | S61117457 | A | 6/1986 |
| JP | S6352890 | A | 3/1988 |
| JP | H0228200 | A | 1/1990 |
| JP | H02163085 | A | 6/1990 |
| JP | H03500644 | A | 2/1991 |
| JP | H03504332 | A | 9/1991 |
| JP | H0441000 | A | 2/1992 |
| JP | H05504579 | A | 7/1993 |
| JP | H0636741 | A | 2/1994 |
| JP | H06104071 | A | 4/1994 |
| JP | H0767688 | A | 3/1995 |
| JP | H08217799 | A | 8/1996 |
| JP | 2559537 | B2 | 12/1996 |
| JP | 2638680 | B2 | 8/1997 |
| JP | 2003512019 | A | 4/2003 |
| JP | 2004073210 | A | 3/2004 |
| JP | 2004511426 | A | 4/2004 |
| JP | 2005501514 | A | 1/2005 |
| JP | 2005510212 | A | 4/2005 |
| JP | 3697555 | B2 | 9/2005 |
| JP | 2005535341 | A | 11/2005 |
| JP | 2006512407 | A | 4/2006 |
| JP | 2006517525 | A | 7/2006 |
| JP | 2006519583 | A | 8/2006 |
| JP | 3865418 | B2 | 1/2007 |
| JP | 2007252368 | A | 10/2007 |
| JP | 2007532139 | A | 11/2007 |
| JP | 2008504002 | A | 2/2008 |
| JP | 2008505174 | A | 2/2008 |
| JP | 2008511292 | A | 4/2008 |
| JP | 2008514201 | A | 5/2008 |
| JP | 4179517 | B2 | 11/2008 |
| JP | 2009500344 | A | 1/2009 |
| JP | 2009504164 | A | 2/2009 |
| JP | 2009511067 | A | 3/2009 |
| JP | 2009541352 | A | 11/2009 |
| JP | 2010505436 | A | 2/2010 |
| JP | 2010081866 | A | 4/2010 |
| JP | 2010514460 | A | 5/2010 |
| JP | 2010521194 | A | 6/2010 |
| JP | 4547561 | B2 | 9/2010 |
| JP | 4580340 | B2 | 11/2010 |
| JP | 2011504096 | A | 2/2011 |
| JP | 2011529700 | A | 12/2011 |
| JP | 4886986 | B2 | 2/2012 |
| JP | 2012021004 | A | 2/2012 |
| JP | 4961501 | B | 6/2012 |
| JP | 2012116837 | A | 6/2012 |
| JP | 2012512641 | A | 6/2012 |
| JP | 5017116 | B2 | 9/2012 |
| JP | 5048866 | B | 10/2012 |
| JP | 5055603 | B2 | 10/2012 |
| JP | 5144499 | B2 | 2/2013 |
| JP | 2013518131 | A | 5/2013 |
| JP | 2013518606 | A | 5/2013 |
| JP | 2013521772 | A | 6/2013 |
| JP | 5229888 | B2 | 7/2013 |
| JP | 5239086 | B2 | 7/2013 |
| JP | 2013165716 | A | 8/2013 |
| JP | 2013531486 | A | 8/2013 |
| JP | 2013537425 | A | 10/2013 |
| JP | 5334319 | B2 | 11/2013 |
| JP | 5357778 | B2 | 12/2013 |
| JP | 5367982 | B2 | 12/2013 |
| JP | 5421105 | B | 2/2014 |
| JP | 2014055145 | A | 3/2014 |
| JP | 2014528906 | A | 10/2014 |
| JP | 5756291 | B2 | 7/2015 |
| JP | 2015130883 | A | 7/2015 |
| JP | 5815403 | B2 | 11/2015 |
| JP | 2016026190 | A | 2/2016 |
| JP | 5882247 | B2 | 3/2016 |
| JP | 5932670 | B2 | 6/2016 |
| JP | 2016528247 | A | 9/2016 |
| JP | 6082447 | B2 | 2/2017 |
| JP | 6088703 | B1 | 3/2017 |
| JP | 2017112996 | A | 6/2017 |
| JP | 2017113013 | A | 6/2017 |
| JP | 6204350 | B2 | 9/2017 |
| JP | 6527643 | B | 6/2019 |
| JP | 2019523295 | A | 8/2019 |
| JP | 6823167 | B2 | 1/2021 |
| JP | 6879751 | B2 | 6/2021 |
| KR | 100261941 | B1 | 7/2000 |
| KR | 20100074220 | A | 7/2010 |
| KR | 20110004435 | A | 1/2011 |
| KR | 20110103431 | A | 9/2011 |
| KR | 20120035192 | A | 4/2012 |

(56) References Cited

FOREIGN PATENT DOCUMENTS

| | | | |
|---|---|---|---|
| KR | 101282320 | B1 | 7/2013 |
| KR | 20140005864 | A | 1/2014 |
| KR | 101575914 | B1 | 12/2015 |
| MX | 2013006109 | A | 1/2014 |
| MX | 365235 | B | 5/2019 |
| RU | 2147442 | C1 | 4/2000 |
| RU | 2225721 | C2 | 3/2004 |
| RU | 2236222 | C2 | 9/2004 |
| RU | 2266298 | C2 | 12/2005 |
| RU | 2005112742 | A | 1/2006 |
| RU | 2005130173 | A | 3/2006 |
| RU | 2005137578 | A | 6/2007 |
| RU | 2006127314 | A | 2/2008 |
| RU | 2325186 | C2 | 5/2008 |
| RU | 2337107 | C2 | 10/2008 |
| RU | 2360925 | C2 | 7/2009 |
| RU | 2008104038 | A | 8/2009 |
| RU | 2008128133 | A | 1/2010 |
| RU | 2008139118 | A | 4/2010 |
| RU | 2008139901 | A | 4/2010 |
| RU | 2390527 | C2 | 5/2010 |
| RU | 2399381 | C2 | 9/2010 |
| RU | 2009112723 | A | 10/2010 |
| RU | 2422460 | C2 | 6/2011 |
| RU | 2430111 | C1 | 9/2011 |
| RU | 2010116152 | A | 11/2011 |
| RU | 2440824 | C2 | 1/2012 |
| RU | 2445975 | C2 | 3/2012 |
| RU | 2010150931 | A | 6/2012 |
| RU | 2477137 | C2 | 3/2013 |
| RU | 2495882 | C2 | 10/2013 |
| RU | 2505603 | C2 | 1/2014 |
| RU | 2519645 | C2 | 6/2014 |
| SG | 192945 | A1 | 9/2013 |
| TW | 416960 | B | 1/2001 |
| TW | 201202419 | A | 1/2012 |
| TW | 201206466 | A | 2/2012 |
| TW | 201638107 | A | 11/2016 |
| TW | 201643190 | A | 12/2016 |
| TW | 201712032 | A | 4/2017 |
| TW | 201726718 | A | 8/2017 |
| TW | I605057 | B | 11/2017 |
| TW | I611811 | B | 1/2018 |
| TW | 201808331 | A | 3/2018 |
| TW | 201808992 | A | 3/2018 |
| TW | 201819409 | A | 6/2018 |
| TW | I656133 | B | 4/2019 |
| TW | 202039553 | A | 11/2020 |
| WO | WO-8303678 | A1 | 10/1983 |
| WO | WO-8901343 | A1 | 2/1989 |
| WO | WO-9007524 | A1 | 7/1990 |
| WO | WO-9112023 | A2 | 8/1991 |
| WO | WO-9113631 | A1 | 9/1991 |
| WO | WO-9207084 | A1 | 4/1992 |
| WO | WO-9219759 | A1 | 11/1992 |
| WO | WO-9301161 | A1 | 1/1993 |
| WO | WO-9308829 | A1 | 5/1993 |
| WO | WO-9316185 | A2 | 8/1993 |
| WO | WO-9317105 | A1 | 9/1993 |
| WO | WO-9411026 | A2 | 5/1994 |
| WO | WO-9421681 | A1 | 9/1994 |
| WO | WO-9429351 | A2 | 12/1994 |
| WO | WO-9514710 | A1 | 6/1995 |
| WO | WO-9529697 | A1 | 11/1995 |
| WO | WO-9602576 | A1 | 2/1996 |
| WO | WO-9611020 | A1 | 4/1996 |
| WO | WO-9612503 | A1 | 5/1996 |
| WO | WO-9720858 | A1 | 6/1997 |
| WO | WO-9730087 | A1 | 8/1997 |
| WO | WO-9734631 | A1 | 9/1997 |
| WO | WO-9803546 | A1 | 1/1998 |
| WO | WO-9805787 | A1 | 2/1998 |
| WO | WO-9846257 | A1 | 10/1998 |
| WO | WO-9858964 | A1 | 12/1998 |
| WO | WO-9918212 | A1 | 4/1999 |
| WO | WO-9922764 | A1 | 5/1999 |
| WO | WO-9951642 | A1 | 10/1999 |
| WO | WO-9951743 | A1 | 10/1999 |
| WO | WO-9958572 | A1 | 11/1999 |
| WO | WO-0014220 | A1 | 3/2000 |
| WO | WO-0015214 | A1 | 3/2000 |
| WO | WO-0042072 | A2 | 7/2000 |
| WO | WO-0061739 | A1 | 10/2000 |
| WO | WO-0129246 | A1 | 4/2001 |
| WO | WO-0130854 | A2 | 5/2001 |
| WO | WO-0170968 | A2 | 9/2001 |
| WO | WO-0182899 | A2 | 11/2001 |
| WO | WO-0209641 | A2 | 2/2002 |
| WO | WO-0230985 | A2 | 4/2002 |
| WO | WO-0231140 | A1 | 4/2002 |
| WO | WO-02060919 | A2 | 8/2002 |
| WO | WO-03000883 | A1 | 1/2003 |
| WO | WO-03011878 | A2 | 2/2003 |
| WO | WO-03015819 | A1 | 2/2003 |
| WO | WO-03020949 | A2 | 3/2003 |
| WO | WO-03027248 | A2 | 4/2003 |
| WO | WO-03070760 | A2 | 8/2003 |
| WO | WO-03074679 | A2 | 9/2003 |
| WO | WO-03084570 | A1 | 10/2003 |
| WO | WO-03085107 | A1 | 10/2003 |
| WO | WO-03085119 | A1 | 10/2003 |
| WO | WO-03105757 | A2 | 12/2003 |
| WO | WO-03107009 | A2 | 12/2003 |
| WO | WO-2004007553 | A1 | 1/2004 |
| WO | WO-2004016740 | A2 | 2/2004 |
| WO | WO-2004024890 | A2 | 3/2004 |
| WO | WO-2004029207 | A2 | 4/2004 |
| WO | WO-2004035752 | A2 | 4/2004 |
| WO | WO-2004037861 | A2 | 5/2004 |
| WO | WO-2004039826 | A1 | 5/2004 |
| WO | WO-2004056312 | A2 | 7/2004 |
| WO | WO-2004058797 | A2 | 7/2004 |
| WO | WO-2004068931 | A2 | 8/2004 |
| WO | WO-2004092219 | A2 | 10/2004 |
| WO | WO-2004096273 | A1 | 11/2004 |
| WO | WO-2004099249 | A2 | 11/2004 |
| WO | WO-2004108157 | A2 | 12/2004 |
| WO | WO-2005020936 | A2 | 3/2005 |
| WO | WO-2005023193 | A2 | 3/2005 |
| WO | WO-2005035586 | A1 | 4/2005 |
| WO | WO-2005035756 | A1 | 4/2005 |
| WO | WO-2005035778 | A1 | 4/2005 |
| WO | WO-2005037867 | A1 | 4/2005 |
| WO | WO-2005047307 | A2 | 5/2005 |
| WO | WO-2005047327 | A2 | 5/2005 |
| WO | WO-2005053742 | A1 | 6/2005 |
| WO | WO-2005056606 | A2 | 6/2005 |
| WO | WO-2005056759 | A2 | 6/2005 |
| WO | WO-2005059106 | A2 | 6/2005 |
| WO | WO-2005066204 | A2 | 7/2005 |
| WO | WO-2005067620 | A2 | 7/2005 |
| WO | WO-2005074607 | A2 | 8/2005 |
| WO | WO-2005077981 | A2 | 8/2005 |
| WO | WO-2005080429 | A2 | 9/2005 |
| WO | WO-2005092925 | A2 | 10/2005 |
| WO | WO-2005094446 | A2 | 10/2005 |
| WO | WO-2005100402 | A1 | 10/2005 |
| WO | WO-2005112564 | A2 | 12/2005 |
| WO | WO-2005115452 | A2 | 12/2005 |
| WO | WO-2005121180 | A1 | 12/2005 |
| WO | WO-2005123126 | A2 | 12/2005 |
| WO | WO-2005123780 | A2 | 12/2005 |
| WO | WO-2006004663 | A2 | 1/2006 |
| WO | WO-2006019447 | A1 | 2/2006 |
| WO | WO-2006020114 | A2 | 2/2006 |
| WO | WO-2006023403 | A2 | 3/2006 |
| WO | WO-2006023420 | A2 | 3/2006 |
| WO | WO-2006029879 | A2 | 3/2006 |
| WO | WO-2006030200 | A1 | 3/2006 |
| WO | WO-2006030220 | A1 | 3/2006 |
| WO | WO-2006031370 | A2 | 3/2006 |
| WO | WO-2006036834 | A2 | 4/2006 |
| WO | WO-2006044908 | A2 | 4/2006 |
| WO | WO-2006047350 | A2 | 5/2006 |

(56) References Cited

FOREIGN PATENT DOCUMENTS

| | | | |
|---|---|---|---|
| WO | WO-2006050166 | A2 | 5/2006 |
| WO | WO-2006050491 | A2 | 5/2006 |
| WO | WO-2006053301 | A2 | 5/2006 |
| WO | WO-2006066598 | A2 | 6/2006 |
| WO | WO-2006067913 | A1 | 6/2006 |
| WO | WO-2006071877 | A2 | 7/2006 |
| WO | WO-2006076594 | A2 | 7/2006 |
| WO | WO-2006082052 | A1 | 8/2006 |
| WO | WO-2006083182 | A1 | 8/2006 |
| WO | WO-2006083183 | A1 | 8/2006 |
| WO | WO-2006085967 | A2 | 8/2006 |
| WO | WO-2006102095 | A2 | 9/2006 |
| WO | WO-2006105338 | A2 | 10/2006 |
| WO | WO-2006106905 | A1 | 10/2006 |
| WO | WO-2006109592 | A1 | 10/2006 |
| WO | WO-2006113643 | A2 | 10/2006 |
| WO | WO-2006116269 | A2 | 11/2006 |
| WO | WO-2006121852 | A2 | 11/2006 |
| WO | WO-2006130834 | A2 | 12/2006 |
| WO | WO-2007001422 | A2 | 1/2007 |
| WO | WO2007005612 | A2 | 1/2007 |
| WO | WO-2007008943 | A2 | 1/2007 |
| WO | WO-2007022070 | A2 | 2/2007 |
| WO | WO-2007022520 | A2 | 2/2007 |
| WO | WO-2007024249 | A2 | 3/2007 |
| WO | WO-2007024535 | A2 | 3/2007 |
| WO | WO-2007041635 | A2 | 4/2007 |
| WO | WO-2007044411 | A2 | 4/2007 |
| WO | WO-2007044616 | A2 | 4/2007 |
| WO | WO-2007047112 | A2 | 4/2007 |
| WO | WO-2007047578 | A2 | 4/2007 |
| WO | WO-2007060411 | A1 | 5/2007 |
| WO | WO-2007068411 | A2 | 6/2007 |
| WO | WO-2007076524 | A2 | 7/2007 |
| WO | WO-2007084253 | A2 | 7/2007 |
| WO | WO-2007092772 | A2 | 8/2007 |
| WO | WO-2007103134 | A2 | 9/2007 |
| WO | WO-2007103549 | A2 | 9/2007 |
| WO | WO-2007106585 | A1 | 9/2007 |
| WO | WO-2007114319 | A1 | 10/2007 |
| WO | WO-2007114325 | A1 | 10/2007 |
| WO | WO-2007142325 | A1 | 12/2007 |
| WO | WO-2007150015 | A2 | 12/2007 |
| WO | WO-2007150016 | A2 | 12/2007 |
| WO | WO-2008002933 | A2 | 1/2008 |
| WO | WO-2008017963 | A2 | 2/2008 |
| WO | WO-2008022152 | A2 | 2/2008 |
| WO | WO-2008030706 | A2 | 3/2008 |
| WO | WO-2008031056 | A2 | 3/2008 |
| WO | WO-2008036688 | A2 | 3/2008 |
| WO | WO-2008043822 | A2 | 4/2008 |
| WO | WO-2008060785 | A2 | 5/2008 |
| WO | WO-2008069889 | A2 | 6/2008 |
| WO | WO-2008077546 | A1 | 7/2008 |
| WO | WO-2008091798 | A2 | 7/2008 |
| WO | WO-2008091954 | A2 | 7/2008 |
| WO | WO-2008092117 | A2 | 7/2008 |
| WO | WO-2008098115 | A2 | 8/2008 |
| WO | WO-2008113834 | A2 | 9/2008 |
| WO | WO-2008121160 | A2 | 10/2008 |
| WO | WO-2008130969 | A2 | 10/2008 |
| WO | WO-2008150494 | A1 | 12/2008 |
| WO | WO-2009000098 | A2 | 12/2008 |
| WO | WO-2009000099 | A2 | 12/2008 |
| WO | WO-2009006338 | A1 | 1/2009 |
| WO | WO-2009011941 | A2 | 1/2009 |
| WO | WO-2009026117 | A2 | 2/2009 |
| WO | WO-2009032145 | A1 | 3/2009 |
| WO | WO-2009032782 | A2 | 3/2009 |
| WO | WO-2009041062 | A1 | 4/2009 |
| WO | WO-2009041613 | A1 | 4/2009 |
| WO | WO-2009041643 | A1 | 4/2009 |
| WO | WO-2009058346 | A1 | 5/2009 |
| WO | WO-2009058492 | A2 | 5/2009 |
| WO | WO-2009062083 | A2 | 5/2009 |
| WO | WO-2009086320 | A1 | 7/2009 |
| WO | WO-2009089004 | A1 | 7/2009 |
| WO | WO-2009095235 | A1 | 8/2009 |
| WO | WO-2009125825 | A1 | 10/2009 |
| WO | WO-2009131702 | A2 | 10/2009 |
| WO | WO-2009137880 | A1 | 11/2009 |
| WO | WO-2009139822 | A1 | 11/2009 |
| WO | WO-2009155513 | A2 | 12/2009 |
| WO | WO-2010015608 | A1 | 2/2010 |
| WO | WO-2010033736 | A1 | 3/2010 |
| WO | WO-2010043977 | A2 | 4/2010 |
| WO | WO-2010045193 | A1 | 4/2010 |
| WO | WO-2010054403 | A1 | 5/2010 |
| WO | WO-2010058860 | A1 | 5/2010 |
| WO | WO-2010070094 | A1 | 6/2010 |
| WO | WO-2010077854 | A1 | 7/2010 |
| WO | WO2010085682 | A2 | 7/2010 |
| WO | WO-2010106180 | A2 | 9/2010 |
| WO | WO-2010107109 | A1 | 9/2010 |
| WO | WO-2010151338 | A2 | 12/2010 |
| WO | WO-2011008517 | A2 | 1/2011 |
| WO | WO-2011021009 | A1 | 2/2011 |
| WO | WO-2011063980 | A1 | 6/2011 |
| WO | WO-2011091078 | A2 | 7/2011 |
| WO | WO-2011094593 | A2 | 8/2011 |
| WO | WO-2011100271 | A2 | 8/2011 |
| WO | WO-2011109338 | A1 | 9/2011 |
| WO | WO-2011111007 | A2 | 9/2011 |
| WO | WO-2011122011 | A2 | 10/2011 |
| WO | WO-2011137362 | A1 | 11/2011 |
| WO | WO-2011150008 | A1 | 12/2011 |
| WO | WO-2011151432 | A1 | 12/2011 |
| WO | WO-2012016227 | A2 | 2/2012 |
| WO | WO-2012024242 | A1 | 2/2012 |
| WO | WO-2012044831 | A1 | 4/2012 |
| WO | WO-2012073992 | A1 | 6/2012 |
| WO | WO-2012082073 | A1 | 6/2012 |
| WO | WO-2012088247 | A2 | 6/2012 |
| WO | WO-2012093704 | A1 | 7/2012 |
| WO | WO-2012115241 | A1 | 8/2012 |
| WO | WO-2012132067 | A1 | 10/2012 |
| WO | WO-2012133782 | A1 | 10/2012 |
| WO | WO-2012151481 | A1 | 11/2012 |
| WO | WO-2012177653 | A2 | 12/2012 |
| WO | WO-2013012733 | A1 | 1/2013 |
| WO | WO-2013046704 | A2 | 4/2013 |
| WO | WO-2013046722 | A1 | 4/2013 |
| WO | WO-2013047729 | A1 | 4/2013 |
| WO | WO-2013047748 | A1 | 4/2013 |
| WO | WO-2013047752 | A1 | 4/2013 |
| WO | WO-2013081143 | A1 | 6/2013 |
| WO | WO-2013089647 | A1 | 6/2013 |
| WO | WO-2013125667 | A1 | 8/2013 |
| WO | WO-2013138680 | A1 | 9/2013 |
| WO | WO-2013138681 | A1 | 9/2013 |
| WO | WO-2013149111 | A2 | 10/2013 |
| WO | WO-2013151764 | A1 | 10/2013 |
| WO | WO-2013152001 | A2 | 10/2013 |
| WO | WO-2013166099 | A1 | 11/2013 |
| WO | WO-2013173348 | A1 | 11/2013 |
| WO | WO-2013180200 | A1 | 12/2013 |
| WO | WO-2013180201 | A1 | 12/2013 |
| WO | WO-2013186719 | A1 | 12/2013 |
| WO | WO-2014006217 | A1 | 1/2014 |
| WO | WO-2014025546 | A2 | 2/2014 |
| WO | WO-2014028354 | A1 | 2/2014 |
| WO | WO-2014030728 | A1 | 2/2014 |
| WO | WO-2014030750 | A1 | 2/2014 |
| WO | WO2014037899 | A2 | 3/2014 |
| WO | WO-2014043344 | A1 | 3/2014 |
| WO | WO-2014047500 | A1 | 3/2014 |
| WO | WO-2014074532 | A2 | 5/2014 |
| WO | WO-2014100689 | A1 | 6/2014 |
| WO | WO-2014114651 | A1 | 7/2014 |
| WO | WO-2014119969 | A1 | 8/2014 |
| WO | WO-2014140366 | A1 | 9/2014 |
| WO | WO-2014144080 | A2 | 9/2014 |
| WO | WO-2014144575 | A1 | 9/2014 |
| WO | WO-2014144577 | A1 | 9/2014 |

(56) References Cited

FOREIGN PATENT DOCUMENTS

| | | |
|---|---|---|
| WO | WO-2014144903 A1 | 9/2014 |
| WO | WO-2014145159 A2 | 9/2014 |
| WO | WO-2014145806 A2 | 9/2014 |
| WO | WO-2014150983 A2 | 9/2014 |
| WO | WO-2014160958 A1 | 10/2014 |
| WO | WO-2014163101 A1 | 10/2014 |
| WO | WO-2014164959 A2 | 10/2014 |
| WO | WO-2014182676 A2 | 11/2014 |
| WO | WO-2014184384 A1 | 11/2014 |
| WO | WO-2014190441 A1 | 12/2014 |
| WO | WO-2015022658 A2 | 2/2015 |
| WO | WO-2015023972 A1 | 2/2015 |
| WO | WO-2015034000 A1 | 3/2015 |
| WO | WO-2015042250 A1 | 3/2015 |
| WO | WO-2015077491 A1 | 5/2015 |
| WO | WO-2015089492 A2 | 6/2015 |
| WO | WO-2015111008 A2 | 7/2015 |
| WO | WO-2015122995 A1 | 8/2015 |
| WO | WO-2015123362 A1 | 8/2015 |
| WO | WO-2015127134 A2 | 8/2015 |
| WO | WO-2015134894 A1 | 9/2015 |
| WO | WO-2015162590 A1 | 10/2015 |
| WO | WO-2016012800 A1 | 1/2016 |
| WO | WO-2016073853 A1 | 5/2016 |
| WO | WO-2016073879 A2 | 5/2016 |
| WO | WO-2016073906 A2 | 5/2016 |
| WO | WO-2016092439 A1 | 6/2016 |
| WO | WO-2016098356 A1 | 6/2016 |
| WO | WO-2016098357 A1 | 6/2016 |
| WO | WO-2016117346 A1 | 7/2016 |
| WO | WO-2016125495 A1 | 8/2016 |
| WO | WO-2016148653 A1 | 9/2016 |
| WO | WO-2016160756 A2 | 10/2016 |
| WO | WO-2016168613 A1 | 10/2016 |
| WO | WO-2017046994 A1 | 3/2017 |
| WO | WO-2017049011 A1 | 3/2017 |
| WO | WO2017064615 A1 | 4/2017 |
| WO | WO-2017104779 A1 | 6/2017 |
| WO | WO-2017104783 A1 | 6/2017 |
| WO | WO-2017110981 A1 | 6/2017 |
| WO | WO-2017120523 A2 | 7/2017 |
| WO | WO-2017123636 A1 | 7/2017 |
| WO | WO2017205101 A1 | 11/2017 |
| WO | WO-2017212291 A1 | 12/2017 |
| WO | WO-2017217524 A1 | 12/2017 |
| WO | WO-2017217525 A1 | 12/2017 |
| WO | WO-2017218515 A1 | 12/2017 |
| WO | WO-2017218592 A1 | 12/2017 |
| WO | WO-2018025982 A1 | 2/2018 |
| WO | WO-2018052375 A1 | 3/2018 |
| WO | WO-2018143266 A1 | 8/2018 |
| WO | WO-2018167322 A1 | 9/2018 |
| WO | WO-2018169993 A1 | 9/2018 |
| WO | WO-2018184739 A1 | 10/2018 |
| WO | WO 2019177543 A1 | 9/2019 |
| WO | WO-2020027279 A1 | 2/2020 |
| WO | WO-2020209318 A1 | 10/2020 |

OTHER PUBLICATIONS

Kim, J. H., et al., "Enhanced humanization and affinity maturation of neutralizing anti-hepatitis B virus preS1 antibody based on antigen-antibody complex structure," FEBS Lett., 589(2):193-200 (2015).

Putnam, F. W., et al., "Complete Amino Acid Sequence of the Mu Heavy Chain of a Human IgM Immunoglobulin," Science, 182(4109):287-291 (1973).

Ricklin, D. and Lambris, J. D., "Complement-targeted therapeutics," Nat Biotechnol., 25(11):1265-1275 (2007).

Roitt, et al., Immunology, Moscow, Mir, 110-111, 151 (2000), with English translation, Immunology, 62-68 (2006).

Sun, W., et al., "Therapeutic antibody: new opportunity for immunity and inflammatory diseases," Acta Pharmaceutica Sinica,47(10):1306-1316 (2012).

Wagner, E. and Frank, M. M., "Therapeutic potential of complement modulation," Nat Rev Drug Discov., 9(1):43-56 (2010).

U.S. Appl. No. 16/323,142, filed Feb. 4, 2019, Kakiuchi et al., related application.

U.S. Appl. No. 17/333,256, filed May 28, 2021, Kakiuchi et al., related application.

U.S. Appl. No. 18/390,581, filed Dec. 20, 2023, Igawa et al., related application.

U.S. Appl. No. 18/425,859, filed Jan. 29, 2024, Igawa et al., related application.

U.S. Appl. No. 18/432,567, filed Feb. 5, 2024, Igawa et al., related application.

U.S. Appl. No. 18/453,418, filed Aug. 22, 2023, Sampei et al., related application.

U.S. Appl. No. 18/545,077, filed Dec. 19, 2023, Fink et al., related application.

U.S. Appl. No. 18/883,787, filed Sep. 12, 2004, Igawa et al., related application.

U.S. Appl. No. 18/929,733, filed Oct. 29, 2024, Ruike et al., related application.

Aleshin, A.E., et al., "Crystal Structure of C5b-6 Suggests Structural Basis for Priming Assembly of the Membrane Attack Complex," J Biol Chem., 287(23):19642-19652 (2012).

Almagro, J.C., et al., "Design and Validation of a Synthetic VH Repertoire with Tailored Diversity for Protein Recognition," J Mol Recog., 19(5):413-422 (2006).

Altshuler, D.V., et al., "Advances in Biological Chemistry (Uspekhi biologitsheskoy khimii)," 50:203-204, 215, 219-228 (2010).

Altshuler, Y.P., et al., "Advances in Biological Chemistry (Uspekhi biologitsheskoy khimii)," 50:207 (2010).

Anderson, C.L., et al., "Perspective-FcRn Transports Albumin: Relevance to Immunology and Medicine," Trends Immunol., 27(7):343-348 (2006).

Annex 1—screenshots of Genetyx Software, cited by the opponent during opposition procedure of EP2202245 on May 22, 2020.

Annex 2—Sections of the Genetyx manual pertaining to isoelectric point, cited by the opponent during opposition procedure of EP2202245 on May 22, 2020.

Annex 3—screenshots of the web-based calculator, cited by the opponent during opposition procedure of EP2202245 on May 22, 2020.

Arduin, E., et al., "Highly Reduced Binding to High and Low Affinity Mouse Fc Gamma Receptors by L234A/L235A and N297A Fc Mutations Engineered Into Mouse IgG2a," Mol Immunol., 63(2):456-463 (2015).

Ausubel, F.M., et al., "Current Protocols in Molecular Biology," John Wiley & Sons Inc., Dec. 4, 2003, 4,648 pages.

Barba-Spaeth, G., et al., " Structural Basis of Potent Zika-dengue Virus Antibody Cross- neutralization," Nature, 536(7614):48-53 (2016).

Bazin, R., et al., "Use of hu-IgG-SCID Mice to Evaluate the in Vivo Stability of Human Monoclonal IgG Antibodies," J Immunol Methods, 172(2):209-217 (1994).

Birn, H., et al., "Renal Albumin Absorption in Physiology and Pathology," Kidney Int'l, 69(3):440-449 (2006).

Bork, P., "Powers and Pitfalls in Sequence Analysis: the 70% Hurdle," Genome Res., 10(4):398-400 (2000).

Bournazos, S., et al., "The Role of Igg Fc Receptors in Antibody-dependent Enhancement," Nat Rev Immunol., 20(10):633-643 (2020).

Chaudhury, C., et al., "The Major Histocompatibility Complex-related Fc Receptor for Igg (FcRn) Binds Albumin and Prolongs Its Lifespan," J Exp Med., 197(3):315-322 (2003).

Chien, N.C., et al., "Significant Structural and Functional Change of an Antigen-binding Site by a Distant Amino Acid Substitution: Proposal of a Structural Mechanism," PNAS USA, 86(14):5532-5536 (1989).

Chilukuri, N., et al., "Polyethylene Glycosylation Prolongs the Circulatory Stability of Recombinant Human Butyrylcholinesterase," Chem-Biol Interact., 157-158:115-121 (2005).

Chinese Medicated Bath Encyclopedia-Take Medicated Bath without Getting Sick, Editor-in-chief: Junxia Xu, 177, Oct. 31, 2013.

(56) References Cited

OTHER PUBLICATIONS

Chaudhury, C., "The Major Histocompatibility Complex-related Fc Receptor for IgG (FcRn) Binds Albumin and Prolongs Its Lifespan," J Exp Med., 197(3):315-322 (2003).
Chowdhury, P.S., "Engineering Hot Spots for Affinity Enhancement of Antibodies," Methods Mol Biol., 207:179-196 (2003).
Chuang, V.T.G., et al., "Pharmaceutical Strategies Utilizing Recombinant Human Serum Albumin," Pharm Res., 19(5):569-577 (2002).
Coico, R., et al., Immunology Manual, Publishing Center "Academy", "Antibody Structure and Function," 4:61-62 (2008).
Coloma, M.J., et al., "Design and Production of Novel Tetravalent Bispecific Antibodies," Nat Biotechnol., 15(2):159-163 (1997).
Aikawa, E., Immunohistochemistry, Comprehensive Materials, Editor: Paul Ducheyne, Affinity section of chapter 3.316, p. 278 (2011).
Crowe, J.S., et al., "Humanized Monoclonal Antibody CAMPATH-1H: Myeloma Cell Expression of Genomic Constructs, Nucleotide Sequence of cDNA Constructs and Comparison of Effector Mechanisms of Myeloma and Chinese Hamster Ovary Cell-derived Material," Clin Exp Immunol., 87(1):105-110 (1992).
D'Angelo, S., et al., "Many Routes to an Antibody Heavy-Chain CDR3: Necessary, Yet Insufficient, for Specific Binding," Front Immunol., 9:395 (2018).
Datta-Mannan, A., et al., "FcRn Affinity-Pharmacokinetic Relationship of Five Human IgG4 Antibodies Engineered for Improved In Vitro FcRn Binding Properties in Cynomolgus Monkeys," Drug Metab Dispos., 40(8):1545-1555 (2012).
De Alwis, R., et al., "Identification of Human Neutralizing Antibodies That Bind to Complex Epitopes on Dengue Virions," Pnas USA, 109(19):7439-7444 (2012).
De Haas, et al., "Fc Gamma Receptors of Phagocytes," The Journal of Laboratory and Clinical Medicine, 126(4):330-341 (1995).
Dejnirattisai, W., et al., "Dengue Virus Sero-cross-reactivity Drives Antibody-dependent Enhancement of Infection With Zika Virus," Nat Immunol., 17(9):1102-1108 (2016).
Dennis, M.S., et al., "Albumin Binding as a General Strategy for Improving the Pharmacokinetics of Proteins," J Biol Chem., 277(38):35035-35043 (2002).
Derer, S., et al., "A Complement-Optimized EGFR Antibody Improves Cytotoxic Functions of Polymorphonuclear Cells against Tumor Cells," J Immunol. 195(10):5077-5087 (2015).
Dirnberger, D., et al., "Secretion of Biologically Active Glycoforms of Bovine Follicle Stimulating Hormone in Plants," Eur J Biochem., 268(16):4570-4579 (2001).
Dmytrijuk, A., et al., "FDA Report: Eculizumab (Soliris®) for the Treatment of Patients with Paroxysmal Nocturnal Hemoglobinuria," The Oncologist, 13(9):993-1000 (2008).
Document Establishing that (Product Information Sheet Sigma) was Published in 1998.
Dondelinger, M., et al., "Understanding the Significance and Implications of Antibody Numbering and Antigen-binding Surface/residue Definition," Front Immunol., 16;9:2278 (2018).
Fakhouri, F., et al., "C3 Glomerulopathy: A New Classification," Nat Rev Nephrol., 6(8):494-499 (2010).
Fernandez, E., et al., Human Antibodies to the Dengue Virus E-dimer Epitope Have Therapeutic Activity Against Zika Virus Infection, Nat Immunol., 18(11):1261-1269 (2017).
Fischer, N., et al., "Bispecific Antibodies: Molecules That Enable Novel Therapeutic Strategies," Pathobiology: Journal of Immunopathology, Mol Cell Biol., 74(1):3-14 (2007).
Franks, F., "Conformational Stability of Proteins," Chapter 11 in Protein Biotechnology, 395-436 (1993).
Freifelder, D., "Biochemistry and molecular biology techniques (Tecnicas de bioquimica y biologia molecular)," 3:262-264 (1979).
Fukuzawa, T. et al., "Long Lasting Neutralization of CS by SKY59, a Novel Recycling Antibody is a Potential Therapy for Complement-mediated Diseases," Sci Rep., 7:1080 (2017).
Gekle, M., "Renal Tubule Albumin Transport," Annu Rev Physiol., 67:573-594 (2005).
Genbank, "Complement Component C5 [*Homo sapiens*]," Accession No. AAA51925.1, Accessed from the Internet: URL: https://www.ncbi.nlm.nih.gov/protein/AAA51925.1, Oct. 31, 1994, 3 pages.
Gershoni, J.M., et al., "Epitope Mapping: The First Step in Developing Epitope-Based Vaccines," BioDrugs, 21(3):145-156 (2007).
Giclas, P.C., et al., "Preparation of Characterization of Monoclonal Antibodies Against the Fifth Component of Rabbit Complement (C5)," J Immunol Methods, 105:201-209 (1987).
Green, L.L., et al., "Antibody Engineering via Genetic Engineering of the Mouse: XenoMouse Strains are a Vehicle for the Facile Generation of Therapeutic Human Monoclonal Antibodies," J Immunol Methods, 231(1-2):11-23 (1999).
Guasch, A., et al., "Charge Selectivity of the Glomerular Filtration Barrier in Healthy and Nephrotic Humans," J Clin Invest., 92(5):2274-2282 (1993).
Haviland, D.L., et al., "Complete eDNA Sequence of Human Complement Pro-C5 Evidence of Truncated Transcripts Derived from a Single Copy Gene," J Immunol., 146(1):362-368 (1991).
Ho, M., et al., "In Vitro Antibody Evolution Targeting Germline Hot Spots to Increase Activity of an Anti-CD22 Immunotoxin," J Biol Chem., 280(1):607-617 (2005).
Holers, V. M., "The Spectrum of Complement Alternative Pathway-mediated Diseases," Immunol Rev., 223:300-316 (2008).
Holt, L.J., et al., "Anti-Serum Albumin Domain Antibodies for Extending the Half-Lives of Short Lived Drugs," Protein Eng Des Sel., 21(5):283-288 (2008).
Horiuchi, T. and Tsukamoto, H., "Complement-targeted Therapy: Development of CS- and GSa-targeted Inhibition," Inflammation and Regeneration, 36:11 (2016).
Huang, S., et al., "Fully Humanized Neutralizing Antibodies to Interleukin-8 (ABX-IL8) Inhibit Angiogenesis, Tumor Growth, and Metastasis of Human Melanoma," Amer J Pathol., 161(1):125-134 (2002).
Huang, Y.J., et al., "Recombinant Human Butyrylcholinesterase From Milk of Transgenic Animals to Protect Against Organophosphate Poisoning," PNAS, 104(34):13603-13608 (2007).
Inoue, M., et al., "Synthesis of a Superoxide Dismutase Derivative That Circulates Bound to Albumin and Accumulates in Tissues Whose pH Is Decreased," Biochemistry, 28(16):6619-6624 (1989).
Iwayanagi, Y., et al., "Inhibitory FcyRIIb-Mediated Soluble Antigen Clearance from Plasma by a pH-Dependent Antigen-Binding Antibody and Its Enhancement by Fc Engineering," J Immunol., 195(7):3198-3205 (2015).
Jakubke, et al., "Physicochemical Properties," Amino Acids, Peptides and Proteins, Moscow, Mir, 356-363 (1985).
James, L.C., et al., "1.9 A Structure of the Therapeutic Antibody CAMPATH-1H Fab in Complex with a Synthetic Peptide Antigen," J Mol Biol., 289(2):293-301 (1999).
Janeway, C.A., et al., "The Immune System in Health and Disease," Immunobiology, 5th Edition, 122 (2001).
Janeway, Jr., C.A. and Travers, P., "Immunobiology—The Immune System in Health and Disease," 3rd Edition, Garland Press, 3:1-3:11 (1997).
Japanese Patent Application No. 2014-257647, filed Dec. 19, 2014.
Kam, Y.W., et al., "Cross-Reactive Dengue Human Monoclonal Antibody Prevents Severe Pathologies and Death From Zika Virus Infections," JCI Insight, 2(8): e92428 (2017).
Kawamoto, M., "Circulatory Stability and Plasma Lidocaine Levels During Continuous and Intermittent Thoracic Epidural Analgesia," J Anesth., 5(2):166-171 (1991).
Kim, H.J., et al., "The Glycosylation and Pharmacokinetics of CTLA4Ig Produced in Rice Cells," Biol Pharm Bulletin, 30(10):1913-1917 (2007).
King, D.J., "Applications and Engineering of Monoclonal Antibodies," Bioscience, 68-71 (1998).
King, D.J., "Applications and Engineering of Monoclonal Antibodies," Taylor & Francis, 151-159, 162-164 (2005).
Knudsen, L.B., et al., "Potent Derivatives of Glucagon-Like Peptide-1 with Pharmacokinetic Properties Suitable for Once Daily Administration," J Med Chem., 43(9):1664-1669 (2000).
Kratz, J., "Albumin as a Drug Carrier: Design of Prodrugs, Drug Conjugates and Nanoparticles," J Control Release, 132(3):171-183 (2008).

(56) References Cited

OTHER PUBLICATIONS

Krieg, C., et al., "Functional Analysis of B and T Lymphocyte Attenuator Engagement on CD4+ and CD8+ T Cells," J Immunol., 175(10):6420-6427 (2005).
Kroetsch, A., et al., "Engineered pH-Dependent Recycling Antibodies Enhance Elimination of Staphylococcal Enterotoxin B Superantigen in Mice," mAbs, 11(2):411-421 (2019).
Kunik, V., et al., "Structural Consensus among Antibodies Defines the Antigen Binding Site," PLoS Comput Biol., 8(2):e1002388 (2012).
Kurtzhals, P., et al., "Albumin Binding and Time Action of Acylated Insulins in Various Species," J Pharm Sci., 85(3):304-308 (1996).
Kurtzhals, P., et al., "Effect of Fatty Acids and Selected Drugs on the Albumin Binding of a Long-Acting, Acylated Insulin Analogue," J Pharm Sci., 86(12):1365-1368 (1997).
Latres, E., et al., "Myostatin blockade with a fully human monoclonal antibody induces muscle hypertrophy and reverses muscle atrophy in young and aged mice," Skeletal Muscle, 5:34 (2015).
Lederman, S., et al., "A Single Amino Acid Substitution in a Common African Allele of the CD4 Molecule Ablates Binding of the Monoclonal Antibody, OKT4," Mol Immunol., 28(11):1171-1181 (1991).
Lee, C.H., et al., "IgG Fc Domains That Bind C1q but Not Effector Fcγ Receptors Delineate the Importance of Complement-mediated Effector Functions," Nat Immunol., 18(8):889-898 (2017).
Li, C.H., et al., "Beta-Endorphin Omission Analogs: Dissociation of Immunoreactivity From Other Biological Activities," PNAS USA, 77(6):3211-3214 (1980).
Liberti, P.A., et al., "Antigenicity of Polypeptides (Poly-alpha-amino Acids). Physicochemical Studies of a Calcium-dependent Antigen-antibody Reaction," Biochemistry, 10(9):1632-1639 (1971).
Machado, N.P., et al., "Monoclonal antibodies: physical development and therapeutic perspectives," Colombian Association of Infectology (Asociacion Colombiana de Infectologia) Infectio, 10(3):186-197 (2006).
Makarova, T.P., et al., "Experience of Using Eculizumab in a Child with Atypical Hemolytic Uremic Syndrome," Nephrology, 18(3):84-88 (2014).
Makrides, S.C., et al., "Extended in Vivo Half-Life of Human Soluble Complement Receptor Type 1 Fused to a Serum Albumin-Binding Receptor," J Pharmacol Exp Ther., 277(1):534-542 (1996).
Manning, M.C., et al., "Stability of Protein Pharmaceuticals," Pharm Res., 6(11):903-918 (1989).
Mazda, O., et al., "Regulation of Muscle Homeostasis and Metabolism by the TGF-beta Superfamily Cytokine, Myostatin/growth Differentiation Factor 8 (GDF8)," Journal of Kyoto Prefectural University of Medicine 122(3):133-141 (2013).
Mayilyan, K.R., "Complement Genetics, Deficiencies, and Disease Associations," Protein & Cell, 3(7):487-496 (2012).
Mollnes, T.E., et al., "Identification of a Human C5 B-Chain Epitope Exposed in the Native Complement Component but Concealed in the SC5b-9 Complex," Scand J Immunol., 28: 307-312 (1988).
Morris, G.E., "The Protein Protocols Handbook—Epitope Mapping of Protein Antigens by Competition ELISA," 96:595-600 (1996).
Müller, D., et al., "Bispecific Antibodies: Handbook of Therapeutic Antibodies" Chapter 2:345-378 (2007).
Murray, P., et al., Human Biochemistry, Moscow "Mir", 1(4):34 (1993).
Nishimura, J., et al., "Genetic Variants in C5 and Poor Response to Eculizumab," New Engl J Med., 370(7):632-639 (2014).
O'Hear, C.E., et al., "Antibody Buffering of a Ligand in Vivo," PNAS, 102(1):40-44 (2005).
Padlan, E.A., "Anatomy of the Antibody Molecule," Mol Immunol., 31(3):169-217 (1994).
Peters, Jr., T., "All About Albumin—Biochemistry, Genetics, and Medical Applications," Academic Press, 76-79 (1996).
Piche-Nicholas, N.M., et al., "Changes in Complementarity-determining Regions Significantly Alter IgG Binding to the Neonatal Fc Receptor (FcRn) and Pharmacokinetics," mAbs 10(1):81-94 (2018).
Priyamvada, L., et al., "Human Antibody Responses After Dengue Virus Infection are Highly Cross-Reactive to Zika Virus," PNAS USA, 113(28):7852-7857 (2016).
Product Labelling Information for Rituxan (Rituximab), dated Nov. 1997.
Raghavan, M., et al., "Analysis of the pH Dependence of the Neonatal Fc Receptor/Immunoglobulin G Interaction Using Antibody and Receptor Variants," Biochemistry, 34(45):14649-14657 (1995).
Rehlaender, B.N., et al., "Antibodies as Carrier Proteins," Pharm Res., 15(11):1652-1656 (1998).
Roth, A., et al., "The Complement C5 Inhibitor Crovalimab in Paroxysmal Nocturnal Hemoglobinuria," Blood, 135(12): 912-920 (2020).
Rother, R.P., et al., "Discovery and Development of the Complement Inhibitor Eculizumab for the Treatment of Paroxysmal Nocturnal Hemoglobinuria," Nat Biotechnol., 25(11):1256-1264 (2007).
Saxena, A., et al., "Role of Oligosaccharides in the Pharmacokinetics of Tissue-Derived and Genetically Engineered Cholinesterases," Mol Pharmacol., 53(1):112-122 (1998).
Schultze, H.E., et al., "Turnover of Plasma Proteins," Molecular Biology of Human Proteins with Special Reference to Plasma Proteins, Nature and Metabolism of Extracellular Proteins, 1:476-477 (1996).
Singer, M. and Berg, P., "Genes and Genomes," Moscow, Mir, 1:63-64 (1998).
Singer, M. and Berg, P., "Genes and Genomes," Moscow, Mir, 1:63 (1998).
Smith, B.J., et al., "Prolonged in Vivo Residence Times of Antibody Fragments Associated With Albumin," Bioconj Chem., 12(5):750-756 (2001).
Stavenhagen, J. B., et al., "Enhancing the Potency of Therapeutic Monoclonal Antibodies via Fc Optimization," Adv Enzyme Regul., 48:152-164 (2008).
Stork, R., et al., "A Novel Tri-Functional Antibody Fusion Protein With Improved Pharmacokinetic Properties Generated by Fusing a Bispecific Single-chain Diabody With an Albumin-binding Domain From Streptococcal Protein G," Protein Eng Des Sel., 20(11):569-576 (2007).
Tamura, M., et al., "Structural Correlates of an Anticarcinoma Antibody: Identification of Specificity-determining Residues (SDRs) and Development of a Minimally Immunogenic Antibody Variant by Retention of SDRs Only," J Immunol., 164(3):1432-1441 (2000).
Tarantul, V.Z., Explanatory Biotechnological Dictionary of Russian-English (Tolkovyj Biotechnologicheshkiy Slovar), Languages of Slavic Cultures, 228 (2009).
Vaccaro, C., et al., "Engineering the Fc Region of Immunoglobulin G to Modulate in Vivo Antibody Levels," Nat Biotechnol., 23(10):1283-1288 (2005).
Vidarsson, G., et al., "IgG subclasses and allotypes: from structure to effector functions," Front Immunol., 5(520) (2014).
Wang, Y. and Lv, L., "Applications of Eculizumab, a humanized anti-complement factor C5 monoclonal antibody," Chinese Journal of Clinical Pharmacology and Therapeutics, 20(4):455-459 (2015).
Warmerdam, P.A., et al., "The Human Low Affinity Immunoglobulin G Fc Receptor IIC Gene is a Result of an Unequal Crossover Event," J Biol Chem., 268(10):7346-7349 (1993).
Wines, B.D., et al., "The IgG Fc Contains Distinct Fc Receptor (FcR) Binding Sites: The Leukocyte Receptors Fc Gamma RI and Fc Gamma RIIa Bind to a Region in the Fc Distinct from that Recognized by Neonatal FcR and Protein A," J Immunol., 164(10):5313-5318 (2000).
Xu, M., et al., "A Potent Neutralizing Antibody With Therapeutic Potential Against All Four Serotypes of Dengue Virus," NPJ Vaccines, 2:2 (2017).
Xu, M., et al., "Plasmablasts Generated During Repeated Dengue Infection are Virus Glycoprotein-Specific and Bind To Multiple Virus Serotypes," J Immunol., 189(12):5877-5885 (2012).

(56) References Cited

OTHER PUBLICATIONS

Yoon, S.O., et al., "Construction, Affinity Maturation, and Biological Characterization of an Anti-tumor-associated Glycoprotein-72 Humanized Antibody," J Biol Chem., 281(11):6985-6992 (2006).
Zwolak, A., et al., "Rapid Purification of Human Bispecific Antibodies via Selective Modulation of Protein a Binding," Sci Rep., 7(1):15521 (2017).
U.S. Appl. No. 08/487,283, filed Jun. 7, 1995, Evans et al.
U.S. Appl. No. 10/222,464, filed Aug. 17, 2002, Fung et al.
U.S. Appl. No. 11/124,620, filed May 5, 2005, Lazar et al.
U.S. Appl. No. 11/436,266, filed May 17, 2006, Chamberlain et al.
U.S. Appl. No. 12/532,261, filed Sep. 21, 2009, Guild et al.
U.S. Appl. No. 12/679,922, filed Oct. 1, 2010, Igawa et al., related application.
U.S. Appl. No. 13/509,237, filed Aug. 23, 2012, Weaver et al.
U.S. Appl. No. 13/557,562, filed Jul. 25, 2012, Diefenbach-Streiber et al.
U.S. Appl. No. 13/972,524, filed Aug. 21, 2013, McConnell et al.
U.S. Appl. No. 14/428,050, filed Mar. 13, 2015, Tamburini.
U.S. Appl. No. 14/626,514, filed Feb. 19, 2015, Baciu et al.
U.S. Appl. No. 14/764,885, filed Jul. 30, 2015, Chung et al.
U.S. Appl. No. 14/789,329, filed Jan. 7, 2015, Andrien et al.
U.S. Appl. No. 14/974,350, filed Dec. 18, 2015, Ruike et al., related application.
U.S. Appl. No. 15/379,597, filed Dec. 15, 2016, Shusta et al.
U.S. Appl. No. 15/544,930, filed Jul. 20, 2017, Murata, et al., related application.
U.S. Appl. No. 15/688,004, filed Aug. 28, 2017, Ruike et al., related application.
U.S. Appl. No. 15/977,757, filed May 11, 2018, Igawa et al., related application.
U.S. Appl. No. 16/019,752, filed Jun. 27, 2018, Ruike et al., related application.
U.S. Appl. No. 16/108,897, filed Aug. 22, 2018, Igawa et al.
U.S. Appl. No. 16/480,047, filed Jul. 23, 2019, Shinomiya et al., related application.
U.S. Appl. No. 16/514,467, filed Jul. 17, 2019, Ruike et al., related application.
U.S. Appl. No. 16/928,129, filed Jul. 14, 2020, Shinomiya et al., related application.
U.S. Appl. No. 17/066,092, filed Oct. 8, 2020, Sampei et al., related application.
U.S. Appl. No. 17/263,691, filed Jan. 27, 2021, Shinomiya et al., related application.
U.S. Appl. No. 17/359,867, filed Jun. 28, 2021, Igawa et al., related application.
U.S. Appl. No. 17/494,199, filed Oct. 5, 2021, Igawa et al., related application.
U.S. Appl. No. 17/561,207, Igawa et al., filed Dec. 23, 2021, Igawa et al., related application.
U.S. Appl. No. 17/578,524, filed Jan. 19, 2022, Igawa et al., related application.
U.S. Appl. No. 17/602,196, filed Jul. 10, 2021, Wakabayashi et al., related application.
U.S. Appl. No. 17/671,185, filed Feb. 14, 2022, Mimoto et al., related application.
U.S. Appl. No. 17/742,824, filed May 12, 2022, Ruike et al., related application.
U.S. Appl. No. 17/846,672, filed Jun. 22, 2022, Mimoto et al., related application.
U.S. Appl. No. 17/854,023, filed Jun. 30, 2022, Igawa et al., related application.
U.S. Appl. No. 18/059,677, filed Nov. 29, 2022, Shibahara et al., related application.
U.S. Appl. No. 14/850,949, filed Sep. 10, 2015, Cheng et al.
Becker, J.M., et al., "Prevention of Postoperative Abdominal Adhesions by a Sodium Hyaluronate-based Bioresorbable Membrane: a Prospective, Randomized, Double-blind Multicenter Study," Journal of the American College of Surgeons 183(4):297-306, Elsevier, United States (Oct. 1996).
Bonvin, P., et al., "De Novo Isolation of Antibodies With pH-Dependent Binding Properties," mAbs 7(2):294-302, Taylor & Francis, United States (Mar.-Apr. 2015).
Bulun, S.E., "Endometriosis," The New England Journal of Medicine 360(3):268-279, Massachusetts Medical Society, United States (Jan. 2009).
Chaparro-Riggers, J., et al., "Increasing Serum Half-life and Extending Cholesterol Lowering in Vivo by Engineering Antibody With pH-sensitive Binding in PCSK9," The Journal of biological chemistry 287(14):11090-11097, American Society for Biochemistry and Molecular Biology, United States (Mar. 2012).
Decision of the Opposition Division in EP2275443 dated Apr. 26, 2018.
Declaration of Mr. Taichi Kuramochi, co-inventor of EP2202245 (submitted by the Patentee during EPO opposition procedure for EP2202245).
Donnez, J., et al., "Current thinking on the pathogenesis of endometriosis," Gynecologic and Obstetric Investigation 54 Suppl 1:52-62, Karger, Switzerland (2002).
Examination report for the AU application No. AU2013306700 issued on Jun. 7, 2018.
Ferl, G.Z., et al., "A Predictive Model of Therapeutic Monoclonal Antibody Dynamics and Regulation by the Neonatal Fc Receptor (FcRn)," Annals of Biomedical Engineering 33(11):1640-1652, Academic Press, United States (Nov. 2005).
Giudice, L.C., et al., "Endometriosis," Lancet 364(9447):1789-1799, Elsevier, London (Nov. 2004).
Guo, S.W., "Recurrence of Endometriosis and Its Control," Human Reproduction Update 15(4):441-461, Published for the European Society of Human Reproduction and Embryology by Oxford University Press, England (Jul.-Aug. 2009).
Hinton, P.R., et al., "Engineered Human IgG Antibodies With Longer Serum Half-lives in Primates," The Journal of Biological Chemistry 279(8):6213-6216, American Society for Biochemistry and Molecular Biology, United States (Feb. 2004).
Iwabe, T., et al., "Pathogenetic Significance of Increased Levels of Interleukin-8 in the Peritoneal Fluid of Patients With Endometriosis," Fertility and Sterility 69(5):924-930, Elsevier for the American Society for Reproductive Medicine, New York (May 1998).
Jaeger, "Clinical Immunology and Allergology," 2nd edition, M.: Medicina, 1990,2:484-5 (with English translation).
Murtaugh, M.L., et al., "A Combinatorial Histidine Scanning Library Approach to Engineer Highly pH-Dependent Protein Switches," Protein Science 20(9):1619-1631, Cold Spring Harbor Laboratory Press, United States (Sep. 2011).
Non-Final Office Action mailed Mar. 18, 2019 in U.S. Appl. No. 14/001,218, filed Dec. 2, 2013, Mimoto et al.
Raposo, B., et al., "Epitope-Specific Antibody Response is Controlled by Immunoglobulin V(H) Polymorphisms," The Journal of experimental medicine 211(3):405-411, Rockefeller University Press, United States (Mar. 2014), Supplemental Material.
Russo, R.C., et al., "The Cxcl8/il-8 Chemokine Family and Its Receptors in Inflammatory Diseases," Expert Review of clinical Immunology 10(5):593-619, Oxford, London (May 2014).
Sazinsky, S.L., et al., "Aglycosylated Immunoglobulin G1 Variants Productively Engage Activating Fc Receptors," Proceedings of the National Academy of Sciences of the United States of America 105(51):20167-20172, National Academy of Sciences, United States (Dec. 2008).
Schröter, C., et al., "A Generic Approach to Engineer Antibody Ph-switches Using Combinatorial Histidine Scanning Libraries and Yeast Display," mAbs 7(1):138-151, Taylor & Francis, United States (Jan.-Feb. 2015).
Declaration of Dr. Anette Henriksen, dated Apr. 17, 2019, which was submitted by the Opponent during EPO opposition for EP2006381.
Yarilin, "Osnovy immunologii," M.Meditsina, 1999, pp. 354-358/ Fundamentals of Immunology, M:Medicina, 1999, pp. 354-358.
Yarilin, "Osnovy immunologii," M.Meditsina, 1999, pp. 181-184.
Travis, J., et al., "Isolation of Albumin from Whole Human Plasma and Fractionation of Albumin-Depleted Plasma," Biochemical Journal 157(2):301-306, Portland Press, England (Aug. 1976).

(56) References Cited

OTHER PUBLICATIONS

Vercellini, et al., "Postoperative Oral Contraceptive Exposure and Risk of Endometrioma Recurrence," American Journal of Obstetrics and Gynecology 198(5):504.e1-5, Elsevier, United States (May 2008).
Weiss, G.A., et al., "Rapid Mapping of Protein Functional Epitopes by Combinatorial Alanine Scanning," Proceedings of the National Academy of Sciences of the United States of America 97(16):8950-8954, National Academy of Sciences, United States (Aug. 2000).
Claims granted in European Patent No. 2275443, Written Submission for Oral Proceedings in European Patent No. 3127921, Jul. 2019.
U.S. Appl. No. 15/393,380, filed Dec. 29, 2016, related application.
U.S. Appl. No. 08/765,783, 371 date Mar. 7, 1997, related application.
U.S. Appl. No. 11/929,742, filed Oct. 30, 2007, related application.
Abelev, G.I., Monoclonal Antibodies, Sorosovsky Educational Journal, 1:16-20 (1998).
Aboud-Pirak, E., et al., "Binding and Endocytosis of a Monoclonal Antibody to a High Molecular Weight Human Milk Fat Globule Membrane-associated Antigen by Cultured MCF-7 Breast Carcinoma Cells," Cancer Research 48(11):3188-3196 (1988).
Adams, C.W., et al., "Humanization of a Recombinant Monoclonal Antibody to Produce a Therapeutic HER Dimerization Inhibitor, Pertuzumab," Cancer Immunology Immunotherapy, 55(6):717-727 (2006).
Algonomics—Tripole® applications [Online], Retrieved from the Internet on Feb. 29, 2012: http://www.algonomics.com/proteinengineering/tripole_applications.php, 2 pages, available online on Feb. 21, 2009.
Alignment sequence 1047 and 30 executed Jan. 26, 2021, cited in corresponding European application Office Action.
Alignment sequence 472 and 24 executed Jan. 26, 2021, cited in corresponding European application Office Action.
Almagro, J.C. and Fransson, J., "Humanization of Antibodies," Frontiers in BioScience 13:1619-1633 (2008).
Amersham Biosciences, "Affinity Chromatography: Principles and Methods," Edition AD 137:16-18 (2002).
Amersham Biosciences, "Antibody Purification Handbook," Edition 18-1037-46, accessed at http://www.promix.ru/manuf/ge/chrom/lit/Antibody Purification.pdf [online], accessed on Nov. 5, 2015.
Amigorena, S., et al., "Fc Gamma RII Expression in Resting and Activated B Lymphocytes," European Journal of Immunology, 19(8):1379-1385 (1989).
Amigorena, S., et al., "Cytoplasmic Domain Heterogeneity and Functions of IgG Fc Receptors in B Lymphocytes," Science, 256(5065):1808-1812 (1992).
Anchin, J.M., et al., "Recognition of Superpotent Sweetener Ligands by a Library of Monoclonal Antibodies," Journal of Molecular Recognition, 10(5): 235-242 (1997).
Arici, A., "Local Cytokines in Endometrial Tissue: the Role of Interleukin-8 in the Pathogenesis of Endometriosis," Annals of the New York Academy of Sciences, 955:101-109; Discussion, 118, 396-406 (2002).
AP02123SU-N Origene polyclonal Antibody to Human Pro-Myostatin (amino acids 79-92). Mar. 19, 2013.
Armour, K.L., et al., "Differential binding to human FcgammaRIIa and FcγRIIb receptors by human IgG wildtype and mutant antibodies," Molecular Immunology, 40(9):585-593 (2003).
Armour, K.L., et al., "Recombinant Human IgG Molecules Lacking Fcgamma Receptor I Binding and Monocyte Triggering Activities," European Journal of Immunology, 29(8):2613-2624 (1999).
Baca, M., et al., "Antibody Humanization Using Monovalent Phage Display," The Journal of Biological Chemistry 272(16):10678-10684 (1997).
Balint, R.F., et al., "Antibody Engineering by Parsimonious Mutagenesis," Gene, 137(1):109-118 (1993).
Barrabes, S., et al., "Effect of Sialic Acid Content on Glycoprotein Pi Analyzed by Two-Dimensional Electrophoresis," Electrophoresis, 31(17):2903-2912 (2010).
Bartelds, G.M., et al., "Clinical Response to Adalimumab: Relationship to Anti-Adalimumab Antibodies and Serum Adalimumab Concentrations in Rheumatoid Arthritis," Annals of the Rheumatic Diseases, 66(7):921-926 (2007).
Batra, S.K., et al., "Pharmacokinetics and Biodistribution of Genetically Engineered Antibodies," Current Opinion in Biotechnology, 13(6):603-608 (2002).
Bayry, J., et al., "Immuno Affinity Purification of Foot and Mouth Disease Virus Type-Specific Antibodies Using Recombinant Protein Adsorbed to Polystyrene Wells," Journal of Virological Methods 81(1-2):21-30 (1999).
Beck, A., et al., "Strategies and Challenges for the Next Generation of Therapeutic Antibodies," Nature Reviews Immunology 10(5):345-352 (2010).
Bender, N.K., et al., "Immunogenicity, Efficacy and Adverse Events of Adalimumab in RA Patients," Rheumatology International, 27(3):269-274 (2007).
Experimental data characterizing the binding of rituximab to its antigen CD20 and to human FcRn, Shire (2018) (submitted by the Opponent during EP opposition procedure for EP2708558 and posted by EPO on Jan. 15, 2019), 6 pages.
Binz, H.K., et al., "Engineering Novel Binding Proteins From Nonimmunoglobulin Domains," Nature Biotechnology, 23(10):1257-1268 (2005).
Blank, M., et al., "Decreased Transcription of the Human Fcgr2b Gene Mediated by the -343 G/c Promoter Polymorphism and Association With Systemic Lupus Erythematosus," Human Genetics, 117(2-3):220-227 (2005).
Blog entry, Jun. 1, 2014 (Jun. 1, 2014), Retrieved from the Internet: URL:https://www.thundersplace.org/male-supplements/the-chemical-pe thread-7.html92 [retrieved on May 23, 2018].
Boerner, P., et al., "Production of Antigen-specific Human Monoclonal Antibodies From in Vitro-Primed Human Splenocytes," Journal of Immunology 147(1):86-95 (1991).
Bogdanovich, S., et al., "Functional Improvement of Dystrophic Muscle by Myostatin Blockade," Nature, 420: 418-421 (2002).
Borrok, M.J., et al., "pH-Dependent Binding Engineering Reveals an FcRn Affinity Threshold That Governs IgG Recycling," The Journal of Biological Chemistry 290(7):4282-4290 (2015).
Boruchov, A., et al., "Activating and Inhibitory Igg Fc Receptors on Human Dos Mediate Opposing Functions," The Journal of Clinical Investigation, 115(10):2914-2923 (2005).
Boumpas, T., et al., "A Short Course of Bg9588 (Anti-cd40 Ligand Antibody) Improves Serologic Activity and Decreases Hematuria in Patients With Proliferative Lupus Glomerulonephritis," Arthritis and Rheumatism, 48(3):719-727 (2003).
Bowie, J. U., et al., "Deciphering the Message in Protein Sequences: Tolerance to Amino Acid Substitutions," Science, 247(4948):1306-1310 (1990).
Breitbart, A., et al., "Highly Specific Detection of Myostatin Prodomain by an Immunoradiometric Sandwich Assay in Serum of Healthy Individuals and Patients," Plos One, 8(11):e80454 (2013).
Brooks, D.G., et al., "Structure and Expression of Human IgG FcRII(CD32). Functional Heterogeneity is Encoded by the Alternatively Spliced Products of Multiple Genes," The Journal of Experimental Medicine 170(4):1369-1385 (1989).
Brown, M., et al., "Tolerance of Single, but Not Multiple, Amino Acid Replacements in Antibody Vh Cdr 2: a Means of Minimizing B Cell Wastage From Somatic Hypermutation?," Journal of Immunology 156(9):3285-3291 (1996).
Brown, N.L., et al., "A Study of the Interactions Between an IgG-Binding Domain Based on the B Domain of Staphylococcal Protein A and Rabbit IgG," Molecular Biotechnology 10(1):9-16 (1998).
Bruggemann, M., et al., "Comparison of the Effector Functions of Human Immunoglobulins Using a Matched Set of Chimeric Antibodies," The Journal of Experimental Medicine 166(5):1351-1361 (1987).
Bruhns, P., et al., "Specificity and Affinity of Human Fcgamma Receptors and Their Polymorphic Variants for Human IgG Subclasses," Blood, 113(16):3716-3725 (2009).

(56) References Cited

OTHER PUBLICATIONS

Bruhns, P., et al., "Properties of Mouse and Human IgG Receptors and Their Contribution to Disease Models," Blood, 119(24):5640-5649 (2012).
Buckler, D.R., et al., "Antibody Drug Discovery" edited by Wood, C. R., Molecular Medicine and Medicinal Chemistry—vol. 4, Section 2.4. Library Selection, p. 49-57 (2012).
Burgess, W. H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol., 111:2129-2138 (1990).
Burmeister, W.P., et al., "Crystal Structure of the Complex of Rat Neonatal Fc Receptor With Fc," Nature, 372: 379-383 (1994).
Capel, P.J.A., et al., "Heterogeneity of Human IgG Fc Receptors," ImmunoMethods, 4(1):25-34 (1994).
Carter, P., et al., "Humanization of an Anti-P185HER2 Antibody for Human Cancer Therapy," Proceedings of the National Academy of Sciences of the United States of America 89(10):4285-4289 (1992).
Cartron, G., et al., "Therapeutic Activity of Humanized Anti-CD20 Monoclonal Antibody and Polymorphism in IgG Fc Receptor FcgammaR IIa Gene," Blood, 99(3):754-758 (2002).
Cemerski, S., et al., "Suppression of Mast Cell Degranulation Through a Dual-targeting Tandem IgE-IgG Fc Domain Biologic Engineered to Bind With High Affinity to FcγRIIb," Immunology Letters, 143(1):34-43 (2012).
Chan, K.R., et al., "Therapeutic Antibodies as a Treatment Option for Dengue Fever," Expert Review of Anti-infective Therapy 11(11):1147-1157 (2013).
Chang, B.S. and Shenson, S., "Practical Approaches to Protein Formulation Development," Pharmaceutical Biotechnology 13:1-25 (2002).
Chari, R.V., et al., "Immunoconjugates Containing Novel Maytansinoids: Promising AntiCancer Drugs," Cancer Research 52(1):127-131 (1992).
Chau, L.A., et al., "HuM291 (Nuvion), a Humanized Fc Receptor-Nonbinding Antibody Against CD3, Anergizes Peripheral Blood T Cells as Partial Agonist of the T Cell Receptor," Transplantation 71(7):941-950 (2001).
Chen, C., et al., "Defective Secretion of an Immunoglobulin Caused by Mutations in the Heavy Chain Complementarity Determining Region 2," The Journal of Experimental Medicine, 180(2):577-586 (1994).
Chen, C., et al., "Enhancement and Destruction of Antibody Function by Somatic Mutation: Unequal Occurrence is Controlled by V Gene Combinatorial Associations," The EMBO Journal, 14(12):2784-2794 (1995).
Chen, C., et al., "Generation and Analysis of Random Point Mutations in an Antibody CDR2 Sequence: Many Mutated Antibodies Lose Their Ability to Bind Antigen," The Journal of Experimental Medicine, 176(3):855-866 (1992).
Chen, J.Y., et al., "Association of a transmembrane polymorphism of Fcgamma receptor IIb (FCGR2B) with systemic lupus erythematosus in Taiwanese patients," Arthritis and Rheumatology, 54(12):3908-3917 (2006).
Chen, Y., et al., "Selection and Analysis of an Optimized Anti-VEGF Antibody: Crystal Structure of an Affinity-Matured Fab in Complex With Antigen," Journal of Molecular Biology 293(4):865-881 (1999).
Chirino, A.J., et al., "Minimizing the Immunogenicity of Protein Therapeutics," Drug Discovery Today, 9(2):82-90 (2004).
Chothia, C. and Lesk, A.M., "Canonical Structures for the Hypervariable Regions of Immunoglobulins," Journal of Molecular Biology 196(4):901-917 (1987).
Chu, S.Y., et al., "Inhibition of B Cell Receptor-Mediated Activation of Primary Human B Cells by Coengagement of CD19 and FcgammaRIIb With Fc-engineered Antibodies," Molecular Immunology, 45(15):3926-3933 (2008).
Chu, G.C., et al., "Accumulation of Succinimide in a Recombinant Monoclonal Antibody in Mildly Acidic Buffers Under Elevated Temperatures," Pharmaceutical Research 24(6):1145-1156 (2007).
Chu, S.Y., et al., "Reduction of Total IgE by Targeted Coengagement of IgE B-Cell Receptor and FcγRIIb with Fc-Engineered Antibody," The Journal of Allergy and Clinical Immunology, 129(4):1102-1115 (2012).
Chuntharapai, A., et al., "Isotype-dependent inhibition of tumor growth in vivo by monoclonal antibodies to death receptor 4," Journal of Immunology, 166(8):4891-4898 (2001).
Clackson, T., et al., "Making Antibody Fragments Using Phage Display Libraries," Nature 352(6336):624-628 (1991).
Originally filed claims of European Application No. 13195713.6, European Publication No. 2708558, submitted by opponent in European opposition in EP2708558 on Dec. 20, 2018.
Originally filed description of European Application No. 13195713.6, European Publication No. 2708558, submitted by opponent in European opposition in EP2708558 on Dec. 20, 2018.
Clark, R., "IgG Effector Mechanisms," Chemical Immunology, 65:88-110 (1997).
Clynes, R., et al., "Fc Receptors Are Required in Passive and Active Immunity to Melanoma," Proceedings of the National Academy of Sciences of the United States of America 95(2):652-656 (1998).
Clynes, R.A., et al., "Inhibitory Fc Receptors Modulate in Vivo Cytotoxicity Against Tumor Targets," Nature Medicine 6(4):443-446 (2000).
Cole, M.S., et al., "Human IgG2 Variants of Chimeric Anti-CD3 are Nonmitogenic to T Cells," Journal of Immunology 159(7):3613-3621 (1997).
Tan, et al., editors Coligan, J.E., et al., "Current Protocols in Immunology," John Wiley and Sons, 1991.
Colman, P.M., "Effects of amino acid sequence changes on antibody-antigen interactions," Res Immunol., 145:33-36 (1994).
Coloma, M.J., et al., "Position Effects of Variable Region Carbohydrate on the Affinity and in Vivo Behavior of an Anti-(1--6) Dextran Antibody," Journal of Immunology, 162(4):2162-2170 (1999).
Comper, W.D., et al., "Charge Selectivity in Kidney Ultrafiltration," Kidney International, 47(5):1242-1251 (1995).
Concordance table showing Kabat numbering for antibody Hyb C1, cited by Opponent on Sep. 1, 2016 in EP Opposition in EP2275443.
Concordance table showing Kabat numbering for antibody 300N, cited by Opponent on Sep. 1, 2016 in EP Opposition in EP2275443.
Cooper, L.J., et al., "Variable domain-identical antibodies exhibit IgG subclass-related differences in affinity and kinetic constants as determined by surface plasmon resonance," Molecular Immunology, 31(8):577-584 (1994 ).
Co-pending Application, CL Application No. CL20080002873 inventors Tomoyuki Igawa., filed on Sep. 26, 2008.
Co-pending Application, CL Application No. CL20080002885 inventors Tomoyuki Igawa., filed on Sep. 26, 2008.
Co-pending Application, CL Application No. CL20080002886 inventors Tomoyuki Igawa., filed on Sep. 26, 2008.
Co-pending Application, CO Application No. 07124506.
Co-pending Application, CO Application No. 15075851.
Co-pending Application, CO Application No. CO20110080753 inventors Tomoyuki Igawa., filed on Jun. 28, 2011.
Co-pending Application, CO Application No. CO20130047993 inventors Tomoyuki Igawa., filed on Mar. 11, 2013.
U.S. Appl. No. 06/483,457 inventors Cabilly, Shmuel, filed Apr. 8, 1983.
U.S. Appl. No. 06/534,658 inventors Insel, Richard A., filed Sep. 22, 1983.
U.S. Appl. No. 06/732,471 inventors Weng, Litai, filed May 9, 1985.
U.S. Appl. No. 06/778,670 inventors Segal, David M., filed Sep. 23, 1985.
U.S. Appl. No. 07/139,504 inventors Ngo, That T., filed Dec. 30, 1987.
U.S. Appl. No. 07/157,273 inventors Alton C. Morgan, filed Feb. 17, 1988.
U.S. Appl. No. 07/665,939 inventors Robinson, Randy R., filed Mar. 5, 1991.
U.S. Appl. No. 07/730,040 inventors Esmon, Charles T., filed Jul. 12, 1991.

(56) References Cited

OTHER PUBLICATIONS

U.S. Appl. No. 07/911,380 inventors Chari, Ravi J., filed Jul. 13, 1992.
U.S. Appl. No. 07/934,373 inventors Carter, Paul J., filed Aug. 21, 1992.
U.S. Appl. No. 07/942,245 inventors Pedersen, Jan T., filed Sep. 9, 1992.
U.S. Appl. No. 07/985,827 inventors Pettit, George R., filed Dec. 3, 1992.
U.S. Appl. No. 07/986,578 inventors Chari, Ravi J., filed Dec. 7, 1992.
U.S. Appl. No. 07/998,754 inventors Raso, Victor A., filed Dec. 28, 1992.
U.S. Appl. No. 08/009,296 inventors Pettit, George R., filed Jan. 26, 1993.
U.S. Appl. No. 08/050,058 inventors Garrard, Lisa J., filed Apr. 30, 1993.
U.S. Appl. No. 08/061,092 inventors King, C Richter., filed May 14, 1993.
U.S. Appl. No. 08/137,117 inventors Tsuchiya, Masayuki, filed Dec. 20, 1993.
U.S. Appl. No. 08/235,838 inventors Wels, Winfried S., filed Apr. 29, 1994.
U.S. Appl. No. 08/253,877 inventors Hamann, Philip Ross., filed Jun. 3, 1994.
U.S. Appl. No. 08/329,610 inventors McGahren, William James., filed Oct. 26, 1994.
U.S. Appl. No. 08/341,560 inventors Ward, E. Sally, filed Nov. 17, 1994.
U.S. Appl. No. 08/398,615 inventors Simmons, Laura C., filed Mar. 1, 1995.
U.S. Appl. No. 08/399,106 inventors Carter, Paul J., filed Mar. 1, 1995.
U.S. Appl. No. 08/422,092 inventors Presta, Leonard G., filed Apr. 14, 1995.
U.S. Appl. No. 08/433,781 inventors Carter, Paul J., filed May 3, 1995.
U.S. Appl. No. 08/452,164 inventors Hamann, Philip Ross, filed May 26, 1995.
U.S. Appl. No. 08/461,284 inventors Haman, Philip Ross, filed Jun. 5, 1995.
U.S. Appl. No. 08/462,863 inventors McGahren, William James, filed Jun. 5, 1995.
U.S. Appl. No. 08/462,939 inventors Hamann, Philip Ross, filed Jun. 5, 1995.
U.S. Appl. No. 08/470,031 inventors Winter, Gregory Paul, filed Jun. 6, 1995.
U.S. Appl. No. 08/472,523 inventors Raso, Victor A., filed Jun. 7, 1995.
U.S. Appl. No. 08/475,005 inventors Kuntsmannm Martin P., filed Jun. 7, 1995.
U.S. Appl. No. 08/477,728 inventors Queen, Cary L., filed Jun. 7, 1995.
U.S. Appl. No. 08/478,825 inventors Winter, Gregory Paul, filed Jun. 7, 1995.
U.S. Appl. No. 08/479,752 inventors Winter, Gregory P., filed Jun. 7, 1995.
U.S. Appl. No. 08/484,891 inventors Connelly, Sheila, filed Jun. 7, 1995.
U.S. Appl. No. 08/486,857 inventors Kucherlapati, Raju, filed Jun. 7, 1995.
U.S. Appl. No. 08/525,596 inventors Lee, Se-Jin., filed Oct. 26, 1995.
U.S. Appl. No. 08/544,404 inventors Lonberg, Nils, filed Oct. 10, 1995.
U.S. Appl. No. 08/615,369 inventors Andya, James, filed Mar. 14, 1996.
U.S. Appl. No. 08/642,406 inventors Hein, Mich B., filed May 3, 1996.
U.S. Appl. No. 08/654,505 inventors Kunstmann, Martin P., filed May 28, 1996.
U.S. Appl. No. 08/724,752 inventors Kucherlapati, Raju, filed Oct. 2, 1996.
U.S. Appl. No. 08/741,727 inventors Joly, John C., filed Oct. 31, 1996.
U.S. Appl. No. 08/781,449 inventors Khawli, Leslie A., filed Jan. 10, 1997.
U.S. Appl. No. 08/905,293 inventors Rosok, Mae Joanne, filed Aug. 1, 1997.
U.S. Appl. No. 08/908,469 inventors Baca, Manuel, filed Aug. 6, 1997.
U.S. Appl. No. 08/921,100 inventors Matsushima, Kouji, filed Aug. 29, 1997.
U.S. Appl. No. 09/097,171 inventors Lam, Xanthe M., filed Jun. 12, 1998.
U.S. Appl. No. 09/132,536 inventors Stomp, Anne-Marie, filed Aug. 11, 1998.
U.S. Appl. No. 09/177,860 inventors Lee, Se-Jin, filed Oct. 23, 1998.
U.S. Appl. No. 09/199,534 inventors Hein, Mich B., filed Nov. 25, 1998.
U.S. Appl. No. 09/274,163 inventors Stevens, Fred J., filed Mar. 22, 1999.
U.S. Appl. No. 09/282,505 inventors Idusogie, Esohe Ekinaduese, filed Mar. 31, 1999.
U.S. Appl. No. 09/294,584 inventors Umana, Pablo, filed Apr. 20, 1999.
U.S. Appl. No. 09/339,596 inventors Co, Man Sung, filed Jun. 24, 1999.
U.S. Appl. No. 09/375,924 inventors Gallo, Michael, filed Aug. 17, 1999.
U.S. Appl. No. 09/416,557 inventors Matsushima, Kouji, filed Oct. 12, 1999.
U.S. Appl. No. 09/450,520 inventors Vasquez, Maximiliano, filed Nov. 29, 1999.
U.S. Appl. No. 09/509,098 inventors Tsuchiya, Masayuki, filed Mar. 22, 2000.
U.S. Appl. No. 09/647,468 inventors Sato, Koh, filed Sep. 29, 2000.
U.S. Appl. No. 09/678,300 inventors Vezina, Louis-Philippe, filed Oct. 3, 2000.
U.S. Appl. No. 09/678,303 inventors Vezina, Louis-Philippe., filed Oct. 3, 2000.
U.S. Appl. No. 09/740,991 inventors Chari, Ravi V.J., filed Dec. 21, 2000.
U.S. Appl. No. 09/880,748 inventors Ruben, Steven M., filed Jun. 15, 2001.
U.S. Appl. No. 09/933,497 inventors Ward, Elizabeth Sally., filed Aug. 20, 2001.
U.S. Appl. No. 09/956,206 inventors do Couto, Fernando, filed Sep. 17, 2001.
U.S. Appl. No. 09/970,154 inventors Shinkawa, Toyohide, filed Oct. 4, 2001.
U.S. Appl. No. 09/971,773 inventors Kanda, Yutaka, filed Oct. 9, 2001.
U.S. Appl. No. 10/000,433 inventors Tomizuka, Kazuma, filed Nov. 30, 2001.
U.S. Appl. No. 10/078,757 inventors Barbas, Carlos F. III, filed Feb. 19, 2002.
U.S. Appl. No. 10/227,370 inventors Presta, Leonard G., filed Oct. 22, 2002.
U.S. Appl. No. 10/251,526 inventors Rodman, Toby C., filed Sep. 20, 2002.
U.S. Appl. No. 10/253,532 inventors Aghajanian, Jane, filed Sep. 25, 2002.
U.S. Appl. No. 10/327,663 inventors Shitara, Kenya, filed Dec. 24, 2002.
U.S. Appl. No. 10/351,748 inventors Winter, Gregory Paul, filed Jan. 24, 2003.
U.S. Appl. No. 10/364,953 inventors Lowman, Henry B., filed Feb. 11, 2003.
U.S. Appl. No. 10/379,392 inventors Lazar, Gregory Alan, filed Mar. 3, 2003.

(56) References Cited

OTHER PUBLICATIONS

U.S. Appl. No. 10/409,598 inventors Niwa, Rinpei, filed Apr. 9, 2003.
U.S. Appl. No. 10/409,600 inventors Kanda, Yutaka, filed Apr. 9, 2003.
U.S. Appl. No. 10/409,609 inventors Yamane, Naoko, filed Apr. 9, 2003.
U.S. Appl. No. 10/409,616 inventors Satoh, Mitsuo, filed Apr. 9, 2003.
U.S. Appl. No. 10/474,832 inventors Karpusas, Michael, filed Oct. 14, 2003.
U.S. Appl. No. 10/481,524 inventors Aburatani, Hiroyuki, filed Jun. 30, 2004.
U.S. Appl. No. 10/514,516 inventors Edwards, Cynthia, filed Oct. 28, 2005.
U.S. Appl. No. 10/575,193 inventors Hattori, Kunihiro, filed Oct. 8, 2004.
U.S. Appl. No. 10/576,372 inventors Rossi, Mara, filed Nov. 4, 2004.
U.S. Appl. No. 10/672,280 inventors Lazar, Gregory Alan, filed Sep. 26, 2003.
U.S. Appl. No. 10/688,925 inventors Veldman, Geertruida M., filed Oct. 21, 2003.
U.S. Appl. No. 10/723,434 inventors Zhong, Pingyu, filed Nov. 26, 2003.
U.S. Appl. No. 10/738,120 inventors Teeling, Jessica, filed Dec. 16, 2003.
U.S. Appl. No. 10/759,731 inventors Bond, Christopher J., filed Jan. 16, 2004.
U.S. Appl. No. 10/822,231 inventors Lazar, Gregory Alan, filed Mar. 26, 2004.
U.S. Appl. No. 10/822,300 inventors Hinton, Paul R., filed Apr. 9, 2004.
U.S. Appl. No. 10/861,049 inventors Chan, Andrew, filed Jun. 4, 2004.
U.S. Appl. No. 10/902,588 inventors Stavenhagen, Jeffrey, filed Jul. 28, 2004.
U.S. Appl. No. 10/902,682 inventors Rabbani, Elazar, filed Jul. 29, 2004.
U.S. Appl. No. 10/939,309 inventors Fuh, Germaine, filed Sep. 9, 2004.
U.S. Appl. No. 10/981,738 inventors Umana, Pablo, filed Nov. 5, 2004.
U.S. Appl. No. 10/983,340 inventors Doronina, Svetlana O., filed Nov. 5, 2004.
U.S. Appl. No. 11/065,716 inventors Bookbinder, Louis H., filed Feb. 23, 2005.
U.S. Appl. No. 11/089,426 inventors Gillies, Stephen D., filed Mar. 24, 2005.
U.S. Appl. No. 11/090,981 inventors Lazar, Gregory Alan, filed Mar. 24, 2005.
U.S. Appl. No. 11/094,625 inventors Datta, Deepshikha, filed Mar. 30, 2005.
U.S. Appl. No. 11/096,046 inventors Adams, Camellia W., filed Mar. 31, 2005.
U.S. Appl. No. 11/102,502 inventors Bond, Christopher J., filed Apr. 8, 2005.
U.S. Appl. No. 11/108,135 inventors Koenig, Scott, filed Apr. 15, 2005.
U.S. Appl. No. 11/149,309 inventors Kasaian, Marion T., filed Jun. 9, 2005.
U.S. Appl. No. 11/155,909 inventors Cho, Ho Sung, filed Jun. 17, 2005.
U.S. Appl. No. 11/158,839 inventors Presta, Leonard, filed Jun. 22, 2005.
U.S. Appl. No. 11/165,023 inventors Dall'Acqua, William, filed Jun. 24, 2005.
U.S. Appl. No. 11/218,821 inventors Miller, Kathy L., filed Sep. 2, 2005.
U.S. Appl. No. 11/226,886 inventors Johnson, Leslie S., filed Sep. 13, 2005.
U.S. Appl. No. 11/233,258 inventors Eigenbrot, Charles W., filed Sep. 22, 2005.
U.S. Appl. No. 11/238,171 inventors Bookbinder, Louis H., filed Sep. 27, 2005.
U.S. Appl. No. 11/397,328 inventors Dall'Acqua, William, filed on Apr. 3, 2006.
U.S. Appl. No. 11/410,886 inventors Chin, Eva Rose, filed Apr. 24, 2006.
U.S. Appl. No. 11/429,793 inventors Presta, Leonard, filed May 8, 2006.
U.S. Appl. No. 11/432,872 inventors Farrington, Graham K., filed May 12, 2006.
U.S. Appl. No. 11/483,250 inventors Lazar, Gregory Alan, filed Jul. 7, 2006.
U.S. Appl. No. 11/499,064 inventors Kambadur, Ravi, filed Aug. 3, 2006.
U.S. Appl. No. 11/503,062 inventors Walsh, Frank S., filed Aug. 14, 2006.
U.S. Appl. No. 11/520,121 inventors Presta, Leonard, filed Sep. 13, 2006.
U.S. Appl. No. 11/536,603 inventors Baca, Manuel, filed Sep. 28, 2006.
U.S. Appl. No. 11/557,466 inventors Dennis, Mark S., filed Nov. 7, 2006.
U.S. Appl. No. 11/557,559 inventors Sidhu, Sachdev S., filed Nov. 8, 2006.
U.S. Appl. No. 11/565,880 inventors Birtalan, Sara C., filed Dec. 1, 2006.
U.S. Appl. No. 11/595,427 inventors Murphy, Andrew J., filed Nov. 9, 2006.
U.S. Appl. No. 11/713,577 inventors Krummen, Lynne A., filed Feb. 28, 2007.
U.S. Appl. No. 11/745,644 inventors Barthelemy, Pierre A., filed May 8, 2007.
U.S. Appl. No. 11/754,015 inventors Johnson, Leslie S., filed May 25, 2007.
U.S. Appl. No. 11/764,001 inventors Lazar, Gregory Alan, filed Jun. 15, 2007.
U.S. Appl. No. 11/765,353 inventors Lazar, Gregory Alan, filed Jun. 19, 2007.
U.S. Appl. No. 11/793,649 inventors Tsuchiya, Masayuki, filed Oct. 26, 2005.
U.S. Appl. No. 11/893,693 inventors Fuh, Germaine, filed Aug. 17, 2007.
U.S. Appl. No. 11/911,940 inventors Babcook, John, filed Apr. 18, 2006.
U.S. Appl. No. 11/932,151 inventors Chamberlain, Aaron Keith, filed Oct. 31, 2007.
U.S. Appl. No. 11/952,568 inventors Stavenhagen, Jeffrey B., filed Dec. 7, 2007.
U.S. Appl. No. 11/981,647 inventors Desjarlais, John R., filed Oct. 31, 2007.
U.S. Appl. No. 12/018,754 inventors Bernett, Matthew J., filed Jan. 23, 2008.
U.S. Appl. No. 12/020,443 inventors Lazar, Gregory Alan, filed Jan. 25, 2008.
U.S. Appl. No. 12/033,642 inventors Presta, Leonard, filed Feb. 19, 2008.
U.S. Appl. No. 12/066,838 inventors Davies, Julian, filed Oct. 5, 2006.
U.S. Appl. No. 12/154,836 inventors Chen, Eddy Giing-Lii, filed May 27, 2008.
U.S. Appl. No. 12/156,183 inventors Chu, Seung Yup, filed May 30, 2008.
U.S. Appl. No. 12/186,058 inventors Koenig, Scott, filed Aug. 5, 2008.
U.S. Appl. No. 12/262,712 inventors LaVallie, Edward Roland, filed Oct. 31, 2008.
U.S. Appl. No. 12/295,039 inventors Igawa, Tomoyuki, filed Mar. 30, 2007, related application.

(56) References Cited

OTHER PUBLICATIONS

U.S. Appl. No. 12/295,075 inventors Igawa, Tomoyuki, filed Mar. 30, 2007.
U.S. Appl. No. 12/311,768 inventors Lasters, Ignace Joseph Isabella, filed Oct. 11, 2007.
U.S. Appl. No. 12/532,022 inventors Guler-Gane, Gulin, filed Mar. 19, 2008.
U.S. Appl. No. 12/559,411 inventors Hariharan, Kandasamy, filed Sep. 14, 2009.
U.S. Appl. No. 12/559,415 inventors Hariharan, Kandasamy, filed Sep. 14, 2009.
U.S. Appl. No. 12/577,967 inventors Lowman, Henry B., filed Oct. 13, 2009.
U.S. Appl. No. 12/611,090 inventors Kim, Myung, filed Nov. 2, 2009.
U.S. Appl. No. 12/660,528 inventors Sabbadini, Roger A., filed Feb. 26, 2010.
U.S. Appl. No. 12/673,599 inventors Clegg, Stephanie Jane, filed Aug. 15, 2008.
U.S. Appl. No. 12/679,922 inventors Igawa, Tomoyuki, filed Sep. 26, 2008.
U.S. Appl. No. 12/680,082 inventors Igawa, Tomoyuki, filed Sep. 26, 2008.
U.S. Appl. No. 12/680,087 inventors Igawa, Tomoyuki, filed Sep. 25, 2009.
U.S. Appl. No. 12/680,112 inventors Igawa, Tomoyuki, filed Sep. 26, 2008.
U.S. Appl. No. 12/733,865 inventors Chung, Young Min, filed Aug. 24, 2008.
U.S. Appl. No. 12/733,933 inventors Igawa, Tomoyuki, filed Sep. 26, 2008.
U.S. Appl. No. 12/792,810 inventors Bohrmann, Bernd, filed Jun. 3, 2010.
U.S. Appl. No. 12/809,563 inventors Biere-Citron, Anja Leona, filed Dec. 19, 2008.
U.S. Appl. No. 12/864,075 inventors Bernett, Matthew J., filed Jan. 21, 2009.
U.S. Appl. No. 12/896,610 inventors Lazar, Gregory Alan, filed Oct. 1, 2010.
U.S. Appl. No. 12/913,145 inventors Finney, Helene M., filed Oct. 27, 2010.
U.S. Appl. No. 12/936,587 inventors Igawa, Tomoyuki, filed Apr. 10, 2009, related application.
U.S. Appl. No. 12/990,137 inventors Foltz, Ian, filed Apr. 28, 2009.
U.S. Appl. No. 13/045,345 inventors Pons, Jaume, filed Mar. 10, 2011.
U.S. Appl. No. 13/077,644 inventors Beliard, Roland, filed Mar. 31, 2011.
U.S. Appl. No. 13/192,429 inventors Dall'Acqua, William, filed Jul. 27, 2011.
U.S. Appl. No. 13/194,904 inventors Dahiyat, Bassil I., filed Jul. 29, 2011.
U.S. Appl. No. 13/388,270 inventors Schebye, Xiao Min, filed Aug. 31, 2010.
U.S. Appl. No. 13/458,730 inventors Zhang, Yongke, filed Apr. 27, 2012.
U.S. Appl. No. 13/480,356 inventors Walker, Wynn L., filed May 24, 2012.
U.S. Appl. No. 13/595,139 inventors Igawa, Tomoyuki, filed Aug. 27, 2012, related application.
U.S. Appl. No. 13/637,415 inventors Igawa, Tomoyuki, filed Mar. 30, 2011.
U.S. Appl. No. 13/764,693 inventors Lazar, Gregory Alan, filed Feb. 11, 2013.
U.S. Appl. No. 13/791,312 inventors Grabstein, Kenneth, filed Mar. 8, 2013.
U.S. Appl. No. 13/795,674 inventors Feldhaus, Andrew Lawrence, filed Mar. 12, 2013.
U.S. Appl. No. 13/816,894 inventors Han, Huiquan, filed Aug. 15, 2011.
U.S. Appl. No. 13/889,484 inventors Igawa, Tomoyuki, filed May 8, 2013, related application.
U.S. Appl. No. 13/889,512 inventors Igawa, Tomoyuki, filed May 8, 2013, related application.
U.S. Appl. No. 13/918,751 inventors Lazar, Gregory Alan, filed Jun. 14, 2013.
U.S. Appl. No. 13/990,158 inventors Igawa, Tomoyuki, filed Nov. 30, 2011, related application.
U.S. Appl. No. 14/001,218 inventors Mimoto, Futa, filed Feb. 24, 2012, related application.
U.S. Appl. No. 14/007,947 inventors Igawa, Tomoyuki, filed Mar. 30, 2012.
U.S. Appl. No. 14/021,777 inventors Flanagan, Kenneth, filed Sep. 9, 2013.
U.S. Appl. No. 14/078,501 inventors Lazar, Gregory Alan, filed Nov. 12, 2013.
U.S. Appl. No. 14/127,576 inventors Mimoto, Futa, filed Jun. 29, 2012.
U.S. Appl. No. 14/155,344 inventors Desjarlais, John R., filed Jan. 14, 2014.
U.S. Appl. No. 14/165,487 inventors Lazar, Gregory A., filed Jan. 27, 2014.
U.S. Appl. No. 14/212,189 inventors Dutzar, Benjamin H., filed Mar. 14, 2014.
U.S. Appl. No. 14/216,705 inventors Moore, Gregory, filed Mar. 17, 2014.
U.S. Appl. No. 14/340,872 inventors Lowman, Henry Bernard, filed Jul. 25, 2014.
U.S. Appl. No. 14/347,034 inventors Igawa, Tomoyuki, filed Sep. 28, 2012.
U.S. Appl. No. 14/347,187 inventors Igawa, Tomoyuki, filed Sep. 28, 2012.
U.S. Appl. No. 14/347,321 inventors Igawa, Tomoyuki, filed Sep. 28, 2012, related application.
U.S. Appl. No. 14/349,884 inventors Igawa, Tomoyuki, filed Oct. 5, 2012.
U.S. Appl. No. 14/361,013 inventors Igawa, Tomoyuki, filed Nov. 30, 2012.
U.S. Appl. No. 14/377,556 inventors Kuramochi, Taichi, filed Feb. 8, 2013.
U.S. Appl. No. 14/379,825 inventors Igawa, Tomoyuki, filed Feb. 22, 2013, related application.
U.S. Appl. No. 14/402,574 inventors Igawa, Tomoyuki, filed May 30, 2013.
U.S. Appl. No. 14/404,051 inventors Igawa, Tomoyuki, filed May 30, 2013.
U.S. Appl. No. 14/406,232 inventors Igawa, Tomoyuki, filed Jun. 14, 2013.
U.S. Appl. No. 14/422,207 inventors Igawa, Tomoyuki, filed Aug. 23, 2013, related application.
U.S. Appl. No. 14/423,269 inventors Katada, Hitoshi, filed Aug. 23, 2013, related application.
U.S. Appl. No. 14/629,967 inventors Igawa, Tomoyuki, filed Feb. 24, 2015.
U.S. Appl. No. 14/654,895 inventors Igawa, Tomoyuki, filed Dec. 26, 2013.
U.S. Appl. No. 14/727,313 inventors Andrien, Jr., Bruce A., filed Jun. 1, 2015.
U.S. Appl. No. 14/741,786 inventors Igawa, Tomoyuki, filed Jun. 17, 2015, related application.
U.S. Appl. No. 14/781,069 inventors Mimoto, Futa, filed Apr. 2, 2014, related application.
U.S. Appl. No. 14/974,488 inventors Ruike, Yoshinao, filed Dec. 18, 2015, related application.
U.S. Appl. No. 15/015,287 inventors Igawa, Tomoyuki, filed Feb. 4, 2016, related application.
U.S. Appl. No. 15/050,145 inventors Igawa, Tomoyuki, filed Feb. 22, 2016.
U.S. Appl. No. 15/210,360 inventors Igawa, Tomoyuki, filed Jul. 14, 2016.
U.S. Appl. No. 15/230,904 inventors Igawa, Tomoyuki, filed Aug. 8, 2016.

(56) References Cited

OTHER PUBLICATIONS

U.S. Appl. No. 15/725,692 inventors Igawa, Tomoyuki, filed Oct. 5, 2017, related application.
U.S. Appl. No. 15/952,945 inventors Igawa, Tomoyuki, filed on Apr. 13, 2018, related application.
U.S. Appl. No. 15/952,951 inventors Igawa, Tomoyuki, filed Apr. 13, 2018, related application.
U.S. Appl. No. 15/963,449 inventors Ruike, Yoshinao, filed Apr. 26, 2018, related application.
U.S. Appl. No. 15/963,455 inventors Ruike, Yoshinao, filed Apr. 26, 2018, related application.
U.S. Appl. No. 15/976,288 inventors Igawa, Tomoyuki, filed May 10, 2018, related application.
U.S. Appl. No. 15/988,348 inventors Igawa, Tomoyuki, filed May 24, 2018, related application.
U.S. Appl. No. 16/065,192 inventors Ruike, Yoshinao, filed Dec. 22, 2016, related application.
U.S. Appl. No. 16/333,736 inventors Sampei, Zenjiro, filed Sep. 15, 2017, related application.
U.S. Appl. No. 16/361,498 inventors Igawa, Tomoyuki, filed Mar. 22, 2019, related application.
U.S. Appl. No. 16/435,979 inventors Sampei, Zenjiro, filed Jun. 10, 2019, related application.
U.S. Appl. No. 16/697,310 inventors Igawa, Tomoyuki, filed Nov. 27, 2019, related application.
U.S. Appl. No. 16/889,066, inventors Ruike, Y., et al., filed Jun. 1, 2020, related application.
U.S. Appl. No. 17/020,497 inventors Igawa, Tomoyuki, filed Sep. 14, 2020, related application.
U.S. Appl. No. 17/020,543 inventors Igawa, Tomoyuki, filed Sep. 14, 2020, related application.
U.S. Appl. No. 17/028,210 inventors Katada, et al., filed Sep. 22, 2020, related application.
Cordoba, A.J., et al., "Non-Enzymatic Hinge Region Fragmentation of Antibodies in Solution," Journal of Chromatography B, 818(2):115-121 (2005).
Couto, J.R., et al., "Anti-BA46 Monoclonal Antibody Mc3: Humanization Using a Novel Positional Consensus and in Vivo and in Vitro Characterization," Cancer Research, 55(8):1717-1722, American Association for Cancer Research, United States (Apr. 15, 1995).
Cragg, M.S. and Glennie, M.J., "Antibody Specificity Controls in Vivo Effector Mechanisms of Anti-CD20 Reagents," Blood 103(7):2738-2743, American Society of Hematology, United States (Apr. 2004).
Cragg, M.S., et al., "Complement-mediated Lysis by Anti-CD20 mAb Correlates With Segregation Into Lipid Rafts," Blood 101(3):1045-1052, American Society of Hematology, United States (Feb. 2003).
Cruse et al., "Antigens and Immunogens," Atlas of Immunology, CRC Press LLC, excerpt from Chapter 3, p. 109 (2004).
Cuatrecasas, P and Anfinsen, C.B., "Affinity Chromatography," Methods in Enzymology, 22:345-378, Elsevier, Netherlands (1971).
Curtiss, F.R., "Selectivity and Specificity are the Keys to Cost-Effective Use of Omalizumab for Allergic Asthma," Journal of Managed Care Pharmacy, 11(9):774-776, United States, Academy of Managed Care Pharmacy (Nov. 2005).
Dall'Acqua, W.F., et al., "Antibody Humanization by Framework Shuffling," Methods 36(1):43-60, Academic Press, United States (May 2005).
Dall'Acqua, W.F., et al., "Increasing the Affinity of a Human IgG1 for the Neonatal Fc Receptor: Biological Consequences," Journal of Immunology 169(9):5171-5180, American Association of Immunologists, United States (Nov. 2002).
Dall'Acqua, W.F., et al., "Properties of Human IgG1s Engineered for Enhanced Binding to the Neonatal Fc Receptor (FcRn)," The Journal of Biological Chemistry 281(33):23514-23524, American Society for Biochemistry and Molecular Biology, United States (Aug. 2006).
Damschroder, M.M., et al., "Framework Shuffling of Antibodies to Reduce Immunogenicity and Manipulate Functional and Biophysical Properties," Molecular Immunology, 44(11):3049-3060, Pergamon Press, England (Apr. 2007).
Daeron, M., "Fc Receptor Biology," Annual Review of Immunology 15:203-234, Annual Reviews Inc., United States (1997), Abstract.
Datta-Mannan, A., et al., "Monoclonal Antibody Clearance. Impact of Modulating the Interaction of IgG With the Neonatal Fc Receptor," The Journal of Biological Chemistry 282(3):1709-1717, American Society for Biochemistry and Molecular Biology, United States (Jan. 2007).
De Groot, A.S. and Martin W., et al., "Reducing Risk, Improving Outcomes: Bioengineering Less Immunogenic Protein Therapeutics," Clinical Immunology 131(2):189-201, Academic Press, United States (May 2009).
De Groot, A.S., et al., "De-Immunization of Therapeutic Proteins by T-cell Epitope Modification," Developments in Biologicals, 122:171-194, Karger, c2000-, Switzerland (2005).
Decision of the EPO Opposition Division for EP2006381 on Jul. 25, 2018, 17 pages.
Declaration by Madhusudan Natarajan, Ph.D. (submitted by the Opponent during EP opposition procedure for EP2708558 and posted by EPO on Jan. 15, 2019), 3 pages.
Declaration of Mr. Taichi Kuramochi dated May 23, 2019, co-inventor of EP2202245 (submitted by the Patentee during EPO opposition procedure for EP2202245).
Declaration of Nimish Gera, Ph.D., CV and Exhibits, dated Sep. 1, 2016, submitted by the opponent in opposition for EP2275443 24 pages.
Declaration of Muramatsu Hiroyasu dated Oct. 21, 2020, cited in corresponding European application Office Action.
Deen, W.M., et al., "Structural Determinants of Glomerular Permeability," American Journal of Physiology. Renal Physiology, 281(4):F579-F596, American Physiological Society, c1997-, United States (Oct. 2001).
Del Rio, G., et al., "An Engineered Penicillin Acylase With Altered Surface Charge is More Stable in Alkaline PH," Annals of the New York Academy of Sciences, 799:61-64, Blackwell, United States (Oct. 12, 1996).
Deng, R., et al. , "Pharmacokinetics of Humanized Monoclonal Anti-tumor Necrosis Factor-{alpha} Antibody and Its Neonatal Fc Receptor Variants in Mice and Cynomolgus Monkeys," Drug Metabolism and Disposition 38(4):600-605, American Society for Pharmacology and Experimental , United States (Apr. 2010).
Desai, D.D., et al., "Fc Gamma Receptor IIB on Dendritic Cells Enforces Peripheral Tolerance by Inhibiting Effector T Cell Responses," Journal of Immunology 178(10):6217-6226, American Association of Immunologists, United States (May 2007).
Devanaboyina, S,C., et al., "The Effect of pH Dependence of Antibody-Antigen Interactions on Subcellular Trafficking Dynamics", mAbs 5:851-859, Taylor & Francis, United States (Nov. 2013).
Dhodapkar, K., et al., "Selective Blockade of Inhibitory Fcgamma Receptor Enables Human Dendritic Cell Maturation With IL-12p70 Production and Immunity to Antibody-coated Tumor Cells," Proceedings of the National Academy of Sciences of the United States of America, 102(8):2910-2915, National Academy of Sciences, United States (Feb. 2005).
Di Stefano, A., et al., "Role of Interleukin-8 in the Pathogenesis and Treatment of COPD," Chest, 126(3):676-678 (2004).
Diamond B. and Scharff, M. D., "Somatic Mutation of the T15 Heavy Chain Gives Rise to an Antibody With Autoantibody Specificity," Proceedings of the National Academy of Sciences of the United States of America, 81(18):5841-5844, United States, National Academy of Sciences (Sep. 1984).
Van Dijk, M., et al., "Human Antibodies as Next Generation Therapeutics," Current Opinion in Chemical Biology, 5(4):368-374, Elsevier, England (Aug. 2001).
Drake, A.W and Papalia, G.A., "Chapter 5: Biophysical Considerations for Development of Antibody-Based Therapeutics," Biophysical Considerations for Development of Antibody-Based Therapeutics, 95-97, Springer Science & Business Media, New York (2012).

(56) References Cited

OTHER PUBLICATIONS

Dubowchik, M., et al., "Doxorubicin Immunoconjugates Containing Bivalent, Lysosomally-cleavable Dipeptide Linkages," Bioorganic & Medicinal Chemistry Letters, 12(11):1529-1532, England, Elsevier Science Ltd (Jun. 2002).
Duffau, P., et al., "Platelet CD154 Potentiates Interferon-alpha Secretion by Plasmacytoid Dendritic Cells in Systemic Lupus Erythematosus," Science Translational Medicine, 2(47):47ra63, American Association for the Advancement of Science, United States (Sep. 2010).
Duncan, A.R. and Winter, G., "The Binding Site for C1q on IgG," Nature 332(6166):738-740, Nature Publishing Group, England (Apr. 1988).
Durkee, K.H., et al., "Immunoaffinity Chromatographic Purification of Russell's Viper Venom Factor X Activator Using Elution in High Concentrations of Magnesium Chloride," Protein Expression and Purification 4(5):405-411, Academic Press, United States (Oct. 1993).
Edwards, B.M., et al., "The Remarkable Flexibility of the Human Antibody Repertoire; Isolation of Over One Thousand Different Antibodies to a Single Protein, BLyS," Journal of Molecular Biology 334(1):103-118, Elsevier, England (Nov. 2003).
Ejima, D., et al., "Effective Elution of Antibodies by Arginine and Arginine Derivatives in Affinity col. Chromatography," Analytical Biochemistry, 345(2):250-257, Elsevier, Netherlands (2005).
EP 1870459 English language translation of priority document Japanese patent application 2005101105.
EP 1870459 English language translation of priority document Japanese patent application 2005378266.
EPO Register Extract EP1915397.
Ewert, S., et al., "Stability Improvement of Antibodies for Extracellular and Intracellular Applications: CDR Grafting to Stable Frameworks and Structure-based Framework Engineering," Methods (San Diego, Calif.), 34(2):184-199, Academic Press, c1990-, United States (Oct. 2004).
Example antibody family tree, attached to the written submission for Opposition against EP 2708559 on Mar. 12, 2020.
Declaration of Joachim Boucneau, dated Mar. 11, 2020, submitted by opponent in European opposition in EP2708559 on Mar. 11, 2020.
Feinberg, H., et al., "Mechanism of pH-dependent N-Acetylgalactosamine Binding by a Functional Mimic of the Hepatocyte Asialoglycoprotein Receptor," The Journal of Biological Chemistry 275(45):35176-35184, American Society for Biochemistry and Molecular Biology, United States (Nov. 2000).
Fellouse, F.A., et al., "Synthetic Antibodies From a Four-Amino-Acid Code: a Dominant Role for Tyrosine in Antigen Recognition," Proceedings of the National Academy of Sciences of the United States of America 101(34):12467-12472, National Academy of Sciences, United States (Aug. 2004).
Fiedler, M., et al., "An Engineered in-1 F(Ab) Fragment With Improved Affinity for the Nogo-a Axonal Growth Inhibitor Permits Immunochemical Detection and Shows Enhanced Neutralizing Activity," Protein Engineering, 15(11): 931-941, England, Oxford University Press (Nov. 2002).
Fillipovic, Biochemical basis of human life activity, Vlados, 2005; 38-43.
Fillipovich., Biochemical basis of human life, Vlados 2005:49-50.
Finkelman, F,D., et al., "Anti-cytokine Antibodies as Carrier Proteins. Prolongation of in Vivo Effects of Exogenous Cytokines by Injection of Cytokine-Anti-cytokine Antibody Complexes," Journal of Immunology 151:1235-1244, American Association of Immunologists, United States (Aug. 1993).
Fisher, P.A and Smith, D.E., "Affinity Purification of Antibodies Using Antigens Immobilized on Solid Supports," Biochemical Society Transactions, 16(2):134-138, Portland Press On The Behalf Of The Biochemical Society, England (Apr. 1988).
Flatman, S., et al., "Process Analytics for Purification of Monoclonal Antibodies," Journal of Chromatography B 848(1):79-87, Elsevier, Netherlands (Mar. 2007).
Flores, M., et al., "Dominant Expression of the Inhibitory FcγRIIB Prevents Antigen Presentation by Murine Plasmacytoid Dendritic Cells," J Immunol., 183:7129-7139 (2009).
Floto, R.A., et al., "Loss of Function of a Lupus-associated Fcγ RIIb Polymorphism Through Exclusion From Lipid Rafts," Nature Medicine, 11(10):1056-1058, Nature Publishing Company, United States (Oct. 2005).
Foote, J. and Winter, G., "Antibody Framework Residues Affecting the Conformation of the Hypervariable Loops," Journal of Molecular Biology 224(2):487-499, Elsevier, England (Mar. 1992).
Fournier, E., et al., "Activation of Human Peripheral IgM+ B Cells is Transiently Inhibited by Bcr-independent Aggregation of Fc gammaRIIB," Journal of Immunology, 181(8):5350-5359, American Association of Immunologists, United States (Oct. 2008).
Fujii, I., "Antibody Affinity Maturation by Random Mutagenesis," Methods in Molecular Biology, 248:345-359, Humana Press, United States (2004).
Gazzano-Santoro H., et al., "A Non-Radioactive Complement-Dependent Cytotoxicity Assay for Anti-CD20 Monoclonal Antibody," Journal of Immunological Methods 202(2):163-171, Elsevier, Netherlands (Mar. 1997).
GE Healthcare. Application note 28-9277-92 AA. "High-throughput screening of elution pH for monoclonal antibodies on MabSelect SuRe using PreDictor plates" [online], [retrieved on Nov. 5, 2015]. Retrieved from the Internet: https :/ /www. gelifesciences. com/ gehc Is images/GELS/Related %2 OContent/F iles/1314 78 7 4 24 814/lit doc28927792AA20110831131840.pdf.
GE Healthcare, "Biacore, Sensor Surface Handbook," BR-1005-71, Edition AB, Feb. 2005, pp. 1-100.
Gera, N., et al., "Design of pH Sensitive Binding Proteins From the Hyperthermophilic Sso7d Scaffold," PLoS One, 7(11):e48928, Public Library of Science, United States (2012).
Gerngross, T.U., "Advances in the Production of Human Therapeutic Proteins in Yeasts and Filamentous Fungi," Nature Biotechnology 22(11):1409-1414, Nature America Publishing, United States (Nov. 2004).
Gerstner, R.B., et al., "Sequence Plasticity in the Antigen-binding Site of a Therapeutic Anti-HER2 Antibody," Journal of Molecular Biology, 321(5):851-862, Elsevier, England (Aug. 30, 2002).
Gessner, J.E., et al., "The IgG Fc Receptor Family," Annals of Hematology 76(6):231-248, Springer Verlag, Germany (Jun. 1998).
Ghetie, V. and Ward, E.S., "Fcrn: the Mhc Class I-related Receptor That is More Than an IgG Transporter," Immunology Today 18(12):592-598, Elsevier Science Publishers, England (Dec. 1997).
Ghetie, V., et al., "Increasing the Serum Persistence of an IgG Fragment by Random Mutagenesis," Nature Biotechnology 15(7):637-640, Nature America Publishing, United States (Jul. 1997).
Ghetie, V., et al., "Multiple Roles for the Major Histocompatibility Complex Class I-Related Receptor FcRn," Annual Review of Immunology, 18:739-766, Annual Reviews Inc., c1983-, United States (2000).
Glick, B. R., et al., "Molecular Biotechnology—Principles and Applications of Recombinant DNA," edited, p. 168, paragraph 5, (Mar. 2005), with English translation thereof.
Gobburu, J.V., et al., "Pharmacokinetics/dynamics of 5c8, a Monoclonal Antibody to CD154 (CD40 Ligand) Suppression of an Immune Response in Monkeys," The Journal of pharmacology and experimental therapeutics, 286(2):925-930, American Society for Pharmacology and Experimental Therapeutics, United States (Aug. 1998).
Gonzalez, E.M., et al., "BMP-1/Tolloid-like metalloproteases process endorepellin, the angiostatic C-terminal fragment of perlecan," The Journal of Biological Chemistry, 280(8):7080-7087, American Society for Biochemistry and Molecular Biology, United States (Feb. 2005).
Goode, N.P., et al., "The Glomerular Basement Membrane Charge-selectivity Barrier: an Oversimplified Concept," Nephrology Dialysis Transplantation, 11(9):1714-1716, Oxford University Press, England (Sep. 1996).
Gopferich, A., et al., "Drug Delivery from Bioerodible Polymers," Chapter 15 in Formulation and Delivery of Proteins and Peptides, 567:242-277, American Chemical Society, eds. Cleland et al., (Aug. 1994).

(56) References Cited

OTHER PUBLICATIONS

Graham, F.L., et al., "Characteristics of a Human Cell Line Transformed by Dna From Human Adenovirus Type 5," The Journal of General virology 36(1):59-74, Microbiology Society, England (Jul. 1977).
Graves, S.S., et al., "Molecular Modeling and Preclinical Evaluation of the Humanized NR-LU-13 Antibody," Clinical Cancer Research, 5(4):899-908, The Association, c1995-, United States (Apr. 1999).
Greenwood, J., et al., "Structural Motifs Involved in Human IgG Antibody Effector Functions," European Journal of Immunology, 23(5):1098-1104, Germany, Wiley-VCH Verlag (May 1993).
Griffiths, A.D., et al., "Human Anti-Self Antibodies With High Specificity From Phage Display Libraries," The EMBO Journal 12(2):725-734, Wiley Blackwell, England (Feb. 1993).
Gruber, M., et al., "Efficient Tumor Cell Lysis Mediated by a Bispecific Single Chain Antibody Expressed in *Escherichia coli*," Journal of Immunology 152(11):5368-5374, American Association of Immunologists, United States (Jun. 1994).
Guidance on the Use of International Nonproprietary Names (INNs) for Pharmaceutical Substances, World Health Organization, 2017, 55 pages, submitted by opponent in European opposition in EP2708559 on Mar. 11, 2020.
Guyer, R., et al., "Immunoglobulin Binding by Mouse Intestinal Epithelial Cell Receptors," Journal of Immunology, 117(2):587-593, American Association of Immunologists, United States (Aug. 1976).
Guyre, P.M., et al., "Increased Potency of Fc-Receptor-Targeted Antigens," Cancer Immunology 45(3-4):146-148, Springer Verlag, Germany (Nov.-Dec. 1997).
Hamers-Casterman, C., et al., "Naturally Occurring Antibodies Devoid of Light Chains," Nature, 363(6428):446-448, Nature Publishing Group, England (Jun. 3, 1993).
Han, H.Q. & Mitch, W.E., "Targeting the Myostatin Signaling Pathway to Treat Muscle Wasting Diseases," Current Opinion in Supportive and Palliative Care, 5(4):334-341, United States, Lippincott Williams & Wilkins (Dec. 2011).
Hanson, C.V., et al., "Catalytic Antibodies and Their Applications," Biotechnology Letters, 16:631-636 (Dec. 2005).
Harvey, et al., Lippincott's Illustrated Reviews: Immunology Second Edition Chapter 2 "Antigens and Receptors" pp. 11-23 Chapter11 "Lymphocyte Effector Functions"pp. 141-157 (2013).
Hasemann, C.A., et al., "Mutational analysis of arsonate binding by a CRIA+ antibody. VH and VL junctional diversity are essential for binding activity," Journal of Biological Chemistry, 266(12):7626-7632, American Society for Biochemistry and Molecular Biology, United States (Apr. 1991).
Hashimoto-Gotoh, T., et al., "An Oligodeoxyribonucleotide-directed Dual Amber Method for Site-directed Mutagenesis," Gene 152(2):271-275, Elsevier/North-Holland, Netherlands (Jan. 1995).
He, X.Y., et al., "Humanization and Pharmacokinetics of a Monoclonal Antibody With Specificity for Both E- and P-selectin," Journal of Immunology (Baltimore, Md. : 1950), 160(2):1029-1035, American Association of Immunologists, United States (Jan. 15, 1998).
Hellstrom, I., et al., "Antitumor Effects of L6, an IgG2a Antibody That Reacts With Most Human Carcinomas," Proceedings of the National Academy of Sciences of the United States of America 83(18):7059-7063, National Academy of Sciences, United States (Sep. 1986).
Hellstrom, I., et al., "Strong Antitumor Activities of IgG3 Antibodies to a Human Melanoma- associated Ganglioside," Proceedings of the National Academy of Sciences of the United States of America 82(5):1499-1502, National Academy of Sciences, United States (Mar. 1985).
Heyman, B., "Feedback Regulation by IgG Antibodies," Immunology Letters, 88(2):157-161, Elsevier/North-Holland Biomedical Press, Netherlands (Aug. 2003).
Hill, J., et al., "The Myostatin Propeptide and the Follistatin-related Gene Are Inhibitory Binding Proteins of Myostatin in Normal Serum," The Journal of Biological Chemistry, 277(43):40735-40741, American Society for Biochemistry and Molecular Biology, United States (Oct. 2002).
Hinman, L.M., et al., "Preparation and Characterization of Monoclonal Antibody Conjugates of the Calicheamicins: a Novel and Potent Family of Antitumor Antibiotics," Cancer Research 53(14):3336-3342, American Association for Cancer Research, United States (Jul. 1993).
Hinton, P.R., et al., "An Engineered Human IgG1 Antibody With Longer Serum Half-life," Journal of Immunology, 176(1):346-356, American Association of Immunologists, United States (Jan. 2006).
Hird, V., et al., "Tumour Localisation With a Radioactively Labelled Reshaped Human Monoclonal Antibody," British Journal of Cancer, 64(5):911-914, Nature Publishing Group on behalf of Cancer Research UK, England (Nov. 1991).
Hironiwa et al., "Calcium-dependent Antigen Binding as a Novel Modality for Antibody Recycling by Endosomal Antigen Dissociation," MAbs, 8(1):65-73 (2016).
Hjelm, F., et al., "Antibody-mediated Regulation of the Immune Response," Scandinavian Journal of Immunology, 64(3):177-84, England, Blackwell Scientific Publications (Sep. 2006).
Holash, J., et al., "Vegf-Trap: A Vegf Blocker With Potent Antitumor Effects," Proceedings of the National Academy of Sciences of the United States of America 99(7):11393-11398, National Academy of Sciences, United States (Aug. 2002).
Hollinger, P., et al., ""Diabodies": Small Bivalent and Bispecific Antibody Fragments," Proceedings of the National Academy of Sciences of the United States of America 90(14):6444-6448, National Academy of Sciences, United States (Jul. 1993).
Hong, G., et al., "Enhanced Cellular Uptake and Transport of Polyclonal Immunoglobulin G and Fab After Their Cationization," Journal of Drug Targeting, 8(2):67-77, Informa Healthcare, England (2000).
Hoodless, A., and Wrana, J.L, "Mechanism and Function of Signaling by the TGF Beta Superfamily," Current Topics in Microbiology and Immunology, 228:235-272, Germany, Heidelberg : Springer Verlag (1998).
Hoogenboom, H.R., "Selecting and Screening Recombinant Antibody Libraries," Nature Biotechnology 23(9):1105-1116, Nature America Publishing, United States (Sep. 2005).
Hoogenboom, H.R., et al., "By-Passing Immunisation. Human Antibodies from Synthetic Repertoires of Germline VH Gene Segments Rearranged in Vitro," Journal of Molecular Biology, 227(2):381-388, Amsterdam, Elsevier (Sep. 1992).
Hoogenboom, H.R., "Overview of antibody phage-display technology and its applications," Methods in Molecular Biology, 178:1-37, Humana Press, United States (2002).
Horton, H.M., et al., "Potent in vitro and in vivo activity of an Fc-engineered anti-CD19 monoclonal antibody against lymphoma and leukemia," Cancer Research, 68(19):8049-8057, American Association for Cancer Research, United States (Oct. 2008).
Hotzel, I., et al., "A Strategy for Risk Mitigation of Antibodies With Fast Clearance," mAbs, 4(6):753-760, Taylor & Francis, United States (Nov.-Dec. 2012).
Howard, G. C. and Kaser, M. R., editors, "Making and Using Antibodies: A Practical Handbook," CRC Press, 157-177 (2007).
Sigma-Aldrich®, Product Information, Monoclonal Anti-Flag® M1, Clone M1, accessed at http://www.sigmaaldrich.com/content/dam/sigmaaldrich/ does/Sigma/Datasheet/f3040dat.pdf, 1 page (2008).
Hudson, P.J., et al., "Engineered Antibodies," Nature Medicine 9(1):129-134, Nature Publishing Company, United States (Jan. 2003).
Hughes-Jones, N.C., et al., "The Effect of pH and Ionic Strength on the Reaction between Anti-D and Erythrocytes," Immunology, 7:72-81, Blackwell Scientific Publications, England (Jan. 1964).
Huse, K., et al., "Purification of Antibodies by Affinity Chromatography," Journal of Biochemical and Biophysical Methods 51(3):217-231, (May 2002).
Hwang, W.Y., et al., "Use of Human Germline Genes in a CDR Homology-based Approach to Antibody Humanization," Methods (San Diego, Calif.), 36(1):35-42, Academic Press, United States (May 2005).

(56) References Cited

OTHER PUBLICATIONS

Idusogie, E. E., et al., "Engineered Antibodies with Increased Activity to Recruit Complement," Journal of Immunology 166(4):2571-2575, American Association of Immunologists, United States (Feb. 2001).
Idusogie, E.E., et al., "Mapping of the C1q Binding Site on Rituxan, a Chimeric Antibody With a Human IgG1 Fc," Journal of Immunology 164(8):4178-4184, American Association of Immunologists, United States (Apr. 2000).
Igawa, et al., "Antibody Optimization Technologies for Developing Next Generation Antibody Therapeutics", Bio Industry 28:15-21, (2011) (with English translation).
Igawa, T., et al., "Engineering the Variable Region of Therapeutic IgG Antibodies," MAbs, 3(3):243-52 (2011).
Igawa, T., et al., "Reduced Elimination of IgG Antibodies by Engineering the Variable Region," Protein engineering, design & selection, 23(5):385-92 (2010).
Igawa, T., et al., "Antibody Recycling by Engineered pH-Dependent Antigen Binding Improves the Duration of Antigen Neutralization," Nature Biotechnology 28(11):1203-1207, Nature America Publishing, United States (Nov. 2010).
Igawa, T., et al., "Engineered Monoclonal Antibody With Novel Antigen-sweeping Activity in Vivo," PLoS One 8(5):e63236, Public Library of Science, United States (May 2013).
Igawa, T., et al., "pH-dependent Antigen-binding Antibodies as a Novel Therapeutic Modality," Biochimica Et Biophysica Acta, 1844(11):1943-1950, Elsevier Pub. Co., Netherlands (Nov. 2014).
Igawa, T., et al., "Sweeping Antibody as a Novel Therapeutic Antibody Modality Capable of Eliminating Soluble Antigens From Circulation," Immunological Reviews, 270(1):132-151, Blackwell, England (Mar. 2016).
Ishii-Watabe, A., et al., "FcRn, a Critical Regulator of Antibody Pharmacokinetics," Nihon Yakurigaku Zasshi. Folia Pharmacologica Japonica 136(5):280-284, Nippon Yakuri Gakkai, Japan (Nov. 2010 (with English translation)).
Ito, W., et al., "The His-probe Method: Effects of Histidine Residues Introduced Into the Complementarity-Determining Regions of Antibodies on Antigen-antibody Interactions at Different Ph Values," FEBS letters, 309(1):85-88, John Wiley & Sons Ltd., England (Aug. 31, 1992).
Jain, M., et al., "Engineering Antibodies for Clinical Applications," Trends in Biotechnology, 25(7):307-316, Elsevier Science Publishers, England (Jul. 2007).
Janeway, et al Immunobiology, 5th edition. 2001 :Extract from Chapter 3.
Janeway, et al Immunobiology, 5th edition. 2001:Extract from Chapter 4.
Jefferis, R and Lund, J., "Interaction Sites on Human IgG-Fc for FcgammaR: Current Models," Immunology Letters, 82(1-2):57-65, Elsevier/North-Holland Biomedical Press, Netherlands (Jun. 2002).
Jeffrey, S.C., et al., "Dipeptide-Based Highly Potent Doxorubicin Antibody Conjugates," Bioorganic & Medicinal Chemistry Letters, 16(2):358-362, England, Elsevier Science Ltd (Jan. 2006).
Johnson, K.A., et al., "Cation Exchange-HPLC and Mass Spectrometry Reveal C-Terminal Amidation of an IgG1 Heavy Chain," Analytical Biochemistry 360(1):75-83, Academic Press, United States (Jan. 2007).
Jones, T.D., et al., "Identification and Removal of a Promiscuous CD4+ T Cell Epitope From the C1 Domain of Factor VIII," Journal of Thrombosis and Haemostasis, 3(5):991-1000, Blackwell Pub, England (May 2005).
Junghans, R.P. and Anderson, C.L., "The Protection Receptor for IgG Catabolismis the Beta2-Microglobulin-Containing Neonatal Intestinal Transport Receptor," Proceedings of the National Academy of Sciences of the United States of America 93(11):5512-5516, National Academy of Sciences, United States (May 1996).
Kabat, E.A., et al., "Sequences of Proteins of Immunological Interest," National Institute of Health, Publ'n No. 91-3242, 5th ed. 1991, vol. 1, pp. 647-660.
Kabat, et al., Sequences of proteins of immunological interest, Diane publishing, 5th ed., 1991, vol. 1, pp. 679-687.
Kakita, M., et al., "Isolation of a Human Monoclonal Antibody With Strong Neutralizing Activity Against Diphtheria Toxin", Infection and Immunity, 74:3682-3683, American Society For Microbiology, United States (Jun. 2006).
Kam, N.W., et al., "Carbon Nanotubes as Multifunctional Biological Transporters and Near-Infrared Agents for Selective Cancer Cell Destruction," Proceedings of the National Academy of Sciences of the United States of America 102(33):11600-11605, National Academy of Sciences, United States (Aug. 2005).
Kamata, N., et al., "Comparison of pH and ionic strength dependence of interactions between monoclonal antibodies and bovine beta-lactoglobulin," Bioscience, Biotechnology, and Biochemistry, 60(1):25-29, Taylor & Francis, United States (Jan. 1996).
Kanda, Y., et al., "Comparison of Cell Lines for Stable Production of Fucose-Negative Antibodies With Enhanced ADCC," Biotechnology and Bioengineering 94(4):680-688, Wiley, United States (Jul. 2006).
Kashmiri, S.V., et al., "SDR Grafting—a New Approach to Antibody Humanization," Methods 36(1):25-34, Academic Press, United States (May 2005).
Kashmiri, S.V., et al., "Generation, Characterization, and in Vivo Studies of Humanized Anticarcinoma Antibody CC49," Hybridoma, 14(5):461-473, Mary Ann Liebert, United States (Oct. 1995).
Katayose, Y., et al., "MUC1-specific Targeting Immunotherapy With Bispecific Antibodies: Inhibition of Xenografted Human Bile Duct Carcinoma Growth," Cancer Research, 56(18):4205-4212, American Association for Cancer Research, United States (Sep. 15, 1996).
Khawli, L.A., et al., "Improved Tumor Localization and Radioimaging With Chemically Modified Monoclonal Antibodies," Cancer Biotherapy & Radiopharmaceuticals, 11(3):203-215, Mary Ann Liebert, Inc., c1996-, United States (Jun. 1996).
Kim, I., et al., "Lowering of Pi by Acylation Improves the Renal Uptake of 99m Tc-labeled Anti-Tac DsFv: Effect of Different Acylating Reagents," Nuclear Medicine and Biology, 29(8):795-801, Elsevier, United States (Nov. 2002).
Kim, I.S., et al., "Chemical Modification to Reduce Renal Uptake of Disulfide-bonded Variable Region Fragment of Anti-Tac Monoclonal Antibody Labeled With 99m Tc," Bioconjugate Chemistry, 10(3):447-453, American Chemical Society, c1990-, United States (May-Jun. 1999).
Kim, S.J., et al., "Antibody Engineering for the Development of Therapeutic Antibodies," Molecules and Cells 20(1):17-29, Korean Society for Molecular and Cellular Biology, Korea (Aug. 2005).
Kim, Y.S., et al., "Production of a Monoclonal Anti-myostatin Antibody and the Effects of in Ovo Administration of the Antibody on Posthatch Broiler Growth and Muscle Mass," Poultry Science, 85(6):1062-1071, Elsevier, England (Jun. 2006).
Kim, Y.S., et al., "Production of a Polyclonal Anti-Myostatin Antibody and the Effects of in Ovo Administration of the Antibody on Posthatch Broiler Growth and Muscle Mass," Poultry Science, 86(6):1196-1205, England, Elsevier (Jun. 2007).
King, "Applications and Engineering of Monoclonal Antibodies" Taylor & Francis, ISBN 0-203-21169-3, pp. 1-236 (2005).
King, D., "Antibody Engineering: Design for Specific Applications," Applications and Engineering of Monoclonal Antibodies, 27-75, Chapter 2, (1998).
King, D.J., et al., "Preparation, Structure and Function of Monoclonal Antibodies," Applications and Engineering of Monoclonal Antibodies, London, CRC Press, pp. 2, 13 and 14 (1998).
King, H.D., et al., "Monoclonal Antibody Conjugates of Doxorubicin Prepared With Branched Peptide Linkers: Inhibition of Aggregation by Methoxytriethyleneglycol Chains," Journal of Medicinal Chemistry 45(19):4336-4343, American Chemical Society, United States (Sep. 2002).
Kingsley, D.M., "The TGF-beta Superfamily: New Members, New Receptors, and New Genetic Tests of Function in Different Organisms," Genes & Development, 8(2):133-146, Cold Spring Harbor Laboratory Press, United States (Jan. 1994).
Klimka, A., et al., "Human Anti-CD30 Recombinant Antibodies by Guided Phage Antibody Selection Using Cell Panning," British

(56) References Cited

OTHER PUBLICATIONS

Journal of Cancer 83(2):252-260, Nature Publishing Group on behalf of Cancer Research UK, England (Jul. 2000).
Knappik et al., "Fully Synthetic Human Combinatorial Antibody Libraries (HuCAL) Based on Modular Consensus Frameworks and CDRs Randomized with Trinucleotides," Journal of Molecular Biology, Feb. 11, 2000;296(1):57-86.
Kobayashi et al., "A Monoclonal Antibody Specific for a Distinct Region of Hen Egg-white Lysozyme," Molecular Immunology, 19:619-30 (1982).
Kobayashi, H., et al., "The Pharmacokinetic Characteristics of Glycolated Humanized Anti-tac Fabs Are Determined by Their Isoelectric Points," Cancer Research, 59(2):422-430, American Association for Cancer Research, United States (Jan. 15, 1999).
Kohler, G. and Milstein, C., "Continuous Cultures of Fused Cells Secreting Antibody of Predefined Specificity," Nature 256(5517):495-497, Nature Publishing Group, England (Aug. 1975).
Kohrt, H., et al., "Stimulation of Natural Killer Cells With a CD137-specific Antibody Enhances Trastuzumab Efficacy in Xenotransplant Models of Breast Cancer," The Journal of Clinical Investigation, 122(3):1066-1075, American Society for Clinical Investigation, United States (Mar. 2012).
Komissarov, A.A., et al., "Site-Specific Mutagenesis of a Recombinant Anti-single-stranded DNA Fab. Role of Heavy Chain Complementarity-determining Region 3 Residues in Antigen Interaction," The Journal of Biological Chemistry, 272(43):26864-26870, American Society for Biochemistry and Molecular Biology, United States (Oct. 24, 1997).
Kono, H., et al., "FcgammaRIIB iie232Thr Transmembrane Polymorphism Associated With Human Systemic Lupus Erythematosus Decreases Affinity to Lipid Rafts and Attenuates Inhibitory Effects on B Cell Receptor Signaling," Human Molecular genetics 14(19):2881-2892, IRL Press at Oxford University Press, England (Oct. 2005).
Kostelny, S.A., et al., "Formation of a Bispecific Antibody by the Use of Leucine Zippers," Journal of Immunology 148(5):1547-1553, American Association of Immunologists, United States (Mar. 1992).
Kozbor, D., "A Human Hybrid Myeloma for Production of Human Monoclonal Antibodies," Journal of Immunology 133(6):3001-3005, American Association of Immunologists, United States (Dec. 1984).
Kramer, W., et al., "The Gapped Duplex Dna Approach to Oligonucleotide-directed Mutation Construction," Nucleic Acids Research 12(24):9441-9456, Oxford University Press, England (Dec. 1984).
Kramer, W., et al., "Oligonucleotide-directed construction of mutations via gapped duplex DNA," Methods in Enzymology, 154:350-367, Academic Press, United States (1987).
Kranz, D.M., et al., "Mechanisms of Ligand Binding by Monoclonal Anti-fluorescyl Antibodies," The Journal of Biological Chemistry, 257(12):6987-6995, American Society for Biochemistry and Molecular Biology, United States (Jun. 1982).
Kratz, F., et al., "Prodrugs of Anthracyclines in Cancer Chemotherapy," Current Medicinal Chemistry, 13(5):477-523, Bentham Science Publishers, United Arab Emirates (2006).
Kunkel, T.A., "Rapid and Efficient Site-specific Mutagenesis Without Phenotypic Selection," Proceedings of the National Academy of Sciences of the United States of America 82(2):488-492, National Academy of Sciences, United States (Jan. 1985).
Kuroda, D., et al., "Computer-Aided Antibody Design," Protein Engineering, Design & Selection 25:507-521, Oxford University Press, England (Oct. 2012).
Kussie, P., et al., "A Single Engineered Amino Acid Substitution Changes Antibody Fine Specificity," Journal of Immunology, 152(1):146-152, American Association of Immunologists, United States (Jan. 1994).
Kyogoku, C., et al., "Fcgamma Receptor Gene Polymorphisms in Japanese Patients With Systemic Lupus Erythematosus: Contribution of Fcgr2b to Genetic Susceptibility," Arthritis and Rheumatism 46(5):1242-1254, Wiley-Blackwell, United States (May 2002).
Laitinen et al., "Brave New (Strept) Avidins in Biotechnology," Trends Biotechnol., Jun. 2007;25(6):269-77. Epub Apr. 12, 2007.
Lazar, G.A., et al., "Engineered Antibody Fc Variants With Enhanced Effector Function," Proceedings of the National Academy of Sciences of the United States of America, 103(11):4005-4010, National Academy of Sciences, United States (Mar. 2006).
Lazar, E., et al., "Transforming Growth Factor α: Mutation of Aspartic Acid 47 and Leucine 48 Results in Different Biological Activities," Mol Cell Biol., 8(3):1247-1252 (1988).
Lee, C.V., et al., "High-Affinity Human Antibodies From Phage-displayed Synthetic Fab Libraries With a Single Framework Scaffold," Journal of Molecular biology 340(5):1073-1093, Elsevier, England (Jul. 2004).
Lee, S.J., "Genetic Analysis of the Role of Proteolysis in the Activation of Latent Myostatin," PLOS One, 3(2):e1628, San Francisco, Public Library of Science (Feb. 2008).
Lee, S.J., and Mcpherron, A.C., "Regulation of Myostatin Activity and Muscle Growth," Proceedings of the National Academy of Sciences of the United States of America, 98(16):9306-9311, United States, National Academy of Sciences (Jul. 2001).
Lee, V., et al., "Bivalent Antibody Phage Display Mimics Natural Immunoglobulin," Journal of Immunological Methods, 284(1-2):119-132, Netherlands, Elsevier (Jan. 2004).
Leong, S.R., et al., "Adapting Pharmacokinetic Properties of a Humanized Anti-interleukin-8 Antibody for Therapeutic Applications Using Site-specific Pegylation," Cytokine, 16(3):106-119, Elsevier Science Ltd, England (Nov. 7, 2001).
Li, B., et al., "Construction and Characterization of a Humanized Anti-human Cd3 Monoclonal Antibody 12f6 With Effective Immunoregulation Functions," Immunology 116(4):487-498, Blackwell Scientific Publications, England (Dec. 2005).
LI., et al., "CD72 Down-modulates BCR-induced Signal Transduction and Diminishes Survival in Primary Mature B Lymphocytes," Journal of Immunology (Baltimore, Md. : 1950), 176(9):5321-5328, United States, American Association of Immunologists (May 2006).
Li, F. and Ravetch, J.V., "Apoptotic and Antitumor Activity of Death Receptor Antibodies Require Inhibitory Fcγ Receptor Engagement," Proceedings of the National Academy of Sciences of the United States of America 109(27):10966-10971, National Academy of Sciences, United States (Jul. 2012).
Li, F., et al., "Inhibitory Fcγ Receptor Engagement Drives Adjuvant and Anti-Tumor Activities of Agonistic CD40 Antibodies," Science, 333(6045):1030-1034, United States, American Association for the Advancement of Science (Aug. 2011).
Li, H., et al., "Optimization of Humanized IgGs in Glycoengineered Pichia Pastoris," Nature Biotechnology 24(2):210-215, Nature America Publishing, United States (Feb. 2006).
Li, J., et al., "Human Antibodies for Immunotherapy Development Generated via a Human B Cell Hybridoma Technology," Proceedings of the National Academy of Sciences of the United States of America 103(10):3557-3562, National Academy of Sciences, United States (Feb.-Mar. 2006).
Li, X., et al., "A Novel Polymorphism in the Fcgamma Receptor IIB (CD32B) Transmembrane Region Alters Receptor Signaling," Arthritis and Rheumatism 48(11):3242-3252, Wiley-Blackwell, United States (Nov. 2003).
Lin, Y.S., et al., "Preclinical Pharmacokinetics, Interspecies Scaling, and Tissue Distribution of a Humanized Monoclonal Antibody Against Vascular Endothelial Growth Factor," The Journal of Pharmacology and Experimental Therapeutics, 288(1):371-378, Williams & Wilkins, United States (Jan. 1999).
Linder, M., et al., "Design of a pH-dependent Cellulose-Binding Domain," FEBS Letters, 447(1):13-16, Wiley Publishing Company, England (Mar. 1999).
Liu, H., et al., "Heterogeneity of Monoclonal Antibodies," Journal of Pharmaceutical Sciences, 97(7):2426-2447, Elsevier, United States (Jul. 2008).
Lloyd, C., et al., "Modelling the Human Immune Response: Performance of a 1011 Human Antibody Repertoire Against a Broad Panel of Therapeutically Relevant Antigens," Protein Engineering, Design & Selection 22(3) :159-168, Oxford University Press, England (Mar. 2009).

(56) References Cited

OTHER PUBLICATIONS

Lobo, E.D., et al., "Antibody Pharmacokinetics and Pharmacodynamics," Journal of Pharmaceutical Sciences, 93(11):2645-2668, Elsevier, United States (Nov. 2004).
Lode, H.N., et al., "Targeted Therapy with a Novel Enediyene Antibiotic Calicheamicin Theta(I)1 Effectively Suppresses Growth and Dissemination of Liver Metastases in a Syngeneic Model of Murine Neuroblastoma," Cancer Research 58(14):2925-2928, American Association for Cancer Research, Chicago (Jul. 1998).
Lonberg, N., "Fully Human Antibodies From Transgenic Mouse and Phage Display Platforms," Current Opinion in Immunology 20(4):450-459, Elsevier, England (Aug. 2008).
Lonberg, N., "Human Antibodies From Transgenic Animals," Nature Biotechnology 23(9):1117-1125, Nature America Publishing, United States (Sep. 2005).
Lund, J., et al., "Multiple Binding Sites on the CH2 Domain of IgG for Mouse Fc Gamma R11," Molecular Immunology, 29(1):53-59, England, Pergamon Press (Jan. 1992).
Maccallum, R.M., et al., "Antibody-antigen Interactions: Contact Analysis and Binding Site Topography," Journal of Molecular Biology 262(5):732-745, Academic Press, England (Oct. 1996).
Mackay, M., et al., "Selective Dysregulation of the FcgammaIIB Receptor on Memory B Cells in SLE," The Journal of Experimental Medicine, 203(9):2157-2164, New York, Rockefeller University Press (Sep. 2006).
Maeda, K., et al., "pH-Dependent Receptor/Ligand Dissociation as a Determining Factor for Intracellular Sorting of Ligands for Epidermal Growth Factor Receptors in Rat Hepatocytes," Journal of Controlled Release, 82(1):71-82, Elsevier Science Publishers, Netherlands (Jul. 2002).
Maier, J.K.X. and Labute, P., "Assessment of Fully Automated Antibody Homology Modeling Protocols in Molecular Operating Environment," Proteins 82(8):1599-1610, Wiley-Liss, United States (Aug. 2014).
Maini, R.N., et al., "Double-blind Randomized Controlled Clinical Trial of the Interleukin-6 Receptor Antagonist, Tocilizumab, in European Patients With Rheumatoid Arthritis Who Had an Incomplete Response to Methotrexate," Arthritis and Rheumatism, 54(9):2817-2829, Wiley- Blackwell, United States (Sep. 2006).
Malbec, O., et al., "Antibodies against growth factor receptors can inhibit the proliferation of transformed cells via a cis-interaction with inhibitory FcR," Immunology Letters, 143(1):28-33, Elsevier (Mar. 2012).
Manger, K., et al., "Fcgamma Receptor IIa Polymorphism in Caucasian Patients With Systemic Lupus Erythematosus Association With Clinical Symptoms," Arthritis and Rheumatism, 41(7):1181-1189, United States, Wiley-Blackwell (Jul. 1998).
Marks, J.D., et al., "Selection of Human Antibodies From Phage Display Libraries," Methods in Molecular Biology, 248:161-176, United States, Humana Press (2004).
Marks, J.D., et al., "By-Passing Immunization. Human Antibodies From V-Gene Libraries Displayed on Phage," Journal of Molecular biology 222(3):581-597, Elsevier, England (Dec. 1991).
Mariuzza, R. A., et al., "The Structural Basis of Antigen-Antibody Recognition," Ann Rev Biophys Biophys Chem., 16:139-159 (1987).
Marshall, S.A, et al., "Rational Design and Engineering of Therapeutic Proteins," Drug Discovery Today, 8(5):212-221, Distributed by Virgin Mailing and Distribution, c1996-, England (Mar. 1, 2003).
Martin, W.L., et al., "Crystal Structure at 2.8 a of an Forn/heterodimeric Fc Complex: Mechanism of Ph-dependent Binding," Molecular Cell, 7(4):867-877, Cell Press, United States (Apr. 2001).
Mather, J.P., "Establishment and Characterization of Two Distinct Mouse Testicular Epithelial Cell Lines," Biology of Reproduction 23(1):243-252, Oxford University Press, United States (Aug. 1980).
Mather, J.P., et al., "Culture of testicular cells in hormone-supplemented serum-free medium," Annals of the New York Academy of Sciences, 383:44-68, New York Academy of Sciences, United States (1982).
Matsumiya, S., et al., "Structural Comparison of Fucosylated and Nonfucosylated Fc Fragments of Human Immunoglobulin G1," Journal of Molecular Biology, 368(3):767-779, Amsterdam, Elsevier (May 2007).
Maurer, P., et al., "Antigenicity of Polypeptides (Poly Alpha Amino Acids): Calcium-dependent and Independent Antibodies," Journal of Immunology, 105(3):567-573, American Association of Immunologists, United States (Sep. 1970).
Maxfield, F.R. and McGraw, T.E., "Endocytic Recycling," Nature Reviews Molecular Cell Biology 5(2):121-132, Nature Pub. Group, England (Feb. 2004).
Maxwell, K.F., et al., "Crystal Structure of the Human Leukocyte Fc Receptor, Fc gammaRlla," Nature Structural Biology, 6(5):437-442, Nature Pub. Co., United States (May 1999).
McCafferty, J., et al., "Phage Antibodies: Filamentous Phage Displaying Antibody Variable Domains," Nature 348(6301):552-554, Nature Publishing Group, England ( Dec. 1990).
Mccroskery., et al., "Improved Muscle Healing Through Enhanced Regeneration and Reduced Fibrosis in Myostatin-Null Mice," Journal of Cell Science, 118(Pt 15):3531-3541, England, Company of Biologists (Aug. 2005).
Mcpherron, A.C., et al., "Double Muscling in Cattle Due to Mutations in the Myostatin Gene," Proceedings of the National Academy of Sciences of the United States of America, 94(23):12457-12461, National Academy of Sciences, United States (Nov. 1997).
Mcpherron, C., et al., "Regulation of Skeletal Muscle Mass in Mice by a New TGF-Beta Superfamily Member," Nature, 387(6628):83-90, England, Nature Publishing Group (May 1997).
Mellman, I., "The Importance of Being Acid: The Role of Acidification in Intracellular Membrane Traffic," The Journal of Experimental Biology 172:39-45, Company Of Biologists Limited, England (Nov. 1992).
Mendez-Fernandez, Y. V., et al., "The inhibitory FcyRIIb modulates the inflammatory response and influences atherosclerosis in male apoE-/- mice," Atherosclerosis, 214(1):73-80 (2011).
Merchant, A.M., et al., "An Efficient Route to Human Bispecific IgG," Nature Biotechnology, 16(7):677-681, Nature America Publishing, United States (Jul. 1998).
Certificate of Analysis, Meridian Life Science Inc., "Rabbit Antibody to Human pro-Myostatin (amino acids 79-92)", Nov. 13, 2015 (Nov. 13, 2015), XP055478289, Retrieved from the Internet: URL:https://meridianlifescience.com/biospecs.com/K24340R.pdf [retrieved on May 24, 2018].
Meyer, T., et al., "Bevacizumab immune complexes activate platelets and induce thrombosis in FCGR2A transgenic mice," Journal of Thrombosis and Haemostasis, 7(1):171-181, Blackwell Pub, England (Jan. 2009).
Mi, W., et al., "Targeting the Neonatal Fc Receptor for Antigen Delivery Using Engineered Fc Fragments," Journal of Immunology, 181(11): 7550-7561, United States, American Association of Immunologists (Dec. 2008).
Milstein, C. and Cuello, A.C., "Hybrid Hybridomas and Their Use In Immunohistochemistry," Nature 305:537-540, Nature Publishing Group, England ( Oct. 1983).
Mimoto, F., et al., "Engineered Antibody Fc Variant With Selectively Enhanced FcyRllb Binding Over Both FcγRIIa(R131) and FcγRIIa(H131)," Protein Engineering, Design & Selection, 26(10):589-598, England, Oxford University Press, c2003- (Oct. 2013).
Mohan, et al., Calbiochem Buffers, "A guide for the preparation and use of buffers in biological systems," by chandra Mohan, Ph.D., Copyright 2003 EMD Biosciences, Inc., an Affliate of Merck K GaA, Darmastadt, Germany ,37pages (Calbiochem Buffers Booklet, 2003).
Montero-Julian et al., "Pharmacokinetic Study of Anti-interleukin-6 (II-6) Therapy With Monoclonal Antibodies: Enhancement Ofil-6 Clearance by Cocktails of Anti-il-6 Antibodies," Blood, Feb. 15, 1995;85(4):917-24.
Moore, G.L., et al., "Engineered Fc Variant Antibodies With Enhanced Ability to Recruit Complement and Mediate Effector Functions," mAbs 2(2):181-189, Taylor & Francis, United States (Mar.-Apr. 2010).
Morgan, A., et al., "The N-Terminal End of the CH2 Domain of Chimeric Human IgG1 Anti-HLA-DR is Necessary for C1q, Fc

(56) References Cited

OTHER PUBLICATIONS

Gamma RI and Fc Gamma RIII Binding," Immunology, 86(2):319-324, England, Blackwell Scientific Publications (Oct. 1995).
Morrison, S.L., et al., "Chimeric Human Antibody Molecules: Mouse Antigen-binding Domains With Human Constant Region Domains," Proceedings of the National Academy of Sciences of the United States of America 81(21):6851-6855, National Academy of Sciences, United States (Nov. 1984).
Mouse GDF-8/Myostatin Propeptide Antibody, R&D Catalogue AF 1539,Feb. 6, 2018 (Feb. 6, 2018), XP055478493, Retrieved from the Internet: URL:https://resources.rndsystems.com/pdfs/datasheets/af1539.pdf [retrieved on May 25, 2018].
Muller, Y.A., et al., "VEGF and the Fab Fragment of a Humanized Neutralizing Antibody: Crystal Structure of the Complex at 2.4 a Resolution and Mutational Analysis of the Interface," Structure, 6(9):1153-1167, Cell Press, United States (Sep. 1998).
Munson, P.J. and Rodbard, D. , "Ligand: a Versatile Computerized Approach for Characterization of Ligand-binding Systems," Analytical Biochemistry 107(1):220-239, Elsevier, United States (Sep. 1980).
Muramatsu, H., "P.129Latent Myostatin Specific Elimination by Sweeping Antibody® is a Novel Therapeutic Approach to Improve Muscle Strength," Neuromuscular Disorders, 29(1):S86, Elsevier Inc (Oct. 2019).
Murata, V.M., et al., "Anti-digoxin Fab Variants Generated by Phage Display," Molecular Biotechnology, 54(2):269-277, Humana Press, c1994-, United States (Jun. 2013).
Muta, et al., "A 13-Amino-Acid Motif in the Cytoplasmic Domain of Fc Gamma RIIB Modulates B-cell Receptor Signalling," Nature, 368(6466):70-73, England, Nature Publishing Group (Mar. 1994).
Nagy, A., et al., "Stability of Cytotoxic Luteinizing Hormone-releasing Hormone Conjugate (an-152) Containing Doxorubicin 14-0-hemiglutarate in Mouse and Human Serum in Vitro: Implications for the Design of Preclinical Studies," Proceedings of the National Academy of Sciences of the United States of America, 97(2):829-834, National Academy of Sciences, United States (Jan. 2000).
Nakamura, A., et al., "Fcgamma Receptor IIB-deficient Mice Develop Goodpasture's Syndrome Upon Immunization With Type IV Collagen: a Novel Murine Model for Autoimmune Glomerular Basement Membrane Disease," The Journal of Experimental Medicine, 191(5):899-906, United States, Rockefeller University Press (Mar. 2000).
Narhi, L,O., et al., "Effect of Three Elution Buffers on the Recovery and Structure of Monoclonal Antibodies," Analytical Biochemistry 253(2):236-245, Elsevier, United States (Nov. 1997).
Nesterova et al., "Glypican-3 as a Novel Target for an Antibody-Drug Conjugate," American Association for Cancer Research Abstract No. 656, Los Angeles, CA (Apr. 4-18, 2007).
Nicholas, R., et al., "Regulation of the immune response. I. Reduction in ability of specific antibody to inhibit long-lasting IgG immunological priming after removal of the Fc fragment," Journal of Experimental Medicine, 129(6):1183-1201, Rockefeller University Press, United States (Jun. 1969).
Nimmerjahn, F and Ravetch, J.V., "Fcgamma Receptors as Regulators of Immune Responses," Nature Reviews. Immunology 8(1):34-47, Nature Publishing Group, England (Jan. 2008).
Nimmerjahn, F., et al., "Divergent Immunoglobulin G Subclass Activity Through Selective Fc Receptor Binding," Science, 310(5753):1510-1512, United States, American Association for the Advancement of Science (Dec. 2005).
Nishimoto, N., et al., "Humanized Anti-interleukin-6 Receptor Antibody Treatment of Multicentric Castleman Disease," Blood, 106(8):2627-2632, American Society of Hematology, United States (Oct. 15, 2005).
Nishimoto, N., et al., "Interleukin 6: From Bench to Bedside," Nature Clinical Practice. Rheumatology, 2(11):619-626., Nature Pub. Group, c2005-, United States (Nov. 2006).
Nordlund, H.R., et al., "Introduction of Histidine Residues Into Avidin Subunit Interfaces Allows Ph-dependent Regulation of Quaternary Structure and Biotin Binding," FEBS Letters, 555(3):449-454, John Wiley & Sons Limited, England (Dec. 2003).
Ober, R.J., et al., "Visualizing the Site and Dynamics of IgG Salvage by the MHC Class I-related Receptor, FcRn," Journal of Immunology 172(4):2021-2029, American Association of Immunologists, United States (Feb. 2004).
Ohno et al., "Antigen-Binding Specificities of Antibodies Are Primarily Determined by Seven Residues of VH," Proceedings of the National Academy of Sciences U.S.A., 82(9):2945-9 (May 1985).
Okazaki, A., et al., "Fucose Depletion From Human IgG1 Oligosaccharide Enhances Binding Enthalpy and Association Rate Between IgG1 and FcgammaRIIIa," Journal of Molecular Biology 336(5):1239-1249, Elsevier, England (Mar. 2004).
Olferiev, M., et al., "The Role of Activating Protein 1 in the Transcriptional Regulation of the Human FCGR2B Promoter Mediated by the -343 G-C Polymorphism Associated With Systemic Lupus Erythematosus," The Journal of Biological Chemistry, 282(3):1738-1746, United States, American Society for Biochemistry and Molecular Biology (Jan. 2007).
Onda, M., et al., "Lowering the Isoelectric Point of the Fv Portion of Recombinant Immunotoxins Leads to Decreased Nonspecific Animal Toxicity Without Affecting Antitumor Activity," Cancer Research, 61(13):5070-5077, American Association for Cancer Research, United States (Jul. 2001).
Ono, K., et al., "The Humanized Anti-hm1.24 Antibody Effectively Kills Multiple Myeloma Cells by Human Effector Cell-mediated Cytotoxicity," Molecular Immunology, 36(6):387-395, Pergamon Press, England (Apr. 1999).
Ory, P.A., et al., "Sequences of Complementary DNAs That Encode the NA1 and NA2 Forms of Fc Receptor III on Human Neutrophils," Journal of Clinical Investigation 84(5):1688-1691, American Society for Clinical Investigation, United States (Nov. 1989).
Osbourn, J., et al., "From rodent reagents to human therapeutics using antibody guided selection," Methods, 36(1):61-68, Academic Press, United States (May 2005).
Osbourn, J.K., et al., "Generation of a Panel of Related Human scFv Antibodies With High Affinities for Human CEA," Immunotechnology, 2(3):181-96, Elsevier, Netherlands (Sep. 1996).
Ozhegov et al., "Tolkovyi Slovar Russkogo iazyka," p. 292 (2004)(with English translation of the relevant passage defining "control").
Pace, C.N., et al., "How to Measure and Predict the Molar Absorption Coefficient of a Protein," Protein Science 4(11):2411-2423, Cold Spring Harbor Laboratory Press, United States (Nov. 1995).
Padlan, E.A., "A Possible Procedure for Reducing the Immunogenicity of Antibody Variable Domains While Preserving Their Ligand-Binding Properties," Molecular Immunology 28(4-5):489-498, Pergamon Press, England (Apr.-May 1991).
Pakula, A.A., et al., "Genetic Analysis of Protein Stability and Function," Annual Review of Genetics, 23:289-310, Annual Reviews, United States (1989).
Palladino et al., "Anti-TNF-Alpha Therapies: the Next Generation," Nature Reviews Drug Discovery, Sep. 2003;2(9):736-746.
Pancook, J.D., et al., "In Vitro Affinity Maturation of Human IgM Antibodies Reactive with Tumor-Associated Antigens," Hybridoma and Hybridomics, 20(5-6):383-396, Mary Ann Liebert, United States (2001).
Pardridge, W.M., et al., "Enhanced Cellular Uptake and in Vivo Biodistribution of a Monoclonal Antibody Following Cationization," Journal of Pharmaceutical Sciences, 84(8):943-948, Elsevier, United States (Aug. 1995).
Pardridge, W.M., et al., "Enhanced Endocytosis in Cultured Human Breast Carcinoma Cells and in Vivo Biodistribution in Rats of a Humanized Monoclonal Antibody After Cationization of the Protein," The Journal of Pharmacology and Experimental Therapeutics, 286(1):548-554, American Society for Pharmacology and Experimental Therapeutics, United States (Jul. 1998).
Patel, T.V., et al., "A Forgotten Cause of Kidney Injury in Chronic Myelomonocytic Leukemia," Am J Kidney Dis, Jul. 2009, 54(1):159-64. doi: 10.1053/j.ajkd.2008.11.013. Epub Jan. 29, 2009.
Patentee submission dated Jul. 16, 2015, submitted on May 6, 2020 in opposition of EP2679681.

(56) References Cited

OTHER PUBLICATIONS

Pavlinkova, G., et al., "Charge-modified Single Chain Antibody Constructs of Monoclonal Antibody CC49: Generation, Characterization, Pharmacokinetics, and Biodistribution Analysis," Nuclear Medicine and Biology, 26(1):27-34, Elsevier, United States (Jan. 1999).
Pavlou, A.K and Belsey, M.J, "The Therapeutic Antibodies Market to 2008," European Journal of Pharmaceutics and Biopharmaceutics, 59(3):389-396, Elsevier Science, Netherlands (Apr. 2005).
Pejchal, R., et al., "A Conformational Switch in Human Immunodeficiency Virus Gp41 Revealed by the Structures of Overlapping Epitopes Recognized by Neutralizing Antibodies," Journal of Virology, 83(17):8451-8462, American Society For Microbiology, United States (Sep. 2009).
Petkova, S.B., et al., "Enhanced Half-life of Genetically Engineered Human IgG1 Antibodies in a Humanized Forn Mouse Model: Potential Application in Humorally Mediated Autoimmune Disease," International Immunology 18(12):1759-1769, Oxford University Press, England (Dec. 2006).
Pirruccello-Straub, M., et al., "Blocking Extracellular Activation of Myostatin as a Strategy for Treating Muscle Wasting," Scientific Reports, 8(1):2292, England, Nature Publishing Group (Feb. 2018).
Plückthun, A., Antibodies from *Escherichia coli*. In: Rosenberg M., Moore G.P. (eds) The Pharmacology of Monoclonal Antibodies. Handbook of Experimental Pharmacology, 113:269-315 (1994).
Poduslo, J.F., and Curran, G.L., "Polyamine Modification Increases the Permeability of Proteins at the Blood-nerve and Blood-brain Barriers," Journal of Neurochemistry, 66(4):1599-1609, Wiley on behalf of the International Society for Neurochemistry, England (Apr. 1996).
Polyclonal human pro-Myostatin (aa 79-92) antibody, Immun Diagnostik Antibodies catalogiue, Jun. 30, 2016 (Jun. 30, 2016), Retrieved from the Internet: URL:https://www.immundiagnostik.com/fileadmin/pdf/AK3004.pdf [retrieved on May 24, 2018].
Pons, J., et al., "Energetic Analysis of an Antigen/antibody Interface: Alanine Scanning Mutagenesis and Double Mutant Cycles on the HyHEL-10/lysozyme Interaction," Protein Science : a Publication of the Protein Society, 8(5):958-968, Cold Spring Harbor Laboratory Press, United States (May 1999).
Poosarla, V.G., et al., "Computational de novo Design of Antibodies binding to a Peptide with High Affinity," Biotechnol Bioeng., 114(6):1331-1342 (2017).
Portolano, S., et al., "Lack of Promiscuity in Autoantigen-specific H and L Chain Combinations as Revealed by Human H and L Chain "Roulette".," Journal of Immunology 150(3):880-887, American Association of Immunologists, United States (Feb. 1993).
Presta, L.G., "Engineering of Therapeutic Antibodies to Minimize Immunogenicity and Optimize Function," Advanced drug delivery Reviews 58(5-6) :640-656, Elsevier Science Publishers, Netherlands (Aug. 2006).
Presta, L.G., et al., "Humanization of an Antibody Directed Against IgE," Journal of Immunology 151(5):2623-2632, American Association of Immunologists, United States (Sep. 1993).
Presta, L.G., et al., "Humanization of an Anti-Vascular Endothelial Growth Factor Monoclonal Antibody for the Therapy of Solid Tumors and Other Disorders," Cancer Research 57(20):4593-4599, American Association for Cancer Research, United States (Oct. 1997).
Product Information Sheet from Sigma-H-Y Medium (1998) and document establishing that it was published in 1998, 4 pages (submitted by the Opponent during EP opposition procedure for EP2708558 and posted by EPO on Jan. 15, 2019).
Promega Protocols and Applications Guide, 1991, 2nd Edition (submitted by the Opponent during EP opposition procedure for EP2708558 and posted by EPO on Jan. 14, 2019), 3 pages.
Queen, C., et al., "A Humanized Antibody That Binds to the Interleukin 2 Receptor," Proceedings of the National Academy of Sciences of the United States of America, 86(24):10029-10033, National Academy of Sciences, United States (Dec. 1989).
Radaev, S., et al., "Recognition of IgG by Fcgamma Receptor. The Role of Fc Glycosylation and the Binding of Peptide Inhibitors," The Journal of Biological Chemistry, 276(19):16478-16483, American Society for Biochemistry and Molecular Biology, United States (May 2001).
Radaev, S., et al., "The Structure of a Human Type lii Fcgamma Receptor in Complex With Fc," The Journal of Biological Chemistry, 276(19):16469-16477, American Society for Biochemistry and Molecular Biology, United States (May 2001).
Rajpal, A., et al., "A General Method for Greatly Improving the Affinity of Antibodies by Using Combinatorial Libraries," Proceedings of the National Academy of Sciences of the United States of America 102(24):8466-8471, National Academy of Sciences, United States (Jun. 2005).
Supplemental material to Raposo, B., et al., "Epitope-specific antibody response is controlled by immunoglobulin VH polymorphisms," J Exp Med 211(3):405-411 (2014).
Raso, V., "Intracellular Targeting Using Bispecific Antibodies," Methods in Molecular Medicine, vol. 25: Drug Targeting: Strategies, Principles, and Applications, 37-50 (2000).
Raso, V., et al., "Antibodies Capable of Releasing Diphtheria Toxin in Response to the Low pH Found in Endosomes," Journal of Biological Chemistry 272:27618-27622 (Oct. 1997).
Raso, V., et al., "Intracellular Targeting with Low pH-Triggered Bispecific Antibodies," The Journal of Biological Chemistry 272(44):27623-27628, American Society for Biochemistry and Molecular Biology, United States (Oct. 1997).
Rathanaswami, P., et al., "Demonstration of an in Vivo Generated Sub-picomolar Affinity Fully Human Monoclonal Antibody to Interleukin-8," Biochemical and Biophysical Research Communications, 334:1004-1013 (2005).
Ravetch, J. V. and Lanier, L.L., et al., "Immune Inhibitory Receptors," Science, 290(5489):84-89, United States, American Association for the Advancement of Science (Oct. 2000).
Ravetch, J.V. and Kinet, J.P., "Fc Receptors," Annual Review of Immunology 9:457-492, (1991).
Reddy, M.P., et al., "Elimination of Fc Receptor-Dependent Effector Functions of a Modified lgG4 Monoclonal Antibody to Human CD4," Journal of Immunology 164:1925-1933, American Association of Immunologists, United States (Feb. 2000).
Reichert, J.M., et al., "Development Trends for Monoclonal Antibody Cancer Therapeutics," Nature Reviews Drug Discovery 6(5):349-356, Nature Pub. Group, England (May 2007).
Reichert, J.M., et al., "Monoclonal Antibody Successes in the Clinic," Nature Biotechnology, 23(9):1073-1078, Nature America Publishing, United States (Sep. 2005).
Reimann, K.A., et al., "A Humanized Form of a CD4-specific Monoclonal Antibody Exhibits Decreased Antigenicity and Prolonged Plasma Half-life in Rhesus Monkeys While Retaining Its Unique Biological and Antiviral Properties," AIDS Research and Human Retroviruses, 13(11):933-943, Mary Ann Liebert, United States (Jul. 20, 1997).
Reverberi, R., et al., "Factors Affecting the Antigen-Antibody reaction," Blood Transfusion 5:227-240, SIMTI servizi, Italy (Nov. 2007).
Rich, R.L. and Myszka D.G., "Grading the Commercial Optical Biosensor Literature-Class of 2008: 'The Mighty Binders'," Journal of Molecular Recognition 23(1):1-64, John Wiley & Sons, England (Jan./Feb. 2010).
Rich, R.L., et al., "A global benchmark study using affinity-based biosensors," Analytical Biochemistry, 386(2):194-216, Elsevier, United States (Mar. 2009).
Richards, J.O., et al., "Optimization of Antibody Binding to FcgammaRlla Enhances Macrophage Phagocytosis of Tumor Cells," Molecular Cancer Therapeutics, 7(8):2517-2527, Philadelphia, American Association for Cancer Research (Aug. 2008).
Riechmann, L., et al., "Reshaping human antibodies for therapy," Nature, 332(6162):323-327, Nature Publishing Group, England (Mar. 1988).
Ripka, J., et al., "Two Chinese Hamster Ovary Glycosylation Mutants Affected in the Conversion of GDP-mannose to GDP-Fucose," Archives of Biochemistry and Biophysics, 249(2):533-545, San Diego, Elsevier (Sep. 1986).

(56) References Cited

OTHER PUBLICATIONS

Rituximab biologic license application approval, dated Nov. 26, 1997 (submitted by the Opponent during EP opposition procedure for EP2708558 and posted by EPO on Jan. 15, 2019), 2 pages.
Rituximab product information, IDEC Pharmaceuticals Corporation, Nov. 1997, (submitted by the Opponent during EP opposition procedure for EP2708558 and posted by EPO on Jan. 15, 2019, 2 pages Japanese Patent office, Tokyo mailed on Jan. 15, 2019, 2 pages.
Rituximab, Wikipedia (https://de.wikipedia.org/wiki /Rituximab), accessed on Oct. 24, 2018, (submitted by the Opponent during EP opposition procedure for EP 2708558 and posted by EPO on Jan. 15, 2019), 7 pages (with English translation).
Robles-Carrillo, L., et al., "Anti-CD40L Immune Complexes Potently Activate Platelets in Vitro and Cause Thrombosis in FCGR2A Transgenic Mice," J. Immunol., 185(3):1577-1583 (2010).
Roche Media Release (retrieved from https://www.roche.com/media/releases/med-cor-2011-01-05.htm.
Roitt, A., et al., Extract from Chapter 6, Immunology (2000), Moscow, Mir, pp. 110-111 and English translation of section bridging pp. 110-111.
Roitt, et al., Immunology 5th edition, pp. 80-81 (1998).
Roitt, et al., Immunology. Moscow, Mir, p. 9 (2000).
Roitt, et al., Immunology. Moscow, Mir, p. 110 (2000).
Roitt, et al., Immunology, Moscow, Mir, 373-374 (2000).
Rojas, J.R., et al., "Formation, Distribution, and Elimination of Infliximab and Anti-Infliximab Immune Complexes in Cynomolgus Monkeys," The Journal of Pharmacology and Experimental Therapeutics 313(2):578-585, American Society for Pharmacology and Experimental Therapeutics, United States (May 2005).
Roopenian, D.C., et al., "FcRn: the Neonatal Fc Receptor Comes of Age," Nature reviews. Immunology, 7(9):715-725, Nature Pub. Group, [c2001-, England (Sep. 2007).
Rosok, M.J., et al., "A Combinatorial Library Strategy for the Rapid Humanization of Anticarcinoma BR96 Fab," The Journal of Biological Chemistry 271(37):22611-22618, American Society for Biochemistry and Molecular Biology, United States (Sep. 1996).
Rothe, A., et al., "Ribosome Display for Improved Biotherapeutic Molecules," Expert Opinion on Biological Therapy, 6(2):177-187, Oxford : Taylor & Francis, England (Feb. 2006).
Rudikoff, S., et al., "Single Amino Acid Substitution Altering Antigen-binding Specificity," Proceedings of the National Academy of Sciences of the United States of America 79(6):1979-1983, National Academy of Sciences, United States (Mar. 1982).
Ryman, J.T., and Meibohm, B., "Pharmacokinetics of Monoclonal Antibodies," CPT: Pharmacometrics & Systems Pharmacology, 6(9):576-588, Wiley, United States (Sep. 2017).
Sada, E., et al., "Effect of Histidine Residues in Antigenic Sites on pH Dependence of Immuno-Adsorption Equilibrium," Applied Microbiology and Biotechnology 27:528-532, Springer (Feb. 1988).
Safdari, Y., et al., "Antibody Humanization Methods—A Review and Update," Biotechnology & Genetic Engineering Reviews, 29(2):175-186, England, Taylor & Francis (2013).
Salfeld, J. G., "Isotype Selection in Antibody Engineering," Nature Biotechnology, 25(12):1369-1372, Nature America Publishing, United States (Dec. 2007).
Salmon, J.E., et al., "Fc Gamma RIIA Alleles are Heritable Risk Factors for Lupus Nephritis in African Americans," The Journal of Clinical Investigation, 97(5):1348-1354, United States, American Society for Clinical Investigation (Mar. 1996).
Sarkar, C.A., et al., "Rational Cytokine Design for Increased Lifetime and Enhanced Potency Using Ph-activated "Histidine Switching"," Nature Biotechnology, 20(9):908-913, Nature America Publishing (Sep. 2002).
Sato, K., et al., "Reshaping a Human Antibody to Inhibit the Interleukin 6-dependent Tumor Cell Growth," Cancer Research, 53(4):851-856, American Association for Cancer Research, United States (Feb. 15, 1993).
Scappaticci, F.A., et al., "Arterial Thromboembolic Events in Patients With Metastatic Carcinoma Treated With Chemotherapy and Bevacizumab," Journal of the National Cancer Institute 99(16):1232-1239, Oxford University Press, United States (Aug. 2007).
Schaeffer, R.C et al., "The Rat Glomerular Filtration Barrier Does Not Show Negative Charge Selectivity," Microcirculation (New York, N.Y. : 1994), 9(5):329-342, Wiley-Blackwell, United States (Oct. 2002).
Schier, et al., "Isolation of Picomolar Affinity Anti-c-erbB-2 Single-chain Fv by Molecular Evolution of the Complementarity Determining Regions in the Center of the Antibody Binding Site," Journal of Molecular Biology 263:551-567, Elsevier, England (Nov. 1996).
Schlothauer, T., et al., "Novel Human IgG1 and IgG4 Fc-engineered Antibodies With Completely Abolished Immune Effector Functions," Protein Engineering, Design & Selection: PEDS, 29(10):457-466, Oxford University Press, England (Oct. 2016).
Schmitz, U., et al., "Phage Display: a Molecular Tool for the Generation of Antibodies—a Review," Placenta, 21:106-112, Elsevier, Netherlands (Mar.-Apr. 2000).
Schrama., et al., "Antibody Targeted Drugs as Cancer Therapeutics," Nature Reviews Drug Discovery, 5(2):147-159, England, Nature Pub. Group, [2002—(Feb. 2006).
Schroeder, H.W., "Similarity and Divergence in the Development and Expression of the Mouse and Human Antibody Repertoires," Developmental and Comparative Immunology 30(1-2):119-135, Elsevier Science, United States (Jan. 2006).
Sequence alignments and modification scheme (Document filed during Oral Proceedings in EPO opposition for EP2006381 and mentioned in minutes of the Oral Proceedings) posted by EPO on Jul. 25, 2018, 3 pages.
Shadduck, R.K., et al., "Fractionation of Antibodies to L-cell Colony-Stimulating Factor by Affinity Chromatography," Blood 53(6):1182-1190, American Society of Hematology, United States (Jun. 1979).
Sharifi, J., et al., "Improving Monoclonal Antibody Pharmacokinetics via Chemical Modification," The Quarterly Journal of Nuclear Medicine : Official Publication of the Italian Association of Nuclear Medicine (AIMN) [and] the International Association of Radiopharmacology (IAR), 42(4):242-249, Minerva Medica, c1995-c2003, Italy (Dec. 1998).
Shields, R. L., et al., "High Resolution Mapping of the Binding Site on Human IgG1 for Fc Gamma RI, Fc Gamma RIII, Fc Gamma RIII, and FcRn and Design of Igg1 Variants With Improved Binding to the Fc Gamma R," The Journal of Biological Chemistry, 276(9):6591-6604, American Society for Biochemistry and Molecular Biology, United States (Mar. 2001).
Shinkawa, T., et al., "The Absence of Fucose but Not the Presence of Galactose or Bisecting N-acetylglucosamine of Human IgG1 Complex-type Oligosaccharides Shows the Critical Role of Enhancing Antibody-dependent Cellular Cytotoxicity," The Journal of Biological Chemistry 278(5):3466-3473, American Society for Biochemistry and Molecular Biology, United States (Jan. 2003).
Shire, S.J., et al., "Challenges in the Development of High Protein Concentration Formulations," Journal of Pharmaceutical Sciences 93(6):1390-1402, American Pharmaceutical Assn, United States (Jun. 2004).
Siberil, et al., "Molecular Aspects of Human FcgammaR Interactions With IgG Functional and Therapeutic Consequences," Immunology Letters, 106(2):106(2), Netherlands, Elsevier/North-Holland Biomedical Press (Aug. 2006).
Sidhu, S.S., et al., "Phage-Displayed Antibody Libraries of Synthetic Heavy Chain Complementarity Determining Regions," Journal of Molecular biology 338(2):299-310, Elsevier, England (Apr. 2004).
Singer, M., and Berg, P., "Genes & Genomes," Structure of Proteins, 67-69, University Science Books, United States (1991).
Singer, et al., "Genes & Genomes," Moscow, Mir, 115-188 (1998).
Smith, K., et al., "FcgammaRIIB in Autoimmunity and Infection: Evolutionary and Therapeutic Implications," Nature Reviews. Immunology, 10(5):328-343, Nature Pub. Group, England (May 2010).
Sondermann, P., et al., "Crystal Structure of the Soluble Form of the Human Fcgamma-receptor IIb: a New Member of the Immunoglobulin Superfamily at 1.7 a Resolution," The EMBO Journal, 18(5):1095-1103, Wiley Blackwell, England (Mar. 1999).

(56) References Cited

OTHER PUBLICATIONS

Sondermann, P., et al., "Molecular basis for immune complex recognition: a comparison of Fc-receptor structures," Journal of Molecular Biology, 309(3):737-749, Elsevier, England (Jun. 2001).
Sondermann, P., et al., "The 3.2-A crystal structure of the human IgG1 Fc fragment-Fc gammaRIII complex," Nature, 406(6793):267-273, Nature Publishing Group, England (Jul. 2000).
Stearns, D.J., et al., "The Interaction of a Ca2+-Dependent Monoclonal Antibody with the Protein C Activation Peptide Region. Evidence for Obligatory Ca2+ Binding to Both Antigen and Antibody," Journal of Biological Chemistry 263:826-832, American Society for Biochemistry and Molecular Biology, United States (Jan. 1988).
Stepanov, V.M., Molecular Biology. Structure and Functions of Proteins. Moscow, Science, 61-62 (2005).
Stewart, J.D., et al., "Site-directed Mutagenesis of a Catalytic Antibody: an Arginine and a Histidine Residue Play Key Roles," Biochemistry 33:1994-2003, American Chemical Society, United States (Mar. 1994).
Story, C.M., et al., "A Major Histocompatibility Complex Class I-like Fc Receptor Cloned From Human Placenta: Possible Role in Transfer of Immunoglobulin G From Mother to Fetus," Journal of Experimental Medicine 180(6):2377-2381, Rockefeller University Press, United States (Dec. 1994).
Strand, V., et al., "Biologic Therapies in Rheumatology: Lessons Learned, Future Directions," Nature Reviews. Drug discovery 6(1):75-92, Nature Pub. Group, England (Jan. 2007).
Strausberg, R. L., et al., "Generation and Initial Analysis of More Than 15,000 Full-length Human and Mouse cDNA Sequences," Proceedings of the National Academy of Sciences of the United States of America 99(26):16899-16903 (2002).
Su, K., et al., "Expression Profile of FcgammaRIIb on Leukocytes and Its Dysregulation in Systemic Lupus Erythematosus," Journal of Immunology, 178(5):3272-3280, United States, American Association of Immunologists (Mar. 2007).
Summary of information about antibodies in Examples of patent EP2006381 (document submitted in EP opposition and posted by EPO on Apr. 13, 2018).
Suzuki, T., et al., "Importance of Neonatal For in Regulating the Serum Half-life of Therapeutic Proteins Containing the Fc Domain of Human Igg1: a Comparative Study of the Affinity of Monoclonal Antibodies and Fc-fusion Proteins to Human Neonatal For," Journal of Immunology, 184(4):1968-1976, American Association of Immunologists, United States (Feb. 2010).
Szlama, et al., "Latent Myostatin Has Significant Activity and This Activity is Controlled More Efficiently by Wfikkn1 Than by Wfikkn2," The FEBS Journal, 280(16):3822-3839, England, Published by Blackwell Pub. On Behalf of the Federation of European Biochemical Societies, C2005—(Aug. 2013).
Tabrizi, M.A., et al., "Elimination Mechanisms of Therapeutic Monoclonal Antibodies," Drug Discovery Today, 11(1-2):81-88, Distributed by Virgin Mailing and Distribution, c1996-, England (Jan. 2006).
Tackenberg, B., et al., "Impaired inhibitory Fcγ receptor IIB expression on B cells in chronic inflammatory demyelinating polyneuropathy," PNAS, 106(12):4788-4792 (2009).
Tan, G.K., et al., "A Non Mouse-adapted Dengue Virus Strain as a New Model of Severe Dengue Infection in AG129 Mice," PLOS Neglected Tropical Diseases 4(4):e672, Public Library of Science, United States (Apr. 2010).
Tan, P.H., et al., "Engineering the Isoelectric Point of a Renal Cell Carcinoma Targeting Antibody Greatly Enhances ScFv Solubility," Immunotechnology : an International Journal of Immunological Engineering, 4(2):107-114, Elsevier, c1995-, Netherlands (Oct. 1998).
Tarantul, V. Z., Explanatory Biotechnological Dictionary of Russian-English, Languages of Slavic Cultures, Moscow, 72 (2009).
Tarditi, L., et al., "Selective High-performance Liquid Chromatographic Purification of Bispecific Monoclonal Antibodies," Journal of Chromatography, 599(1-2):13-20, Elsevier, Netherlands (May 1992).
Teeling, J.L., et al., "The Biological Activity of Human CD20 Monoclonal Antibodies is Linked to Unique Epitopes on CD20," Journal of Immunology (Baltimore, Md. : 1950), 177(1):362-371, American Association of Immunologists, United States (Jul. 1, 2006).
Ten Kate, C.I., et al., "Effect of Isoelectric Point on Biodistribution and Inflammation: Imaging With Indium-111-labelled IgG," European Journal of Nuclear Medicine, 17(6-8):305-309, Springer Verlag, Germany (1990).
Torgov, M.Y., et al., "Generation of an Intensely Potent Anthracycline by a Monoclonal Antibody-beta-galactosidase Conjugate," Bioconjugate Chemistry 16(3):717-721, American Chemical Society, United States (May 2005).
Torres, M. and Casadevall, A., "The immunoglobulin constant region contributes to affinity and specificity," Trends in Immunol., 29(2):91-97 (2008).
Traunecker, A., et al., "Bispecific Single Chain Molecules (Janusins) Target Cytotoxic Lymphocytes on Hiv Infected Cells," The EMBO Journal 10(12):3655-3659, Wiley Blackwell, England (Dec. 1991).
Tsuchiya, M., "Therapeutic Antibody," Credit Suisse Seminar at Fuji-Gotemba Research Laboratories, p. 21, Shizuoka, Japan (2006) (with English translation).
Tsurushita, N., et al., "Design of Humanized Antibodies: From Anti-tac to Zenapax," Methods (San Diego, Calif.), 36(1):69-83, Academic Press, United States (May 2005).
Tutt, A., et al., "Trispecific F(Ab')3 Derivatives That Use Cooperative Signaling via the TCR/CD3 Complex and CD2 to Activate and Redirect Resting Cytotoxic T Cells," Journal of Immunology 147(1):60-69, American Association of Immunologists, United States (Jul. 1991).
Urlaub, G. and Chasin, L.A., "Isolation of Chinese Hamster Cell Mutants Deficient in Dihydrofolate Reductase Activity," Proceedings of the National Academy of Sciences of the United States of America 77(7):4216-4220, National Academy of Sciences, United States (Jul. 1980).
Vaisitti, T., et al., "Cationization of Monoclonal Antibodies: Another Step Towards the "Magic Bullet"," Journal of Biological Regulators and Homeostatic Agents, 19(3-4):105-112, Biolife, Italy (Jul.-Dec. 2005).
Vajdos, F.F., et al., "Comprehensive Functional Maps of the Antigen-binding Site of an Anti-ErbB2 Antibody Obtained With Shotgun Scanning Mutagenesis," Journal of Molecular Biology, 320(2):415-428, Elsevier, England (Jul. 2002).
Van Assche, G., et al., "Adalimumab in Crohn's disease," Biologics Target and Therapy, 1(4):355-365, Dove Medical Press, New Zealand (Dec. 2007).
Van Den Abbeele, A.D., et al., "Antigen-binding Site Protection During Radiolabeling Leads to a Higher Immunoreactive Fraction," Journal of Nuclear Medicine, 32(1):116-122, Society of Nuclear Medicine, United States (Jan. 1991).
Van Walle, I., et al., "Immunogenicity Screening in Protein Drug Development," Expert Opinion on Biological Therapy, 7(3):405-418, Taylor & Francis, United States (Mar. 2007).
Vaughn, D.E., et al., "Structural Basis of pH-Dependent Antibody Binding by the Neonatal Fc Receptor", Structure 6:63-73, Cell Press, United States (Jan. 1998).
Venturi, M., et al., "The Monoclonal Antibody 1f6 Identifies a pH-dependent Conformational Change in the Hydrophilic NH(2) terminus of NhaA Na(+)/H(+) Antiporter of *Escherichia coli*," The Journal of Biological Chemistry 275(7):4734-4742, American Society for Biochemistry and Molecular Biology, United States (Feb. 2000).
Verhoeyen, et al., "Monoclonal Antibodies in Clinical Oncology," 1991, Edited by AA Epenetos, Chapter 5, pp. 37-43, Chapman and Hall.
Verhoeyen, M.E., et al., "Construction of a Reshaped HMFG1 Antibody and Comparison of Its Fine Specificity With That of the Parent Mouse Antibody," Immunology, 78(3):364-370, Blackwell Scientific Publications, England (Mar. 1993).
Veri, M., et al., "Monoclonal Antibodies Capable of Discriminating the Human Inhibitory Fcgamma-receptor Iib (Cd32b) From the Activating Fcgamma-receptor Iia (Cd32a): Biochemical, Biological

(56) References Cited

OTHER PUBLICATIONS and Functional Characterization," Immunology, 121(3):392-404, Blackwell Scientific Publications, England (Jul. 2007).
Veri, M.C., et al., "Therapeutic control of B cell activation via recruitment of Fcgamma receptor IIb (CD32B) inhibitory function with a novel bispecific antibody scaffold," Arthritis and Rheumatology, 62(7):1933-1943, Wiley-Blackwell, United States (Jul. 2010).
Vincent, K.J., et al., "Current Strategies in Antibody Engineering: Fc Engineering and pH-dependent Antigen Binding, Bispecific Antibodies and Antibody Drug Conjugates," Biotechnol Journal, 7(12):1444-1450, Germany, Wiley-VCH Verlag (Dec. 2012).
Vitetta, E.S., et al., "Redesigning Nature's Poisons to Create Anti-Tumor Reagents," Science, 238(4830):1098-1104, United States, American Association for the Advancement of Science (Nov. 1987).
Vollmers, H.P. & Brandlein, S., "Death by Stress: Natural Igm-induced Apoptosis," Methods and Findings in Experimental and Clinical Pharmacology, 27(3):185-191, Spain, Reuters (Apr. 2005).
Vollmers, H.P. and Brandlein, S., "The "Early Birds": Natural IgM Antibodies and Immune Surveillance," Histology and Histopathology 20(3):927-937, Histology and Histopathology, Spain (Jul. 2005).
Wagner, K.R., et al., "Loss of Myostatin Attenuates Severity of Muscular Dystrophy in mdx Mice," Annals of Neurology, 52(6):832-836, Wiley-Liss, United States (Dec. 2002).
Wang, et al., "Monoclonal Antibodies With Identical Fc Sequences Can Bind to FcRn Differentially With Pharmacokinetic Consequences," Drug Metabolism and Disposition the Biological Fate of Chemicals, 39(9):1469-1477, United States, American Society for Pharmacology and Experimental Therapeutics (Sep. 2011).
Wang, W., "Instability, Stabilization, and Formulation of Liquid Protein Pharmaceuticals," International Journal of Pharmaceutics 185(2):129-188, Elsevier/North-Holland Biomedical Press, Netherlands (Aug. 1999).
Ward, et al., "A Calcium-binding Monoclonal Antibody That Recognizes a Non-calcium-binding Epitope in the Short Consensus Repeat Units (Scrs) of Complement C1r," Molecular Immunology, 29(1):83-93, (Jan. 1992).
Warmerdam, P.A., et al., "Molecular Basis for a Polymorphism of Human Fc Gamma Receptor II (CD32)," Journal of Experimental Medicine 172(1):19-25, Rockefeller University Press, United States (Jul. 1990).
Wenink, H., et al., "The Inhibitory Fc Gamma Iib Receptor Dampens TLR4-mediated Immune Responses and is Selectively Up-regulated on Dendritic Cells From Rheumatoid Arthritis Patients With Quiescent Disease," Journal of Immunology , 183(7):4509-4520, United States, American Association of Immunologists (Oct. 2009).
Wernersson, S., et al., "IgG-mediated Enhancement of Antibody Responses is Low in Fc Receptor Gamma Chain-deficient Mice and Increased in Fc Gamma RII-deficient Mice," Journal of Immunology, 163(2):618-622, American Association of Immunologists, United States (Jul. 1999).
Whittemore, et al., "Inhibition of myostatin in adult mice increases skeletal muscle mass and strength," Biochemical and Biophysical Research Communications, 300(4):965-971, Elsevier, United States (Jan. 2003).
Wiens, G.D., et al., "Mutation of a Single Conserved Residue in VH Complementarity-determining Region 2 Results in a Severe Ig Secretion Defect," Journal of Immunology, 167(4):2179-2186, Williams & Wilkins, United States (Aug. 15, 2001).
Wiens, G.D., et al., "Somatic Mutation in VH Complementarity-determining Region 2 and Framework Region 2: Differential Effects on Antigen Binding and Ig Secretion," Journal of Immunology, 159(3):1293-1302, American Association of Immunologists, United States (Aug. 1, 1997).
Wikipedia, "Chaotropic agent," [online], [retrieved on Nov. 2, 2015]. Retrieved from the Internet: https://en.wikipedia.org/wiki/Chaotropicagent.
Wilson, N.S., et al., "An Fcγ Receptor-Dependent Mechanism Drives Antibody-Mediated Target-Receptor Signaling in Cancer Cells," Cancer Cell, 19(1):101-113, Cambridge, Mass:Cell Press (Jan. 2011).
Winter, G., et al., "Making Antibodies by Phage Display Technology," Annual Review of Immunology 12:433-455, Annual Reviews Inc., United States (1994).
Wojciak, et al., "The Crystal Structure of Sphingosine-1-Phosphate in Complex With a Fab Fragment Reveals Metal Bridging of an Antibody and Its Antigen," Proceedings of the National Academy of Sciences of the United States of America, 106(42):17717-17722-2009.
Wolfman, N., et al., "Activation of Latent Myostatin by the Bmp-1/tolloid Family of Metalloproteinases," Proceedings of the National Academy of Sciences of the United States of America, 100(26):15842-15846, National Academy of Sciences, United States (Dec. 2003).
Wright, A., et al. , "Effect of Glycosylation on Antibody Function: Implications for Genetic Engineering," Trends in Biotechnology 15(1):26-32, Elsevier Science Publishers, England (Jan. 1997).
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu, et al., "Stepwise in Vitro Affinity Maturation Ofvitaxin, an Av-33-specific Humanized Mab," Proceedings of the National Academy of Sciences USA, May 26, 1998; 95(11):6037-6042.
Wu, H., et al., "Development of Motavizumab, an Ultra-potent Antibody for the Prevention of Respiratory Syncytial Virus Infection in the Upper and Lower Respiratory Tract," Journal of Molecular Biology 368:652-665, Elsevier, England (May 2007).
Wu, H., et al., "Humanization of a Murine Monoclonal Antibody by Simultaneous Optimization of Framework and CDR Residues," Journal of Molecular Biology 294(1):151-162, Elsevier, England (Nov. 1999).
Wu, H., et al., "Ultra-potent Antibodies Against Respiratory Syncytial Virus: Effects of Binding Kinetics and Binding Valence on Viral Neutralization," Journal of Molecular Biology, 350(1):126-144, Elsevier, England (Jul. 1, 2005).
Wu, J., et al., "A Novel Polymorphism of Fcgammarilia (CS16) Alters Receptor Function and Predisposes to Autoimmune Disease," Journal of Clinical Investigation 100(5):1059-1070, American Society for Clinical Investigation, United States ( Sep. 1997).
Wu, S.J., et al., "Structure-Based Engineering of a Monoclonal Antibody for Improved Solubility," Protein Engineering 23(8):643-651, Oxford University, England (Aug. 2010).
Xiang, J., et al., "Study of B72.3 Combining Sites by Molecular Modeling and Site-directed Mutagenesis," Protein Engineering, 13(5):339-344 (May 2000).
Xu, Y., et al., "Fc Gamma Rs Modulate Cytotoxicity of anti-Fas Antibodies: Implications for Agonistic Antibody-based Therapeutics," Journal of Immunology, 171(2):562-568, American Association of Immunologists, United States (Jul. 2003).
Yada, et al., Lippincott's Illustrated Reviews: Immunology Second Edition, Nov. 30, 2013, p. 18, 19, 152, 153 (Chapter 2 pp. 11-23, Chapter 11 pp. 149-165) (see Harvey 2013 for English translation).
Yamamoto, et al., "Molecular Studies of PH-dependent Ligand Interactions With the Low-density Lipoprotein Receptor," Biochemistry, 47(44):11647-11652 (Nov. 2008).
Yamane-Ohnuki, N., et al. , "Establishment of FUT8 Knockout Chinese Hamster Ovary Cells: an Ideal Host Cell Line for Producing Completely Defucosylated Antibodies With Enhanced Antibody-dependent Cellular Cytotoxicity," Biotechnology and bioengineering 87(5):614-622, Wiley, United States (Sep. 2004).
Yamasaki, Y., et al., "Pharmacokinetic Analysis of in Vivo Disposition of Succinylated Proteins Targeted to Liver Nonparenchymal Cells via Scavenger Receptors: Importance of Molecular Size and Negative Charge Density for in Vivo Recognition by Receptors," The Journal of Pharmacology and Experimental Therapeutics, 301(2):467-477, American Society for Pharmacology and Experimental Therapeutics, United States (May 2002).

(56) References Cited

OTHER PUBLICATIONS

Yang, K., et al., "Tailoring Structure-function and Pharmacokinetic Properties of Single-chain Fv Proteins by Site-specific PEGylation," Protein Engineering, 16(10):761-770, Oxford University Press, England (Oct. 2003).
Yang, W.P., et al., "CDR Walking Mutagenesis for the Affinity Maturation of a Potent Human Anti-HIV-1 Antibody Into the Picomolar Range," Journal of Molecular Biology, 254(3):392-403, Elsevier, England (Dec. 1995).
Yang, M., et al., "Effect of anti CD20 antibody Fab' fragment on apoptosis of B lymphoma cells and intracellular calcium," Tumor, 26(2):116-119 (2006).
Yarilin, A., "Osnovy Immunologii," M.: Meditsina (Fundamentals of Immunology. M: Medicina) 172-174 (1999).
Yarilin, A. A., Fundamentals of Immunology (Osnovy immunologii), Moscow, Medicina, 171 (1999).
Yazaki, P.J., et al., "Expression of recombinant antibodies in mammalian cell lines," Methods in Molecular Biology, 248:255-268, Humana Press, United States (2004).
Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671, American Association of Immunologists, United States (Jun. 2009).
Ying, J. and Xue, L., "Large Yellow Croaker MSTN-1 Prodomain Prokaryotic Expression, Polyclonal Antibody Preparation and Antibody Function Identification," Chinese Journal of Cell Biology. Oct. 2014;36(10):1344-1349, English abstract.
Yu, X., et al., "Development and Validation of a Cell-Based Fluorescent Method for Measuring Antibody Affinity," Journal of Immunological Methods, 442:49-53, Netherlands, Elsevier (Mar. 2017).
Yuasa, T., et al., "Deletion of Fcgamma Receptor IIB renders H-2(b) Mice Susceptible to Collagen-induced Arthritis," The Journal of Experimental Medicine, 189(1):187-194, Rockefeller University Press, United States (Jan. 1999).
Zalevsky, J., et al., "Enhanced Antibody Half-life Improves in Vivo Activity," Nature Biotechnology 28(2):157-159, Nature America Publishing, United States (Feb. 2010).
Zalevsky, J., et al., "The Impact of Fc Engineering on an Anti-cd19 Antibody: Increased Fcgamma Receptor Affinity Enhances B-cell Clearing in Nonhuman Primates," Blood, 113(16):3735-3743, American Society of Hematology, United States (Apr. 2009).
Zhang, et al., "Immune Complex/Ig Negatively Regulate TLR4-Triggered Inflammatory Response in Macrophages Through Fc Gamma Rllb-Dependent PGE2 Production," Journal of Immunology, 182(1):554-562, United States, American Association of Immunologists (Jan. 2009).
Zhang, et al., "Monoclonal Antibodies as Therapeutic Agents in Oncology and Antibody Gene Therapy," Cell Research, 17(2):89-99, England, Nature Publishing Group (Feb. 2007).
Zhang, M., et al., "Effective Therapy for a Murine Model of Human Anaplastic Large-Cell Lymphoma with the Anti-CD30 Monoclonal Antibody, HeFi-1, Does Not Require Activating Fc Receptors," Blood, 108(2):705-710, United States, American Society of Hematology (Jul. 2006).
Zheng, et al., "Translational Pharmacokinetics and Pharmacodynamics of an Forn-variant Anti-cd4 Monoclonal Antibody From Preclinical Model to Phase I Study," Clinical Pharmacology and Therapeutics 89(2):283-290, Wiley, United States (Feb. 2011).
Zhou, T., et al., "Interfacial Metal and Antibody Recognition," Proceedings of the National Academy of Sciences of the United States of America, 102(41):14575-14580, National Academy of Sciences, United States (Oct. 2005).
Zhu, X., et al., "MHC Class I-Related Neonatal Fc Receptor for IgG Is Functionally Expressed in Monocytes, Intestinal Macrophages, and Dendritic Cells", Journal of Immunology 166:3266-3276, American Association of Immunologists, United States (Mar. 2001).
Zimmers, T.A., et al., "Induction of Cachexia in Mice by Systemically Administered Myostatin," Science, 296 (5572):1486-1488, American Association for the Advancement of Science (May 2002).
Zola, Monoclonal Antibodies: A Manual of Techniques, 147-58, 1987.
Zoller, M.J. and Smith M., "Oligonucleotide-directed mutagenesis of DNA fragments cloned into M13 vectors," Methods in enzymology 100:468-500, Academic Press, United States (1983).
Zuckier, L.S., et al., "Chimeric Human-mouse IgG Antibodies With Shuffled Constant Region Exons Demonstrate That Multiple Domains Contribute to in Vivo Half-life," Cancer Research, 58(17):3905-3908, American Association for Cancer Research, United States (Sep. 1, 1998).
Zust, R., et al., "Type I Interferon Signals in Macrophages and Dendritic Cells Control Dengue Virus Infection: Implications for a New Mouse Model to Test Dengue Vaccines," Journal of Virology 88(13):7276-7285, American Society For Microbiology, United States ( Jul. 2014).
Zwick, M.B., et al., "The Long Third Complementarity-determining Region of the Heavy Chain is Important in the Activity of the Broadly Neutralizing Anti-human Immunodeficiency Virus Type 1 Antibody 2F5," Journal of Virology, 78(6):3155-3161, American Society For Microbiology, United States (Mar. 2004).
Dagbay, K. B., et al., "Structural basis of specific inhibition of extracellular activation of pro- or latent myostatin by the monoclonal antibody SRK-015," J Biol Chem., 295(16):5404-5418 (2020).
Nagaoka, M. and Akaike, T., "Single amino acid substitution in the mouse IgG1 Fc region induces drastic enhancement of the affinity to protein A.," Protein Eng., 16(4):243-245 (2003).
Sikkink, L. A. and Ramirez-Alvarado, M., "Biochemical and aggregation analysis of Bence Jones proteins from different light chain disease," Amyloid, 15(1):29-39 (2008).
U.S. Appl. No. 16/980,611, 371 (c) date Sep. 14, 2020, Fink, et al., related application.
U.S. Appl. No. 18/156,138, filed Jan. 18, 2023, Igawa et al., related application.
U.S. Appl. No. 18/157,320, filed Jan. 20, 2023, Ruike et al., related application.
U.S. Appl. No. 18/181,641, filed Mar. 10, 2023, Shinomiya et al., related application.
Devita, V.T., et al., "Cancer: Principles and Practice of Oncology," J.B. Lippincott Company, 1993.
Mimoto, F., et al., "Fc Engineering to Improve the Function of Therapeutic Antibodies," Curr Pharm Biotechnol., 17:1298-1314 (2016).
Third-Party Submission Under 37 C.F.R. 1.290 submitted Jan. 17, 2019 in U.S. Appl. No. 15/952,951.
Third-Party Submission Under 37 C.F.R. 1.290 submitted Apr. 3, 2019 in U.S. Appl. No. 15/952,951.
WHO Drug Information, 32(2):283, 303, 304, International Nonproprietary Names (2018).
Restriction Requirement dated Mar. 13, 2017 in U.S. Appl. No. 15/015,287, filed Feb. 4, 2016, Igawa et al.

FIG. 31

Size

| Area | | Depth | Size | | | Total score |
|---|---|---|---|---|---|---|
| | | | <3mm | 3-10mm | >10mm | |
| Other peritoneal walls | | Superficial | 1 | 2 | 4 | |
| | | Deep | 2 | 4 | 6 | |
| Ovary | Left | Superficial | 1 | 2 | 4 | |
| | | Deep | 4 | 16 | 20 | |
| | Right | Superficial | 1 | 2 | 4 | |
| | | Deep | 4 | 16 | 20 | |

Adhesion

| Area | | | Unobliterated | Partially obliterated | Obliterated | Total score |
|---|---|---|---|---|---|---|
| Douglas' pouch | | | 0 | 4 | 40 | |
| Vesicouterine pouch | | | 0 | 4 | 40 | |
| Area | | Depth | <1/3 | 1/3-2/3 | >2/3 | |
| Ovary | Left | Film-like | 1 | 2 | 4 | |
| | | Dense | 4 | 8 | 16 | |
| | Right | Film-like | 1 | 2 | 4 | |
| | | Dense | 4 | 8 | 16 | |
| Oviduct | Left | Film-like | 1 | 2 | 4 | |
| | | Dense | 4 | 8 | 16 | |
| | Right | Film-like | 1 | 2 | 4 | |
| | | Dense | 4 | 8 | 16 | |

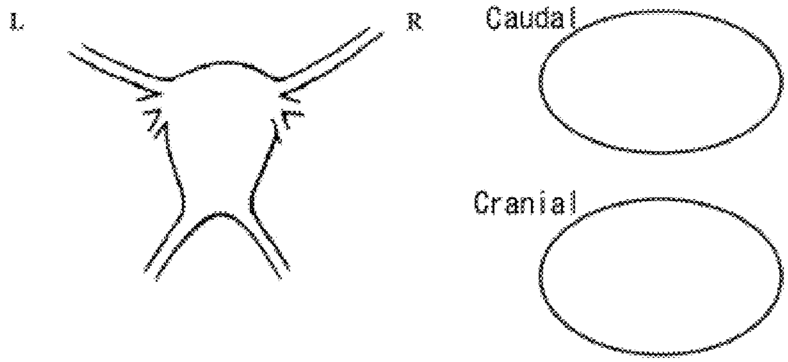

Data sheet of laparoscopic observation

N: Nodular lesion
Dotted line: Cystic adhesion
Solid arrow: Adhesion
Dotted arrow: Superficial lesion (ITL): Initial transplant
(N): Nodule
(PR): Peritoneum
(M): Abdominal wall muscle Vehicle H1009/L395-F1974m 10mg/kg ➢: Ectopic endometriosis lesion, ee: Entopic endometrium, m: Myometriu ➔: Epithelial tissue, sc: Stromal cell area    Bar = 10 $\mu$m

COMPOSITION FOR PROPHYLAXIS OR TREATMENT OF IL-8 RELATED DISEASES

CROSS REFERENCE TO RELATED APPLICATIONS

This application is a divisional of U.S. patent application Ser. No. 17/333,256, filed May 28, 2021, which is a divisional of U.S. patent application Ser. No. 16/323,142, § 371 date Feb. 4, 2019, now U.S. Pat. No. 11,053,308 B2, issue date Jul. 6, 2021, which is a U.S. National Phase of PCT Application No. PCT/JP2017/028346, filed Aug. 4, 2017, which claims priority to Japanese Patent Application No. 2016-154174, filed Aug. 5, 2016, each of which is incorporated herein by reference.

REFERENCE TO SEQUENCE LISTING SUBMITTED ELECTRONICALLY

The content of the electronically submitted sequence listing (Name: 6663_0253_Sequence_Listing.xml; Size: 146 kilobytes; and Date of Creation: Aug. 2, 2023) filed with the application is incorporated herein by reference in its entirety.

TECHNICAL FIELD

The present disclosure relates to therapeutic or preventive compositions for IL-8-related diseases and such.

BACKGROUND ART

Endometriosis is known not only for its estrogen dependency (Non-Patent Documents 1 and 2) but also as an inflammatory disease (Non-Patent Document 3).

In one aspect, without any limitation intended, endometriosis refers to a disease where uterine endometrial tissues occur and grow ectopically outside the uterine cavity (typically within the pelvis, occasionally in the peritoneal cavity, and rarely in the thoracic cavity). Endometriosis is not malignant tumor, but is a disease progressing over time and causing tumor formation and adhesion of adjacent tissues, severe abdominal and pelvic pain during menstrual and non-menstrual periods, and infertility (impaired fertility). Endometriosis develops mostly in women at reproductive age of 20 years or older, causes reduced QOL associated with pain and other symptoms, and leads to chronic pain and infertility due to aggravation of adhesion. In one aspect, without any limitation intended, adenomyosis refers to a disease that is similar to endometriosis but involves occurrence of endometrium within the myometrium. Adenomyosis causes severe menstrual pain, hypermenorrhea, anemia, and chronic pain. (The terms "endometriosis" and "adenomyosis" used herein are defined by descriptions below in the "Mode for Carrying Out the Invention".)

Conventional therapy for endometriosis or adenomyosis includes analgesics, hormonal therapy, and surgical treatments. Analgesics have only limited effects and cannot prevent progression of the disease state. Hormonal therapy is effective to relieve pains and to delay progression of the disease state; however, it has problems in that the ability to conceive is lost during the therapy since it stops menstruation, the disease state is likely to progress again after discontinuation of the therapy, and hormone drugs have adverse effects. Furthermore, there is no previous report of improvement of the ability to conceive after administration of hormone drugs. Even in the case of surgical treatments, the chance of recurrence is as high as about 50% three to five years after surgery (Non-Patent Documents 4 and 5). In order to prevent post-surgery recurrence, patients need to continue to take hormone drugs and tolerate their adverse effects.

IL-8 (interleukin 8) is a chemokine, and is a protein known to have 72- and 77-amino acid forms. IL-8 is also referred to as CXCL8. The monomer of IL-8 has two disulfide bridges between cysteines 7 and 34 and between cysteines 9 and 50, when numbered in accordance with the 72-amino acid form. It is known that IL-8 can also be present in the form of homodimer in a solution. The homodimer has no intermolecular covalent bond and is stabilized by non-covalent interaction between the β sheets of two monomers.

IL-8 is produced by various cells such as peripheral blood monocytes, tissue macrophages, NK cells, fibroblasts, and vascular endothelial cells, upon stimulation with inflammatory cytokines and such (Non-Patent Document 6). IL-8 is considered to have the activity of primarily activating neutrophils, elevating their expression of cell adhesion molecules, and thereby enhancing their adhesion to vascular endothelial cells. IL-8 also has chemotactic activity for neutrophils. IL-8 produced in damaged tissues promotes migration of neutrophils that have adhered to vascular endothelial cells toward the tissues, and thus induces inflammation associated with neutrophil infiltration. Furthermore, IL-8 is a major angiogenic factor for endothelial cells, and is also known to be involved in tumor angiogenesis.

It has been reported that when human proliferative-phase endometrial tissue was intraperitoneally transplanted into ovariectomized nude mice implanted with estradiol-releasing capsules and then an anti-IL-8 antibody was administered to them, regression of endometrial lesions was observed (Patent Document 1).

However, menstruation similar to that of human does not occur in non-primate experimental animal models. Therefore, in the aim of elucidating the cause of human endometriosis, animals such as rats and mice cannot serve as a true animal model for human endometriosis. Rats and mice do not have IL-8 in the first place. Furthermore, since until recently there has been no in vivo non-human primate model with which human endometriosis can be assessed properly, there is no previous report of confirming the effect of IL-8 signal on endometriosis using an in vivo non-human primate model.

Moreover, adhesion caused by surgical operations and such is problematic in various disease conditions. Adhesion prevention sheet is one method for treating or preventing adhesion. Although adhesion prevention sheet is effective in reducing post-surgical adhesion, the effect is still insufficient as dense adhesion is still formed at a frequency of 15% (Non-Patent Document 7).

CITATION LIST

Patent Documents

Patent Document 1: WO2009/026117

Non-Patent Documents

Non-Patent Document 1: Bulun et al., Endometriosis. N Engl J Med 2009; 360:268-279

Non-Patent Document 2: Giudice et al., Endometriosis. Lancet 2004; 364:1789-1799

Non-Patent Document 3: Donnez et al., Gynecol Obstet Invest 2002; 54 Suppl. 1:52-58; discussion 59-62

Non-Patent Document 4: Vercellini et al., Am J Obstet Gynecol. 2008 May; 198(5): 504.e1-5

Non-Patent Document 5: Guo et al., Hum Reprod Update. 2009 July-August; 15(4): 441-461

Non-Patent Document 6: Remo et al., Expert Rev. Clin. Immunol. 2014 10(5):593-619

Non-Patent Document 7: Becker et al., J Am Coll Surg. 1996 October; 183(4): 297-306

SUMMARY OF THE INVENTION

Problems to be Solved by the Invention

The present invention was achieved in view of various circumstances including those described above. In one non-limiting aspect, an objective of the present invention is to provide novel methods and such for treating IL-8-related diseases using an IL-8 signal inhibitor.

More specifically, in one non-limiting embodiment, an objective of the present invention is to provide novel therapeutic methods and such for novel IL-8-related diseases by using an IL-8 signal inhibitor. Alternatively, in another non-limiting embodiment, an objective of the present invention is to provide novel therapeutic methods and such for novel or known IL-8-related diseases by using a novel anti-IL-8 antibody.

Means for Solving the Problems

Without necessarily intending to be bound by theory, the present inventors have been proposing that the true pathology of endometriosis is conceptually a chronic inflammatory proliferative disease as reported previously (Odagiri, Fertil Steril. 2009; 92(5):1525-31). The pathology of endometriosis is immunological response following chronic inflammation, and is manifested as fibrosis, smooth muscle metaplasia, neuronal regeneration, angiogenesis, etc. Based on the concept that IL-8 is involved in an important part of the mechanism of chronic inflammation and endometriosis is a chronic inflammatory disease, the present inventors have performed pathological and clinical evaluation (observation using a laparoscope or MR) of drug effectiveness.

The present invention is, without any limitation intended, based on comprehensive studies ranging from basic studies to clinical studies using animal models, which include creation of a non-human primate model to elucidate the pathology of endometriosis and such, and preparation and improvement of highly functional anti-IL-8 antibodies as well as assessment of their pharmacological effects. Since true assessment of human uterus-related diseases cannot be achieved with animal model experiments using rats, mice, or other small animals, the present inventors created a cynomolgus monkey model with surgically-induced endometriosis, and conducted trial and error and dedicated studies while gathering each one's excellent techniques, knowledge, etc., such as those from basic reproduction studies of primates including cynomolgus monkey, the concept of the pathological conditions of human endometriosis etc., and their assessment and clinical management (laparoscopic surgery and observation, MRI (magnetic resonance imaging) assessment, etc.), then completing the present invention.

Specifically, in one non-limiting embodiment, the present inventors adopted an approach from the aspect of anti-inflammation with a focus on IL-8, which is a major inflammatory cytokine in endometriosis, to seek a therapeutic agent for endometriosis or adenomyosis that improves its pathological conditions without affecting the sexual cycle, unlike existing hormonal therapies. As a result, the present inventors surprisingly found that the pathological conditions were ameliorated by administering an IL-8 signal inhibitor.

Furthermore, in another non-limiting embodiment, the present inventors adopted an approach from the aspect of anti-inflammation to address adhesion caused by surgical operations and such, and as a result surprisingly found that adhesion was ameliorated by administering an IL-8 signal inhibitor.

Moreover, in another non-limiting embodiment, the present inventors conceived that highly functional anti-IL-8 antibodies in the present disclosure were useful for treatment etc. of novel or known IL-8-related diseases. Such highly functional anti-IL-8 antibodies include pH-dependent anti-IL-8 antibodies (anti-IL-8 antibodies that bind to IL-8 in a pH-dependent manner). The pH-dependent anti-IL-8 antibodies are advantageous when administered to an individual because as compared to a reference antibody they can have at least one or more of the following properties: they rapidly eliminate IL-8; they stably keep their IL-8-neutralizing activity; their immunogenicity is low; and their expression levels are high. Alternatively, such highly functional anti-IL-8 antibodies may be antibodies that have at least one or more of the following properties: anti-IL-8 antibodies containing an Fc domain whose FcRn-binding affinity at an acidic pH is greater than that of a native Fc domain; anti-IL-8 antibodies containing an Fc domain whose binding affinity for a pre-existing ADA is lower than that of a native Fc domain; anti-IL-8 antibodies containing an Fc domain whose half-life in plasma is longer than that of a native Fc domain; and pH-dependent anti-IL-8 antibodies containing an Fc domain whose binding affinity for an effector receptor is lower than that of a native Fc domain.

In one non-limiting specific embodiment, the present invention relates to:

[1] A composition for treating or preventing an IL-8-related disease, which comprises as an active ingredient an isolated anti-IL-8 antibody that binds to human IL-8, wherein the IL-8-related disease is selected from the group consisting of: endometriosis; adenomyosis; dysmenorrhea; adhesion; fibrotic diseases; pain in endometriosis, adenomyosis, or dysmenorrhea; infertility; and pain resulting from adhesion, fibrosis, or inflammation;

wherein the anti-IL-8 antibody is selected from the group consisting of:

(1) an anti-IL-8 antibody which binds to IL-8 in a pH-dependent manner, and comprises at least one amino acid substitution in at least one of:

(a) HVR-H1 comprising the amino acid sequence of SEQ ID NO: 23, (b) HVR-H2 comprising the amino acid sequence of SEQ ID NO: 24, (c) HVR-H3 comprising the amino acid sequence of SEQ ID NO: 25, (d) HVR-L1 comprising the amino acid sequence of SEQ ID NO: 26, (e) HVR-L2 comprising the amino acid sequence of SEQ ID NO: 27, and (f) HVR-L3 comprising the amino acid sequence of SEQ ID NO: 28;

(2) an anti-IL-8 antibody which binds to IL-8 in a pH-dependent manner, and comprises at least one amino acid substitution in at least one of:

(a) HVR-H1 comprising the amino acid sequence of SEQ ID NO: 23, (b) HVR-H2 comprising the amino acid sequence of SEQ ID NO: 24,
(c) HVR-H3 comprising the amino acid sequence of SEQ ID NO: 25,
(d) HVR-L1 comprising the amino acid sequence of SEQ ID NO: 26,
(e) HVR-L2 comprising the amino acid sequence of SEQ ID NO: 27, and
(f) HVR-L3 comprising the amino acid sequence of SEQ ID NO: 28,
wherein the anti-IL-8 antibody at least comprises amino acid substitutions of:
tyrosine at position 3 in the amino acid sequence of SEQ ID NO: 25,
asparagine at position 1 and leucine at position 5 in the amino acid sequence of SEQ ID NO: 27, and
glutamine at position 1 in the amino acid sequence of SEQ ID NO: 28;

(3) an anti-IL-8 antibody which binds to IL-8 in a pH-dependent manner, and comprises at least one amino acid substitution in at least one of:
(a) HVR-H1 comprising the amino acid sequence of SEQ ID NO: 23,
(b) HVR-H2 comprising the amino acid sequence of SEQ ID NO: 24,
(c) HVR-H3 comprising the amino acid sequence of SEQ ID NO: 25,
(d) HVR-L1 comprising the amino acid sequence of SEQ ID NO: 26,
(e) HVR-L2 comprising the amino acid sequence of SEQ ID NO: 27, and
(f) HVR-L3 comprising the amino acid sequence of SEQ ID NO: 28,
wherein the anti-IL-8 antibody at least comprises amino acid substitutions of:
tyrosine at position 9 and arginine at position 11 in the amino acid sequence of SEQ ID NO: 24, and tyrosine at position 3 in the amino acid sequence of SEQ ID NO: 25;

(4) an anti-IL-8 antibody which binds to IL-8 in a pH-dependent manner, and comprises at least one amino acid substitution in at least one of:
(a) HVR-H1 comprising the amino acid sequence of SEQ ID NO: 23,
(b) HVR-H2 comprising the amino acid sequence of SEQ ID NO: 24,
(c) HVR-H3 comprising the amino acid sequence of SEQ ID NO: 25,
(d) HVR-L1 comprising the amino acid sequence of SEQ ID NO: 26,
(e) HVR-L2 comprising the amino acid sequence of SEQ ID NO: 27, and
(f) HVR-L3 comprising the amino acid sequence of SEQ ID NO: 28,
wherein the anti-IL-8 antibody at least comprises amino acid substitutions of:
alanine at position 6, glycine at position 8, tyrosine at position 9, and arginine at position 11 in the amino acid sequence of SEQ ID NO: 24, and tyrosine at position 3 in the amino acid sequence of SEQ ID NO: 25;

(5) an anti-IL-8 antibody which binds to IL-8 in a pH-dependent manner, and comprises at least one amino acid substitution in at least one of:
(a) HVR-H1 comprising the amino acid sequence of SEQ ID NO: 23,
(b) HVR-H2 comprising the amino acid sequence of SEQ ID NO: 24,
(c) HVR-H3 comprising the amino acid sequence of SEQ ID NO: 25,
(d) HVR-L1 comprising the amino acid sequence of SEQ ID NO: 26,
(e) HVR-L2 comprising the amino acid sequence of SEQ ID NO: 27, and
(f) HVR-L3 comprising the amino acid sequence of SEQ ID NO: 28,
wherein the anti-IL-8 antibody at least comprises amino acid substitutions of:
asparagine at position 1 and leucine at position 5 in the amino acid sequence of SEQ ID NO: 27, and
glutamine at position 1 in the amino acid sequence of SEQ ID NO: 28;

(6) an anti-IL-8 antibody which binds to IL-8 in a pH-dependent manner, and comprises at least one amino acid substitution in at least one of:
(a) HVR-H1 comprising the amino acid sequence of SEQ ID NO: 23,
(b) HVR-H2 comprising the amino acid sequence of SEQ ID NO: 24,
(c) HVR-H3 comprising the amino acid sequence of SEQ ID NO: 25,
(d) HVR-L1 comprising the amino acid sequence of SEQ ID NO: 26,
(e) HVR-L2 comprising the amino acid sequence of SEQ ID NO: 27, and
(f) HVR-L3 comprising the amino acid sequence of SEQ ID NO: 28,
wherein the anti-IL-8 antibody at least comprises amino acid substitutions of:
tyrosine at position 9 and arginine at position 11 in the amino acid sequence of SEQ ID NO: 24, tyrosine at position 3 in the amino acid sequence of SEQ ID NO: 25,
asparagine at position 1 and leucine at position 5 in the amino acid sequence of SEQ ID NO: 27, and glutamine at position 1 in the amino acid sequence of SEQ ID NO: 28; and (7) an anti-IL-8 antibody which binds to IL-8 in a pH-dependent manner, and comprises at least one amino acid substitution in at least one of:
(a) HVR-H1 comprising the amino acid sequence of SEQ ID NO: 23,
(b) HVR-H2 comprising the amino acid sequence of SEQ ID NO: 24,
(c) HVR-H3 comprising the amino acid sequence of SEQ ID NO: 25,
(d) HVR-L1 comprising the amino acid sequence of SEQ ID NO: 26,
(e) HVR-L2 comprising the amino acid sequence of SEQ ID NO: 27, and
(f) HVR-L3 comprising the amino acid sequence of SEQ ID NO: 28, wherein the anti-IL-8 antibody at least comprises amino acid substitutions of: ala-nine at
position 6, glycine at position 8, tyrosine at position 9, and arginine at position 11 in the amino acid sequence of SEQ ID NO: 24, tyrosine at position 3 in the amino acid sequence of SEQ ID NO: 25, asparagine at position 1 and leucine at position 5 in the amino acid sequence of SEQ ID NO: 27, and glutamine at position 1 in the amino acid sequence of SEQ ID NO: 28.

[2] The composition of [1], wherein the anti-IL-8 antibody is selected from the group consisting of:

(8) the anti-IL-8 antibody of any one of (1) to (7) of [1], which comprises:
(a) the amino acid sequence of SEQ ID NO: 23 as HVR-H1,
(b) the amino acid sequence of SEQ ID NO: 29 as HVR-H2, and
(c) the amino acid sequence of SEQ ID NO: 30 as HVR-H3;

(9) the anti-IL-8 antibody of any one of (1) to (7) of [1], which comprises:
(d) the amino acid sequence of SEQ ID NO: 26 as HVR-L1,
(e) the amino acid sequence of SEQ ID NO: 31 as HVR-L2, and
(f) the amino acid sequence of SEQ ID NO: 32 as HVR-L3;

(10) the anti-IL-8 antibody of any one of (1) to (7) of [1], which comprises:
(a) the amino acid sequence of SEQ ID NO: 23 as HVR-H1,
(b) the amino acid sequence of SEQ ID NO: 24 as HVR-H2, and
(c) the amino acid sequence of SEQ ID NO: 30 as HVR-H3;

(11) the anti-IL-8 antibody of any one of (1) to (7) of [1], which comprises:
(d) the amino acid sequence of SEQ ID NO: 26 as HVR-L1,
(e) the amino acid sequence of SEQ ID NO: 107 as HVR-L2, and
(f) the amino acid sequence of SEQ ID NO: 32 as HVR-L3;

(12) the anti-IL-8 antibody of any one of (1) to (7) of [1], which comprises:
(a) the amino acid sequence of SEQ ID NO: 23 as HVR-H1,
(b) the amino acid sequence of SEQ ID NO: 29 as HVR-H2,
(c) the amino acid sequence of SEQ ID NO: 30 as HVR-H3,
(d) the amino acid sequence of SEQ ID NO: 26 as HVR-L1,
(e) the amino acid sequence of SEQ ID NO: 31 as HVR-L2, and
(f) the amino acid sequence of SEQ ID NO: 32 as HVR-L3;

(13) the anti-IL-8 antibody of (1) or (2) of [1], which comprises:
(a) the amino acid sequence of SEQ ID NO: 23 as HVR-H1,
(b) the amino acid sequence of SEQ ID NO: 24 as HVR-H2,
(c) the amino acid sequence of SEQ ID NO: 30 as HVR-H3,
(d) the amino acid sequence of SEQ ID NO: 26 as HVR-L1,
(e) the amino acid sequence of SEQ ID NO: 107 as HVR-L2, and
(f) the amino acid sequence of SEQ ID NO: 32 as HVR-L3;

(14) the anti-IL-8 antibody of any one of (1) to (7) of [1], which comprises a heavy chain variable region comprising the amino acid sequence of SEQ ID NO: 34 and a light chain variable region comprising the amino acid sequence of SEQ ID NO: 35;

(15) the anti-IL-8 antibody of (1) or (2) of [1], which comprises a heavy chain variable region comprising the amino acid sequence of SEQ ID NO: 108 and a light chain variable region comprising the amino acid sequence of SEQ ID NO: 109;

(16) the anti-IL-8 antibody of any one of (1) to (7) of [1], which comprises HVR-H1, HVR-H2, HVR-H3, HVR-L1, HVR-L2, and HVR-L3 which have at least 80% sequence identity with (a) HVR-H1 comprising the amino acid sequence of SEQ ID NO: 23, (b) HVR-H2 comprising the amino acid sequence of SEQ ID NO: 29, (c) HVR-H3 comprising the amino acid sequence of SEQ ID NO: 30, (d) HVR-L1 comprising the amino acid sequence of SEQ ID NO: 26, (e) HVR-L2 comprising the amino acid sequence of SEQ ID NO: 31, and (f) HVR-L3 comprising the amino acid sequence of SEQ ID NO: 32, respectively;

(17) the anti-IL-8 antibody of any one of (1) to (7) of [1], which comprises HVR-H1, HVR-H2, HVR-H3, HVR-L1, HVR-L2, and HVR-L3 which have at least 80% sequence identity with (a) HVR-H1 comprising the amino acid sequence of SEQ ID NO: 23, (b) HVR-H2 comprising the amino acid sequence of SEQ ID NO: 24, (c) HVR-H3 comprising the amino acid sequence of SEQ ID NO: 30, (d) HVR-L1 comprising the amino acid sequence of SEQ ID NO: 26, (e) HVR-L2 comprising the amino acid sequence of SEQ ID NO: 107, and (f) HVR-L3 comprising the amino acid sequence of SEQ ID NO: 32, respectively;

(18) the anti-IL-8 antibody of any one of (1) to (7) of [1], which comprises a heavy chain variable region and a light chain variable region which have at least 80% sequence identity with a heavy chain variable region comprising the amino acid sequence of SEQ ID NO: 34 and a light chain variable region comprising the amino acid sequence of SEQ ID NO: 35, respectively; and

(19) the anti-IL-8 antibody of any one of (1) to (7) of [1], which comprises a heavy chain variable region and a light chain variable region which have at least 80% sequence identity with a heavy chain variable region comprising the amino acid sequence of SEQ ID NO: 108 and a light chain variable region comprising the amino acid sequence of SEQ ID NO: 109, respectively.

[3] A composition for treating or preventing an IL-8-related disease, which comprises as an active ingredient an isolated anti-IL-8 antibody that binds to human IL-8, wherein the IL-8-related disease is selected from the group consisting of: endometriosis; adenomyosis; dysmenorrhea; adhesion; fibrotic diseases; pain in endometriosis, adenomyosis, or dysmenorrhea; infertility; and pain resulting from adhesion, fibrosis, or inflammation, and wherein the anti-IL-8 antibody is selected from the group consisting of:

(I) an anti-IL-8 antibody which comprises an Fc region comprising amino acid substitution at one or more positions selected from the group consisting of positions 235, 236, 239, 327, 330, 331, 428, 434, 436, 438, and 440 according to EU numbering;

(II) an anti-IL-8 antibody which comprises an Fc region comprising amino acid substitution at all positions selected from the group consisting of positions 434, 438, and 440 according to EU numbering;

(III) an anti-IL-8 antibody which comprises an Fc region comprising all of amino acid substitution with Ala at position 434; amino acid substitution with Glu, Arg, Ser, or Lys at position 438; and amino acid substitution with Glu, Asp, or Gln at position 440, according to EU numbering;

(IV) an anti-IL-8 antibody which comprises an Fc region comprising all of amino acid substitution with Ala at position 434; amino acid substitution with Glu, Arg, Ser, or Lys at position 438; and amino acid substitution with Glu, Asp, or Gln at position 440, and further comprising Ile or Leu at position 428, and/or Ile, Leu, Val, Thr, or Phe at position 436, according to EU numbering;

(V) an anti-IL-8 antibody which comprises an Fc region comprising one or more amino acid substitutions selected from the group consisting of L235R, G236R, S239K, A327G, A330S, P331S, M428L, N434A, Y436T, Q438R, and S440E according to EU numbering;

(VI) an anti-IL-8 antibody which comprises an Fc region comprising a combination of amino acid substitutions selected from the group consisting of:

N434A/Q438R/S440E;
N434A/Q438R/S440D;
N434A/Q438K/S440E;
N434A/Q438K/S440D;
N434A/Y436T/Q438R/S440E;
N434A/Y436T/Q438R/S440D;
N434A/Y436T/Q438K/S440E;
N434A/Y436T/Q438K/S440D;
N434A/Y436V/Q438R/S440E;
N434A/Y436V/Q438R/S440D;
N434A/Y436V/Q438K/S440E;
N434A/Y436V/Q438K/S440D;
N434A/R435H/F436T/Q438R/S440E; N434A/R435H/F436T/Q438R/S440D;
N434A/R435H/F436T/Q438K/S440E; N434A/R435H/F436T/Q438K/S440D;
N434A/R435H/F436V/Q438R/S440E; N434A/R435H/F436V/Q438R/S440D;
N434A/R435H/F436V/Q438K/S440E; N434A/R435H/F436V/Q438K/S440D;
M428L/N434A/Q438R/S440E;
M428L/N434A/Q438R/S440D;
M428L/N434A/Q438K/S440E;
M428L/N434A/Q438K/S440D;
M428L/N434A/Y436T/Q438R/S440E; M428L/N434A/Y436T/Q438R/S440D;
M428L/N434A/Y436T/Q438K/S440E; M428L/N434A/Y436T/Q438K/S440D;
M428L/N434A/Y436V/Q438R/S440E; M428L/N434A/Y436V/Q438R/S440D;
M428L/N434A/Y436V/Q438K/S440E; and
M428L/N434A/Y436V/Q438K/S440D
according to EU numbering;

(VII) an anti-IL-8 antibody which comprises an Fe region comprising a combination of amino acid substitutions:

L235R/G236R/S239K/M428L/N434A/Y436T/Q438R/S440E; or
L235R/G236R/A327G/A330S/P331S/M428L/N434A/Y436T/Q438R/S440E, according to EU numbering; and (VIII) an anti-IL-8 antibody comprising the Fc region of any one of (I) to (VII) above, wherein the Fc region has at least one property selected from the group consisting of (a) to (e) below:

(a) the FcRn-binding affinity of the Fc region at an acidic pH has been increased relative to the FcRn-binding affinity of a native Fc region;

(b) the binding affinity of the Fc region for a pre-existing ADA has been reduced relative to the binding affinity of a native Fc region for the pre-existing ADA;

(c) the plasma half-life of the Fc region has been increased relative to the plasma half-life of a native Fc region;

(d) the plasma clearance of the Fc region has been reduced relative to the plasma clearance of a native Fc region; and (e) the binding affinity of the Fc region for an effector receptor has been reduced relative to the binding affinity of a native Fc region for the effector receptor.

[4] A composition for treating of preventing an IL-8-related disease, which comprises as an active ingredient an isolated anti-IL-8 antibody that binds to human IL-8, wherein the IL-8-related disease is selected from the group consisting of:

endometriosis; adenomyosis; dysmenorrhea; adhesion; fibrotic diseases; pain in endometriosis, adenomyosis, or dysmenorrhea; infertility; and pain resulting from adhesion, fibrosis, or inflammation, and wherein the anti-IL-8 antibody is selected from the group consisting of:

(A) an anti-IL-8 antibody comprising a heavy chain comprising the amino acid sequence of SEQ ID NO: 36 and a light chain comprising the amino acid sequence of SEQ ID NO: 38;

(B) an anti-IL-8 antibody comprising a heavy chain comprising the amino acid sequence of SEQ ID NO: 37 and a light chain comprising the amino acid sequence of SEQ ID NO: 38;

(C) an anti-IL-8 antibody comprising a heavy chain comprising the amino acid sequence of SEQ ID NO: 106 and a light chain comprising the amino acid sequence of SEQ ID NO: 44;

(D) an anti-IL-8 antibody comprising heavy and light chains which have at least 80% sequence identity with a heavy chain comprising the amino acid sequence of SEQ ID NO: 36 and a light chain comprising the amino acid sequence of SEQ ID NO: 38, respectively;

(E) an anti-IL-8 antibody comprising heavy and light chains which have at least 80% sequence identity to a heavy chain comprising the amino acid sequence of SEQ ID NO: 37 and a light chain comprising the amino acid sequence of SEQ ID NO: 38, respectively; and (F) an anti-IL-8 antibody comprising heavy and light chains which have at least 80% sequence identity with a heavy chain comprising the amino acid sequence of SEQ ID NO: 106 and a light chain comprising the amino acid sequence of SEQ ID NO: 44, respectively.

[5] The composition of any one of [1] to [4], wherein the fibrotic disease is selected from the group consisting of fibrosis in endometriosis or adenomyosis, chronic obstructive pulmonary disease (COPD), cystic fibrosis, psoriasis, hepatic fibrosis, renal fibrosis, and pulmonary fibrosis.

[6] A composition for treating or preventing an IL-8-related disease, which comprises an IL-8 signal inhibitor as an active ingredient, wherein the IL-8-related disease is selected from the group consisting of human endometriosis; adenomyosis; dysmenorrhea; adhesion; pain in human endometriosis, adenomyosis, or dysmenorrhea; infertility; and pain resulting from adhesion, fibrosis, or inflammation.

[7] The composition of [6] for suppressing infiltration of immune cells to a lesion or surrounding environment thereof in an IL-8-related disease.

[8] The composition of [6] or [7] for inhibiting the production of aromatase or a fibrotic factor.

[9] The composition of any one of [6] to [8], which does not affect the sexual cycle.

[10] The composition of any one of [6] to [9] for suppressing adhesion or fibrosis in endometriosis or adenomyosis.

[11] The composition of any one of [6] to [10] for (1) atrophying endometrial epithelial cells or stromal cells in an endometriosis or adenomyosis patient, or (2) reducing endometrial interstitium in endometriosis.

[12] The composition of any one of [6] to [11], wherein dysmenorrhea is dysmenorrhea with endometriosis or adenomyosis, or is dysmenorrhea suspected of endometriosis or adenomyosis.

[13] The composition of [6] wherein adhesion is formed after surgery.

[14] The composition of any one of [6] to [13], wherein the IL-8 signal inhibitor is an IL-8 inhibitor, a CXCR1 inhibitor, or a CXCR2 inhibitor.

[15] The composition of [14] wherein the IL-8 inhibitor, the CXCR1 inhibitor, or the CXCR2 inhibitor is an anti-IL-8 antibody, an anti-CXCR1 antibody, or an anti-CXCR2 antibody, respectively.

[16] The composition of any one of [1] to [5] for suppressing the infiltration of immune cells to a lesion of an IL-8-related disease or adjacent environment thereof.

[17] The composition of any one of [1] to [5] for inhibiting the production of aromatase or a fibrotic factor.

[18] The composition of any one of [1] to [5], which does not affect the sexual cycle.

[19] The composition of any one of [1] to [5] for suppressing adhesion or fibrosis in endometriosis or adenomyosis.

[20] The composition of any one of [1] to [5] for:

(1) atrophying endometrial epithelial cells or stromal cells in an endometriosis or adenomyosis patient, or (2) reducing endometrial interstitium in endometriosis.

[21] The composition of any one of [1] to [5], wherein the dysmenorrhea has endometriosis or adenomyosis, or is suspected of being endometriosis or adenomyosis.

[22] The composition of any one of [1] to [5], wherein the adhesion is formed after surgery.

[23] The composition of any one of [1] to [22], wherein the IL-8-related disease is responsive to an IL-8 signal.

[24] The composition of any one of [1] to [23], which additionally comprises a pharmaceutically acceptable carrier.

[25] The composition of any one of [1] to [5] and [16] to [24], wherein the endometriosis is human endometriosis.

[A1] An anti-IL-8 antibody defined in any one of [1] to [5] and [16] to [25] for use in treating or preventing an IL-8-related disease which is selected from the group consisting of: endometriosis; adenomyosis; dysmenorrhea; adhesion; fibrotic diseases; pain in endometriosis, adenomyosis, or dysmenorrhea; infertility; and pain resulting from adhesion, fibrosis, or inflammation.

[A2] An IL-8 signal inhibitor defined in any one of [6] to [15] and [23] to [25] for use in treating or preventing an IL-8-related disease which is selected from the group consisting of: human endometriosis; adenomyosis; dysmenorrhea; adhesion; pain in human endometriosis, adenomyosis, or dysmenorrhea; infertility; and pain resulting from adhesion, fibrosis, or inflammation.

[A3] A method for treating or preventing an IL-8-related disease which is selected from the group consisting of: endometriosis; adenomyosis; dysmenorrhea; adhesion; fibrotic diseases; pain in endometriosis, adenomyosis, or dysmenorrhea; infertility; and pain resulting from adhesion, fibrosis, or inflammation, wherein the method comprises administering to a subject in need thereof the anti-IL-8 antibody defined in any one of [1] to [5] and [16] to [25], or the composition of any one of [1] to [5] and [16] to [25](wherein the subject in need thereof may be a subject suffering or suspected to suffer from the IL-8-related disease).

[A4] A method for treating or preventing an IL-8-related disease which is selected from the group consisting of: human endometriosis; adenomyosis; dysmenorrhea; adhesion; pain in human endometriosis, adenomyosis, or dysmenorrhea; infertility; and pain resulting from adhesion, fibrosis, or inflammation, wherein the method comprises administering to a subject in need thereof the IL-8 signal inhibitor defined in any one of [6] to [15] and [23] to [25], or the composition of any one of [6] to [15] and [23] to [25] (wherein the subject in need thereof may be a subject suffering or suspected to suffer from the IL-8-related disease).

[A5] Use of the anti-IL-8 antibody defined in any one of [1] to [5] and [16] to [25], in producing a medicament for treating or preventing an IL-8-related disease which is selected from the group consisting of: endometriosis; adenomyosis; dysmenorrhea; adhesion; fibrotic diseases; pain in endometriosis, adenomyosis, or dysmenorrhea; infertility; and pain resulting from adhesion, fibrosis, or inflammation.

[A6] Use of the IL-8 signal inhibitor defined in any one of [6] to [15] and [23] to [25], in producing a medicament for treating or preventing an IL-8-related disease which is selected from the group consisting of: human endometriosis; adenomyosis; dysmenorrhea; adhesion; pain in human endometriosis, adenomyosis, or dysmenorrhea; infertility; and pain resulting from adhesion, fibrosis, or inflammation.

It is intended, and will be naturally understood by persons with ordinary skill in the art, that the present invention includes any combinations of part or all of one or more of the elements described in any of the above unless they are technically contradictory based on the common technical knowledge of persons with ordinary skill in the art.

BRIEF DESCRIPTION OF THE DRAWINGS

FIG. 18-1 shows changes in relative intensity of chemical luminescence depending on antibody concentrations of Hr9, H89/L118, and H553/L118 prior to storage in plasma.

FIG. 18-2 shows changes in relative intensity of chemical luminescence depending on antibody concentrations of Hr9, H89/L118, and H553/L118 after one-week storage in plasma.

FIG. 18-3 shows changes in relative intensity of chemical luminescence depending on antibody concentrations for Hr9, H89/L118, and H553/L118 after two-week storage in plasma.

FIG. 21-1 shows changes in relative intensity of chemical luminescence depending on antibody concentrations of Hr9, H89/L118, and H1009/L395-F1886s prior to storage in plasma.

FIG. 21-2 shows changes in relative intensity of chemical luminescence depending on antibody concentrations of Hr9, H89/L118, and H1009/L395-F1886s after one-week storage in plasma.

FIG. 21-3 shows changes in relative intensity of chemical luminescence depending on antibody concentrations of Hr9, H89/L118, and H1009/L395-F1886s after two-week storage in plasma.

FIG. 31 shows a laparoscopy recording sheet in which lesions formed by seeding endometrial tissues cut into small pieces, and lesions formed by adhesion and suture, are recorded.

FIG. 34-1 is a graph showing a high correlation between adhesion r-AFS score and IL-8 concentration in the cystic fluid in the monkey endometriosis model.

FIG. 34-2 is a graph showing relative volumes of endometriosis nodular lesions after administration of vehicle or antibody H1009/L395-F1974m.

FIG. 35-1 is a set of graphs showing changes in total r-AFS score, adhesion r-AFS score, and size r-AFS score before and after administration of vehicle or antibody H1009/L395-F1974m.

FIG. 35-2 is a graph showing changes in total r-AFS score before and after administration of vehicle or antibody H1009/L395-F1974m.

MODE FOR CARRYING OUT THE INVENTION

Figure 1:
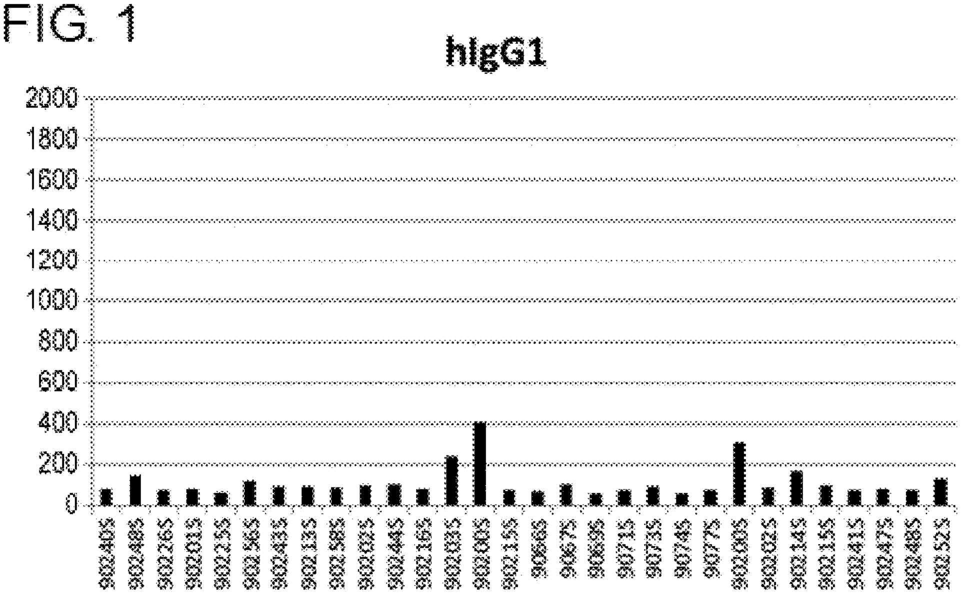
FIG. 1 shows the degree of binding of Fv4-IgG1 having the Fe domain of native human IgG1 to rheumatoid factor in the sera of RA patients.

Preferred non-limiting embodiments of the present disclosure are described below.

It is intended that all elements described in the Examples set forth later will naturally be deemed as also being equally described in this "Mode for Carrying Out the Invention" without being bound by any limitation of patent practice, custom, law, and the like by which one could attempt to interpret what is described in the Examples in a limited manner in countries where patent protection is sought by the present patent application.

It is intended, and is to be naturally understood by persons with ordinary skill in the art, that the present disclosure includes any combinations of some or all of one or more elements described anywhere in the present disclosure as long as they are not technically contradictory based on the common technical knowledge of the skilled persons.

Herein, the term "antibody" is used in the broadest sense, and includes, without limitation, monoclonal antibodies, polyclonal antibodies, multispecific antibodies (for example, bispecific antibodies), and antibody fragments as long as they exhibit desired antigen-binding activity.

In the present disclosure, an "antibody that binds to the same epitope" as a desired reference antibody (for example, a reference anti-IL-8 antibody, anti-CXCR1 antibody, or anti-CXCR2 antibody) refers to, in one embodiment, an antibody that inhibits the antigen binding of a reference antibody which binds to a desired antigen (for example, IL-8, CXCR1, or CXCR2) by, for example, 50%, 60%, 70%, 80%, 90%, 95%, or more. Conversely, the reference antibody inhibits the binding of the antibody to the antigen by, for example, 50%, 60%, 70%, 80%, 90%, 95%, or more. Here, typical competition assays can be used, without limitation thereto.

Herein, the term "monoclonal antibody" refers to an antibody obtained from a substantially homogeneous antibody population. Specifically, for example, the individual antibodies constituting the population are identical and/or bind to the same epitope except for possible variant antibodies, such as variants generally present in a small amount containing naturally occurring mutations or arising during production of a monoclonal antibody preparation. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the characteristic of an antibody obtained from a substantially homogeneous antibody population, and is not to be construed as requiring the antibody to be produced by any particular method. For example, the monoclonal antibodies of the present invention may be produced by various techniques, including but not limited to hybridoma methods, recombinant DNA methods, phage-display methods, and methods using transgenic animals containing all or part of the human immunoglobulin loci. In one embodiment, the antibodies in the present disclosure may be monoclonal antibodies.

Herein, the term "native antibody" refers to naturally occurring immunoglobulin molecules with various structures. In one aspect, native IgG antibodies are, for example, but are not limited to, heterotetrameric glycoproteins of about 150,000 daltons composed of two identical light chains and two identical heavy chains which are linked together via disulfide bonds. In the N- to C-terminus direction, each heavy chain has a variable region (VH) followed by three constant regions (CH1, CH2, and CH3). Likewise, in the N- to C-terminus direction, each light chain has a variable region (VL) followed by a constant region (CL). An antibody light chain may be assigned to one of the two types, called kappa (κ) and lambda (λ), based on the amino acid sequence of its constant region. Constant regions used here may be of any reported allotype (allele) or any subclass/isotype. For example, the heavy-chain constant region used may be, but is not limited to, the constant region of a native IgG antibody (IgG1, IgG2, IgG3, or IgG4). For example, known IgG1 alleles are IGHG1*01 to 05 (see at http://www.imgt.org/), and any of these can be used as a native human IgG1 sequence. Meanwhile, the constant region sequence may be derived from a single allele or subclass/isotype, or from multiple alleles or subclasses/isotypes. Specifically, such antibodies include, but are not limited to, antibodies with CH1 derived from IGHG1*01, CH2 derived from IGHG1*02, and CH3 derived from IGHG1*01. The heavy chain constant regions of native human IgG antibodies include, for example, human IgG1 constant region (SEQ ID NO: 100), human IgG2 constant region (SEQ ID NO: 101), human IgG3 constant region (SEQ ID NO: 102), and human IgG4 constant region (SEQ ID NO: 103). Meanwhile, the light chain constant regions of native human IgG antibodies include, for example, human κ chain constant region (SEQ ID NO: 104) and human λ chain constant region (SEQ ID NO: 105).

Herein, the term "framework" or "FR" refers to variable region portions other than hypervariable region (HVR) residues. The FRs of a variable region generally consist of four FR domains: FR1, FR2, FR3, and FR4. Accordingly, the HVR and FR sequences generally appear in VH (or VL) in the following sequence: FR1-H1(L1)-FR2-H2(L2)-FR3-H3(L3)-FR4.

Herein, the term "human consensus framework" is a framework which represents the most commonly occurring amino acid residues in a selection of human immunoglobulin VL or VH framework sequences. Generally, human immunoglobulin VL or VH sequences are selected from a subgroup of variable region sequences. Generally, the subgroup of sequences is a subgroup as in Kabat et al., Sequences of proteins of Immunological Interest, 5th Ed. Public Health Service, National Institutes of Health, Bethesda, MD (1991). In one embodiment, for the VL, the subgroup may be subgroup KI as in Kabat et al., supra. In one embodiment, for the VH, the subgroup may be subgroup III as in Kabat et al., supra.

Herein, an "acceptor human framework" is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence substitutions. In one embodiment, the number of pre-existing amino acid substitutions is 10, 9, 8, 7, 6, 5, 4, 3, or 2 or less. In one embodiment, the VL acceptor human framework is identical in sequence to the VL human immunoglobulin framework sequence or human consensus framework sequence.

Herein, the term "variable region" refers to a domain of an antibody heavy or light chain that is involved in the binding of the antibody to a desired antigen. The variable regions of the heavy chain and light chain (VH and VL, respectively) of a native antibody generally have similar structures, with each domain comprising four conserved framework regions (FRs) and three hypervariable regions (HVRs) (Kindt et al. Kuby Immunology, 6th ed., W.H. Freeman and Co., 2007 p. 91). In one embodiment, a single VH or VL domain is sufficient to confer antigen-binding specificity, but is not limited thereto. Furthermore, antibodies that bind to a particular antigen may be isolated using a VH or VL domain from an antibody that binds to the antigen, to screen a library of complementary VL or VH domains, respectively (e.g., Portolano et al., J. Immunol. 150:880-887 (1993); Clarkson et al., Nature 1991 352:624-628).

Herein, the term "hypervariable region" or "HVR" refers to each of the regions of an antibody variable domain which are hypervariable in sequence ("complementarity determining region" or "CDR"), and/or form structurally defined loops ("hypervariable loops"), and/or contain antigen-contacting residues ("antigen contacts"). Generally, antibodies comprise six HVRs: three in the VH (H1, H2, and H3), and three in the VL (L1, L2, and L3). Exemplary HVRs include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));
(c) antigen contacts occurring at amino acid residues 27c-36 (L1), 46-55 (L2), 89-96 (L3), 30-35b (H1), 47-58 (H2), and 93-101 (H3) (MacCallum et al., J. Mol. Biol. 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues within the variable regions (for example, FR residues) are numbered herein according to the Kabat et al., supra.

Herein, an "individual" refers to a mammal. Mammals include, but are not limited to, domesticated animals (for example, cows, sheep, cats, dogs, and horses), primates (e.g., humans and non-human primates such as monkeys), rabbits, and rodents (e.g., mice and rats). In one embodiment, the "individual" is preferably a mammal that naturally possesses IL-8 in its body, more preferably an animal with menstruation similar to that of humans, for example, a nonhuman primate, and yet more preferably a human. Herein, the term "individual" is used interchangeably with "subject" unless it is inconsistent with the context.

Herein, an "isolated" antibody is one which has been separated from a component of its natural environment. In one embodiment, an antibody can be purified to, for example, 95% or higher, or 99% or higher purity, for example, in a chromatographic manner (for example, ion-exchange or reverse phase HPLC) or an electrophoretic manner (for example, SDS-PAGE, isoelectric focusing (IEF), or capillary electrophoresis). For methods for assessment of antibody purity, see, for example, Flatman et al., J. Chromatogr. B 848:79-87 (2007). In one aspect, an "isolated" antibody in the present disclosure can be referred to as a "purified" antibody.

Herein, an "isolated" nucleic acid refers to a nucleic acid molecule that has been separated from a component of its natural environment. A nucleic acid includes a nucleic acid molecule that is contained in cells that ordinarily contain the nucleic acid molecule, but the nucleic acid molecule is present extrachromosomally or at a chromosomal location that is different from its natural chromosomal location.

Herein, the term "affinity" may typically refer to the strength of the sum total of noncovalent interactions between a single binding site of a molecule (for example, an antibody or a chemical compound) and its binding partner (for example, an antigen). Unless indicated otherwise, the term "binding affinity" in the present disclosure refers to intrinsic binding affinity which reflects 1:1 interaction between members of a binding pair (for example, an antibody or chemical compound and an antigen). The affinity of a molecule X for its partner Y can generally be represented by the dissociation constant (KD). Binding affinity can be measured using methods known to those skilled in the art, including those described in the present disclosure.

In one embodiment, an antibody that binds to an antigen such as IL-8, CXCR1, or CXCR2 may have a dissociation constant (KD) of, for example, ≤1000 nM, ≤100 nM, ≤10 nM, ≤1 nM, ≤0.1 nM, ≤0.01 nM, or ≤0.001 nM (for example, $10^{-8}$ M or less, from $10^{-8}$ M to $10^{-13}$ M, or from $10^{-9}$ M to $10^{-13}$ M).

Herein, the terms "host cell" and "host cell line" are used interchangeably and refer to cells into which exogenous nucleic acid has been introduced (including the progeny of such cells). Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the original transformed cell are also included herein.

Herein, the term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are also referred to herein as "expression vectors."

In one embodiment, an antibody in the present disclosure (for example, an anti-IL-8 antibody, anti-CXCR1 antibody, or anti-CXCR2 antibody) may be an antibody fragment. Antibody fragments may include, for example, Fab, Fab', Fab'-SH, $F(ab')_2$, Fv, scFv fragments, diabodies, and single-domain antibodies. For a review of antibody fragments, see, for example, Hudson et al., Nat. Med. 9:129-134 (2003). For a review of scFv fragments, see, for example, Pluckthun, in The Pharmacology of Monoclonal Antibodies, vol. 113, Rosenburg and Moore eds., (Springer-Verlag, New York), pp. 269-315 (1994); WO93/16185; U.S. Pat. Nos. 5,571,894; and 5,587,458.

Herein, "diabodies" are antibody fragments with two antigen-binding sites that may be bivalent or bispecific (See, for example, EP404,097; WO1993/01161; Hudson et al., Nat. Med. 9:129-134 (2003); Hollinger et al., Proc. Natl. Acad. Sci. USA 90: 6444-6448 (1993)). Triabodies and tetrabodies are described, for example, in Hudson et al., Nat. Med. 9:129-134 (2003).

Herein, a "single-domain antibody" is an antibody fragment comprising the whole or a portion of the heavy chain variable domain or the whole or a portion of the light chain variable domain of an antibody. In one embodiment, when an antibody in the present disclosure is a single-domain antibody, it may be a human single-domain antibody (see, for example, Domantis, Inc., Waltham, MA; U.S. Pat. No. 6,248,516). Antibody fragments can be made by various techniques, including but not limited to, for example, proteolytic digestion of an intact antibody as well as production using recombinant host cells as described herein.

Herein, the term "chimeric antibody" refers to an antibody in which a portion of the heavy and/or light chain is derived from a particular source or species, while the remainder of the heavy and/or light chain is derived from a different source or species.

Herein, a "humanized" antibody refers to a chimeric antibody comprising amino acid residues from non-human HVRs and amino acid residues from human FRs. In one embodiment, a humanized antibody comprises substantially at least one, and typically two, variable regions, in which all (or substantially all) of the HVRs correspond to the HVRs (for example, CDRs) of a nonhuman antibody, and all (or substantially all) of the FRs correspond to those of a human antibody. A humanized antibody may optionally comprise at least a portion of an antibody constant region derived from a human antibody.

In one embodiment, an antibody in the present disclosure (for example, an anti-IL-8 antibody, anti-CXCR1 antibody, or anti-CXCR2 antibody) may be a chimeric antibody. Chimeric antibodies are described, for example, in U.S. Pat. No. 4,816,567; and Morrison et al., Proc. Natl. Acad. Sci. USA, 81:6851-6855 (1984). A chimeric antibody may comprise a non-human variable region (for example, a variable region derived from a non-human primate such as a monkey, or a mouse, a rat, a hamster, or a rabbit) and a human constant region.

In one embodiment, an antibody in the present disclosure (for example, an anti-IL-8 antibody, anti-CXCR1 antibody, or anti-CXCR2 antibody) may be a humanized antibody. Typically, a non-human antibody is humanized to reduce immunogenicity in humans, while retaining the specificity and affinity of the parental non-human antibody. Typically, a humanized antibody comprises one or more variable regions in which HVRs, for example, CDRs (or portions thereof) are derived from a nonhuman antibody, and FRs (or portions thereof) are derived from human antibody sequences. A humanized antibody may also optionally comprise at least a portion of a human constant region. In one embodiment, some FR amino acid residues in a humanized antibody may be substituted with corresponding amino acid residues from a non-human antibody (for example, the antibody from which the HVR residues are derived), for example, to retain or improve antibody specificity or affinity.

Humanized antibodies and methods of making them are reviewed, for example, in Almagro and Fransson, Front. Biosci. 13:1619-1633 (2008)), and are further described, for example, in: Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

In one embodiment, human framework that may be used for humanization may include, for example, framework regions selected using the "best-fit" method (Sims et al., J. Immunol. 151:2296 (1993)); framework regions derived from the consensus sequence of human antibodies of a particular subgroup of light or heavy chain variable regions (Carter et al., Proc. Natl. Acad. Sci. USA, 89:4285 (1992) and Presta et al., J. Immunol., 151:2623 (1993)); and framework regions derived from screening of FR libraries (Baca et al., J. Biol. Chem. 272:10678-10684 (1997); and Rosok et al., J. Biol. Chem. 271:22611-22618 (1996)).

In one embodiment, an antibody in the present disclosure (for example, an anti-IL-8 antibody, anti-CXCR1 antibody, or anti-CXCR2 antibody) may be a human antibody. Human antibodies can be produced by various techniques. Human antibodies are reviewed, for example, in: van Dijk and van de Winkel, Curr. Opin. Pharmacol. 5: 368-374 (2001); and Lonberg, Curr. Opin. Immunol. 20:450-459 (2008). Human antibodies may be prepared by administering an antigen (for example, IL-8, CXCR1, or CXCR2) to a transgenic animal that has been modified to produce intact human antibodies or intact antibodies with human variable regions in response to the antigen. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology; and US2007/0061900 describing VELOCI-MOUSE® technology. Human variable regions from intact antibodies generated by such animals may be further modified, for example, by combining them with a different human constant region.

In another embodiment, human antibodies can also be made by hybridoma-based methods. Human myeloma and mouse-human heteromyeloma cell lines for the production of human monoclonal antibodies are described below (for example, Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991)). Human antibodies generated via human B-cell hybridoma technology are described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4): 265-268 (2006) (describing human-human hybridomas). Human hybridoma technology (Trioma technology) is described in Vollmers and Brandlein, Histology and Histopathology, 20(3):927-937 (2005), and Vollmers and Brandlein, Methods and Findings in Experimental and Clinical Pharmacology, 27(3):185-91 (2005).

In an alternative embodiment, human antibodies can also be generated by isolating Fv clone variable region sequences selected from human-derived phage display libraries. Such variable region sequences can then be combined with a desired human constant region. Techniques for selecting human antibodies from antibody libraries are described below.

In one embodiment, an antibody in the present disclosure (for example, an anti-IL-8 antibody, anti-CXCR1 antibody, or anti-CXCR2 antibody) may be isolated by screening combinatorial libraries for antibodies with one or more desired activities. For example, a variety of methods are known in the art for generating phage display libraries and screening such libraries for antibodies possessing desired binding characteristics. Such methods are reviewed in Hoogenboom et al., in Methods in Molecular Biology 178:1-37 (O'Brien et al., ed., Human Press, Totowa, N J, 2001), and further described, for example, in McCafferty et al., Nature 348:552-554; Clackson et al., Nature 352: 624-628 (1991); Marks et al., J. Mol. Biol. 222: 581-597 (1992); Marks and Bradbury, Molecular Biology 248:161-175 (Lo, ed., Human Press, Totowa, N J, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods in one embodiment, VH and VL repertoires can be separately cloned by polymerase chain reaction (PCR) and recombined randomly in phage libraries, which may then be screened for antigen-binding phage as described in Winter et al., Ann. Rev. Immunol., 12: 433-455 (1994). The phages display antibody fragments, for example, scFv and Fab. Libraries from immunized sources can provide high-affinity antibodies to the immunogen without the requirement of constructing hybridomas. In an alternative embodiment, the naive repertoire can also be cloned (for example, from human) to provide a single source of antibodies to a wide range of non-self and also self-antigens without any immunization as described in Griffiths et al., EMBO J, 12: 725-734 (1993). In yet another embodiment, naive libraries can also be made synthetically by cloning non-rearranged V-gene segments from stem cells, and using PCR primers containing random sequence to encode the hypervariable region CDR3 and to accomplish rearrangement in vitro, as described in Hoogenboom and Winter, J. Mol. Biol., 227: 381-388 (1992). Patent publications describing human antibody phage libraries include, for example: U.S. Pat. No. 5,750,373; US2005/0079574; US2005/0119455; US2005/0266000; US2007/0117126; US2007/0160598; US2007/0237764; US2007/0292936; and US2009/0002360.

Antibodies or antibody fragments isolated from human antibody libraries are considered human antibodies or human antibody fragments herein.

In one embodiment, an antibody in the present disclosure (for example, an anti-IL-8 antibody, anti-CXCR1 antibody, or anti-CXCR2 antibody) is a multispecific antibody (for example, a bispecific antibody). Multispecific antibodies are antibodies (for example, monoclonal antibodies) that have binding specificities for at least two different sites. In one embodiment, one of the binding specificities is for an antigen (for example, IL-8, CXCR1, or CXCR2) and the other is for any other antigen. In another embodiment, a bispecific antibody may bind to different two epitopes of an antigen (for example, IL-8, CXCR1, or CXCR2). Bispecific antibodies may be used to localize cytotoxic agents to cells which express the antigen (for example, IL-8, CXCR1, or CXCR2). Bispecific antibodies can be prepared as full-length antibodies or antibody fragments.

Techniques for producing multispecific antibodies include, but are not limited to, recombinant co-expression of two immunoglobulin heavy chain-light chain pairs having different specificities (for example, Milstein and Cuello, Nature 305: 537 (1983); WO93/08829; and Traunecker et al., EMBO J. 10: 3655 (1991)), and knob-in-hole engineering (for example, U.S. Pat. No. 5,731,168). Multispecific antibodies may also be made by engineering electrostatic steering effects for making antibody Fc-heterodimeric molecules (for example, WO2009/089004A1); cross-linking two or more antibodies or antibody fragments (for example, U.S. Pat. No. 4,676,980; and Brennan et al., Science, 229: 81 (1985)); using leucine zippers to produce bispecific antibodies (for example, Kostelny et al., J. Immunol., 148(5):1547-1553 (1992)); using "diabody" technology for producing bispecific antibody fragments (for example, Hollinger et al., Proc. Natl. Acad. Sci. USA, 90:6444-6448 (1993)); using scFv dimers (for example, Gruber et al., J. Immunol., 152:5368 (1994)); and preparing trispecific antibodies (for example, Tutt et al., J. Immunol. 147: 60 (1991)). Engineered antibodies with three or more functional antigen binding sites, including "octopus antibodies" are also included herein (for example, US2006/0025576).

In one embodiment, an antibody in the present disclosure (for example, an anti-IL-8 antibody, anti-CXCR1 antibody, or anti-CXCR2 antibody) or an antibody fragment thereof may be a "dual acting Fab" or "DAF" comprising an antigen-binding site that binds to an antigen (for example, IL-8, CXCR1, or CXCR2) as well as another, different antigen (for example, US2008/0069820).

In one embodiment, amino acid sequence variants (mutants) of an antibody in the present disclosure (for example, an anti-IL-8 antibody, anti-CXCR1 antibody, or anti-CXCR2 antibody) may be prepared by introducing appropriate modifications into the nucleotide sequence encoding the antibody, or by peptide synthesis. Such modifications can be achieved by introducing one or more arbitrary deletions, insertions, substitutions of arbitrary amino acids (residues), or combinations thereof into the amino acid sequences. Any combination of deletion, insertion, and substitution can be used as long as the final construct possesses the desired characteristics (for example, antigen binding).

In one embodiment, when antibody variants (mutants) having one or more amino acid substitutions are provided, sites of interest for substitutional mutagenesis may include the HVRs and FRs.

Conservative substitutions in one embodiment are shown in Table 1 under the heading of "Preferred substitutions", and more substantial changes are shown in Table 1 under the heading of "Exemplary substitutions", and further described below in reference to amino acid side chain classes. Amino acid substitutions may be introduced into an antibody of interest and the products may be screened for a desired activity, for example, retained/improved antigen-binding, reduced immunogenicity, or improved ADCC or CDC.

TABLE 1

| Original residue | Exemplary substitutions | Preferred substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids can be grouped based on common side-chain properties:

(1) hydrophobic: Norleucine, Met, Ala, Val, Leu, Ilie;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe

Non-conservative substitutions mean exchanging a member of one of these classes for another class.

In one embodiment, amino acid insertions include amino- and/or carboxyl-terminal fusions of one or two residues, or polypeptides containing three to hundred or more residues, as well as insertions of single or multiple amino acid residues into an amino acid sequence. Examples of terminal insertions include an antibody with an N-terminal methionyl residue. Other examples of insertional variants (mutants) include the fusion of the N- and/or C-terminus of the antibody to an enzyme (for example, an enzyme for ADEPT) or a polypeptide which increases the plasma half-life of the antibody.

Herein, "percent (%) amino acid sequence identity" with respect to a reference polypeptide sequence is defined as the percentage of amino acid residues in a candidate sequence, that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publicly available computer software such as BLAST, BLAST-2, ALIGN, Megalign (DNASTAR) software, or GENETYX®. Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, where it is registered under U.S. Copyright Registration No. TXU510087. The ALIGN-2 program is publicly available from Genentech, Inc. (South San Francisco, California), or may be compiled from the source code. The ALIGN-2 program is compiled for use on a UNIX® operating system, including digital UNIX V4.0D. All sequence comparison parameters are set by ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values herein are obtained using the computer program ALIGN-2.

In one embodiment, an amino acid sequence which has appropriate substitution, deletion, or insertion of one or more amino acids in the amino acid sequence of a CDR region, heavy chain variable region, light chain variable region, heavy chain constant region, light chain constant region, whole heavy chain region, whole light chain region, or any particular region thereof, of an antibody in the present disclosure (for example, an anti-IL-8 antibody, anti-CXCR1 antibody, or anti-CXCR2 antibody), and has binding activity to an antigen (for example, IL-8, CXCR1, or CXCR2), can also be obtained from a nucleic acid that hybridizes under stringent conditions to a nucleic acid that comprises a nucleotide sequence encoding the amino acid sequence of that region. Exemplary stringent hybridization conditions to isolate a nucleic acid that hybridizes under stringent conditions are 6 M urea, 0.4% SDS, 0.5×SSC, and 37° C., or conditions equivalent or corresponding thereto. Isolation of nucleic acids with higher homology can be expected by using more stringent conditions, for example, 6 M urea, 0.4% SDS, 0.1×SSC, and 42° C. Conditions of post-hybridization washes include, for example, 0.5×SSC (where 1×SSC is, for example, 0.15 M NaCl and 0.015 M sodium citrate, pH 7.0) and 0.1% SDS at 60° C., preferably 0.2×SSC and 0.1% SDS at 60° C., more preferably 0.2×SSC and 0.1% SDS at 62° C., even more preferably 0.2×SSC and 0.1% SDS at 65° C., and yet more preferably 0.1×SSC and 0.1% SDS at 65° C. The washing time and the number of washes can be appropriately adjusted; for example, a 20-minute wash may be performed three times. Isolated nucleic acid can be sequenced by known methods.

In an alternative embodiment, instead of the above hybridization techniques, gene amplification methods, for example, PCR, using primers synthesized based on the information of the nucleotide sequence encoding the amino acid sequence of the CDR region, heavy chain variable region, light chain variable region, heavy chain constant region, light chain constant region, whole heavy chain region, whole light chain region, or any particular region thereof, can also be employed to isolate a nucleic acid that hybridizes under stringent conditions to a nucleic acid comprising a nucleotide sequence that encodes the amino acid sequence of that region.

A nucleic acid thus isolated has at least 50% or higher, preferably 70% or higher, 75% or higher, 80% or higher, 85% or higher, and more preferably 90% or higher (for example, 91%, 92%, 93%, 94%, 95%, 96%, 97%, 98%, or 99% or higher) overall sequence identity to the nucleotide sequence of the region of interest. An antibody having the amino acid sequence encoded by such an isolated nucleic acid is advantageous if it is functionally (substantially) equivalent (for example, any one or more indicators or characteristics such as antigen binding or retention in blood are (substantially) equivalent) to the antibody having the amino acid sequence of the region of interest; however, it is not limited thereto. Here, the term "substantially" is intended to mean retaining at least 50% or more, preferably 70% or more, 75% or more, 80% or more, 85% or more, and more preferably 90% or more (for example, 91%, 92%, 93%, 94%, 95%, 96%, 97%, 98%, or 99% or more) of the function (for example, it is possible to focus on any one or more indicators or characteristics such as antigen binding and retention in blood) as compared to the function possessed by the antibody having the amino acid sequence of the region of interest, when assessed by methods known to those skilled in the art.

In one embodiment, an antibody in the present disclosure (for example, an anti-IL-8 antibody, anti-CXCR1 antibody, or anti-CXCR2 antibody) may be glycosylated. Addition or deletion of glycosylation sites to an antibody can readily be accomplished by altering the amino acid sequence such that glycosylation sites are created or removed.

In one embodiment, where an antibody in the present disclosure (for example, anti-IL-8 antibody, anti-CXCR1 antibody, or anti-CXCR2 antibody) comprises an Fc region, sugar chains that can be attached to the Fc domain may vary. Naive antibodies produced by animal cells typically contain a branched, biantennary oligosaccharide, which is attached via an N-linkage to Asn297 of the CH2 domain of the Fc region (Wright et al. TIBTECH 15:26-32 (1997)). The oligosaccharide includes, for example, mannose, N-acetylglucosamine (GlcNAc), galactose, and sialic acid, as well as fucose attached to GlcNAc in the "stem" of the biantennary oligosaccharide structure. In one embodiment, modifications of the oligosaccharide in an antibody of the present disclosure may be made to create antibody variants having certain improved properties.

Herein, "effector functions" refer to biologically activities attributable to the Fc region of an antibody (for example, an anti-IL-8 antibody, anti-CXCR1 antibody, or anti-CXCR2 antibody), and can vary with the antibody isotype. Examples of antibody effector functions include, but are not limited to, C1q binding or complement-dependent cytotoxicity (CDC); Fc receptor binding; antibody-dependent cell-mediated cytotoxicity (ADCC); phagocytosis; down regulation of cell surface receptors (for example, B cell receptor); and B cell activation.

The term "Fc region" herein is used to define the C-terminal region of an immunoglobulin heavy chain that contains at least a portion of the constant region. The term includes native Fc regions and variant Fc regions. The native Fc region refers to the Fc region of a native antibody. Examples of the Fc region of native human IgG include, for example, the Fc region contained in the human IgG1 constant region (SEQ ID NO: 100), human IgG2 constant region (SEQ ID NO: 101), human IgG3 constant region (SEQ ID NO: 102), or human IgG4 constant region (SEQ ID NO: 103) described above. In one embodiment, the Fc region of a human IgG heavy chain extends from Cys226, or from Pro230, to the C terminus of the heavy chain. However, the C-terminal lysine (Lys447) of the Fc region, or the C-terminal glycine (Gly446) and lysine (Lys447) of the Fc domain may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD (1991).

Unlike FcγR which belongs to the immunoglobulin superfamily, "FcRn" herein, human FcRn in particular, is structurally similar to polypeptides of major histoincompatibility complex (MHC) class I, sharing 22% to 29% sequence identity with class I MHC molecules (Ghetie et al., Immunol. Today (1997) 18 (12), 592-598). FcRn is expressed as a heterodimer consisting of soluble β or light chain (β2 microglobulin) complexed with transmembrane α or heavy chain. Like MHC, the α chain of FcRn consists of three extracellular domains (α1, α2, and α3) and its short cytoplasmic domain anchors the protein onto the cell surface. The α1 and α2 domains interact with the FcRn-binding domain of the antibody Fc region (Raghavan et al., Immunity, (1994), 1: 303-15). FcRn is expressed in the maternal placenta or yolk sac of mammals and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG. Typically, binding of FcRn to IgG molecules is strictly pH dependent. The optimal binding is observed in an acidic pH range below 7.0. The polynucleotide and amino acid sequences of human FcRn may be derived, for example, from the precursor shown in NM_004107.4 and NP_004098.1 (containing the signal sequence), respectively (RefSeq accession numbers are shown in parentheses). The precursor forms a complex with human β2-microglobulin in vivo. Thus, soluble human FcRn capable of forming a complex with human β2-microglobulin can be produced using known recombinant expression techniques, and appropriately used in various experimental systems. Such soluble human FcRn capable of forming a complex with human β2-microglobulin may be used to assess antibodies or Fc region variants for their FcRn-binding activity. FcRn is not particularly limited as long as it is in a form capable of binding to the FcRn-binding domain, and preferably human FcRn.

In one embodiment, when an antibody in the present disclosure (for example, an anti-IL-8 antibody, anti-CXCR1 antibody, or anti-CXCR2 antibody) or a Fc region variant thereof has FcRn-binding activity, the antibody or Fc region variant preferably has an "FcRn-binding domain", more preferably has a human FcRn-binding domain. The FcRn-binding domain is not particularly limited as long as the antibody (for example, an anti-IL-8 antibody, anti-CXCR1 antibody, or anti-CXCR2 antibody) has FcRn-binding activity or affinity at an acidic pH and/or a neutral pH. Alternatively, the FcRn-binding domain may have activity to bind to FcRn directly or indirectly. Such domains include, but are not limited to, for example, the Fc regions of IgG-type immunoglobulins, albumin, albumin domain 3, anti-FcRn antibodies, anti-FcRn peptides, and anti-FcRn Scaffold molecules, which have the activity to directly bind to FcRn, and molecules that bind to IgG or albumin, which have the activity of indirectly binding to FcRn. Alternatively, it is possible to use, for example, a domain that has FcRn-binding activity at an acidic pH and/or a neutral pH. If the domain originally has FcRn-binding activity at an acidic pH and/or a neutral pH, it can be used without modification. When the domain has no or weak FcRn-binding activity at an acidic pH and/or a neutral pH, amino acid residues in the FcRn-binding domain of the antibody or the Fc region variant may be modified to give FcRn-binding activity at an acidic pH and/or a neutral pH. Alternatively, amino acids of the domain that originally has FcRn-binding activity at an acidic pH and/or a neutral pH may be modified to increase its FcRn-binding activity. Amino acid modifications desired for the FcRn-binding domain can be identified by comparing the FcRn-binding activity at an acidic pH and/or a neutral pH before and after the amino acid modifications.

The FcRn-binding domain is preferably a region which directly binds to FcRn. Preferred examples of the FcRn-binding domain include the constant regions and Fc regions of antibodies. However, regions capable of binding to a polypeptide that has FcRn-binding activity, such as albumin or IgG, can bind indirectly to FcRn via albumin or IgG. Thus, the FcRn-binding regions may be regions that bind to a polypeptide with binding activity to albumin or IgG. Without limitation, the FcRn-binding activity of an FcRn-binding domain is preferably greater at a neutral pH to enhance antigen elimination from plasma, whereas the FcRn-binding activity of an FcRn-binding domain is preferably greater at an acidic pH to improve antibody retention in plasma. For example, it is possible to select and use a FcRn-binding domain whose FcRn-binding activity is originally greater at a neutral pH or acidic pH. Alternatively, amino acids of an antibody or Fc region may be modified to confer FcRn-binding activity at a neutral pH or acidic pH. Alternatively, the pre-existing FcRn-binding activity at a neutral pH or acidic pH may be increased.

Whether the FcRn-binding activity of an antibody (for example, an anti-IL-8 antibody, anti-CXCR1 antibody, or anti-CXCR2 antibody) or an Fc region (variant) has been increased, (substantially) retained, or reduced as compared to that before its modification can be determined by any methods known to persons skilled in the art without particular limitation and it is also possible to use the methods described in the present Examples. For example, BIACORE, Scatchard plot, flow cytometer, and such may be used (WO2013/046722). In these assays, the extracellular domain of human FcRn may be used as a soluble antigen. The conditions in measuring the FcRn-binding activity of an antibody or Fc region (variant) can be appropriately determined by a person skilled in the art except for pH, and are not particularly limited. Such assays can be carried out, for example, under the condition of MES buffer at 37° C., as described in WO2009/125825. The FcRn-binding activity of an antibody or Fc region (variant) can be assessed, for example, by allowing FcRn to flow as an analyte onto a chip with the antibody immobilized thereon.

Furthermore, the FcRn-binding activity of an antibody or Fc region (variant) can be assessed based on the dissociation constant (KD), apparent dissociation constant (apparent KD), dissociation rate (kd), or apparent dissociation rate (apparent kd).

When the FcRn-binding activity of the FcRn-binding domain in an antibody (for example, an anti-IL-8 antibody, anti-CXCR1 antibody, or anti-CXCR2 antibody) or Fc region (variant) is measured, an acidic or neutral pH may be appropriately used. The temperature used to assess the FcRn-binding activity (binding affinity) of an FcRn-binding domain may be any temperature from 10° C. to 50° C. Preferably, the temperature used to determine the FcRn-binding activity (binding affinity) of a human FcRn-binding domain is 15° C. to 40° C. More preferably, the temperature used to determine the FcRn-binding activity (binding affinity) of an FcRn-binding domain is any temperature from 20° C. to 35° C., such as any one of 20, 21, 22, 23, 24, 25, 26, 27, 28, 29, 30, 31, 32, 33, 34, and 35° C., but is not limited thereto. 25° C. is a non-limiting example.

In one embodiment, amino acids included in the amino acid sequence of an antibody of the present disclosure (for example, an anti-IL-8 antibody, anti-CXCR1 antibody, or anti-CXCR2 antibody) may be subjected to post-translational modifications (for example, modification of N-terminal glutamine to pyroglutamate by pyroglutamylation is well known to those skilled in the art). It is understood that such amino acid sequences with post-translationally modified amino acids are also included as equivalents to the amino acid sequences described in the present disclosure.

In one embodiment, an antibody of the present disclosure (for example, an anti-IL-8 antibody, anti-CXCR1 antibody, or anti-CXCR2 antibody) may be derivatized by containing additional non-proteinaceous moieties. Moieties suitable for antibody derivatization of the antibody include, for example, water soluble polymers. Examples of water soluble polymers include polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyamino acids (either homopolymers or random copolymers), dextran or poly (n-vinyl pyrrolidone) polyethylene glycol, polypropylene glycol homopolymers, polypropylene oxide/ethylene oxide copolymers, polyoxyethylated polyols (for example, glycerol), polyvinyl alcohol, and any mixtures thereof. As an example of the moieties, polyethylene glycol propionaldehyde may have advantages in manufacturing due to its stability in water. The polymers may be of any molecular weight and may be branched or unbranched. The number of polymers attached to the antibody may vary, and if one or more polymers are attached, they can be the same or different molecules. In general, the number and/or type of polymers for use for derivatization may be determined based on considerations of, for example, the particular properties or functions of the antibody to be improved, whether the antibody derivative will be used in a therapy under defined conditions, etc.

In one embodiment, conjugates of an antibody of the present disclosure (for example, an anti-IL-8 antibody, anti-CXCR1 antibody, or anti-CXCR2 antibody) and nonproteinaceous moiety that may be selectively heated by exposure to radiation are provided. The non-proteinaceous moiety may be, for example, a carbon nanotube (Kam et al., Proc. Natl. Acad. Sci. USA 102: 11600-11605 (2005)). The radiation may be of any wavelength as long as it achieves the desired purpose, and may be of wavelengths that do not harm ordinary cells, but which heat the non-proteinaceous moiety to a temperature at which cells proximal to the antibody-non-proteinaceous moiety are killed.

The term “IL-8” in the present disclosure refers to, unless specifically indicated otherwise, native IL-8 derived from any vertebrates, primates (for example, humans, cynomolgus monkeys, and rhesus monkeys), and other mammals (for example, rabbits and dogs; however, mice and rats do not possess endogenous IL-8). IL-8 includes intact IL-8, any in vivo modified form of IL-8, and naturally occurring IL-8 derivatives such as splicing variants and allelic variants. A typical example of human IL-8 amino acid sequence is shown in SEQ ID NO: 22. Furthermore, for a non-limiting example of the human IL-8 amino acid sequence, the sequence of human interleukin-8 precursor is registered as NP_000575.1 in NCBI. In addition, a non-limiting example of the amino acid sequence of cynomolgus monkey IL-8 is registered as XP_005555144.1 in NCBI.

CXCR1 is also known as interleukin 8 receptor alpha, IL8RA, or CD181, and CXCR2 is also known as interleukin 8 receptor beta or IL8RB, both of which are chemokine receptors. IL-8 is known to exert its physiological actions via binding to its receptors CXCR1 and CXCR2 (Science. 1991; 253:1278-80; Science. 1991; 253:1280-3). It has been reported that CXCR1 is only activated by IL-8 and granulocyte chemotactic protein-2, and CXCR2 is activated by binding to IL-8 and various molecules such as GROα, β, and γ, neutrophil-activating peptide, and granulocyte chemotactic protein-2 (Neuro-oncol. 2005; 7:122-33). No other IL-8 receptors than CXCR1 and CXCR2 have been reported so far. As described in the present Examples, the present inventors have demonstrated that the ability of neutrophils to migrate towards IL-8 is blocked by an IL-8-neutralizing antibody and also by a CXCR2 inhibitor, and thus it is easily predicted that not only anti-IL-8 antibodies but also IL-8 signal inhibitors including CXCR1 inhibitors and CXCR2 inhibitors are useful against endometriosis, adhesion, and adenomyosis described in the present Examples.

The term “CXCR1” in the present disclosure refers to, unless specifically indicated otherwise, native CXCR1 present in any vertebrates, primates (for example, humans, cynomolgus monkeys, and rhesus monkeys), and other mammals (for example, rabbits and dogs). CXCR1 includes intact CXCR1, any in vivo modified form of CXCR1, and naturally occurring CXCR1 derivatives such as splicing variants and allelic variants. A non-limiting example of the amino acid sequence of human CXCR1 is registered as NP_000625.1 in NCBI.

The term “CXCR2” in the present disclosure refers to, unless specifically indicated otherwise, native CXCR2 present in any vertebrates, primates (for example, humans, cynomolgus monkeys, and rhesus monkeys), and other mammals (for example, rabbits and dogs). CXCR2 includes intact CXCR2, any in vivo modified form of CXCR2, and naturally occurring CXCR2 derivatives such as splicing variants and allelic variants. Non-limiting examples of the amino acid sequence of human CXCR2 are registered as NP_001161770.1 and NP_001548.1 in NCBI.

IL-8 is produced by immune cells such as monocytes, macrophages, neutrophils, and lymphocytes, skin fibroblasts, keratinocytes, vascular endothelial cells, melanocytes, hepatocytes, and various tumor cell lines. IL-8 is a potent chemokine for neutrophils, and is involved in migration of neutrophils to inflammatory sites. It has been reported that, when IL-8 binds to its high-affinity receptors (CXCR1 and CXCR2) on the surface of neutrophils, it activates neutrophils by promoting degranulation and increasing the concentration of cytoplasmic free $Ca^{2+}$, and induces their migration, thereby destroying infiltrated tissues (WO2004/058797).

As described in the present Examples, the present inventors revealed that CXCR1 and CXCR2 were expressed in immune cells such as neutrophils, mononuclear cells, and macrophages, endometriosis epithelial cells, and vascular endothelial cells, but were not expressed in stromal cells and muscle fibroblasts. Furthermore, addition of IL-8 or anti-IL-8 antibody to endometriosis-derived stromal cells and muscle fibroblasts that had been collected from human endometriosis patients and cultured did not show changes such as cell proliferation or atrophy (data not shown).

These results were not consistent with the report of Ulukus et al. (Human Reproduction 2005 20(3):794-80) that CXCR1 is expressed at high levels in the epithelium, stroma, and fibrotic areas of endometriosis tissues. In the Ulukus's report, the overall staining intensity was high. CXCR2 was also, though weakly positive, stained on stromal cells as well as vascular endothelial cells. In addition, the above results were not consistent with the report of Iwabe et al., Fertility and Sterility 1998 69(5):924-930, that in vitro experiments showed that the proliferation of stromal cells derived from endometriosis patients was enhanced by IL-8 but suppressed by addition of an anti-IL-8 antibody. In the Iwabe's report, endometriosis lesions from human endometriosis patients were subjected to removal of epithelial cells to obtain stromal cells, and then IL-8 was added to examine cell proliferation. The response was as weak as around 20%.

Meanwhile, as described in the present Examples, the present inventors demonstrated in a non-human primate endometriosis model that proliferative epithelial and stromal cells showed atrophic changes upon administration of an IL-8 signal inhibitor such as antibody H1009/L395-F1974m.

Without intending to be bound by theory, it is presumed in one aspect that immune cells might have coexisted in the Iwabe's report because their experiments were carried out soon after cell passage. Since CXCR1 and CXCR2 are not expressed in stromal cells, it is considered that CXCR1- or CXCR2-mediated IL-8 signal does not directly act on stromal cells as its target, but instead acts on endometrial epithelia and immune cells as direct targets and indirectly acts on stromal cells via signal from the endometrial epithelia and immune cells.

The “IL-8 signal inhibitor” in the present disclosure is not particularly limited as long as it can inhibit IL-8 signal directly or indirectly and partially or completely. For example, the IL-8 signal inhibitor may be a nucleic acid (for example, double-stranded nucleic acid such as siRNA), a protein (including antibodies and antibody fragments), a peptide, or other compound (for example, low molecular weight compound). In one aspect, the IL-8 signal inhibitor may be an IL-8 inhibitor, CXCR1 inhibitor, or CXCR2 inhibitor, and in this case, they include, for example, nucleic acids (for example, double-stranded nucleic acids such as siRNAs), proteins (including antibodies and antibody fragments, more specifically, anti-IL-8 antibodies, anti-CXCR1 antibodies, anti-CXCR2 antibodies, and antibody fragments fully or partially retaining their functions), peptides, or other compounds (for example, low molecular weight compounds).

If an IL-8 signal inhibitor partially or fully inhibits the binding of IL-8 to its receptor CXCR1 and/or CXCR2, the inhibition of IL-8 preferably reduces or alters the normal level or type of activity that should occur upon binding of IL-8 to the receptor without the inhibition. Such reduction or change may be observed, for example, as an inhibition of IL-8-induced elastase release or calcium flux, inhibition of IL-8-induced increase in expression of CD11b (Mac-1), or inhibition of decrease in expression of L-selectin. Such inhibition includes decreases or changes in the above-mentioned level or type of activity, for example, by at least 10%, 20%, 30%, 40%, 50%, 60%, 70%, 80%, 90%, 95%, 99%, or 100% as compared to that in the absence of the IL-8 signal inhibitor.

In one embodiment, a CXCR1 inhibitor in the present disclosure may bind (be specific) to CXCR1 but not to CXCR2, or may bind (be specific) to both CXCR1 and CXCR2 (also referred to as CXCR1/CXCR2 inhibitor).

In one embodiment, a CXCR2 inhibitor in the present disclosure may bind (be specific) to CXCR2 but not to CXCR1, or may bind (be specific) to both CXCR1 and CXCR2 (also referred to as CXCR1/CXCR2 inhibitors).

In one embodiment, specific examples of the CXCR1 inhibitor and/or CXCR2 inhibitor in the present disclosure include, for example, anti-CXCR1 antibodies, Repartaxin, and Repartaxin derivatives described in WO2010/056753; CXCR1 and/or CXCR2 inhibitors described in WO2011/042466; CXCR1 and CXCR2 chemokine antagonists described in WO2005/113534 and WO2003/057676; CXCR2-binding polypeptides described in WO2012/062713 and WO2013/168108; CXCR2 inhibitors described in WO2008/061740, WO2008/061741, WO2008/062026, WO2009/106539, WO2010/015613, and WO2013/030803.

In one embodiment, specific examples of the IL-8 inhibitor in the present disclosure include, for example, IL-8 mimetics described in JP2006-117633A; IL-8 expression inhibitors disclosed in JP2013-180992A (or JP5496232B); IL-8 production inhibitors disclosed in JPH9-2954A (or JP3008010B); antibody fragment-polymer complexes disclosed in WO1998/037200; anti-IL-8 antibodies, multispecific antibodies that bind to antigens including IL-8, and variants thereof disclosed in WO1995/023865, WO2009/026117, WO2013/166099, WO2006/113643, WO2004/058797, WO2008/130969, WO2011/100271, WO98/58671, WO2014/149733, US2003/0077283A1, etc. In another embodiment, these anti-IL-8 antibody variants may additionally have one or more of the properties described herein below for highly functional anti-IL-8 antibodies.

In one embodiment, the term “anti-IL-8 antibody” or “antibody that binds to IL-8” in the present disclosure refers to an antibody that can bind with sufficient affinity to IL-8 and thus is useful as a composition for detection, diagnosis, therapy, and/or prevention by targeting IL-8.

In one embodiment, the degree of non-specific binding of an anti-IL-8 antibody to unrelated non-IL-8 proteins may be, for example, below 10% of the degree of binding of the antibody to IL-8.

In one embodiment, an anti-IL-8 antibody in the present disclosure has IL-8-neutralizing activity. The IL-8-neutralizing activity may refer to activity of inhibiting a biological activity shown by IL-8 or may refer to activity of inhibiting the binding of IL-8 to its receptor (CXCR1 or CXCR2).

In one embodiment, an anti-IL-8 antibody in the present disclosure may be a chimeric antibody, a humanized antibody, or a human antibody.

In one embodiment, an anti-IL-8 antibody in the present disclosure preferably has cross-reactivity with animals with endogenous IL-8 (for example, rabbits), or in some cases preferably is an anti-primate IL-8 antibody (preferably an antibody against IL-8 of a nonhuman primate with menstruation similar to human menstruation, such as cynomolgus monkey or baboon, or an anti-human IL-8 antibody (for example, an anti-human IL-8 neutralizing antibody)).

As embodied in the present Examples, without limitation, the present inventors discovered an amino acid modification technology capable of conferring high functionality to an antibody (for example, an anti-IL-8 antibody, anti-CXCR1 antibody, or anti-CXCR2 antibody), and conceived highly functional anti-IL-8 antibodies based on that discovery. Non-limiting examples of such antibodies are described below.

In one embodiment, an anti-IL-8 antibody in the present disclosure may be an anti-IL-8 antibody that may possess pH-dependent affinity for IL-8. Such an anti-IL-8 antibody comprises, for example, sequences comprising substitution of at least one, two, three, four, five, six, seven, eight, or more amino acids in the amino acid sequences of:

(a) HVR-H1 comprising the amino acid sequence of SEQ ID NO: 23;
(b) HVR-H2 comprising the amino acid sequence of SEQ ID NO: 24;
(c) HVR-H3 comprising the amino acid sequence of SEQ ID NO: 25;
(d) HVR-L1 comprising the amino acid sequence of SEQ ID NO: 26;
(e) HVR-L2 comprising the amino acid sequence of SEQ ID NO: 27; and
(f) HVR-L3 comprising the amino acid sequence of SEQ ID NO: 28.

Unless specifically indicated otherwise, the amino acids may be substituted with any other amino acids. In a further embodiment, an anti-IL-8 antibody in the present disclosure may additionally at least comprise substitution with a different amino acid or with an amino acid indicated below at a position(s) selected from the group consisting of the positions described below:

(1) serine at position 8 in the sequence of SEQ ID NO: 26; asparagine at position 1 and leucine at position 5 in the sequence of SEQ ID NO: 27; and glutamine at position 1 in the sequence of SEQ ID NO: 28;
(2) substitution of alanine at position 6 with aspartic acid, and substitution of arginine at position 11 with proline in the sequence of SEQ ID NO: 24; and substitution of tyrosine at position 3 with histidine in the sequence of SEQ ID NO: 25;
(3) substitution of glycine at position 8 with tyrosine and substitution of tyrosine at position 9 with histidine in the sequence of SEQ ID NO: 24;
(4) substitution of alanine at position 6 with aspartic acid, substitution of glycine at position 8 with tyrosine, substitution of tyrosine at position 9 with histidine, and substitution of arginine at position 11 with proline in the sequence of SEQ ID NO: 24; and substitution of tyrosine at position 3 with histidine in the sequence of SEQ ID NO: 25;

(5) substitution of asparagine at position 1 with lysine and substitution of leucine at position 5 with histidine in the sequence of SEQ ID NO: 27; and substitution of glutamine at position 1 with lysine in the sequence of SEQ ID NO: 28;

(6) substitution of serine at position 8 with glutamine acid in the sequence of SEQ ID NO: 26; substitution of asparagine at position 1 with lysine and substitution of leucine at position 5 with histidine in the sequence of SEQ ID NO: 27; and substitution of glutamine at position 1 with lysine in the sequence of SEQ ID NO: 28;

(7) substitution of tyrosine at position 9 with histidine and substitution of arginine at position 11 with proline in the sequence of SEQ ID NO: 24; substitution of tyrosine at position 3 with histidine in the sequence of SEQ ID NO: 25; substitution of asparagine at position 1 with lysine and substitution of leucine at position 5 with histidine in the sequence of SEQ ID NO: 27; and substitution of glutamine at position 1 with lysine in the sequence of SEQ ID NO: 28; and (8) substitution of alanine at position 6 with aspartic acid, substitution of glycine at position 8 with tyrosine, substitution of tyrosine at position 9 with histidine, and substitution of arginine at position 11 with proline in the sequence of SEQ ID NO: 24; substitution of tyrosine at position 3 with histidine in the sequence of SEQ ID NO: 25; substitution of asparagine at position 1 with lysine and substitution of leucine at position 5 with histidine in the sequence of SEQ ID NO: 27; and substitution of glutamine at position 1 with lysine in the sequence of SEQ ID NO: 28.

In a further or alternative embodiment, an anti-IL-8 antibody in the present disclosure that may possess pH-dependent affinity for IL-8 comprises any one or more amino acid sequences selected from the group consisting of:

(a) HVR-H1 comprising the amino acid sequence of SEQ ID NO: 23, or HVR-H1 that has at least 65%, 70%, 75%, or higher, preferably 80%, 85%, 90%, or higher, and more preferably 95% or higher sequence identity thereto;

(b) HVR-H2 comprising the amino acid sequence of SEQ ID NO: 24 or 29, or HVR-H2 that has at least 65%, 70%, 75%, or higher, preferably 80%, 85%, 90%, or higher, and more preferably 95% or higher sequence identity thereto;

(c) HVR-H3 comprising the amino acid sequence of SEQ ID NO: 25 or 30, or HVR-H3 that has at least 65%, 70%, 75%, or higher, preferably 80%, 85%, 90%, or higher, and more preferably 95% or higher sequence identity thereto;

(d) HVR-L1 comprising the amino acid sequence of SEQ ID NO: 26, or HVR-L1 that has at least 65%, 70%, 75%, or higher, preferably 80%, 85%, 90%, or higher, and more preferably 95% or higher sequence identity thereto;

(e) HVR-L2 comprising the amino acid sequence of SEQ ID NO: 27, 31, or 107, or HVR-L2 that has at least 65%, 70%, 75%, or higher, preferably 80%, 85%, 90%, or higher, and more preferably 95% or higher sequence identity thereto; and (f) HVR-L3 comprising the amino acid sequence of SEQ ID NO: 28 or 32, or HVR-L3 that has at least 65%, 70%, 75%, or higher, preferably 80%, 85%, 90%, or higher, and more preferably 95% or higher sequence identity thereto.

Here, an HVR with a particular % sequence identity to a reference amino acid sequence can be functionally equivalent to the HVR comprising the reference amino acid sequence. Furthermore, the anti-IL-8 antibody may comprise, for example, HVR-H2 comprising the amino acid sequence of SEQ ID NO: 29 and HVR-H3 comprising the amino acid sequence of SEQ ID NO: 30, and/or HVR-L2 comprising the amino acid sequence of SEQ ID NO: 31 and HVR-L3 comprising the amino acid sequence of SEQ ID NO: 32. Moreover, the anti-IL-8 antibody may additionally at least comprise substitution with a different amino acid or with an amino acid indicated below at a position(s) selected from the group consisting of the positions described below:

(1) serine at position 8 in the amino acid sequence of SEQ ID NO: 26; asparagine at position 1 and leucine at position 5 in the amino acid sequence of SEQ ID NO: 27; and glutamine at position 1 in the amino acid sequence of SEQ ID NO: 28;

(2) substitution of alanine at position 6 with aspartic acid and substitution of arginine at position 11 with proline in the amino acid sequence of SEQ ID NO: 24; and substitution of tyrosine at position 3 with histidine in the amino acid sequence of SEQ ID NO: 25;

(3) substitution of glycine at position 8 with tyrosine and substitution of tyrosine at position 9 with histidine in the amino acid sequence of SEQ ID NO: 24;

(4) substitution of alanine at position 6 with aspartic acid, substitution of glycine at position 8 with tyrosine, substitution of tyrosine at position 9 with histidine, and substitution of arginine at position 11 with proline in the amino acid sequence of SEQ ID NO: 24; and substitution of tyrosine at position 3 with histidine in the amino acid sequence of SEQ ID NO: 25;

(5) substitution of asparagine at position 1 with lysine and substitution of leucine at position 5 with histidine in the amino acid sequence of SEQ ID NO: 27; and substitution of glutamine at position 1 with lysine in the amino acid sequence of SEQ ID NO: 28;

(6) substitution of serine at position 8 with glutamine acid in the amino acid sequence of SEQ ID NO: 26; substitution of asparagine at position 1 with lysine and substitution of leucine at position 5 with histidine in the amino acid sequence of SEQ ID NO: 27; and substitution of glutamine at position 1 with lysine in the amino acid sequence of SEQ ID NO: 28;

(7) substitution of tyrosine at position 9 with histidine and substitution of arginine at position 11 with proline in the amino acid sequence of SEQ ID NO: 24; substitution of tyrosine at position 3 with histidine in the amino acid sequence of SEQ ID NO: 25; substitution of asparagine at position 1 with lysine and substitution of leucine at position 5 with histidine in the amino acid sequence of SEQ ID NO: 27; and substitution of glutamine at position 1 with lysine in the amino acid sequence of SEQ ID NO: 28; and (8) substitution of alanine at position 6 with aspartic acid, substitution of glycine at position 8 with tyrosine, substitution of tyrosine at position 9 with histidine, and substitution of arginine at position 11 with proline in the amino acid sequence of SEQ ID NO: 24; substitution of tyrosine at position 3 with histidine in the amino acid sequence of SEQ ID NO: 25; substitution of asparagine at position 1 with lysine and substitution of leucine at position 5 with histidine in the amino acid sequence of SEQ ID NO: 27; and substitution of glutamine at position 1 with lysine in the amino acid sequence of SEQ ID NO: 28.

Those skilled in the art will naturally understand all possible combinations of amino acid sequences described herein.

In one embodiment, the term "functionally equivalent" in the present disclosure is, unless specifically indicated otherwise, intended to refer to retaining, when measured by methods known to persons skilled in the art, at least 50% or more, preferably 70% or more, 75% or more, 80% or more, 85% or more, and more preferably 90% or more (for example, 91%, 92%, 93%, 94%, 95%, 96%, 97%, 98%, or 99% or more) of the function possessed by an antibody containing a reference amino acid sequence, which is represented as its physicochemical property and/or biological activity etc. (for example, it is possible to focus on any one or more indicators or properties such as antigen-binding and blood retention.

In a further or alternative embodiment, an anti-IL-8 antibody in the present disclosure that may possess pH-dependent affinity for IL-8 comprises any one or more amino acid sequences selected from the group consisting of:

(A) a heavy chain variable region comprising the amino acid sequence of SEQ ID NO: 33, 34, or 108, or a heavy chain variable region that has at least 65%, 70%, 75%, or higher, preferably 80%, 85%, 90%, or higher, and more preferably 95% or higher sequence identity thereto; and (B) a light chain variable region comprising the amino acid sequence of SEQ ID NO: 35 or 109, or a light chain variable region that has at least 65%, 70%, 75%, or higher, preferably 80%, 85%, 90%, or higher, and more preferably 95% or higher sequence identity thereto.

Here, the variable region with a particular % sequence identity to the reference amino acid sequence may be functionally equivalent to the variable region comprising the reference amino acid sequence. Furthermore, for example, the anti-IL-8 antibody may comprise a heavy chain variable region comprising the amino acid sequence of SEQ ID NO: 34 and a light chain variable region comprising the amino acid sequence of SEQ ID NO: 35. Such an antibody can be advantageous in that its IL-8-neutralizing activity is stably retained in vivo (for example, in the plasma) or in that its immunogenicity is low. Moreover, when the anti-IL-8 antibody comprises a variant of the amino acid sequence of SEQ ID NO: 33, it may additionally at least comprise substitution with a different amino acid or an amino acid indicated below at one or more positions selected from the group consisting of the positions described below:

(i) substitution of alanine at position 55 with a different amino acid, e.g. aspartic acid, in the amino acid sequence of SEQ ID NO: 33;

(ii) substitution of glycine at position 57 with a different amino acid, e.g. tyrosine, in the amino acid sequence of SEQ ID NO: 33;

(iii) substitution of tyrosine at position 58 with a different amino acid, e.g. histidine, in the amino acid sequence of SEQ ID NO: 33;

(iv) substitution of arginine at position 60 with a different amino acid, e.g. proline, in the amino acid sequence of SEQ ID NO: 33;

(v) substitution of glutamine at position 84 with a different amino acid, e.g. threonine, in the amino acid sequence of SEQ ID NO: 33;

(vi) substitution of serine at position 87 with a different amino acid, e.g. aspartic acid, in the amino acid sequence of SEQ ID NO: 33; and (vii) substitution of tyrosine at position 103 with a different amino acid, e.g. histidine, in the amino acid sequence of SEQ ID NO: 33.

Those skilled in the art will naturally understand all possible combinations of amino acid sequences described above.

In another embodiment, an anti-IL-8 antibody in the present disclosure may be an antibody comprising at least one to six of the amino acid sequences of (a) to (f) listed in each of (1) to (7) below, or an antibody comprising at least one amino acid substitution in at least any one or more of the amino acid sequences of (a) to (f) listed in each. The antibody may be an anti-IL-8 antibody with pH-dependent affinity for IL-8. Unless specifically indicated otherwise, amino acids may be substituted with any other amino acids.

(1) (a) HVR-H1 comprising the amino acid sequence of SEQ ID NO: 58,
(b) HVR-H2 comprising the amino acid sequence of SEQ ID NO: 59,
(c) HVR-H3 comprising the amino acid sequence of SEQ ID NO: 60,
(d) HVR-L1 comprising the amino acid sequence of SEQ ID NO: 61,
(e) HVR-L2 comprising the amino acid sequence of SEQ ID NO: 62, and
(f) HVR-L3 comprising the amino acid sequence of SEQ ID NO: 63.

(2) (a) HVR-H1 comprising the amino acid sequence of SEQ ID NO: 64,
(b) HVR-H2 comprising the amino acid sequence of SEQ ID NO: 65,
(c) HVR-H3 comprising the amino acid sequence of SEQ ID NO: 66,
(d) HVR-L1 comprising the amino acid sequence of SEQ ID NO: 67,
(e) HVR-L2 comprising the amino acid sequence of SEQ ID NO: 68, and
(f) HVR-L3 comprising the amino acid sequence of SEQ ID NO: 69.

(3) (a) HVR-H1 comprising the amino acid sequence of SEQ ID NO: 70,
(b) HVR-H2 comprising the amino acid sequence of SEQ ID NO: 71,
(c) HVR-H3 comprising the amino acid sequence of SEQ ID NO: 72,
(d) HVR-L1 comprising the amino acid sequence of SEQ ID NO: 73,
(e) HVR-L2 comprising the amino acid sequence of SEQ ID NO: 74, and
(f) HVR-L3 comprising the amino acid sequence of SEQ ID NO: 75.

(4) (a) HVR-H1 comprising the amino acid sequence of SEQ ID NO: 76,
(b) HVR-H2 comprising the amino acid sequence of SEQ ID NO: 77,
(c) HVR-H3 comprising the amino acid sequence of SEQ ID NO: 78,
(d) HVR-L1 comprising the amino acid sequence of SEQ ID NO: 79,
(e) HVR-L2 comprising the amino acid sequence of SEQ ID NO: 80, and
(f) HVR-L3 comprising the amino acid sequence of SEQ ID NO: 81.

(5) (a) HVR-H1 comprising the amino acid sequence of SEQ ID NO: 82,
(b) HVR-H2 comprising the amino acid sequence of SEQ ID NO: 83,
(c) HVR-H3 comprising the amino acid sequence of SEQ ID NO: 84,
(d) HVR-L1 comprising the amino acid sequence of SEQ ID NO: 85,
(e) HVR-L2 comprising the amino acid sequence of SEQ ID NO: 86, and
(f) HVR-L3 comprising the amino acid sequence of SEQ ID NO: 87.

(6) (a) HVR-H1 comprising the amino acid sequence of SEQ ID NO: 88,
(b) HVR-H2 comprising the amino acid sequence of SEQ ID NO: 89,
(c) HVR-H3 comprising the amino acid sequence of SEQ ID NO: 90,
(d) HVR-L1 comprising the amino acid sequence of SEQ ID NO: 91,
(e) HVR-L2 comprising the amino acid sequence of SEQ ID NO: 92, and
(f) HVR-L3 comprising the amino acid sequence of SEQ ID NO: 93.

(7) (a) HVR-H1 comprising the amino acid sequence of SEQ ID NO: 94,
(b) HVR-H2 comprising the amino acid sequence of SEQ ID NO: 95,
(c) HVR-H3 comprising the amino acid sequence of SEQ ID NO: 96,
(d) HVR-L1 comprising the amino acid sequence of SEQ ID NO: 97,
(e) HVR-L2 comprising the amino acid sequence of SEQ ID NO: 98, and
(f) HVR-L3 comprising the amino acid sequence of SEQ ID NO: 99.

Herein, the term “acidic pH” refers to a pH that is selected between, for example, pH 4.0 and pH 6.5. In one embodiment, the acidic pH refers to, but is not limited to, pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, or pH 6.5.

Herein, the term “neutral pH” refers to a pH that is selected between, for example, pH 6.7 and pH 10.0. In one embodiment, the neutral pH refers to, but is not limited to, for example, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0, pH 9.5, or pH 10.0.

In one embodiment, an anti-IL-8 antibody of the present disclosure is an anti-IL-8 antibody that binds to IL-8 in a pH-dependent manner. In one aspect of the present disclosure, an anti-IL-8 antibody that binds to IL-8 in a pH-dependent manner refers to an antibody whose IL-8-binding affinity at an acidic pH has been decreased as compared to that at a neutral pH. Such pH-dependent anti-IL-8 antibodies include, for example, antibodies that possess higher affinity for IL-8 at a neutral pH than at an acidic pH. In one embodiment, the anti-IL-8 antibodies of the present disclosure have affinity for IL-8 at a neutral pH which is at least 2 times, 3 times, 5 times, 10 times, 15 times, 20 times, 25 times, 30 times, 35 times, 40 times, 45 times, 50 times, 55 times, 60 times, 65 times, 70 times, 75 times, 80 times, 85 times, 90 times, 95 times, 100 times, 200 times, 400 times, 1000 times, 10000 times, or more times greater than the affinity at an acidic pH. Without limitations, the binding affinity can be determined by using surface plasmon resonance assays (BIACORE, etc.). The association rate constant (kon) and dissociation rate constant (koff) can be calculated using a simple one-to-one Langmuir binding model (Biacore T200 Evaluation Software (GE Healthcare)) by simultaneously fitting the association and dissociation sensorgrams. The equilibrium dissociation constant (KD) is calculated as the ratio of koff/kon. Screening for antibodies whose binding affinity varies depending on pH can be carried out using, for example, without limitations, ELISA, kinetic exclusion assay (KinExA™) as well as surface plasmon resonance assays (BIACORE, etc.). The pH-dependent IL-8-binding ability refers to the property of binding to IL-8 in a pH-dependent manner. Meanwhile, whether an antibody can bind to IL-8 multiple times can be assessed by the method described in WO2009/125825.

In one embodiment, an anti-IL-8 antibody of the present disclosure preferably has a small dissociation constant (KD) for IL-8 at a neutral pH (for example, pH 7.4). The dissociation constant of the antibody for IL-8 at a neutral pH (for example, pH 7.4) may be, for example, 0.3 nM or less, 0.1 nM or less, or 0.03 nM or less.

In one embodiment, an anti-IL-8 antibody of the present disclosure preferably has a large dissociation constant (KD) for IL-8 at an acidic pH (for example, pH 5.8). The dissociation constant of the antibody for IL-8 at an acidic pH (for example, pH 5.8) may be, for example, 3 nM or greater, 10 nM or greater, or 30 nM or greater.

In one embodiment, an anti-IL-8 antibody of the present disclosure has a ratio of dissociation constant at an acidic pH (for example, pH 5.8) to the dissociation constant at a neutral pH (for example, pH 7.4), [KD(acidic pH)/KD(neutral pH)] (for example, [KD(pH5.8)/KD(pH7.4)]) that is, for example, 30 or greater, 50 or greater, or, for example, 100 or greater, for example, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, or 9500 or greater.

In one embodiment, an anti-IL-8 antibody of the present disclosure preferably has a large dissociation rate constant (koff) at an acidic pH (for example, pH 5.8). The dissociation rate constant of the antibody at an acidic pH (for example, pH 5.8) may be, for example, 0.003 (l/s) or greater, 0.005 (l/s) or greater, or 0.01 (l/s) or greater.

WO2013/046704 reports that an Fc region variant introduced with a specific mutation (a representative example is a dual residue mutation Q438R/S440E according to EU numbering) in combination with a mutation that increases the FcRn binding at an acidic pH showed significant reduction in its rheumatoid factor binding. However, WO2013/046704 did not show that the Fc region variant whose rheumatoid factor binding has been reduced by the modification Q438R/S440E is superior in plasma retention as compared to an antibody containing the native Fc region. Thus, there has been a demand for safe and more advantageous Fc region variants that allow improved plasma retention, but do not bind to pre-existing ADA. The inventors conceived that Fc region variants which comprise a substitution of Ala (A) for the amino acid at position 434 according to EU numbering and a specific dual residue mutation (a representative example is Q438R/S440E) as a combination of amino acid residue mutations, are preferable as safe and more advantageous Fc region variants that allow improved plasma retention, but do not bind to anti-drug antibodies (pre-existing ADA, etc.).

Thus, in a further or an alternative embodiment, an anti-IL-8 antibody of the present disclosure comprises an Fc region variant comprising an FcRn-binding domain, and the FcRn-binding domain may comprise, for example, Ala at position 434; Glu, Arg, Ser, or Lys at position 438; and Glu, Asp, or Gln at position 440 according to EU numbering as compared to a native Fc region. For the anti-IL-8 antibody, the FcRn-binding domain can be an FcRn-binding domain having an increased FcRn-binding activity at an acidic pH and neutral pH, in particular, at an acidic pH. Alternatively, in the antibody, its FcRn-binding domain preferably contains an Fc region variant comprising Ala at position 434; Glu, Arg, Ser, or Lys at position 438; and Glu, Asp, or Gln at position 440, more preferably comprising Ala at position 434; Arg or Lys at position 438; and Glu or Asp at position 440 according to EU numbering. Alternatively, the Fc region variant preferably further contains Ile or Leu at position 428; and/or Ile, Leu, Val, Thr, or Phe at position 436, more preferably, further contains Leu at position 428; and/or Val or Thr at position 436 according to EU numbering.

In one embodiment, the Fe region variant of an anti-IL-8 antibody of the present disclosure is preferably the Fc region variant of a native Ig antibody, more preferably the Fc region variant of a native IgG (IgG1, IgG2, IgG3, or IgG4 type) antibody, and yet more preferably it is derived from a native human IgG1, IgG2, IgG3, or IgG4. The Fc region variant may be derived from, for example, human IgG1.

Regarding Fc regions of native human IgG1, IgG2, IgG3, and IgG4-type antibodies, except for position 436, positions 428, 434, 438, and 440 according to EU numbering, which are the modification sites described above, are common to the Fc regions of all native human IgG1, IgG2, IgG3, and IgG4-type antibodies. On the other hand, at position 436 in the Fc region, native human IgG1, IgG2, and IgG4-type antibodies have Tyr (Y), whereas native human IgG3-type antibody has Phe (F). However, Stapleton et al. (Competition for FcRn-mediated transport gives rise to short half-life of human IgG3 and offers therapeutic potential, Nature Communications, 2011, December, number 599) reported that human IgG3 allotypes containing the amino acid substitution of R435H according to EU numbering showed a plasma half-life in human that is comparable to IgG1. Thus, the plasma retention can be improved by increasing the FcRn binding under an acidic condition by introducing the R435H amino acid substitution in addition to the amino acid substitution at position 436.

WO2013/046704 specifically reported Q438R/S440E, Q438R/S440D, Q438K/S440E, and Q438K/S440D according to EU numbering as dual amino acid residue substitutions that could result in a significant reduction of the rheumatoid factor binding when combined with an amino acid substitution that can increase the FcRn binding at an acidic pH.

Thus, in one embodiment, as compared to the native Fc region, the amino acid sequence of the Fc region variant of an anti-IL-8 antibody of the present disclosure may comprise, in its FcRn-binding domain, a combination of substituted amino acids selected from the group consisting of:

N434A/Q438R/S440E;
N434A/Q438R/S440D;
N434A/Q438K/S440E;
N434A/Q438K/S440D;
N434A/Y436T/Q438R/S440E;
N434A/Y436T/Q438R/S440D;
N434A/Y436T/Q438K/S440E;
N434A/Y436T/Q438K/S440D;
N434A/Y436V/Q438R/S440E;
N434A/Y436V/Q438R/S440D;
N434A/Y436V/Q438K/S440E;
N434A/Y436V/Q438K/S440D;
N434A/R435H/F436T/Q438R/S440E;
N434A/R435H/F436T/Q438R/S440D;
N434A/R435H/F436T/Q438K/S440E;
N434A/R435H/F436T/Q438K/S440D;
N434A/R435H/F436V/Q438R/S440E;
N434A/R435H/F436V/Q438R/S440D;
N434A/R435H/F436V/Q438K/S440E;
N434A/R435H/F436V/Q438K/S440D;
M428L/N434A/Q438R/S440E;
M428L/N434A/Q438R/S440D;
M428L/N434A/Q438K/S440E;
M428L/N434A/Q438K/S440D;
M428L/N434A/Y436T/Q438R/S440E;
M428L/N434A/Y436T/Q438R/S440D;
M428L/N434A/Y436T/Q438K/S440E;
M428L/N434A/Y436T/Q438K/S440D;
M428L/N434A/Y436V/Q438R/S440E;
M428L/N434A/Y436V/Q438R/S440D;
M428L/N434A/Y436V/Q438K/S440E; and
M428L/N434A/Y436V/Q438K/S440D;
L235R/G236R/S239K/M428L/N434A/Y436T/Q438R/S440E; and
L235R/G236R/A327G/A330S/P331S/M428L/N434A/Y436T/Q438R/S440E, according to EU numbering.

Alternatively, in another embodiment, the Fe region variant of an anti-IL-8 antibody of the present disclosure may comprise substitutions for other amino acids at one or more positions (for example, six, seven, or all positions) selected from the group consisting of positions 235, 236, 239, 327, 330, 331, 428, 434, 436, 438, and 440 according to EU numbering as compared to a native Fc region, for example, one or more amino acid substitutions (for example, six, seven, or all substitutions) selected from the group consisting L235R, G236R, S239K, A327G, A330S, P331S, M428L, N434A, Y436T, Q438R, and S440E.

In one embodiment, it is preferable that the FcRn-binding activity of the Fc region variant of an anti-IL-8 antibody of the present disclosure has been increased at an acidic pH as compared to the Fc region of a native IgG.

An increase in the FcRn-binding affinity of an FcRn-binding domain at a certain pH may correspond to an increase in the measured FcRn-binding affinity compared to the measured FcRn-binding affinity of a native FcRn-binding domain. In this case, KD (native Fc region)/KD (Fc region variant of anti-IL-8 antibody of the present disclosure), which represents a difference in the binding affinity, may be at least 1.5-fold, 2-fold, 3-fold, 4-fold, 5-fold, 10-fold, 15-fold, 20-fold, 50-fold, 70-fold, 80-fold, 100-fold, 500-fold, or 1000-fold. Such an increase in the FcRn-binding affinity of an FcRn-binding domain may be provided at an acidic pH and/or at a neutral pH; however, in particular, it is preferable that the FcRn-binding activity is increased at an acidic pH.

Furthermore, the FcRn-binding affinity of the Fc region variant of an anti-IL-8 antibody of the present disclosure whose FcRn-binding affinity has been increased at an acidic pH may be greater than that of the Fc region of a native IgG, for example, at pH 6.0 and 25° C. by 1.5-fold, 2-fold, 3-fold, 4-fold, 5-fold, 6-fold, 7-fold, 8-fold, 9-fold, 10-fold, 20-fold, 30-fold, 50-fold, 75-fold, 100-fold, 200-fold, 500-fold, 1000-fold or more.

As used herein, “anti-drug antibody” or “ADA” refers to an endogenous antibody that has binding activity to an epitope located on a therapeutic antibody and thus can bind to the therapeutic antibody. As used herein, “pre-existing anti-drug antibody” or “pre-existing ADA” refers to an anti-drug antibody that is present and detectable in the blood of a patient prior to administration of the therapeutic antibody to the patient. In an embodiment, the pre-existing ADA is a rheumatoid factor, a polyclonal or monoclonal autoantibody against the Fc region of a human IgG antibody. The rheumatoid factor epitope is located in the CH2/CH3 interface region and in the CH3 domain, and can vary depending on the clone. For "an Fc region variant whose binding affinity for a pre-existing ADA is low", the affinity may have been reduced, for example, to 1/10 or less, 1/50 or less, or 1/100 or less as compared to the ADA-binding affinity of an antibody comprising a native IgG Fc region.

In one embodiment, the binding affinity of an antibody Fc region (variant) for a pre-existing ADA can be demonstrated, for example, by electrochemiluminescence (ECL) reaction at an acidic pH and/or at a neutral pH; however, it is also possible to use other appropriate methods known to those skilled in the art for determining the binding affinity for a pre-existing ADA. ECL assays are described, for example, in Moxness et al. (Clin Chem, 2005, 51:1983-85), and in the Examples herein. Assays can be performed, for example, under the conditions at 37° C. with MES buffer. The antigen-binding activity of an antibody can be determined, for example, by BIACORE. In an embodiment, the binding affinity for a pre-existing ADA can be assessed at any temperature from 10° C. to 50° C. The binding activity between a human Fc region and a pre-existing human ADA is preferably determined at a temperature of 15° C. to 40° C. The temperature is preferably 20° C. to 25° C., more preferably 25° C. The activity may be measured at pH 7.4 (or pH 7.0) and 25° C.

In one embodiment, it is preferable that the Fc region variant of an anti-IL-8 antibody of the present disclosure does not have significantly increased binding affinity for a pre-existing ADA, preferably, rheumatoid factor (RF) at a neutral pH, and/or has increased FcRn-binding activity at an acidic pH as compared to the Fc region of a native IgG; as a result, it preferably exhibits reduced clearance (CL) in plasma, prolonged retention time in plasma, or prolonged half-life in plasma (t½). The correlation among antibody clearance (CL) in plasma, retention time in plasma, and half-life in plasma (t½) is known to those skilled in the art.

In one embodiment, the Fc region variant of an anti-IL-8 antibody of the present disclosure has improved plasma retention as compared to a reference Fc region variant comprising a combination of amino acid substitutions N434Y/Y436V/Q438R/S440E according to EU numbering.

Examples 1 to 3 herein compare the plasma retention of the two Fc region variants below: the Fc region variant called F1718 (an Fc region with mutations introduced at four sites: N434Y/Y436V/Q438R/S440E) described in WO2013/046704; and the Fc region variant F1848m (an Fc region with mutations introduced at four sites: N434A/Y436V/Q438R/S440E). The difference in amino acid mutations between the two Fc region variants is only at position 434 according to EU numbering, where the introduced amino acid mutation is Y (tyrosine) for F1718 and A (alanine) for F1848m. Nevertheless, as compared to a native IgG1, F1848m exhibited improved plasma retention, while F1718 showed no improvement in plasma retention (see, in particular, Example (3-2) herein). Furthermore, the results of Examples (1-2) and (3-3) herein demonstrate that, of various Fc region variants, the plasma retention of F1847m, F1886m, F1889m, and F1927m was more improved than F1848m. Thus, those skilled in the art can naturally predict that Fc region variants including F1847m, F1886m, F1889m, and F1927m as well as F1848m have improved plasma retention as compared to the reference Fc region variant containing the combination of amino acid substitutions N434Y/Y436V/Q438R/S440E according to EU numbering.

Antibodies whose half-life in blood have been prolonged and FcRn binding at an acidic pH have been improved are also described in US2005/0014934 (Hinton et al.). The antibodies may contain an Fc region variant which comprises one or more amino acid substitutions that increase the binding of the Fc region to FcRn, and may comprise one or more amino acid substitutions at a position(s) selected from positions 238, 256, 265, 272, 286, 303, 305, 307, 311, 312, 317, 340, 356, 360, 362, 376, 378, 380, 382, 413, 424, and 434 (EU numbering), for example, an amino acid substitution at position 434 in the Fc region. For other examples of Fc region variants, see Duncan & Winter, Nature 322:738-40 (1988); U.S. Pat. Nos. 5,648,260; 5,624,821; and WO 94/29351. Appropriate modification of these amino acids may be introduced into the Fc region (variant) of an anti-IL-8 antibody of the present disclosure.

The binding to FcγR or a complement protein can also cause an unfavorable effect (for example, inappropriate platelet activation). Fc region variants that do not bind to effector receptors such as the FcγRIIa receptor can be safer and/or more advantageous.

In one embodiment, an anti-IL-8 antibody comprising an Fc region variant of the present disclosure has only weak complement protein-binding activity or does not bind to complement proteins. The preferred complement protein is C1q. The low binding activity to a complement protein can refer to the complement protein-binding activity that has been reduced, for example, to 1/10 or less, 1/50 or less, or 1/100 or less as compared to the complement protein-binding activity of a native IgG or an antibody comprising a native IgG Fc region. The complement protein-binding activity of an Fc region (variant) can be reduced by amino acid sequence modification such as amino acid substitution, insertion, and deletion.

In a further or an alternative embodiment, an anti-IL-8 antibody comprising an Fc region variant of the present disclosure preferably has only weak effector receptor-binding activity or does not bind to effector receptors. Effector receptors include, for example, activating FcγR, in particular, FcγRI, FcγRII, and FcγRIII. FcγRI includes, for example, FcγRIa, FcγRIb, and FcγRIc, and subtypes thereof. FcγRII includes, for example, FcγRIIa (two allotypes: R131 and H131) and FcγRIIb. FcγRIII includes, for example, FcγRIIIa (two allotypes: V158 and F158) and FcγRIIIb (two allotypes: FcγIIIb-NA1 and FcγIIIb-NA2). Antibodies that have only weak effector receptor-binding affinity or do not bind to the receptors include antibodies comprising an Fc region variant whose binding affinity has been reduced, for example, to 1/10 or less, 1/50 or less, or 1/100 or less as compared to the binding affinity of an antibody comprising the Fc region of a native IgG. Specific example include antibodies comprising a silent Fc region and antibodies that do not have an Fc region (for example, Fab, $F(ab)'_2$, scFv, $sc(Fv)_2$, and diabodies).

Examples of Fc region variants that have only weak or no effector receptor-binding affinity are described in Strohl et al. (Current Opinion in Biotechnology (2009) 20(6), 685-691), which include deglycosylated Fc regions (N297A and N297Q) and silent Fc regions resulting from manipulation of Fc regions to silence their effector functions (or to suppress immunity) (IgG1-L234A/L235A, IgG1-H268Q/A330S/P331S, IgG1-C226S/C229S, IgG1-C226S/C229S/E233P/L234V/L235A, IgG1-L234F/L235E/P331S, IgG2-V234A/

G237A, IgG2-H268Q/V309L/A330S/A331S, IgG4-L235A/G237A/E318A, and IgG4-L236E). WO2008/092117 describes antibodies containing a silent Fc region that comprises substitutions of G236R/L328R, L235G/G236R, N325A/L328R, or N325L/L328R (according to EU numbering). WO2000/042072 describes antibodies containing a silent Fc region that comprises substitutions at one or more of positions EU233, EU234, EU235, and EU237. WO2009/011941 describes antibodies containing a silent Fc region where the residues of EU231 to EU238 are deleted. Davis et al. (Journal of Rheumatology (2007) 34(11): 2204-2210) describe antibodies with a silent Fc region containing substitutions C220S/C226S/C229S/P238S. Shields et al. (Journal of Biological Chemistry (2001) 276 (9), 6591-6604) describe antibodies containing a silent Fc region which comprises the substitution D265A. U.S. Pat. No. 6,737,056 describes antibodies with reduced effector function which comprise one or more of amino acid substitutions at EU238, EU265, EU269, EU270, EU297, EU327, and EU329. U.S. Pat. No. 7,332,581 describes Fe region variants that contain two or more of amino acid substitutions at EU265, EU269, EU270, EU297, and EU327 as well as so-called "DANA" Fc region variants which have substitutions with alanine at EU265 and EU297. Modification of these amino acid residues may also be appropriately introduced into the Fc region variants of anti-IL-8 antibodies of the present disclosure.

"Weak binding to effector receptors" means that the effector receptor-binding activity is, for example, 95% or less, preferably 90% or less, 85% or less, 80% or less, or 75% or less, more preferably 70% or less, 65% or less, 60% or less, 55% or less, 50% or less, 45% or less, 40% or less, 35% or less, 30% or less, 25% or less, 20% or less, 15% or less, 10% or less, 9% or less, 8% or less, 7% or less, 6% or less, 5% or less, 4% or less, 3% or less, 2% or less, or 1% or less of the effector receptor-binding activity of a native IgG (or an antibody comprising a native IgG Fc region). The FcγR-binding activity may be reduced to 1/10 or less, 1/50 or less, or 1/100 or less as compared to the effector receptor-binding activity of a native IgG (or an antibody comprising a native IgG Fc region).

Herein, the "silent Fc region" is an Fc region variant comprising one or more amino acid substitutions, insertions, deletions, and such that reduce the effector receptor binding as compared to a native Fc region. Since the effector receptor-binding activity can be reduced to a large extent, the Fc region variants (substantially) no longer bind to effector receptors. The silent Fc regions include, for example, an Fc region (variant) comprising amino acid substitutions at one or more positions selected from the group consisting of: EU234, EU235, EU236, EU237, EU238, EU239, EU265, EU266, EU267, EU269, EU270, EU271, EU295, EU296, EU297, EU298, EU300, EU324, EU325, EU327, EU328, EU329, EU331, and EU332. In an embodiment, modifications of these amino acid residues may also be appropriately introduced into an Fc region (variant) of an anti-IL-8 antibody of the present disclosure.

In one embodiment, a method for modifying antibody constant regions to produce the Fc region variant of an anti-IL-8 antibody of the present disclosure may be based, for example, on assessment of several constant region isotypes (IgG1, IgG2, IgG3, and IgG4), followed by introduction of, for example, appropriate amino acid substitutions into their sequences to select isotypes that have a reduced antigen-binding activity at an acidic pH and/or have an increased dissociation rate at an acidic pH.

In a further or an alternative embodiment, an anti-IL-8 antibody of the present disclosure may comprise:

(A) a heavy chain comprising the amino acid sequence of SEQ ID NO: 36, 37, or 106, or a heavy chain that has a sequence identity thereto which is at least 65%, 70%, or 75%, or higher, preferably 80%, 85%, or 90%, or higher, and more preferably 95% or higher; and/or (B) a light chain comprising the amino acid sequence of SEQ ID NO: 38 or 44, or a light chain that has a sequence identity thereto which is at least 65%, 70%, or 75%, or higher, preferably 80%, 85%, or 90%, or higher, and more preferably 95% or higher.

Here, a heavy or light chain with a certain percentage (%) of sequence identity to a reference amino acid sequence can be functionally equivalent to the heavy or light chain comprising the reference amino acid sequence. Furthermore, the anti-IL-8 antibody may contain an Fc region variant having at least one of the five properties below:

(a) the FcRn binding affinity of the Fc region variant has been increased relative to the FcRn binding affinity of the native Fc region at an acidic pH;

(b) the binding affinity of the Fc region variant for a pre-existing ADA has been reduced relative to the binding affinity of the native Fc region for the pre-existing ADA;

(c) the plasma half-life of the Fc region variant has been prolonged relative to the plasma half-life of the native Fc region;

(d) the clearance in plasma of the Fc region variant has been reduced relative to the clearance in plasma of the native Fc region;

(e) the effector receptor binding affinity of the Fc region variant has been reduced relative to the effector receptor binding affinity of the native Fc region; and (f) being capable of binding to IL-8 in a pH-dependent manner.

Those skilled in the art will naturally appreciate all possible combinations of the amino acid sequences described herein.

In one embodiment, an anti-IL-8 antibody of the present disclosure can be produced using, for example, the methods described in U.S. Pat. No. 4,816,567. In an embodiment, isolated nucleic acids encoding an anti-IL-8 antibody of the present disclosure are provided. Such a nucleic acid may encode an amino acid sequence comprising a VL and/or an amino acid sequence comprising a VH of the antibody (for example, antibody light chain and/or heavy chain). An isolated nucleic acid encoding an anti-IL-8 antibody may be inserted into one or more vectors for further cloning and/or expression in host cells. Such a nucleic acid can readily be isolated and sequenced using conventional procedures (for example, by using oligonucleotide probes that specifically bind to genes encoding the heavy and/or light chains of the antibody).

In a further embodiment, one or more vectors containing such a nucleic acid (for example, expression vectors) are provided. In an embodiment, host cells containing such a nucleic acid are provided. The host cells contain: (1) a vector comprising a nucleic acid that encodes an amino acid sequence comprising a VL of the antibody and/or an amino acid sequence comprising a VH of the antibody; or (2) a first vector comprising a nucleic acid that encodes an amino acid sequence comprising a VL of an antibody, and a second vector comprising a nucleic acid that encodes an amino acid sequence comprising a VH of the antibody (for example, the cells have been transformed with the vectors).

In one embodiment, the host is eukaryotic (for example, CHO cells or lymphocytes (for example, Y0, NS0, or SP20 cells)).

In one embodiment, a method for producing an anti-IL-8 antibody of the present disclosure is provided. The method comprises, for example, culturing host cells containing the above-mentioned nucleic acid under conditions suitable for expressing the antibody, and optionally collecting the antibody from the host cells (or host cell culture media).

Suitable host cells for cloning or expression of antibody-encoding vectors include, for example, prokaryotic and eukaryotic cells. Cells derived from multicellular organisms (invertebrates and vertebrates) may be used to express glycosylated antibodies. Invertebrates include, for example, plant and insect cells.

In one embodiment, an anti-IL-8 antibody produced by culturing, under conditions suitable for antibody expression, host cells containing a nucleic acid that encodes the antibody can be isolated from inside of the host cells or outside of the cells (media, milk, etc.) to purify it as a substantially pure, homogeneous antibody. Without limitations, separation/purification methods that are generally used to purify polypeptides can be appropriately used to separate and purify the antibody. The antibody can be appropriately separated and purified, for example, by appropriately selecting and combining column chromatography, filters, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration chromatography, reverse phase chromatography, and adsorption chromatography. Such chromatography can be performed using liquid chromatography, for example, HPLC and FPLC. Columns for use in affinity chromatography include, for example, Protein A column and Protein G column. Protein A columns include, for example, Hyper D, POROS, and Sepharose F. F (Pharmacia).

In one embodiment, the present disclosure focuses on the characteristics of anti-IL-8 antibodies such as increased extracellular matrix binding and enhanced cellular uptake of the complex between IL-8 and an anti-IL-8 antibody, and thus the present disclosure relates to methods for selecting antibodies with increased extracellular matrix binding and antibodies with enhanced cellular uptake. In an embodiment, the present disclosure relates to methods for producing an anti-IL-8 antibody comprising a variable region whose IL-8-binding activity is pH-dependent, which comprise the steps of: (i) assessing the binding between an anti-IL-8 antibody and extracellular matrix; (ii) selecting an anti-IL-8 antibody that strongly binds to extracellular matrix; (iii) culturing a host that comprises a vector comprising a nucleic acid encoding the antibody; and (iv) isolating the antibody from the culture medium (culture supernatant, etc.). The binding to extracellular matrix can be assessed, for example, by an ELISA system in which an antibody is added to a plate immobilized with an extracellular matrix, and then a labeled antibody against the antibody is added thereto to detect the binding between the antibody and the extracellular matrix. Alternatively, the binding can be assessed, for example, as follows: a mixture of the antibody and a ruthenium antibody is added to a plate immobilized with an extracellular matrix, and the binding between the antibody and the extracellular matrix is assessed by an electrochemiluminescence (ECL) method measuring the electrochemiluminescence of ruthenium.

In one embodiment, it is preferable that the IL-8 neutralizing activity of an anti-IL-8 antibody of the present disclosure be retained stably in a solution (for example, in PBS). Whether the activity is retained stably in a solution can be tested by assessing whether the IL-8 neutralizing activity of an anti-IL-8 antibody of the present disclosure added to the solution changes before and after storage for a certain period of time at a certain temperature. In an embodiment, the storage period is, for example, one to four weeks, and the storage temperature is, for example, 25° C., 30° C., 35° C., 40° C., or 50° C.

In one embodiment, it is preferable that the IL-8 neutralizing activity of an anti-IL-8 antibody of the present disclosure be retained stably in vivo (for example, in the plasma). Whether the activity is retained stably in vivo can be tested by assessing whether the IL-8 neutralizing activity of an anti-IL-8 antibody of the present disclosure added to the plasma of a nonhuman animal (for example, mouse) or human changes before and after storage for a certain period of time at a certain temperature. In an embodiment, the storage period is, for example, one to four weeks, and the storage temperature is, for example, 25° C., 30° C., 35° C., or 40° C.

In one embodiment, the rate of cellular uptake of an anti-IL-8 antibody of the present disclosure is greater in a complex with IL-8 than the antibody alone.

In one embodiment, it is preferable that the predicted immunogenicity of an anti-IL-8 antibody of the present disclosure in human hosts be reduced. "Low immunogenicity" can mean, for example, that an administered anti-IL-8 antibody does not induce in vivo immune response in at least a majority of the individuals administered with a sufficient amount of the antibody over a sufficient period of time to achieve therapeutic effect. The induction of immune response can include production of anti-drug antibodies. "Low anti-drug antibody production" can be rephrased as "low immunogenicity". The immunogenicity level in humans can be predicted using a T cell epitope prediction program. Such T cell epitope prediction programs include Epibase (Lonza), iTope/TCED (Antitope), and EpiMatrix (EpiVax). Sequences with reduced immunogenicity can be designed, for example, by analysis using a T cell epitope prediction program. Non-limiting examples of the amino acid modification sites include position 81 and/or position 82b according to Kabat numbering in the heavy-chain sequence of the anti-IL-8 antibody shown in SEQ ID NO: 34.

In one embodiment, a reference antibody for use in functional comparison to an anti-IL-8 antibody described herein may be an antibody comprising the amino acid sequences of SEQ ID NOs: 39 and 40. In a specific embodiment, a reference antibody for use in PK test may be an antibody comprising the amino acid sequences of SEQ ID NOs: 43 and 45.

In some embodiments, IL-8 signal inhibitors (for example, anti-IL-8 antibodies) of the present disclosure are identified, screened, or characterized by various known methods using the physicochemical properties and/or biological activities as indexes.

Binding Measurements and Other Measurements

In one aspect, the antibodies of the present disclosure can be assessed for their antigen-binding activity by any methods, for example, ELISA, Western blotting, kinetic exclusion assay (KinExA™), and surface plasmon resonance using a device such as BIACORE (GE Healthcare).

In one embodiment, the binding affinity can be measured using Biacore T200 (GE Healthcare) in the following manner. An appropriate amount of a trapping protein (for example, Protein A/G (PIERCE)) is immobilized onto a sensor chip CM4 (GE Healthcare) by the amine-coupling method, and an antibody of interest is allowed to be captured by it. Then, a diluted antigen solution and running buffer (as a reference solution, for example, 0.05% tween20, 20 mM ACES, 150 mM NaCl, pH 7.4) are injected to allow the antigen molecule to interact with the antibody trapped on the sensor chip. The sensor chip is regenerated using 10 mM glycine HCl solution (pH 1.5). Measurements are performed at a predetermined temperature (for example, 37° C., 25° C., or 20° C.). The KD (M) of each antibody for the antigen is calculated based on the association rate constant kon (1/Ms) and dissociation rate constant koff (l/s) which are kinetic parameters calculated from a sensorgram obtained by the measurement. Each parameter is calculated using the BIACORE T200 Evaluation Software (GE Healthcare).

In one embodiment, IL-8 can be quantitated as described below. An anti-human IL-8 antibody containing the mouse IgG constant region is immobilized onto a plate. A solution containing IL-8 bound to a humanized anti-IL-8 antibody, which does not compete with the above-described anti-human IL-8 antibody, is aliquoted to the immobilized plate. After stirring, a biotinylated anti-human Igκ light chain antibody is added and allowed to react for a certain period of time. Then, SULFO-Tag-labeled streptavidin is further added and allowed to react for a certain period of time. Then, assay buffer is added and immediately, measurement is performed with SECTOR Imager 2400 (Meso Scale Discovery).

Activity Evaluation Assays

In one aspect, assays are provided to identify an antibody having a biological activity. The biological activity includes, for example, the activity of neutralizing an antigen (for example, IL-8) and the activity of blocking signals from an antigen (for example, IL-8).

In one embodiment, the level of IL-8-neutralizing activity can be determined, for example, by the methods described below. PathHunter™ CHO-KI CXCR2 β-Arrestin Cell Line (DiscoveRx, Cat. #93-0202C2) is an artificial cell line created to express human CXCR2 known as a human IL-8 receptor and emit chemiluminescence when a signal by human IL-8 is transduced. When human IL-8 is added to a culture medium of the cells, chemiluminescence is emitted from the cells in a manner that depends on the concentration of added human IL-8. When human IL-8 is added in combination with an anti-human IL-8 antibody to the culture medium, the chemiluminescence of the cells is reduced or undetectable as compared to when the antibody is not added, since the anti-human IL-8 antibody can block the signal transduction via IL-8. That is, the stronger the human IL-8-neutralizing activity of the antibody is, the weaker the level of chemiluminescence is; and the weaker the human IL-8-neutralizing activity of the antibody is, the greater the level of chemiluminescence is. Thus, the human IL-8-neutralizing activity of the anti-human IL-8 antibody can be assessed by examining this difference.

As used herein, the terms “diagnostic composition”, “therapeutic composition”, and “preventive composition” are interchangeable with “diagnostic agent”, “therapeutic agent”, and “preventive agent”, respectively. In one embodiment, when a “therapeutic composition” or “preventive composition” is intended to treat or prevent a disease or symptom in a desired subject, the composition is also referred to as a “pharmaceutical composition”; in general, a pharmaceutical composition refers to an agent for treating or preventing a disease or symptom.

As used herein, a “pharmaceutically acceptable carrier” refers to a component other than active ingredients contained in a pharmaceutical composition. Pharmaceutically acceptable carriers nontoxic to subjects are typically selected, but the selection will be made in consideration of benefit/risk depending on the purpose. Pharmaceutically acceptable carriers include, for example, buffers, excipients, stabilizers, and preservatives.

In one embodiment, a therapeutic or preventive composition of the present disclosure comprises a pharmaceutically acceptable carrier, and can be prepared in a form of freeze-dried agent or aqueous formulation.

In one embodiment, pharmaceutically acceptable carriers are typically nontoxic to recipients at the used dosages and concentrations, and include, for example, buffers such as phosphate, citrate, and histidine; antioxidants including ascorbic acid and methionine; preservatives (for example, octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum albumin, gelatin, and immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, and dextrins; chelating agents such as EDTA; sugars such as sucrose, mannitol, trehalose, and sorbitol; salt-forming counter-ions such as sodium; metal complexes (for example, Zn-protein complexes); and/or non-ionic detergents such as TWEEN™, PLURONICS™, or polyethylene glycol (PEG). Alternatively, the pharmaceutically acceptable carriers can also include, for example, interstitial drug dispersion agents such as soluble hyaluronidase glycoproteins (sHASEGP) (US2005/0260186; US2006/0104968). It is possible to combine sHASEGP with one or more glycosaminoglycanases such as chondroitinases.

As used herein, “effective amount” of an active ingredient (an IL-8 signal inhibitor such as an IL-8 inhibitor (for example, an anti-IL-8 antibody), a CXCR1 inhibitor, or a CXCR2 inhibitor) in a pharmaceutical composition refers to an amount that is effective when used at a dose and for a period of time necessary to achieve the desired therapeutic or prophylactic result.

In one aspect, the present disclosure is based on the applicability of IL-8 signal inhibitors (for example, IL-8 inhibitors (for example, anti-IL-8 antibodies), CXCR1 inhibitors, and CXCR2 inhibitors) as pharmaceutical compositions. The IL-8 signal inhibitors (for example, IL-8 inhibitors (for example, anti-IL-8 antibodies), CXCR1 inhibitors, and CXCR2 inhibitors) of the present disclosure are useful, for example, in diagnosing, treating, or preventing diseases where IL-8 is present in an excessive amount.

In one embodiment, an IL-8 signal inhibitor (for example, an IL-8 inhibitor (for example, an anti-IL-8 antibody), a CXCR1 inhibitor, or a CXCR2 inhibitor) of the present disclosure is administered by any suitable means, including parenteral, intrapulmonary, and intranasal, and, if local treatment is desired, intralesional administration. Parenteral infusion includes intramuscular, intravenous, intraarterial, intraperitoneal, and subcutaneous administration. Dosing can be by any suitable route, for example, by injections such as intravenous or subcutaneous injections, depending in part on whether the administration is brief or chronic. Various dosing schedules are available.

In one embodiment, an IL-8 signal inhibitor of the present disclosure can be formulated, dosed, and administered in a fashion consistent with medical practicability.

In one embodiment, the present disclosure relates to products containing IL-8 signal inhibitors that are useful for diagnosing, treating, and/or preventing diseases disclosed herein. Such a product includes a container and a label or attached document associated with the container. Suitable containers include, for example, bottles, vials, and intravenous solution bags.

An appropriate dose and administration intervals of an IL-8 signal inhibitor (for example, an IL-8 inhibitor (for example, an anti-IL-8 antibody), a CXCR1 inhibitor, or a CXCR2 inhibitor) of the present disclosure for preventing or treating a disease can be suitably determined based on the type of disease to be treated, the type of inhibitor, the severity and course of the disease, the purpose of administration, previous therapy, the patient's clinical history and response to the inhibitor, and discretion of the attending physician.

In one embodiment, the therapeutic effects include, for example, prevention of disease development or recurrence, remission of symptoms, alleviation of any direct or indirect pathological consequence of the disease, prevention of metastasis, reduction in the rate of progression of the disease, cure, alleviation, and remission of the pathological condition, and improved prognosis.

In an embodiment, in this disclosure, diseases or symptoms where IL-8 is present in an excessive amount and diseases where IL-8 signals are involved or can be involved in the onset, progression, exacerbation, recurrence, and such of pathological conditions, are collectively referred to as "IL-8-related diseases".

In one embodiment in an aspect, the present disclosure relates to therapeutic or preventive compositions for IL-8-related diseases, which comprise an IL-8 signal inhibitor (for example, an IL-8 inhibitor (for example, an anti-IL-8 antibody), a CXCR1 inhibitor, or a CXCR2 inhibitor) as an active ingredient. In a further embodiment, the compositions may additionally comprise a pharmaceutically acceptable carrier.

In one embodiment in an aspect, the present disclosure relates to IL-8 signal inhibitors (for example, IL-8 inhibitors (for example, anti-IL-8 antibodies), CXCR1 inhibitors, and CXCR2 inhibitors) for use in treating or preventing IL-8-related diseases (for example, endometriosis, adenomyosis, dysmenorrhea, adhesion, and fibrotic diseases).

In one embodiment in an aspect, the present disclosure relates to the use of IL-8 signal inhibitors (for example, IL-8 inhibitors (for example, anti-IL-8 antibodies), CXCR1 inhibitor, and CXCR2 inhibitors) as diagnostic, therapeutic, or preventive compositions against IL-8-related diseases (for example, endometriosis, adenomyosis, dysmenorrhea, adhesion, and fibrotic diseases).

In one embodiment in an aspect, the present disclosure relates to methods for treating or preventing an IL-8-related disease (for example, endometriosis, adenomyosis, dysmenorrhea, adhesion, and fibrotic diseases), which comprise administering (in an effective amount) an IL-8 signal inhibitor (for example, an IL-8 inhibitor (for example, an anti-IL-8 antibody), a CXCR1 inhibitor, or a CXCR2 inhibitor), or a therapeutic or preventive composition comprising it to a subject in need thereof. Herein, the subject in need thereof may be a subject suffering from or suspected to suffer from the IL-8-related disease. In a further embodiment, the compositions may additionally comprise a pharmaceutically acceptable carrier.

In one embodiment in an aspect, the present disclosure relates to use of an IL-8 signal inhibitor (for example, an IL-8 inhibitor (for example, an anti-IL-8 antibody), a CXCR1 inhibitor, or a CXCR2 inhibitors) of the present disclosure, or a therapeutic or preventive composition comprising it in the manufacture of pharmaceutical agents for treating or preventing IL-8-related diseases (for example, endometriosis, adenomyosis, dysmenorrhea, adhesion, and fibrotic diseases). In a further embodiment, the compositions may additionally comprise a pharmaceutically acceptable carrier.

In one embodiment, IL-8-related diseases that are the target of the treatment or prevention with an IL-8 signal inhibitor (for example, an IL-8 inhibitor (for example, an anti-IL-8 antibody), a CXCR1 inhibitor, or a CXCR2 inhibitor) of the present disclosure include, for example, the following: endometriosis; adenomyosis; dysmenorrhea; adhesion such as Asherman's syndrome; infertility; pain in endometriosis, adenomyosis, or dysmenorrhea; pain in adhesion, fibrosis, or inflammation; inflammatory skin diseases such as inflammatory keratosis, atopic dermatitis, contact dermatitis, palmoplantar pustulosis, and psoriasis; chronic inflammatory diseases such as chronic rheumatoid arthritis, systemic lupus eryhtematosus (SLE), and Behcet's disease which are autoimmune diseases; inflammatory bowel diseases such as Crohn's disease and ulcerative colitis; inflammatory liver diseases such as hepatitis B and C, alcoholic hepatitis, and drug-induced allergic hepatitis; inflammatory kidney diseases such as glomerulonephritis and ANCA associated nephritis; inflammatory respiratory diseases such as bronchitis and asthma; inflammatory chronic vascular diseases such as atherosclerosis; multiple sclerosis; stomatitis; chorditis; posttransplantational ischemia-reperfusion; inflammations appearing during the use of artificial organs and artificial blood vessels; malignant tumors such as ovary cancer, lung cancer, prostate cancer, stomach cancer, breast cancer, melanoma (malignant melanoma), cancers of the head and neck, kidney cancer, urinary bladder cancer, and glioblastoma; sepsis caused by infection or such (including septic shock); acute lung injury; fibrotic diseases such as fibrosis in endometriosis or adenomyosis, cystic fibrosis, hepatic fibrosis, renal fibrosis, and pulmonary fibrosis such as chronic obstructive pulmonary disease (COPD); brain disorders selected from cerebral stroke, brain infarction (for example, ischemic cerebral infarction), cerebral thrombosis, cerebral embolism, hemorrhagic cerebrovascular damage, intracerebral hemorrhage, and subarachnoid hemorrhage; cardiac infarction (including acute cardiac infarction, unstable angina, and cardiac ischemia/reperfusion injury) (see, for example, the Examples herein; the documents shown herein; Remo et al., Expert Rev. Clin. Immunol. 10(5), pp. 593-619, 2014; Mian et al., Clin Cancer Res. 2003 Aug. 1, 9(8):3167-75; Huang et al., Am J Pathol. 2002 July; 161(1):125-34; WO97/49426; WO97/39775; JP10-045622; JP10-182488; JP10-053536). The IL-8-related diseases may be mammalian diseases, and are preferably primate diseases, and more preferably human diseases (for example, human endometriosis for endometriosis, human adenomyosis for adenomyosis; the same applies hereinafter).

In one embodiment, patients (subjects) with an IL-8-related disease who are the target of therapy or prevention using an IL-8 signal inhibitor of the present disclosure may be subjects suffering from or suspected to suffer from the IL-8-related disease. Herein, the subjects suspected to suffer from the IL-8-related disease include, but are not limited to, subjects who once suffered from the IL-8-related disease and have a possibility of reoccurrence of the disease, and subjects being suspected to have the IL-8-related disease before receiving confirmed diagnosis or such made by a physician or others based on pathological findings indicating the IL-8-related disease. In one embodiment, the prevention and therapy of an IL-8-related disease can be interpreted to be synonymous in some cases. Alternatively, the prevention of an IL-8-related disease can be interpreted based on a general concept well-known to those skilled in the art, if appropriate.

In one embodiment of the present disclosure, IL-8-related diseases are responsive to IL-8 signals.

Herein, endometriosis refers to, but is not limited to, a disease in which symptoms are manifested as tissues having morphology and function which are the same as or similar to those of uterine endometrial tissues develop and grow ectopically outside of the uterus (typically within the pelvis, occasionally in the peritoneal cavity, and rarely in the thoracic cavity) (Japan Society of Obstetrics and Gynecology, 1993). Endometriosis is not malignant tumor; however, this disease progresses over time and causes tumor formation and adhesion of surrounding tissues, severe abdominal and pelvic pain at the time of menstruation and between periods, pain during intercourse, defecation pain, and infertility (impaired fertility). Endometriosis develops mostly in women at a reproductive age of 20 years or older, which causes pain and other symptoms resulting in reduced QOL, and can lead to chronic pain and infertility due to severe adhesion. Fibrosis results from the progression of the pathological condition at the site of adhesion in endometriosis lesions (affected areas). In the fibrotic areas, collagen is generated and results in fibrosis. The progression of fibrosis in endometriosis is generally understood to be irreversible. Thus, there has been no report on methods for arresting the progression of fibrosis or alleviating the fibrosis in endometriosis. As described above, endometriosis is a disease which becomes exacerbated during a course with a variety of stages, while showing various pathological features in the process of progression from the disease onset; nevertheless, the disease has been collectively called endometriosis. Recently, however, an in vivo endometriosis model was created using nonhuman primates with menstruation similar to human menstruation, which has eventually facilitated the elucidation of pathological conditions of the disease. The present inventors created an in vivo cynomolgus monkey endometriosis model with menstruation similar to human menstruation by surgically inducing endometriosis. By using this reliable in vivo model, the present inventors succeeded, for the first time in the world, in proving that the proliferation in endometriosis lesions can be suppressed by administering IL-8 signal inhibitors to the living body, thereby allowing atrophic changes of epithelial cells and stromal cells in endometriosis lesions or reduction of the interstitium in endometriosis leading to a decrease of smooth muscle cells. Due to atrophied endometriosis tissues, in particular, interstitium, reduction of ectopic neurons can also be expected. Furthermore, the present inventors observed muscle tissue regeneration, which was not detectable in the vehicle group, in the group administered with the IL-8 signal inhibitors. Thus, the present inventors considered that the lesions invading up to the myometrium were regressed and replaced with muscular tissues for recovery. The presence of deep lesions was assessed based on whether endometriosis gland ducts have invaded up to the muscle layer of abdominal wall, and it was suggested that the IL-8 signal inhibitors can suppress the formation of deep lesions. Furthermore, surprisingly, the present inventors also proved for the first time that the IL-8 signal inhibitors are capable of suppressing even adhesion and fibrosis in endometriosis. Thus, in an embodiment, the IL-8 signal inhibitors of the present disclosure can be used to treat or prevent the symptom referred to as fibrosis at a particular stage of endometriosis which can be regarded as a fibrotic disease. Moreover, in the in vivo cynomolgus monkey model, one animal had irregular sexual cycle presumably due to the influence of model preparation; however, except for this animal, the sexual cycle was regular, and thus it was considered that the IL-8 signal inhibitors had no influence on the sexual cycle (see the Examples herein). These findings show that the IL-8 signal inhibitors are promising therapeutic or preventive agents as compared to conventional therapeutic agents for endometriosis. Furthermore, it is surprising that endometriosis can be treated or prevented by using an IL-8 signal inhibitor as a single drug without combining it with a hormone drug. In one embodiment, endometriosis of the present disclosure is responsive to IL-8 signals.

Herein, adenomyosis refers to, but is not limited to, a condition where endometrial tissues, specifically, endometrial glands and their circumjacent uterine stroma, are present in the uterine musculature, which is a disease with hypertrophy and hyperplasia of the circumjacent smooth muscles and causes severe menstrual pain, hypermenorrhea, anemia, and chronic pain. Although 6% to 20% of adenomyosis patients also have endometriosis (Taketani, et al., Study report on mental and physical disorders sponsored by the Ministry of Health and Welfare. 1998:99-104), adenomyosis is a disease different from endometriosis in disease classification. It is the recent common technical knowledge of those skilled in the art that the two are separate, distinct diseases (Frankl et al., 1925, 10:680-4; Brosens et al., Lancet. 1993 Jan. 16, 341(8838):181-2; Benagiano et al., Best Pract Res Clin Obstet Gynaecol. 2006 August, 20(4): 449-63). Although adenomyosis resembles endometriosis in that endometrium develops and proliferates ectopically, and changes occur in an estrogen-dependent manner, and menstrual pain is a main symptom, adenomyosis often develops in relatively elderly parous women compared to endometriosis, which is epidemiologically different from endometriosis. It is not possible to specify the cause leading to the disruption of the boundary between the myometrium and the basal layer of the endometrium; however, the following hypothesis has been proposed for the development: uterine damages (excessive curettage or birth injury) result in direct incorporation of the endometrium into the myometrium (Pappas et al., Obset Gynecol. 1959, 13:714; Benagiano et al., Fertil Steril. 2012 September, 98(3):572-9). A condition where endometrial tissues are not present up to 90% of the myometrium on its luminal side and they are only distributed on the myometrium on its serosal side is called pelvic peritoneal endometriosis (Bergeron et al., Best Pract Res Clin Obset Gynaecol 2006; 20(4):511-521).

The present inventors observed and confirmed the spontaneous onset of adenomyosis in the above-described in vivo cynomolgus monkey model, and succeeded for the first time in the world in demonstrating that the proliferation of adenomyosis lesions can be suppressed by administering IL-8 signal inhibitors to the living body. The IL-8 signal inhibitors did not affect the sexual cycle in the in vivo cynomolgus monkey model (see the Examples herein). Thus, the IL-8 signal inhibitors are promising therapeutic or preventive agents as compared to conventional therapeutic agents for adenomyosis. Furthermore, it is surprising that adenomyosis can be treated or prevented by an IL-8 signal inhibitor as a single drug without combining it with a hormone drug. The administration of an IL-8 signal inhibitor can result in thinning of hypertrophied uterine wall in adenomyosis, and thus they are expected to have therapeutic or preventive effects against fibrosis in adenomyosis. In one embodiment of the present disclosure, adenomyosis is responsive to IL-8 signals.

Dysmenorrhea is not limited herein, but may particularly refer to a catamenial symptom that disturbs daily life. Endometriosis, adenomyosis, hypermenorrhea, and such are known to be involved in dysmenorrhea, and the typical symptoms include, for example, lumbar pain, headache, nausea, anemia, and fatigue as well as abdominal pain during menstruation, in particular lower abdominal pain. Based on its cause, dysmenorrhea is roughly classified into the following two types: functional (primary) dysmenorrhea and organic (secondary) dysmenorrhea. The causes of functional dysmenorrhea include, for example, oversecretion of prostaglandins as well as causes associated with progression of a disease such as uterine fibroid and endometriosis. The causes of organic dysmenorrhea include, for example, those associated with progression of a disease such as uterine fibroid and endometriosis. Furthermore, dysmenorrhea is known to be caused by inflammation inside and outside of the uterus. Meanwhile, IL-8 is known as an anti-inflammatory cytokine. In one embodiment, thus, an IL-8 signal inhibitor of the present disclosure can treat or prevent dysmenorrhea. In a preferable non-limiting embodiment, an IL-8 signal inhibitor of the present disclosure can treat or prevent dysmenorrhea with endometriosis or adenomyosis, dysmenorrhea with which endometriosis or adenomyosis is suspected, dysmenorrhea accompanying inflammation, or dysmenorrhea with pain caused by adhesion. Alternatively, in another embodiment of the present disclosure, dysmenorrhea is responsive to IL-8 signals.

Herein, "dysmenorrhea with which endometriosis or adenomyosis is suspected" includes, but is not limited to, dysmenorrhea in a subject who has once suffered from endometriosis or adenomyosis and has a possibility of reactivation of the disease, and dysmenorrhea in a subject with suspected endometriosis or adenomyosis before confirmed diagnosis or such made by a physician or others based, for example, on pathological findings that indicates endometriosis or adenomyosis.

In one embodiment, when an IL-8 signal inhibitor of the present disclosure is used in treating or preventing dysmenorrhea accompanying endometriosis or adenomyosis, or dysmenorrhea with which endometriosis or adenomyosis is suspected, the IL-8 signal inhibitor is advantageous since it does not affect the sexual cycle and can be used to treat or prevent endometriosis or adenomyosis as a single drug without combining it with a hormone drug, as described above.

Furthermore, the present inventors conceived and demonstrated that IL-8 signal inhibitors can treat or prevent adhesion in addition to endometriosis and adenomyosis, as described in the Examples herein. Dysmenorrhea is also characterized by pain such as abdominal pain. Thus, it is naturally thought that not only adhesion in endometriosis but also adhesion by other symptoms or disorders cause pain in patients due to the adhered contact of tissues or organs. For example, it is known that, in pelvic adhesion, pain correlates with adhesion of Douglas' pouch while it does not correlate with adhesion between appendages of the reproductive organ (Porpora et al., The Journal of the American Association of Gynecologic Laparoscopists 1999; 6:429-434), and adhesion between organs causes twitches leading to pain. Furthermore, ectopic nerve fibers and NGF production are known to cause pain and pain exacerbation in endometriosis (Anaf et al., Hum Reprod 2000, 15:1744-1750; Berkley et al., Proc Natl Acad Sci USA 2004, 101:11094-11098; Odagiri et al., Fertil Steril 2009, 92:1525-1531). In addition, there is a previous report (Odagiri et al., Fertil Steril 2009, 92:1525-1531) suggesting that the interstitium with increased smooth muscles circumjacent to endometriosis lesions intensifies pain during contraction. It was confirmed that the administration of anti-IL-8 antibodies described in the Examples herein reduces the interstitium of endometriosis tissues, and it is expected to decrease ectopic neurons, and thus pain reduction can be expected.

In one embodiment, an IL-8 signal inhibitor of the present disclosure can treat or prevent pain in endometriosis or adenomyosis (chronic pain, pain during menstruation, etc.), pain in dysmenorrhea, or pain by adhesion, fibrosis, or inflammation. Here, the chronic pain includes, but is not limited to, chronic lower abdomen pain and chronic pelvic pain.

In one embodiment, herein, "does not affect the sexual cycle" may mean that the periodical menstrual cycle and ovulation are not substantially interfered with in a subject (a woman in human, or a female in a nonhuman animal). The periodicity of the cycle may be assessed based on the presence of bleeding during menstruation as observed in the Examples herein, or based on changes in estrogen or progesterone level in blood or urine. Hormone (for example, estrogen/progesterone combination drug, progesterone preparation, GnRH agonist, and danazol) therapy is known to interfere with the menstrual cycle and inhibit ovulation. Without limitations, the presence of the substantial interference can be assessed, for example, by testing the tendency of, or statistically testing whether the menstrual cycle is interfered with in a group administered with an IL-8 signal inhibitor as compared to a reference group that underwent hormone therapy which is known to affect the sexual cycle. In one embodiment, since an IL-8 signal inhibitor of the present disclosure does not affect the sexual cycle of subjects with endometriosis, adenomyosis, or dysmenorrhea to which it is administered, it is considered that it does not inhibit ovulation and allows chances of pregnancy unlike conventional hormone therapy. Furthermore, the inhibitor is advantageous in that hormone drugs are avoided and thus subjects can obviate adverse effect conditions such as menopause caused by low estrogen conditions.

The body has wound healing functionality to heal the site of injury or wound when cells, tissues, organs, or viscera are damaged or injured. However, during the process of wound healing, normally undesirable attachments can occur between cells, tissues, organs, or viscera. Typically, without limitations, such a condition of attachment is referred to as adhesion. Some patients are asymptomatic for adhesion; however, a non-negligible number of patients need to be treated due to accompanying symptoms such as pain, infertility, and a sense of fullness in the abdomen. Adhesion includes, for example, adhesion formed (forming) after surgery (for example, adhesion that directly or indirectly formed (forms) at the surface of surgical incision, areas around the suture site, sites of abrasion such as by gauze; intrauterine adhesion (Asherman's syndrome)) formed (forming) after uterine curettage; adhesion caused by drugs (for example, local administration of drugs to organs); adhesion caused by diseases (for example, endometriosis, adenomyosis, infiltrating cancer cells or tissues, and inflammatory diseases associated with infection (salpingitis, oophoritis, pelvic peritonitis, etc.); bowel atresia with adhesion; and spontaneous adhesion. The present inventors incidentally found that in vivo administration of an IL-8 signal inhibitor reduced the adhesion at the site of laparotomy, which was different from that in post-surgical endometriosis, in the in vivo cynomolgus monkey model for endometriosis. In one embodiment of the present invention, adhesion is responsive to IL-8 signals.

Herein, without limitations, infertility means that despite having intercourse without contraception, a healthy couple who desire pregnancy do not achieve pregnancy in a certain period of time (generally in one year) (Japan Society of Obstetrics and Gynecology, 2016). In an aspect, infertility includes, but is not limited to, infertility after formation of adhesion (in particular, caused by adhesion) and infertility caused by intraperitoneal inflammation. In one embodiment of the present disclosure, infertility is responsive to IL-8 signals.

Herein, palmoplantar pustulosis refers to, but is not limited to, a disease where uncountable rashes (pus-filled blisters) are formed on the palms or soles. The pus-filled blisters are sterile and contain no bacteria or fungi, where neutrophils have been accumulated within the keratin of skin and IL-8 is present at a high concentration (Skov et al., J Immunol 2008, 181:669-679). The symptom is chronic and recurs repeatedly for a long period of time. In clinical trials against palmoplantar pustulosis, when HuMab10F8 which is an anti-IL-8 antibody was administered, the pathological state was ameliorated (Skov et al., J Immunol 2008; 181: 669-679). Thus, in one embodiment of the present disclosure, palmoplantar pustulosis is responsive to IL-8 signals.

Herein, ANCA-associated nephritis refers to nephritis where ANCA (anti-neutrophil cytoplasmic antibody) is positive. ANCA-associated nephritis is a disease where inflammation occurs in kidney blood vessels such as glomeruli, and its typical pathological condition is necrotizing crescentic glomerulonephritis. As the nephritis becomes chronic, fibrosis progresses and glomeruli harden to leads renal failure ("Evidence-based Clinical Guideline for rapidly progressive glomerulonephritis (PRGN) 2014" in Japanese; Nature Review Rheumatology 10 (2014) 463). In ANCA associated nephritis, IL-8 is expressed at a high level in the lesions, and the migratory competence of patients' neutrophils is augmented by ANCA treatment, and suppressed by anti-IL-8 antibody treatment (Cockwell et al., Kidney Int. 1999 March, 55(3):852-63). In one embodiment of the present disclosure, ANCA-associated nephritis is responsive to IL-8 signals.

Herein, cystic fibrosis refers to a systemic autosomal recessive inherited disorder caused by genetic mutation in cystic fibrosis transmembrane conductance regulator (CFTR). Secretory fluid and mucosal fluid such as airway fluid, intestinal fluid, and pancreatic fluid become extremely viscous throughout the body, resulting in occlusion of lumens, which predisposes to infection and is manifested with symptoms such as meconium ileus, indigestion and malabsorption due to pancreatic atrophy and exocrine failure, and respiratory failure due to recurring respiratory infection. The lesions and their surrounding area, for example, airway fluid or bronchoalveolar lavage fluid, contain a high concentration of IL-8 (Marcos et al., Nat Med. 2010 September, 16(9):1018-23; Khan et al., Am J Respir Crit Care Med. 1995 April, 151(4):1075-82) and a large number of neutrophils migrated by IL-8 are present. It is thought that excessive and persistent inflammation occurs and neutrophils produce enzymes such as elastase and undergo NETosis, and thus the viscosity of body fluid is increased resulting in manifestation of the symptoms (Cheng et al., Front Immunol. 2013 Jan. 24, 4:1). Topical neutrophil migration was observed to be suppressed in clinical trials of the CXCR2 inhibitor Elubrixin against cystic fibrosis (J Cyst Fibros. 2013 May, 12(3):241-8). It is expected that, when the enzyme production and NETosis are suppressed by inhibiting neutrophil migration by blockage of the IL-8 pathway, the local viscosity is decreased, and the symptoms are ameliorated. Thus, in one embodiment of the present disclosure, cystic fibrosis is responsive to IL-8 signals.

Herein, without intending to be limiting, psoriasis is also known as an inflammatory disease. A typical symptom is well-circumscribed red papules or convex prominences covered with silver dander. The common triggers include external injury, infection, and certain drugs. Generally, there is almost no symptom, but occasionally mild itching is experienced. Some major complaints can be from a cosmetic point of view. Some people have arthritis with pain as a complication which increases the severity. US2003/0077283A1 discloses local therapy for psoriasis using an anti-IL-8-neutralizing antibody. Furthermore, a therapeutic agent of an anti-IL-8-neutralizing antibody for infection is available on the market under the name of Abcream™. Thus, in one embodiment of the present disclosure, psoriasis is responsive to IL-8 signals.

The mechanism underlying fibrosis is as follows: inflammation following damage caused by hemorrhage or diseases serves as a trigger, and chemokines and cytokines including IL-8 recruit immune cells such as neutrophils and monocytes from the surrounding tissues; cytokines and chemokines are produced and this induces activation and proliferation of muscle fibroblasts (or fibrotic cells) as well as hyperproduction or hypodegradation of extracellular matrix such as collagen, which results in fibrosis. This is common for fibrosis in various organs (N Engl J Med 2015, 372: 1138-1149 Mar. 19, 2015).

Herein, diseases and conditions with such fibrosis are collectively referred to as "fibrotic diseases", by focusing on the fibrotic condition.

Since IL-8 signal inhibitors exhibited an inhibitory activity on the migration of neutrophils that produce MCP-1 (known as a macrophage-migratory factor and as a fibrosis-enhancing factor) and such in an in vitro assay, in addition to the fact that the IL-8 signal inhibitors suppressed the infiltration of immune cells and reduced the collagen-rich interstitium in the in vivo cynomolgus monkey model (see the Examples herein), the IL-8 signal inhibitors are promising therapeutic or preventive agents for fibrosis as described above.

In addition, various anti-IL-8 antibodies suppressed the increase in expression of connecting tissue growth factor (CTGF) as a fibrosis-enhancing factor in an in vitro assay as described in the Examples herein. This result supports the fact that IL-8 signal inhibitors such as anti-IL-8 antibodies are promising therapeutic or preventive agents for fibrotic diseases.

In one embodiment of the present disclosure, adhesion and fibrosis in endometriosis can occur during a process where uterus-derived tissues develop and proliferate outside of the uterus (for example, pelvic viscera, in the peritoneal cavity, or in the thoracic cavity).

Herein, hepatic fibrosis refers to, but is not limited to, a disease where chronic inflammation caused by viral infection, fat accumulation, or such triggers hyperproduction or hypodegradation of extracellular matrix (ECM) such as collagen in the liver, which leads to fibrosis. Hepatic fibrosis includes, for example, cirrhosis caused by chronic inflammation such as viral hepatitis, alcoholic hepatitis, nonalcoholic fatty liver disease (NAFLD), or primary biliary cirrhosis (PBC).

The following has been reported: IL-8 is increased in chronic liver diseases such as viral hepatitis A and B, alcoholic hepatitis, and primary biliary cirrhosis (Mediators Inflamm. 2015, 2015:276850); and the level of IL-8 in blood is high in chronic liver diseases and particularly high in patients in advanced pathological conditions; and the expression level of the receptor CXCR1 is high in monocytes; and IL-8 strongly enhances inflammation in the liver; and these results suggest the contribution of IL-8 to the progression of fibrosis (PLoS One. 2011; 6(6):e21381).

Furthermore, plasma IL-8 concentration was significantly high in NASH patients with fibrosis (Gastroenterology, 2015 September, 149(3):635-48.e14), which suggests the correlation between IL-8 and fibrosis. In one embodiment of the present disclosure, hepatic fibrosis is responsive to IL-8 signals.

Herein, renal fibrosis refers to, but is not limited to, a disease where inflammation triggers hyperproduction or hypodegradation of extracellular matrix such as collagen in the kidney, which leads to fibrosis. Renal fibrosis includes, for example, chronic kidney diseases caused by chronic inflammation such as chronic nephritis and diabetes. As chronic kidney diseases are advanced, fibrosis occurs in the kidneys regardless of the causative disease. Once started, fibrosis is irreversible, and as for the kidney, dialysis or renal transplantation is needed.

The following reports have been published: kidney fibroblasts enhanced IL-8 production via IL-1 (Kidney Int. 1995 March, 47(3):845-54); renal fibrosis was reduced by suppressing MCP-1 signal (Kitagawa et al., Am J Pathol. 2004 July, 165(1):237-46); and the activation and mechanism of fibrosis in diabetic condition were examined using human fibrous cells and the result suggested that human fibrous cells involve in progression of diabetic nephropathy via elevated blood glucose and MCP-1/CCR2 (Clin Exp Nephrol. 2013 December, 17(6):793-804). Since IL-8 signal inhibitors inhibit the migration of MCP-1-producing neutrophils to the lesions (see the Examples herein), the inhibitors are expected to suppress the progression of or ameliorate renal fibrosis via MCP-1. In one embodiment of the present disclosure, renal fibrosis is responsive to IL-8 signals.

Herein, pulmonary fibrosis refers to, but is not limited to, a disease where fibrosis is caused by hyperproduction or hypodegradation of extracellular matrix such as collagen in the lungs or bronchi which is triggered by inflammation. Pulmonary fibrosis includes, for example, chronic obstructive pulmonary disease (COPD), combined pulmonary fibrosis and emphysema (CPFE), idiopathic interstitial pneumonias (IIPs), and idiopathic pulmonary fibrosis (IPF).

Chronic obstructive pulmonary disease (COPD) refers to, but is not limited to, a pulmonary inflammatory disease caused by long-term inhalation exposure to harmful substances, primarily cigarette smoke (Guideline for diagnosis and therapy of chronic obstructive pulmonary disease (COPD), 4th Ed.). In the respiratory tract and lungs, chronic inflammation reduces alveolar elasticity and narrows bronchial lumen, and as a result, the air flow to the lungs becomes weak, and airflow obstruction causes breathing difficulty, chronic cough, sputum production, etc. It has been reported that in the sputum of COPD patients, IL-8 is increased and a large number of neutrophils are present, and the chemotactic index in a migration assay of patients' neutrophils correlates with pulmonary function FEV1/FVC (Yamamoto et al., Chest. 1997 August, 112(2):505-10; Wu et al., PLoS One. 2015 May 11, 10(5)). Further, it is reported that, in clinical trials of the CXCR2 inhibitor MK7123 for COPD patients, pulmonary function (FEV1) was improved in the active drug group whereas the function was worsened in the placebo group (Am J Respir Crit Care Med. 2015 May 1, 191(9):1001-11).

Combined pulmonary fibrosis and emphysema (CPFE) refers to, but is not limited to, a poor-prognosis disease where pathological change called emphysema which destroys and enlarges the lungs is complicated by pulmonary fibrosis (Cottin et al., Eur Respir J. 2005 October, 26(4): 586-93). There are reports describing that in CPFE, IL-8 is increased in bronchoalveolar lavage fluid of patients, and the concentration of IL-8 in bronchoalveolar lavage fluid correlates with low attenuation area (LAA) which indicates emphysematous lesion in chest CT (Respirology. 2012 July, 17(5):814-20); and LAA which shows emphysematous lesions in chest CT correlates with prognosis (Johannessen A, et al., Am J Respir Crit Care Med 2013, 187: 602-8).

IIPs is a generic name for various interstitial pneumonias whose cause is not identifiable, which are diseases where inflammation and damages occur in alveolar walls, and this results in fibrosis which thickens and hardens the walls, leading to impaired gas-exchange function (Guideline for diagnosis and therapy of idiopathic interstitial pneumonias, revised 2nd Ed.; Travis et al., Am J Respir Crit Care Med. 2013 Sep. 15,188(6):733-48). Of IIPs, IPF is frequent and most difficult to treat, and a poor-prognosis pulmonary disease which follows a chronic and progressive course and progresses to severe fibrosis, leading to irreversible honey comb lung formation (Guideline for diagnosis and therapy of idiopathic interstitial pneumonias, revised 2nd Ed.; Raghu et al., Am J Respir Crit Care Med. 2011 Mar. 15; 183(6): 788-824). The level of IL-8 is high in sera and bronchoalveolar lavage fluid from IPF patients (Car et al., Am J Respir Crit Care Med 1994, 149:655-659; Ziegenhagen et al., Am J Respir Crit Care Med 1998, 157:762-768); and the number of neutrophils that migrate in response to IL-8 is increased in bronchoalveolar lavage fluid, and the prognosis is worse when the number is high (Haslam et al., Thorax 1980, 35: 328-339; Turner-Warwick M et al., Am Rev Respir Dis 1987, 135: 26-34). These suggest that IL-8 and neutrophils are deeply involved in the pathological condition of IPF. IL-8 is also assumed to be the cause of the disease from the finding that IPF patients have an SNIP of IL-8 and the local IL-8 concentration is elevated (Ahn et al., Respir Res. 2011 Jun. 8; 12:73). In one embodiment of the present disclosure, pulmonary fibrosis, COPD, CPFE, IIPs, and IPF are responsive to IL-8 signals.

In a further or an alternative embodiment, the present disclosure relates to IL-8 signal inhibitors (for example, anti-IL-8 antibodies) for use in inhibiting production of a fibrotic factor. Alternatively, the present disclosure relates to methods for inhibiting the production of a fibrotic factor in a subject, which comprise administering an effective amount of an IL-8 signal inhibitor (for example, an anti-IL-8 antibody) to the subject, or relates to IL-8 signal inhibitors (for example, anti-IL-8 antibodies) for use in the methods. Alternatively, the present disclosure relates to pharmaceutical compositions for inhibiting the production of a fibrotic factor, which comprise an effective amount of an IL-8 signal inhibitor (for example, an anti-IL-8 antibody). Alternatively, the present disclosure relates to use of an IL-8 signal inhibitor (for example, an anti-IL-8 antibody) in the manufacture of a pharmaceutical agent for inhibiting the production of a fibrotic factor. Alternatively, the present disclosure relates to use of an IL-8 signal inhibitor (for example, an anti-IL-8 antibody) in inhibiting the production of a fibrotic factor. Alternatively, the present disclosure relates to methods for manufacturing a pharmaceutical composition for inhibiting the production of a fibrotic factor, which comprise the step of mixing an IL-8 signal inhibitor (for example, an anti-IL-8 antibody) with a pharmaceutically acceptable carrier. In an embodiment, the fibrotic factor includes, for example, MCP-1 (Monocyte Chemotactic Protein-1). The inhibition of the production of such a fibrotic factor can occur, for example, in immune cells such as neutrophils.

In a further or an alternative embodiment, the present disclosure relates to IL-8 signal inhibitors (for example, anti-IL-8 antibodies) for use in inhibiting angiogenesis. Alternatively, the present disclosure relates to methods for inhibiting angiogenesis in a subject, which comprise administering to the subject an effective amount of an IL-8 signal inhibitor (for example, an anti-IL-8 antibody), or relates to IL-8 signal inhibitors (for example, anti-IL-8 antibodies) for use in the methods. Alternatively, the present disclosure relates to pharmaceutical compositions for inhibiting angiogenesis, which comprise an effective amount of an IL-8 signal inhibitor (for example, an anti-IL-8 antibody). Alternatively, the present disclosure relates to use of an IL-8 signal inhibitor (for example, an anti-IL-8 antibody) in the manufacture of a pharmaceutical agent for inhibiting angiogenesis. Alternatively, the present disclosure relates to use of an IL-8 signal inhibitor (for example, an anti-IL-8 antibody) in inhibiting angiogenesis. Alternatively, the present disclosure relates to methods for manufacturing a pharmaceutical composition for inhibiting angiogenesis, which comprise the step of mixing an IL-8 signal inhibitor (for example, an anti-IL-8 antibody) with a pharmaceutically acceptable carrier.

As described in the Examples herein, in the in vitro assay, neutrophil migration was demonstrated to be inhibited not only by commercially available anti-IL-8 antibodies but also by IL-8 receptor inhibitors as well as by the anti-IL-8 antibodies used in the in vivo experiments. This means that those skilled in the art naturally understand that the findings from the in vivo model described in the Examples herein can be generalized and expanded to the general application to IL-8 signal inhibitors.

Thus, in a further or an alternative embodiment, the present disclosure relates to IL-8 signal inhibitors (for example, anti-IL-8 antibodies) for use in suppressing the infiltration (which may be, in an aspect, rephrased as migration) of immune cells to a lesion or a surrounding environment thereof in an IL-8-related disease. Alternatively, the present disclosure relates to methods for suppressing in a subject the infiltration of immune cells to a lesion or a surrounding environment thereof in an IL-8-related disease, which comprise administering to the subject an effective amount of an IL-8 signal inhibitor (for example, an anti-IL-8 antibody), or relates to IL-8 signal inhibitors (for example, anti-IL-8 antibodies) for use in the methods. Alternatively, the present disclosure relates to pharmaceutical compositions for suppressing the infiltration of immune cells to a lesion or a surrounding environment thereof in an IL-8-related disease, which comprise an effective amount of an IL-8 signal inhibitor (for example, an anti-IL-8 antibody). Alternatively, the present disclosure relates to use of an IL-8 signal inhibitor (for example, an anti-IL-8 antibody) in the manufacture of a pharmaceutical agent for suppressing the infiltration of immune cells to a lesion or a surrounding environment thereof in an IL-8-related disease. Alternatively, the present disclosure relates to use of an IL-8 signal inhibitor (for example, an anti-IL-8 antibody) in suppressing the infiltration of immune cells to a lesion or a surrounding environment thereof in an IL-8-related disease. Alternatively, the present disclosure relates to methods for manufacturing a pharmaceutical composition for suppressing the infiltration of immune cells to a lesion or a surrounding environment thereof in an IL-8-related disease, which comprise the step of mixing an IL-8 signal inhibitor (for example, an anti-IL-8 antibody) with a pharmaceutically acceptable carrier.

In one embodiment, immune cells preferably include, for example, neutrophils, macrophages, monocytes, helper T cells, killer T cells, dendritic cells, and NK cells, and preferably include, but are not limited to, neutrophils, macrophages, and monocytes. When referring to "the infiltration of immune cells to a lesion in an IL-8-related disease", the IL-8-related disease may be any of the diseases described above, for example, endometriosis, adenomyosis, dysmenorrhea, adhesion, or a fibrotic disease. It should be intended that immune cells infiltrate or migrate to a lesion (a site of the disease) or its surrounding in the IL-8-related disease. Furthermore, when referring to "the infiltration of immune cells to a surrounding environment in an IL-8-related disease", a skilled person can understand that, for example, for endometriosis, the infiltration or migration into the peritoneal cavity or ascites would be intended, or for example, for pulmonary fibrosis, the infiltration or migration into the thoracic cavity or pleural effusion would be intended.

In a further or an alternative embodiment, the present disclosure relates to IL-8 signal inhibitors (for example, anti-IL-8 antibodies) for use in inhibiting the production of aromatase in a lesion of endometriosis or adenomyosis. Alternatively, the present disclosure relates to methods for inhibiting the production of aromatase in a subject, which comprise administering an effective amount of an IL-8 signal inhibitor (for example, an anti-IL-8 antibody) to the subject, or IL-8 signal inhibitors (for example, anti-IL-8 antibodies) for use in the methods. Alternatively, the present disclosure relates to pharmaceutical compositions for inhibiting the production of aromatase, which comprise an effective amount of an IL-8 signal inhibitor (for example, an anti-IL-8 antibody). Alternatively, the present disclosure relates to use of an IL-8 signal inhibitor (for example, an anti-IL-8 antibody) in the manufacture of a pharmaceutical agent for inhibiting the production of aromatase. Alternatively, the present disclosure relates to use of an IL-8 signal inhibitor (for example, an anti-IL-8 antibody) in inhibiting the production of aromatase in a lesion of endometriosis or adenomyosis. Alternatively, the present disclosure relates to methods for manufacturing a pharmaceutical composition for inhibiting the production of aromatase in a lesion of endometriosis or adenomyosis, which comprise mixing an IL-8 signal inhibitor (for example, an anti-IL-8 antibody) with a pharmaceutically acceptable carrier.

Those of ordinary skill in the art will naturally understand that the present disclosure includes any combinations of the whole or part of one or more of any embodiments described herein, unless there is a technical contradiction, based on the common technical knowledge of those skilled in the art.

All prior art documents cited in this specification are incorporated herein by reference to the common technical knowledge of those skilled in the art.

Herein, the meaning of the term "and/or" is understood to include any combinations of terms before and after the phrase "and/or" in which "and" and "or" is appropriately combined.

When terms such as first, second, third, fourth, and so on are used for referring to various elements, it is understood that the elements should not be limited by such terms. These terms are only used to distinguish an element from other elements, and it is appreciated that, for example, a first element can be termed a second element, and similarly, a second element can be termed a first element, without departing from the scope of the present disclosure.

Unless explicitly stated otherwise or unless there are contradictions to the context, the words, “a”, “an”, and “the”, as used herein, mean “at least one”.

Herein, the terminology is used for the purpose of describing particular embodiments but is not intended to limit the present invention or the disclosure herein. Unless defined otherwise, all terms (including technical and scientific terms) used herein are interpreted to have the same meaning commonly understood by those of ordinary skill in the art to which the disclosure herein pertains, and idealized, and should not be interpreted in an overly formal sense.

As used herein, the term “comprises” intends the presence of described items (members, steps, elements, numbers, etc.), unless different understanding should clearly be made in the context, and the term does not preclude the presence of other items (members, steps, elements, numbers, etc.).

Embodiments of the present disclosure are described with reference to schematic illustrations, which may be exaggerated for the clarity of explanation.

Unless contrary to the context, numerical values described herein are understood to be values that have a certain range based on the common technical knowledge of those of ordinary skill in the art. For example, the expression “1 mg” is understood to be described as “about 1 mg” with certain variations. Furthermore, for example, the expression “1 to 5 items” used herein is understood to describe each value specifically and individually such as “1 item, 2 items, 3 items, 4 items, 5 items”, unless contrary to the context.

EXAMPLES

[Example 1] Production of Novel Fc Region Variants with Enhanced FcRn Binding Under Acidic pH Conditions for Improving Retention in the Plasma Under the acidic pH condition in the endosomes, IgG antibodies taken up into cells are known to be returned to the plasma by binding to FcRn. Therefore, IgG antibodies generally have long plasma half-life compared to proteins that do not bind to FcRn. Methods that utilize this property to enhance plasma retention of antibodies by increasing their FcRn binding ability (binding affinity) under acidic pH conditions through the introduction of amino acid modifications in the antibody Fc region are already known. Specifically, methods for improving plasma retention of an antibody by increasing its ability to bind to FcRn under acidic pH conditions through amino acid modifications, such as the M252Y/S254T/T256E (YTE) modification (J. Biol. Chem. 281:23514-23524 (2006)), M428L/N434S (LS) modification (Nat. Biotechnol. 28:157-159 (2010)), and N434H modification (Clinical Pharmacology & Therapeutics 89(2):283-290 (2011)) are known.

On the other hand, as described above, Fc region variants with increased binding to FcRn under acidic pH conditions are also known to show binding to the rheumatoid factor (RF) (WO2013/046704). Therefore, the following examinations were carried out with an objective of producing Fc region variants that can improve plasma retention without showing binding to rheumatoid factor.

(1-1) Production of Novel Fc Region Variant-Containing Antibodies

Fc region variants with increased FcRn binding ability under acidic pH conditions including the known modifications, YTE, LS, or N434H, and several newly-found Fc region variants (F1847m, F1848m, F1886m, F1889m, F1927m, and F1168m) were produced as shown below.

Genes for heavy chains in which the amino acid modifications were introduced into the Fc region of the heavy chain (VH3-IgG1m) of Fv4-IgG1, which is an anti-human IL-6 receptor antibody, were produced by the method of Reference Example 1. These heavy chains were used to produce the following antibodies by the method of Reference Example 2:

Fv4-IgG1 consisting of VH3-IgG1m (SEQ ID NO:2) as the heavy chain and VL3-CK (SEQ ID NO: 110) as the light chain;

Fv4-YTE consisting of VH3-YTE (SEQ ID NO:3) as the heavy chain and VL3-CK as the light chain;

Fv4-LS consisting of VH3-LS (SEQ ID NO:4) as the heavy chain and VL3-CK as the light chain;

Fv4-N434H consisting of VH3-N434H (SEQ ID NO:5) as the heavy chain and VL3-CK as the light chain;

Fv4-F1847m consisting of VH3-F1847m (SEQ ID NO:6) as the heavy chain and VL3-CK as the light chain;

Fv4-F1848m consisting of VH3-F1848m (SEQ ID NO:7) as the heavy chain and VL3-CK as the light chain;

Fv4-F1886m consisting of VH3-F1886m (SEQ ID NO:8) as the heavy chain and VL3-CK as the light chain;

Fv4-F1889m consisting of VH3-F1889m (SEQ ID NO:9) as the heavy chain and VL3-CK as the light chain;

Fv4-F1927m consisting of VH3-F1927m (SEQ ID NO:10) as the heavy chain and VL3-CK as the light chain; and Fv4-F1168m consisting of VH3-F1168m (SEQ ID NO:11) as the heavy chain and VL3-CK as the light chain.

(1-2) Kinetic Analyses of Binding Toward Human FcRn

Antibodies containing VH3-IgG1m or an above-mentioned variant as the heavy chain and L(WT) (SEQ ID NO: 1) as the light chain were produced by the method of Reference Example 2, and the binding activity toward human FcRn was evaluated as follows.

Kinetic analyses of human FcRn and each of the antibodies were carried out using BIACORE T100 (GE Healthcare). An appropriate amount of Protein L (ACTIGEN) was fixed onto Sensor chip CM4 (GE Healthcare) by the amine coupling method to capture the antibodies of interest. Next, human FcRn was made to interact with the antibodies captured on the sensor chip by injecting a diluted FcRn solution and a running buffer (used as a reference solution). For the running buffer, 50 mM sodium phosphate, 150 mM NaCl, and 0.05% (w/v) Tween 20 at pH 6.0 was used, and the respective buffer was also used to dilute FcRn. To regenerate the sensor chip, 10 mM glycine-HCl at pH 1.5 was used. All measurements were carried out at 25° C. KD (M) for human FcRn was calculated for each antibody based on the association rate constant ka (1/Ms) and dissociation rate constant kd (l/s), which are kinetic parameters calculated from sensorgrams obtained by the measurements. The BIACORE T100 Evaluation Software (GE Healthcare) was used to calculate each parameter.

The results are shown in Table 2.

TABLE 2

| Variant Name | Amino Acid Mutation(s) | KD Value (nM) for hFcRn at pH 6.0 |
|---|---|---|
| IgG1 | | 1382 |
| LS | M428L/N434S | 116 |
| YTE | M252Y/S254T/T256E | 148 |
| F1847m | N434A/Y436T/Q438R/S440E | 367 |
| F1848m | N434A/Y436V/Q438R/S440E | 295 |

TABLE 2-continued

| Variant Name | Amino Acid Mutation(s) | KD Value (nM) for hFcRn at pH 6.0 |
|---|---|---|
| F1886m | M428L/N434A/Y436T/Q438R/S440E | 108 |
| F1889m | M428L/N434A/Y436V/Q438R/S440E | 103 |
| F1927m | M428L/N434A/Q438R/S440E | 125 |
| F1168m | N434A/Q438R/S440E | 410 |

[Example 2] Evaluation of the Binding of Antibodies Containing a Novel Fc Region Variant with Enhanced FcRn Binding Under Acidic pH Conditions Toward the Rheumatoid Factor Anti-drug antibodies (ADAs) affect the efficacy and pharmacokinetics of therapeutic antibodies, and lead to serious side-effects at times; therefore, clinical utility and efficacy of therapeutic antibodies may be limited by production of ADAs. Many factors influence the immunogenicity of therapeutic antibodies, and the presence of effector T cell epitopes is one factor. In addition, the presence of ADA in a patient before administration of the therapeutic antibody (also called "Pre-existing ADA") may also have similar problems. Specifically, in the case of therapeutic antibodies for patients with autoimmune diseases such as rheumatoid arthritis (RA), rheumatoid factor (RF) which is an autoantibody against human IgG may become a "pre-existing ADA" problem. Recently, a humanized anti-CD4 IgG1 antibody having an N434H (Asn434His) mutation was reported to induce significant rheumatoid factor binding (Clin Pharm Ther 2011 February; 89(2):283-290). Detailed studies confirmed that the N434H mutation in human IgG1 increases binding of the rheumatoid factor to the Fc region of antibodies as compared to the parent human IgG1.

The rheumatoid factor is a polyclonal autoantibody against human IgG, and its epitopes in human IgG differ depending on the clone and seem to be positioned in the CH2/CH3 interface region, and in the CH3 domain that may overlap with the FcRn-binding epitope. Therefore, mutations that increase the binding activity (binding affinity) towards FcRn may increase the binding activity (binding affinity) towards specific clones of the rheumatoid factor.

In fact, regarding Fc with increased binding to FcRn at acidic pH or neutral pH, not only the N434H modification but many other amino acid modifications are also known to similarly increase the binding to rheumatoid factor (WO2013/046704).

On the other hand, WO2013/046704 also exemplifies several amino acid modifications that selectively suppress the binding toward the rheumatoid factor while not affecting binding toward FcRn, and of these, combinations of two amino acid mutations, namely Q438R/S440E, Q438R/S440D, Q438K/S440E, and Q438K/S440D, have been indicated. Accordingly, it was examined whether the binding of Fc with increased binding ability under acidic pH conditions newly produced this time toward rheumatoid factors could be reduced by introducing Q438R/S440E.

(2-1) Rheumatoid Factor Binding Assay of Antibodies Containing a Novel Fc Region Variant A binding assay toward rheumatoid factor was performed by utilizing electrochemiluminescence (ECL) at pH 7.4 using individual sera (Proteogenex) from 30 RA patients. A 50-fold diluted serum sample, each biotinylated test antibody (1 μg/mL), and each SULFO-TAG NHS Ester (Meso Scale Discovery)-labeled test antibody (1 μg/mL) were mixed and incubated at room temperature for three hours. Thereafter, the mixture was added to a Streptavidin-coated MULTI-ARRAY 96-well plate (Meso Scale Discovery), and the plate was incubated at room temperature for two hours and then washed. After adding Read Buffer T(×4) (Meso Scale Discovery) to each well, the plate was immediately set on the SECTOR imager 2400 Reader (Meso Scale Discovery), and chemiluminescence was measured.

The results of this assay are shown in FIGS. 1 to 10. Fv4-IgG1 (FIG. 1) which has a native human IgG1 only showed weak binding to the rheumatoid factor, whereas the existing Fc variants with increased FcRn binding, Fv4-YTE (FIG. 2), Fv4-LS (FIG. 3), and Fv4-N434H (FIG. 4), all showed significantly increased rheumatoid factor binding in a number of donors. On the other hand, all novel Fc region variants with increased FcRn binding, Fv4-F1847m (FIG. 5), Fv4-F1848m (FIG. 6), Fv4-F1886m (FIG. 7), Fv4-F1889m (FIG. 8), Fv4-F1927m (FIG. 9), and Fv4-F1168m (FIG. 10), showed only weak rheumatoid factor binding, and this showed that binding to the rheumatoid factor as a result of modifications to increase FcRn binding was significantly inhibited.

Figure 11:
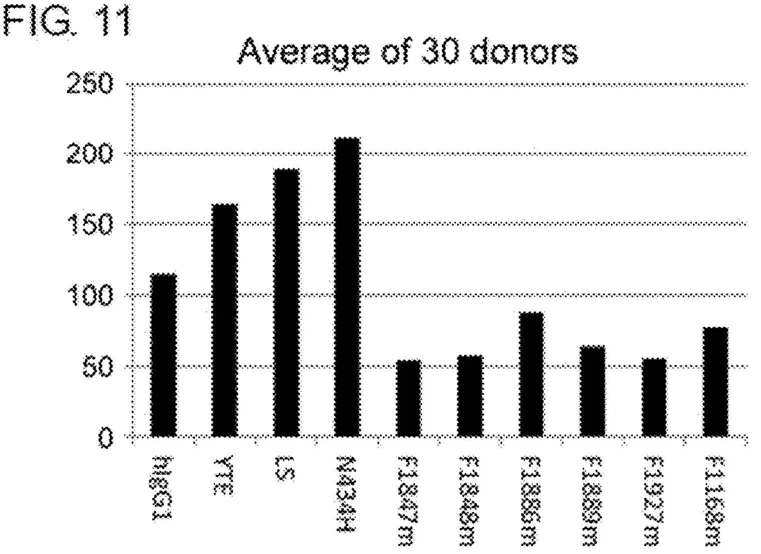
FIG. 11 shows a mean value of binding to rheumatoid factor in the blood of RA patients for each of Fv4-IgG1 and antibodies containing various Fc region variants with increased FcRn binding.

In addition, FIG. 11 shows the average values of rheumatoid factor binding in the blood of 30 RA patients for each of the variants. All of the six new variants showed a lower binding than the three pre-existing variants (YTE, LS, and N434H), and they also showed a lower binding toward the rheumatoid factor as compared with native human IgG1. As such, when considering clinical development of therapeutic antibodies with improved binding ability towards FcRn for autoimmune diseases etc. such as rheumatoid arthritis and the like, the risk associated with the rheumatoid factor, which is of concern in the existing Fc region variants, was suppressed in the Fc region variants newly produced this time, and accordingly they may be used more safely.

[Example 3] PK Evaluation of the Novel Fc Region Variants with Increased FcRn Binding Under Acidic pH Conditions in Cynomolgus Monkeys In Example 3, the effect of improving plasma retention in cynomolgus monkeys was evaluated by the following method using novel Fc region variant-containing antibodies whose binding to rheumatoid factor was confirmed to be suppressed.

(3-1) Production of Novel Fc Region Variant-Containing Antibodies

The following anti-human IgE antibodies were produced:

OHB-IgG1 consisting of OHBH-IgG1 (SEQ ID NO:12) as the heavy chain and OHBL-CK (SEQ ID NO:13) as the light chain;

OHB-LS consisting of OHBH-LS (SEQ ID NO:14) as the heavy chain and OHBL-CK as the light chain;

OHB-N434A consisting of OHBH-N434A (SEQ ID NO:15) as the heavy chain and OHBL-CK as the light chain;

OHB-F1847m consisting of OHBH-F1847m (SEQ ID NO:16) as the heavy chain and OHBL-CK as the light chain;

OHB-F1848m consisting of OHBH-F1848m (SEQ ID NO:17) as the heavy chain and OHBL-CK as the light chain;

OHB-F1886m consisting of OHBH-F1886m (SEQ ID NO:18) as the heavy chain and OHBL-CK as the light chain;

OHB-F1889m consisting of OHBH-F1889m (SEQ ID NO:19) as the heavy chain and OHBL-CK as the light chain; and OHB-F1927m consisting of OHBH-F1927m (SEQ ID NO:20) as the heavy chain and OHBL-CK as the light chain.

(3-2) Monkey PK Assay on Novel Fe Region Variant-Containing Antibodies

The in vivo kinetics of anti-human IgE antibodies in the plasma after administration of the anti-human IgE antibodies to cynomolgus monkeys were evaluated. The anti-human IgE antibody solution was intravenously administered once at 2 mg/kg. Blood collection was performed five minutes, (two hours), seven hours, one day, two days, three days, (four days), seven days, 14 days, 21 days, 28 days, 35 days, 42 days, 49 days, and 56 days after administration. The collected blood was immediately subjected to centrifugation at 4° C. and 15,000 rpm for 5 minutes to obtain plasma. The separated plasma was stored in a freezer set to −80° C. or lower until performing the measurements. Eight types of anti-human IgE antibodies, namely OHB-IgG1, OHB-LS, OHB-N434A, OHB-F1847m, OHB-F1848m, OHB-F1886m, OHB-F1889m, and OHB-F1927m, were used.

Figure 12:
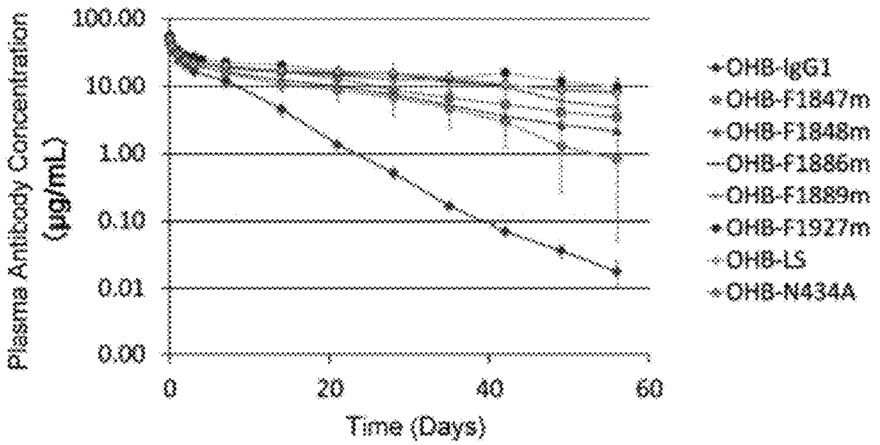
FIG. 12 shows a time course of the concentration of various anti-human IgE antibodies in the plasma of cynomolgus monkeys, where OHB-IgG1, which is an anti-human IgE antibody having the Fc domain of native human IgG1, and antibodies containing various Fc region variants with increased FcRn binding (OHB-LS, OHB-N434A, OHB-F1847m, OHB-F1848m, OHB-F1886m, OHB-F1889m, and OHB-F1927m), were each administered.

(3-3) Measurement of the Anti-Human IgE Antibody Concentration in the Plasma by ELISA The concentration of anti-human IgE antibodies in the plasma of cynomolgus monkeys was measured by ELISA. First, an anti-human IgG kappa chain antibody (Antibody Solution) was dispensed into a Nunc-Immuno Plate, MaxiSorp (Nalge Nunc International) and allowed to stand overnight at 4° C. to produce an anti-human IgG kappa chain antibody-immobilized plate. Calibration curve samples having a plasma concentration of 640, 320, 160, 80, 40, 20 or 10 ng/mL, and cynomolgus monkey plasma measurement samples diluted 100-fold or more were prepared. These calibration curve samples and plasma measurement samples were produced such that cynomolgus monkey IgE (product prepared within the company) was added at a concentration of 1 μg/mL. Subsequently, the samples were dispensed into the anti-human IgG kappa chain antibody-immobilized plate, and allowed to stand at room temperature for two hours. Then, an HRP-anti human IgG gamma chain antibody (Southern Biotech) was dispensed, and allowed to stand at room temperature for one hour. Subsequently, a chromogenic reaction was carried out using the TMB Chromogen Solution (Life Technologies) as a substrate, and after stopping the reaction by adding 1N sulfuric acid (Wako), the absorbance at 450 nm was measured by a microplate reader. The concentration of anti-human IgE antibody in the monkey plasma was calculated from absorbance of the calibration curve using the analytical software SOFTmax PRO (Molecular Devices). The measured change in the concentration of anti-human IgE antibody in the monkey plasma is shown in FIG. 12. From the measured change in the concentration of anti-human IgE antibody in the monkey plasma, elimination clearance was calculated by moment analysis using Phoenix WinNonlin Ver. 6.2 (Pharsight Corporation). The calculated pharmacokinetic parameters are shown in Table 3. Samples from individuals who were positive for antibodies against the administered sample in plasma were excluded from the calculation of the change in the anti-human IgE antibody concentration and clearance in monkey plasma.

TABLE 3

Elimination Clearance of Administered Sample after Anti-Human IgE Antibody Administration

| Sample Name | Elimination Clearance (mL/day/kg) |
|---|---|
| OHB-IgG1 | 9.33 |
| OHB-F1847m | 2.83 |
| OHB-F1848m | 4.02 |
| OHB-F1886m | 1.92 |
| OHB-F1889m | 2.39 |
| OHB-F1927m | 1.51 |
| OHB-LS | 1.80 |
| OHB-N434A | 4.36 |

(3-4) Measurement of Antibodies Against the Administered Samples in Plasma by the Electrochemiluminescence Method Antibodies in monkey plasma against the administered samples were measured by an electrochemiluminescence method. An administered sample that was ruthenium-labeled using SULFO-TAG NHS Ester (Meso Scale Discovery), an administered sample that was biotinylated using EZ-Link Micro Sulfo-NHS-Biotinylation Kit (Pierce), and a cynomolgus monkey plasma measurement sample were mixed in equal amounts, and were left to stand overnight at 4° C. The samples were added to a MULTI-ARRAY 96-well Streptavidin Gold Plate (Meso Scale Discovery), then allowed to react at room temperature for two hours, and washed. Then, immediately after Read Buffer T(×4) (Meso Scale Discovery) was dispensed into the plate, measurements were carried out using SECTOR Imager 2400 (Meso Scale Discovery).

As a result, all of the novel Fc region variants were confirmed to show greatly improved plasma retention in comparison to the case of native IgG1.

(3-5) Mouse PK Assay on Fc Variants

The following experiment was carried out to compare F1718, which is an Fc region variant described in WO2013/046704, and F1848m, which is an Fc region variant newly discovered this time, as Fc variants for increasing FcRn binding at acidic pH.

Genes for heavy chains in which amino acid modifications were introduced into the Fc region of the heavy chain (VH3-IgG1) of Fv4-IgG1, an anti-human IL-6 receptor antibody, were produced by the method of Reference Example 1. Using these heavy chains, the following antibodies were produced by the method of Reference Example 2:

Fv4-IgG1 consisting of VH3-IgG1 as the heavy chain and VL3-CK as the light chain; and Fv4-F1718 consisting of VH3-F1718 (SEQ ID NO:21) as the heavy chain and VL3-CK as the light chain.

The above-mentioned anti-human IL-6 receptor antibodies were administered once at 1 mg/kg into the tail vein of human FcRn transgenic mice (B6.mFcRn−/−.hFcRn Tg line 32+/+mouse; Jackson Laboratories, Methods Mol. Biol. 602:93-104 (2010). Blood was collected 15 minutes, seven hours, one day, two days, three days, seven days, 14 days, 21 days, and 28 days after administration of the anti-human IL-6 receptor antibodies. The collected blood was immediately centrifuged at 15,000 rpm and 4° C. for 15 minutes to obtain plasma. The separated plasma was stored in a freezer set at −20° C. or below until measurements were taken.

(3-6) Measurement of the Anti-Human IL-6 Receptor Antibody Concentration in Plasma by ELISA The concentration of anti-human IL-6 receptor antibodies in the mouse plasma was measured by ELISA. First, an Anti-Human IgG (gamma-chain specific) $F(ab')_2$ Fragment of Antibody (SIGMA) was dispensed into a Nunc-Immuno Plate, MaxiSorp (Nalge nunc International) and allowed to stand overnight at 4° C. to produce an anti-human IgG immobilized plate. Calibration curve samples containing an anti-human IL-6 receptor antibody at a plasma concentration of 0.8, 0.4, 0.2, 0.1, 0.05, 0.025, or 0.0125 μg/mL and mouse plasma measurement samples diluted 100-fold or more were each prepared. 200 μL of 20 ng/mL soluble human IL-6 receptor was added to 100 μL of the calibration curve samples or the plasma measurement samples, and then the mixed solutions were allowed to stand for one hour at room temperature. Subsequently, the mixed solutions were dispensed into each well of the anti-human IgG-immobilized plate, and the plate was allowed to stand for one hour at room temperature. Then, a Biotinylated Anti-Human IL-6R Antibody (R&D) was added to react for one hour at room temperature. Subsequently, Streptavidin-PolyHRP80 (Stereospecific Detection Technologies) was added to react for one hour at room temperature, and chromogenic reaction of this reaction solution was carried out using TMB One Component HRP Microwell Substrate (BioFX Laboratories) as a substrate. After stopping the reaction by adding 1 N sulfuric acid (Showa Chemical), the absorbance at 450 nm of the reaction solution in each well was measured on a microplate reader. The antibody concentration in mouse plasma was calculated from the absorbance of the calibration curve using the analytical software SOFTmax PRO (Molecular Devices).

Figure 13:
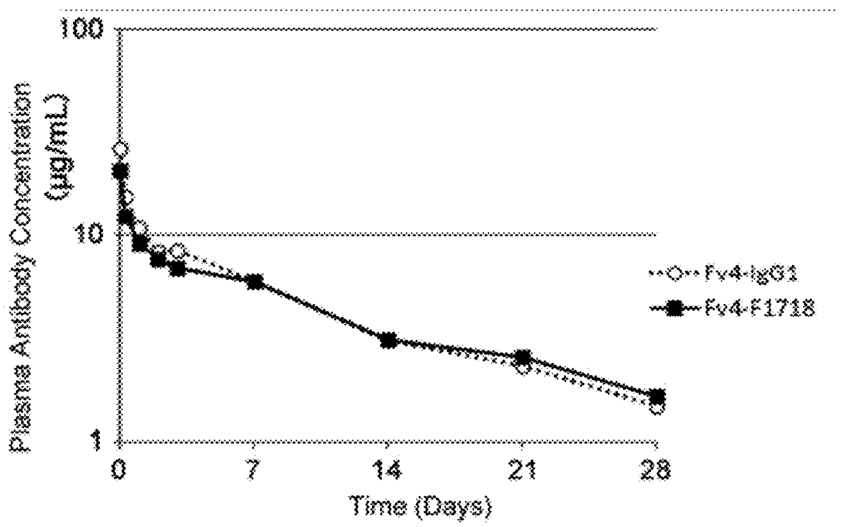
FIG. 13 shows a time course of antibody concentration in the plasma of human FcRn transgenic mice when Fv4-IgG1, which is an anti-human IL-6 receptor antibody, or Fv4-F1718, which resulted from increasing the FcRn-binding activity of Fv4-IgG1 at an acidic pH, was administered.

The results are shown in FIG. 13. F1718, which is an Fc region variant for increasing FcRn binding at acidic pH described in WO2013/046704, did not show any effect of prolonging antibody PK, but showed plasma retention equivalent to that of native IgG1.

Here, F1718 described in WO2013/046704 has four mutations, namely N434Y/Y436V/Q438R/S440E, introduced in the Fc region. By contrast, F1848m, newly discovered this time, has been introduced with four mutations, namely N434A/Y436V/Q438R/S440E. The only difference between the amino acid mutations introduced in these two types of Fc's is that the amino acid mutation introduced at position 434 according to EU numbering is Y (tyrosine) in F1718 and A (alanine) in F1848m. In Example (3-2), F1848m showed improved plasma retention compared to that of the native IgG1, whereas F1718 did not show any improvement in plasma retention. Therefore, without particular limitation, this suggests that A (alanine) is preferred as the amino acid mutation to be introduced at position 434 for improving plasma retention.

[Example 4] Production of Humanized Anti-Human IL-8 Antibodies

(4-1) Production of the Humanized Anti-Human IL-8 Antibody hWS-4

Humanized anti IL-8 antibodies disclosed in U.S. Pat. No. 6,245,894 (WO1996/002576) bind to human IL-8 (hereinafter denoted as hIL-8) and block its physiological function. Humanized anti-IL-8 antibodies can be produced by combining the variable region sequences of the heavy and light chains disclosed in U.S. Pat. No. 6,245,894 with any known human antibody constant region sequences. The human antibody constant region sequences are not particularly limited, but native human IgG1 sequences or native human IgG4 sequences may be used as the heavy chain constant regions, and native human Kappa sequences can be used as the light chain constant region sequence.

Here, from among the humanized IL-8 antibodies disclosed in U.S. Pat. No. 6,245,894, the gene of hWS4H-IgG1 (SEQ ID NO:39), in which the heavy chain variable region RVHg and the native human anti-IgG1 sequence for the heavy chain constant region were combined, was produced by the method of Reference Example 1. Furthermore, the gene of hWS4L-k0MT (SEQ ID NO:40), in which the light chain variable region RVLa and the native human Kappa sequence for the light chain constant region were combined, was produced by the method of Reference Example 1. An antibody, in which the above heavy chain and light chain were combined, was produced, and was named the humanized WS-4 antibody (hereinafter, hWS-4).

(4-2) Production of Humanized Anti-Human IL-8 Antibody Hr9

A new humanized antibody was produced using human consensus framework sequences that are different from the FRs used in hWS-4.

Specifically, a hybrid sequence of VH3-23 and VH3-64 was used as the heavy chain FR1, a sequence seen in VH3-15 and VH3-49 was used as FR2, a sequence seen in VH3-72 was used as FR3 (provided that 82a according to Kabat numbering is excluded), and a sequence seen in JH1 etc. was used as FR4. These were linked to the CDR sequences of the hWS-4 heavy chain to produce Hr9-IgG1 (SEQ ID NO:41), a novel humanized antibody heavy chain.

Next, two types of antibodies were produced, namely, hWS-4 having hWS4H-IgG1 as the heavy chain and hWS4L-k0MT as the light chain, and Hr9 having Hr9-IgG1 as the heavy chain and hWS4L-k0MT as the light chain. Within the present disclosure, when referring to the light chain in particular, Hr9 (its heavy chain variable region sequence is shown in SEQ ID NO: 33) is written as Hr9/hWS4L. The antibodies were expressed using FreeStyle 293F cells (Invitrogen) according to the protocol attached to the product. Antibodies were purified from the culture supernatant by the method of Reference Example 2. As a result, antibodies were obtained in the amounts shown in Table 4. Surprisingly, the expression level of Hr9 was approximately 8 times the expression level of hWS-4.

TABLE 4

| | Antibody Yield per 1 mL Medium (μg) |
|---|---|
| hWS-4 | 6.4 |
| Hr9 | 50 |

(4-3) Human IL-8-Binding Activities of hWS-4 and Hr9

Binding affinities of hWS-4 and Hr9 towards human IL-8 were determined as follows using BIACORE T200 (GE Healthcare).

A running buffer having the composition of 0.05% tween 20, 20 mM ACES, and 150 mM NaCl (pH 7.4) was used. An appropriate amount of Protein A/G (PIERCE) was immobilized onto Sensor chip CM4 (GE Healthcare) by the amine coupling method and the antibody of interest was captured. Next, human IL-8 was made to interact with the antibody captured on the sensor chip by injecting a diluted human IL-8 solution and a running buffer (used as a reference solution). For the running buffer, the solution having the above-described composition was used, and this buffer was also used to dilute human IL-8. To regenerate the sensor chip, 10 mM glycine-HCl at pH 1.5 was used. All measurements were carried out at 37° C. KD (M) of each antibody for human IL-8 was calculated based on the association rate constant kon (1/Ms) and dissociation rate constant koff (l/s), which are kinetic parameters calculated from sensorgrams obtained by the measurements. The BIACORE T200 Evaluation Software (GE Healthcare) was used to calculate each parameter.

The results are shown in Table 5. hWS-4 and Hr9 were confirmed to have equivalent binding affinities toward human IL-8.

TABLE 5

| Antibody Name | kon (1/Ms) | koff (1/s) | KD (M) |
|---|---|---|---|
| hWS-4 | 9.74E+05 | 2.03E−04 | 2.09E−10 |
| Hr9 | 1.11E+06 | 2.17E−04 | 1.95E−10 |

For development of antibody pharmaceuticals, the production level of antibody molecules is an important factor, and generally, a high production level is desirable. It is particularly notable that from the above-mentioned examination, a more appropriate human consensus framework-derived sequence was selected for combination with the HVR sequence of hWS-4, and yielded Hr9 which had an improved production level while maintaining the binding affinity toward human IL-8.

[Example 5] Obtainment of Antibodies with pH-Dependent IL-8 Binding Ability (5-1) Production of Hr9-Modified Antibodies for Conferring pH Dependency Studies were carried out with the objective of conferring pH-dependent IL-8 binding ability to the Hr9 obtained in Example 4.

While not being bound by particular theory, antibodies having pH-dependent binding ability towards IL-8 may be considered to show the following behavior in vivo. The antibodies administered to a living organism can bind strongly to IL-8 in an environment where neutral pH is maintained (for example, in plasma), and block its function. A portion of such IL-8/antibody complexes are taken up into cells by nonspecific interaction with the cell membrane (pinocytosis) (hereinafter, referred to as non-specific uptake). Under the acidic pH conditions in the endosomes, the binding affinities of the aforementioned antibodies toward IL-8 become weak, and therefore the antibodies release IL-8. Then, the antibodies that have released IL-8 can return to the outside of the cell via FcRn. The aforementioned antibodies that returned to the outside of the cell (into the plasma) in this manner can bind again to another IL-8 and block its function. Antibodies having pH-dependent binding ability towards IL-8 are thought to be also capable of binding to IL-8 multiple times by the above-mentioned mechanism.

In contrast, in the case of an antibody that does not have a property like the aforementioned antibody, an antibody molecule is capable of neutralizing an antigen only once, but cannot neutralize the antigen multiple times. Generally, since an IgG antibody has two Fabs, a single antibody molecule can neutralize two molecules of IL-8. On the other hand, antibodies which can bind to IL-8 multiple times could bind to IL-8 any number of times as long as they stay in the living body. For example, a single molecule of a pH-dependent IL-8-binding antibody that is taken up into cells ten times since being administered until being eliminated can neutralize a maximum of 20 molecules of IL-8. Therefore, an antibody that can bind multiple times to IL-8 has the advantage of being able to neutralize several IL-8 molecules even with a small amount of the antibody. From another viewpoint, an antibody that can bind multiple times to IL-8 has the advantage of being able to maintain a state of being able to neutralize IL-8 for a longer period of time when the same amount of antibody is administered. From yet another viewpoint, an antibody that can bind multiple times to IL-8 has the advantage of being able to block the biological activity of IL-8 more strongly than when the same amount of an antibody which does not have the property possessed is administered.

To achieve these advantages, amino acid modifications, mainly histidine, were introduced into the variable regions of Hr9-IgG1 and WS4L-k0MT with the objective of producing antibodies that can bind to IL-8 multiple times. Specifically, the variants shown in Table 6 were produced by the methods of Reference Examples 1 and 2.

Notations such as "Y97H" indicated in Table 6 show the position where the mutation is introduced as defined by Kabat numbering, the amino acid before introduction of the mutation, and the amino acid after introduction of the mutation. Specifically, when denoted as "Y97H", it shows that the amino acid residue at position 97 according to Kabat numbering has been substituted from Y (tyrosine) to H (histidine). Furthermore, when a combination of multiple amino acid substitutions is introduced, it is written in a manner such as "N50H/L54H".

TABLE 6

| Antibody Name | Mutation Introduced into Heavy Chain | Mutation Introduced into Light Chain |
|---|---|---|
| Hr9/WS4L | None | None |
| Hr9/L16 | None | L54H |
| H89/WS4L | Y97H | None |
| H89/L12 | Y97H | N50H |
| H89/L16 | Y97H | L54H |

(5-2) pH-Dependent IL-8 Binding Ability

The human IL-8-binding affinity of the antibodies produced in Example 5-1 was determined as described below using BIACORE T200 (GE Healthcare). The following two running buffers were used:

0.05% tween 20, 20 mM ACES, 150 mM NaCl, pH 7.4;

0.05% tween 20.20 mM ACES, 150 mM NaCl, pH 5.8.

An appropriate amount of Protein A/G (PIERCE) was immobilized onto Sensor chip CM4 (GE Healthcare) by the amine coupling method and the antibodies of interest was captured. Next, human IL-8 was made to interact with the antibodies captured on the sensor chip by injecting a diluted human IL-8 solution and a running buffer (used as a reference solution). For the running buffer, any of the above-mentioned solutions was used, and the respective buffers were also used to dilute human IL-8. To regenerate the sensor chip, 10 mM glycine-HCl at pH 1.5 was used. All measurements were carried out at 37° C. KD (M) of each antibody for human IL-8 was calculated based on the association rate constant kon (1/Ms) and dissociation rate constant koff (l/s), which are kinetic parameters calculated from sensorgrams obtained by the measurements. The BIACORE T200 Evaluation Software (GE Healthcare) was used to calculate each parameter.

The results are shown in Table 7. First, compared to Hr9, Hr9/L16 which contains a L54H modification in the light chain had a slightly enhanced human IL-8-binding affinity at neutral pH (pH 7.4) but a lowered human IL-8-binding affinity at acidic pH (pH 5.8). On the other hand, anti-IL-8 antibodies (H89/WS4L, H89/L12, and H89/L16) produced by combining various light chains with H89 containing the Y97H modification in the heavy chain all showed a decreased human IL-8-binding affinity at acidic pH as well as a decreased human IL-8-binding affinity at neutral pH.

conditions (such as in the endosomes). In comparison to Hr9, H89/L118 had acquired favorable properties in both these neutral pH and acidic pH.

Thus, useful amino acid modifications were identified for Hr9 such as Y97H for its heavy chain and N50H/L54H/Q89K for its light chain. While not being limited thereto, it has been shown that pH-dependent IL-8-binding antibodies that are superior as pharmaceuticals could be generated by introducing a single or a combination of multiple amino acid modifications selected from these modifications.

TABLE 7

| Antibody Name | pH | kon (1/Ms) | koff (1/s) | KD (M) | kon Ratio (pH 7.4/pH 5.8) | Koff Ratio (pH 5.8/pH 7.4) | KD Ratio (pH 5.8/pH 7.4) |
|---|---|---|---|---|---|---|---|
| Hr9 | pH 7.4 | 8.59E+05 | 2.11E−04 | 2.46E−10 | 2.7 | 2.2 | 5.9 |
| (Hr9/WS4L) | pH 5.8 | 3.23E+05 | 4.69E−04 | 1.45E−09 | | | |
| Hr9/L16 | pH 7.4 | 8.90E+05 | 9.57E−05 | 1.08E−10 | 22.8 | 2.1 | 46.8 |
| | pH 5.8 | 3.91E+04 | 1.97E−04 | 5.04E−09 | | | |
| H89/WS4L | pH 7.4 | 8.51E+05 | 7.65E−04 | 8.99E−10 | 5.2 | 9.5 | 49.8 |
| | pH 5 8 | 1.62E+05 | 7.27E−03 | 4.48E−08 | | | |
| H89/L12 | pH 7.4 | 5.95E+05 | 2.48E−04 | 4.17E−10 | 5.0 | 14.2 | 71.0 |
| | pH 5 8 | 1.19E+05 | 3.52E−03 | 2.96E−08 | | | |
| H89/L16 | pH 7.4 | 6.02E+05 | 4.21E−04 | 6.99E−10 | 5.0 | 10.0 | 50.3 |
| | pH 5.8 | 1.20E+05 | 4.22E−03 | 3.51E−08 | | | |
| H89/L63 | pH 7.4 | 5.37E+05 | 1.13E−04 | 2.10E−10 | 2.1 | 18.7 | 38.3 |
| | pH 5.8 | 2.62E+05 | 2.10E−03 | 8.04E−09 | | | |
| H89/L118 | pH 7.4 | 5.80E+05 | 2.13E−05 | 3.67E−11 | 3.2 | 180.3 | 585.0 |
| | pH 5.8 | 1.79E+05 | 3.84E−03 | 2.15E−08 | | | |

(5-3) Production and Evaluation of Further Modified Antibodies for Conferring pH Dependence Next, combinations of promising modifications found in 5-2 and new amino acid mutations were researched, and the following combinations were found as a result.

TABLE 7-2

| Antibody Name | Mutaion(s) Introduced into Heavy Chain | Mutation(s) Introduced into Light Chain |
|---|---|---|
| H89/L63 | Y97H | N50H/L54H |
| H89/L118 | Y97H | N50H/L54H/Q89K |

These variants were produced by the methods of Reference Examples 1 and 2, and the binding affinity towards human IL-8 was evaluated by a method similar to that of Example 5-2.

The results are also shown in Table 7. H89/L63 which has H89-IgG1 (SEQ ID NO:42) as the heavy chain and L63-k0MT (SEQ ID NO:43) as the light chain showed a human IL-8-binding affinity at neutral pH (pH 7.4) equivalent to that of Hr9, and a decreased human IL-8-binding affinity at acidic pH (pH 5.8). Specifically, both the koff (dissociation rate constant) and KD (dissociation constant) of H89/L63 at pH5.8 were higher than those of Hr9. This means that under the acidic pH condition in the endosomes, H89/L63 has a property of readily releasing human IL-8.

Furthermore, surprisingly, H89/L118, which has H89-IgG1 as the heavy chain and L118-k0MT (SEQ ID NO:44) as the light chain, had an enhanced human IL-8-binding affinity (KD) under neutral pH conditions as compared to that of Hr9, but a weakened human IL-8-binding affinity (KD) under acidic pH conditions as compared to that of Hr9. Without particular limitation, generally, when antibodies that can bind multiple times to antigens are used as a pharmaceutical product, the pH-dependent antigen-binding antibodies preferably have a strong binding affinity (small KD) so that they can strongly neutralize the antigens under neutral pH conditions (such as in plasma). On the other hand, the antibodies preferably have a large dissociation rate constant (koff) and/or a weak binding affinity (large KD) so that they can quickly release the antigens under acidic pH While not being bound by a particular theory, it is considered that an important point when using a pH-dependent antigen-binding antibody as a pharmaceutical is whether or not the antibody administered to the body can release the antigen in the endosome. In this regard, a sufficiently weak binding (large dissociation constant (KD)) under acidic pH conditions or a sufficiently fast dissociation rate (large dissociation rate constant (koff)) is thought to be important. Therefore, it was examined in the following experiment whether the KD or koff of H89/L118 obtained by BIACORE is sufficient for dissociating the antigen in the endosome in vivo.

[Example 6] Production of High-Affinity Antibodies for Mouse PK Assay

Methods for confirming the effect of an antibody on the rate of human IL-8 elimination in mice are not particularly limited. For example, there is a method involving administering an antibody in a condition mixed with human IL-8 to mice and then comparing the rate of human IL-8 elimination from mouse plasma.

Here, the reference antibody to be used for the mouse PK assay desirably has a sufficiently strong binding affinity under both neutral pH and acidic pH conditions. Then, a search for modifications that confer Hr9 with high-affinity was conducted, and as a result H998/L63 having H998-IgG1 (SEQ ID NO:45) as the heavy chain and L63-k0MT as the light chain was created.

Figure 14:
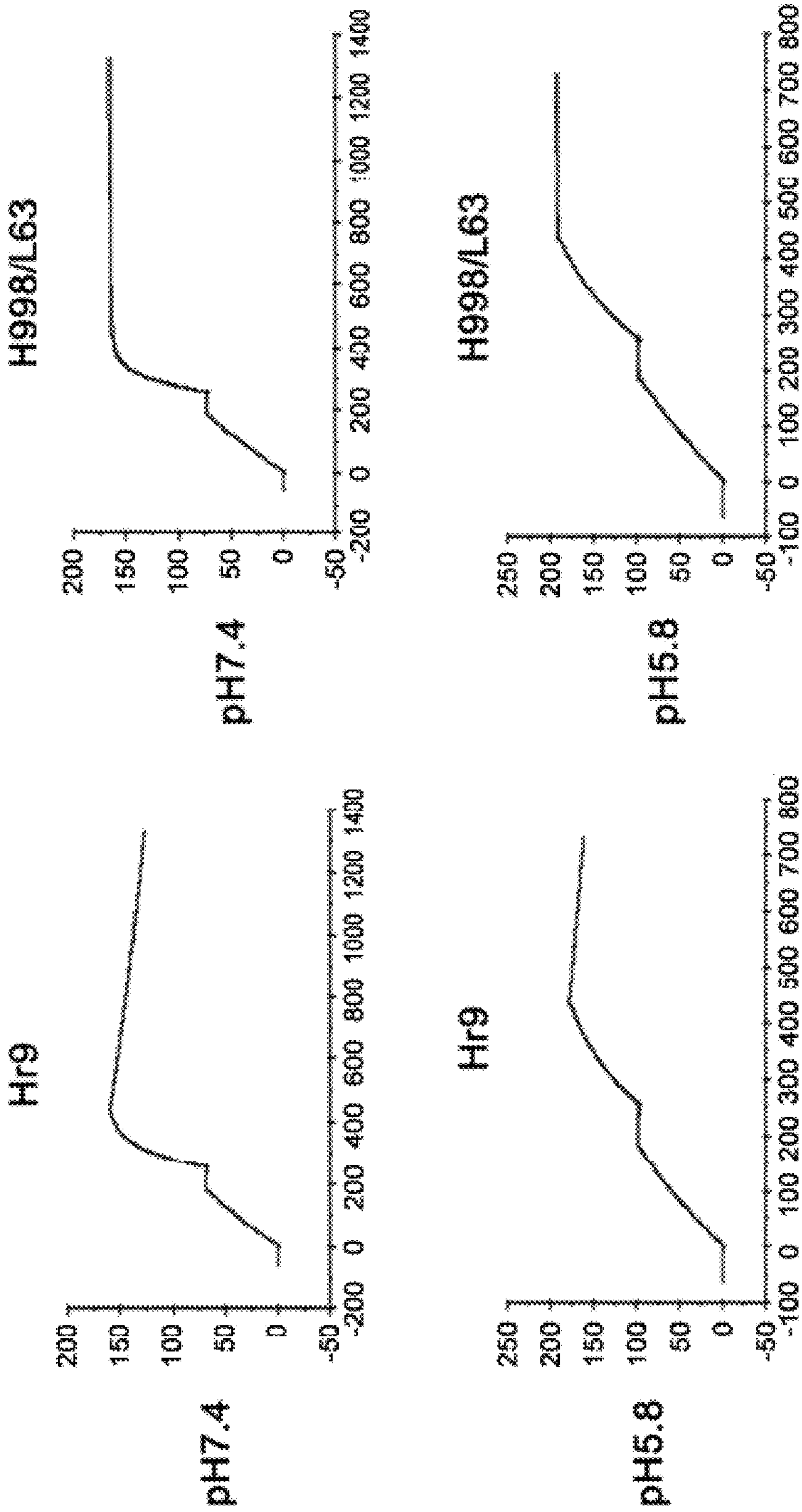
FIG. 14 shows sensorgrams obtained by Biacore measurement of H998/L63 and Hr9 for their binding to IL-8 at pH 7.4 and 5.8.

H998/L63 was used to evaluate the human IL-8-binding affinity by a method similar to that of Example 5-2. The resulting sensorgrams are shown in FIG. 14.

H998/L63 showed a significantly slow dissociation rate under both neutral pH and acidic pH conditions, and was shown to have stronger IL-8-binding affinity than Hr9. However, it is known that, due to the mechanical limits of BIACORE, analytical values such as dissociation rate constant (koff) and dissociation constant (KD) cannot be calculated accurately in such cases where the protein-protein interaction has a slow dissociation rate. As accurate analytical values could not be obtained for H998/L63, its analytical values are not shown here. However, it is confirmed from the results of the experiment that H998/L63 has very strong binding affinity at both neutral pH and acidic pH, and is suitable as an antibody to be used for comparison in mouse PK assays.

[Example 7] Mouse PK Assay Using the pH-Dependent IL-8-Binding Antibody H89/L118

(7-1) Mouse PK Assay Using H89/L118

The rate of human IL-8 elimination in vivo was evaluated using H89/L118 produced in Example 5 and H998/L63 produced in Example 6.

After simultaneous administration of human IL-8 and anti-human IL-8 antibodies to mice (C57BL/6J, Charles river), pharmacokinetics of human IL-8 were evaluated. A mixed solution of human IL-8 and an anti-human IL-8 antibody (10 μg/mL and 200 μg/mL, respectively) was administered in a single dose at 10 mL/kg to the tail vein. At this time, since a sufficiently excessive amount of the anti-human IL-8 antibody is present with respect to human IL-8, almost all the human IL-8 is considered to be bound to the antibody. Blood was collected five minutes, two hours, four hours, seven hours, one day, two days, three days, seven days, 14 days, 21 days, and 28 days after the administration. The collected blood was immediately centrifuged at 15,000 rpm and 4° C. for 15 minutes to obtain plasma. The separated plasma was stored in a freezer set at −20° C. or below until measurements were taken.

(7-2) Measurement of the Human IL-8 Concentration in Plasma

The human IL-8 concentration in mouse plasma was determined by an electrochemiluminescence method. First, an anti-human IL-8 antibody (prepared in-house) having a mouse IgG constant region was dispensed into a MULTI-ARRAY 96-well Plate (Meso Scale Discovery), and was allowed to stand at room temperature for one hour. Then, a PBS-Tween solution containing 5% BSA (w/v) was used for blocking at room temperature for two hours to prepare an anti-human IL-8 antibody-immobilized plate. Calibration curve samples containing human IL-8 at a plasma concentration of 275, 91.7, 30.6, 10.2, 3.40, 1.13, or 0.377 ng/mL and mouse plasma measurement samples diluted 25-fold or more were prepared. The samples were mixed with hWS-4 and allowed to react overnight at 37° C. Subsequently, 50 μL of the mixed solutions were dispensed into each well of the anti-human IL-8 antibody-immobilized plate, and the solution was stirred at room temperature for one hour. The final concentration of hWS-4 was adjusted to 25 μg/mL. Then, after one hour of reaction with a Biotin Mouse Anti-Human Igκ Light Chain (BD Pharmingen) at room temperature, and then one hour of reaction with SULFO-TAG Labeled Streptavidin (Meso Scale Discovery) at room temperature, Read Buffer T (×1) (Meso Scale Discovery) was dispensed, and measurements were performed immediately with SECTOR Imager 2400 (Meso Scale Discovery). The human IL-8 concentration was calculated based on the response in the calibration curve using the analytical software, SOFT Max PRO (Molecular Devices).

Figure 15:
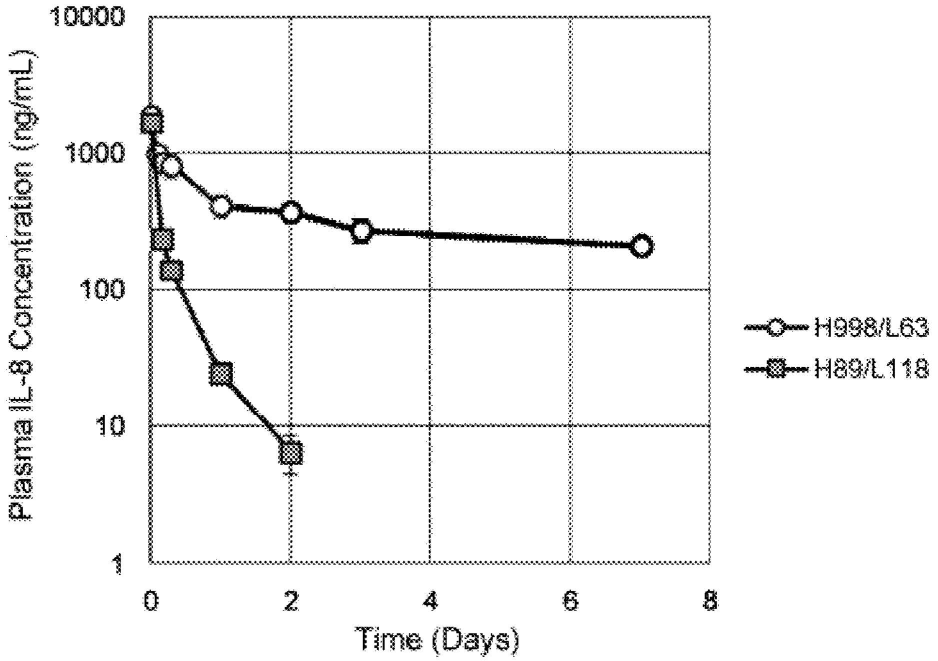
FIG. 15 shows a time course of human IL-8 concentration in the plasma of mice when H998/L63 and H89/L118 were each administered to the mice at 2 mg/kg in combination with human IL-8.

The resulting data on the concentration of human IL-8 in plasma is shown in FIG. 15, and the values of human IL-8 clearance (CL) from mouse plasma are shown in Table 8.

TABLE 8

| | Human IL-8 CL (mL/d/kg) | |
|---|---|---|
| | H998/L63 | H89/L118 |
| #1 | 21.4 | 472.2 |
| #2 | 27.5 | 447.2 |
| #3 | 24.7 | 476.0 |
| Average (N = 3) | 24.5 | 465.1 |
| Standard Deviation | 3.0 | 15.6 |

As clear from FIG. 15, in comparison to human IL-8 administered simultaneously with H998/L63, human IL-8 administered simultaneously with H89/L118 was shown to be eliminated markedly quickly from mouse plasma. Furthermore, CL values which quantitatively represent the rate of human IL-8 elimination from mouse plasma indicate that the rate of human IL-8 elimination was increased about 19-fold for H89/L118 as compared to H998/L63.

Without being bound by a particular theory, the following can be speculated from the obtained data. Most of the human IL-8 administered simultaneously with the antibody binds to the antibody in the plasma and exists in a complexed form. Human IL-8 bound to H998/L63 exists in an antibody-bound state even under the acidic pH condition in the endosome, due to the strong affinity. Thereafter, H998/L63 is returned to the plasma via FcRn while still in the human IL-8-complexed form; therefore, when this occurs, human IL-8 is also returned to the plasma at the same time. Therefore, most of the human IL-8 taken up into the cells again is returned to the plasma. That is, the rate of elimination of human IL-8 from plasma decreases remarkably when H998/L63 is simultaneously administered. On the other hand, as described previously, human IL-8 taken up into cells in a form complexed with H89/L118, a pH-dependent IL-8-binding antibody, dissociates from the antibody under the acidic pH condition in the endosome. Human IL-8 dissociated from the antibody will be degraded after being transferred to the lysosome. Therefore, pH-dependent IL-8-binding antibodies can markedly accelerate the elimination of human IL-8 as compared to an IL-8-binding antibody such as H998/L63 which has strong binding affinity at both acidic pH and neutral pH.

(7-3) Mouse PK Assay with Increased Dose of H89/L118

Next, an experiment that verifies the effect of varying the dose of H89/L118 was carried out as follows. After simultaneous administration of human IL-8 and H89/L118 (2 mg/kg or 8 mg/kg) to mice (C57BL/6J, Charles river), pharmacokinetics of human IL-8 were evaluated. A mixed solution of human IL-8 (2.5 μg/mL) and an anti-human IL-8 antibody (200 μg/mL or 800 μg/mL) was administered to the tail vein in a single dose of 10 mL/kg. At this time, since a sufficiently excessive amount of the anti-human IL-8 antibody is present compared to human IL-8, almost all of the human IL-8 are considered to be bound to the antibody. Blood was collected five minutes, seven hours, one day, two days, three days, seven days, 14 days, 21 days, and 28 days after the administration. The collected blood was immediately centrifuged at 15,000 rpm and 4° C. for 15 minutes to obtain plasma. The separated plasma was stored in a freezer set at −20° C. or below until measurements were taken.

Figure 16:
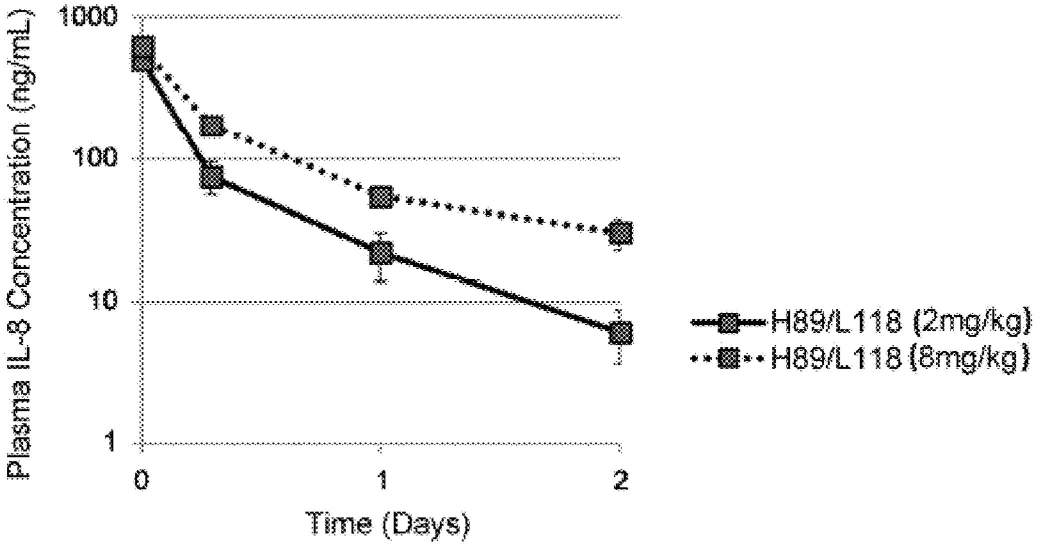
FIG. 16 shows a time course of human IL-8 concentration in the plasma of mice when H89/L118 was administered to the mice at 2 mg/kg or 8 mg/kg in combination with human IL-8.

Measurement of the human IL-8 concentration in mouse plasma was carried out by a method similar to that of Example 7-2. The resulting data on the human IL-8 concentration in plasma is shown in FIG. 16, and the values for human IL-8 clearance (CL) from mouse plasma are shown in Table 9.

TABLE 9

| | Human IL-8 CL (mL/d/kg) | |
|---|---|---|
| Antibody Name | H89/L118 | H89/L118 |
| Antibody Dose | 2 mg/kg | 8 mg/kg |
| #1 | 181.2 | 93.0 |
| #2 | 237 | 101.6 |
| #3 | 247 | 114.5 |
| Average (N = 3) | 221.8 | 103.0 |
| Standard Deviation | 35.6 | 10.8 |

As a result, it was confirmed that as compared to the group administered with 2 mg/kg of H89/L118, the group administered with 8 mg/kg of the antibody had an approximately 2-fold slower rate of human IL-8 elimination.

Herein below, without intending to be bound by theory, contents surmised as one of possible factors that bring about the aforementioned results based on the are described.

Among the antibodies that are returned from inside the endosome into the plasma via FcRn, it is preferred that the proportion of human IL-8-bound antibodies is low. With the focus on human IL-8 present in the endosome, it is desirable to have a high proportion of the free form not bound by an antibody. When human IL-8 is administered together with an antibody that does not have pH-dependent IL-8-binding ability, most (nearly 100%) of the human IL-8 in the endosome is considered to exist in a form complexed with the antibody, and a small amount (close to 0%) is considered to be in the free form. On the other hand, when administered together with the pH-dependent IL-8-binding antibody (for example H89/L118), a certain proportion of human IL-8 should exist in a free form in the endosome. Hypothetically, the proportion of free form in this case can be understood as follows: [proportion of free human IL-8 in the endosome (%)]=[free human IL-8 concentration in the endosome]/[total human IL-8 concentration in the endosome]×100.

The proportion of free human IL-8 in the endosome as understood by the above equation is desirably higher, and for example, 20% is more preferable than 0%, 40% is more preferable than 20%, 60% is more preferable than 40%, 80% is more preferable than 60%, and 100% is more preferable than 80%.

Thus, it is rational to consider that there is a correlation between the proportion of free human IL-8 in the endosome described above and the binding affinity (KD) and/or dissociation rate constant (koff) for human IL-8 at acidic pH. That is, the weaker the binding affinity and/or the greater the dissociation rate for human IL-8 at acidic pH, the higher the proportion of free human IL-8 should be in the endosome. However, in the case of pH-dependent IL-8-binding antibodies where the proportion of free human IL-8 in the endosome is already close to 100%, further weakening the binding affinity and/or increasing the dissociation rate at acidic pH does not necessarily lead to an effective increase in the proportion of free human IL-8. One can easily understand that, for example, even if the proportion of free human IL-8 is improved from 99.9% to 99.99%, such a degree of improvement may not be significant.

Furthermore, according to the general chemical equilibrium theory, when an anti-IL-8 antibody and human IL-8 coexist and their binding reaction and dissociation reaction have reached an equilibrium, the proportion of free human IL-8 is unambiguously determined by three parameters: antibody concentration, antigen concentration, and dissociation constant (KD). Here, when the antibody concentration is high, when the antigen concentration is high, or when the dissociation constant (KD) is small, complexes are readily formed and the proportion of free human IL-8 decreases. On the other hand, when the antibody concentration is low, when the antigen concentration is low, or when the dissociation constant (KD) is large, complex formation becomes difficult, and the proportion of free human IL-8 increases.

Meanwhile, in this experiment, the rate of elimination of human IL-8 when H89/L118 was administered at 8 mg/kg was slower than when the antibody was administered at 2 mg/kg. This therefore suggests that in the endosome, the proportion of free human IL-8 was decreased when antibody was administered at 8 mg/kg compared to when the antibody was administered at 2 mg/kg. The reason may be that increasing the antibody dosage by four-fold increased the antibody concentration in the endosome, and thereby facilitated formation of the IL-8-antibody complex in the endosome. That is, it is considered that in the group administered with an increased dose of the antibody, the proportion of free human IL-8 in the endosome decreased, and therefore the rate of elimination of human IL-8 has been decreased. This also suggests that when the antibody is administered at 8 mg/kg, the degree of the dissociation constant (KD) of H89/L118 under acidic pH conditions is insufficient for bringing free human IL-8 to nearly 100%. More specifically, if it is an antibody that has a larger dissociation constant (KD) (weaker binding) under acidic pH conditions, it may achieve a state of nearly 100% free IL-8 even when the antibody is administered at 8 mg/kg, and a rate of human IL-8 elimination equivalent to that when the antibody is administered at 2 mg/kg.

Based on the above, to confirm whether the pH-dependent IL-8-binding antibody of interest can accomplish a proportion of nearly 100% free human IL-8 in the endosome as mentioned above, without being particularly limited, one can verify whether there is room for increasing the degree of the antigen-eliminating effect in vivo or not. For example, there is a method of comparing the rate of human IL-8 elimination when using a novel pH-dependent IL-8-binding antibody to that when H89/L118 is used, where the novel antibody has a weaker binding affinity at acidic pH and/or an increased dissociation rate at acidic pH compared to that of H89/L118. In case that the aforementioned novel pH-dependent IL-8 antibody shows an equivalent rate of human IL-8 elimination to that for H89/L118, this suggests that the binding affinity and/or dissociation rate of H89/L118 at acidic pH is already at a level sufficient for achieving a proportion of nearly 100% free human IL-8 in the endosome. On the other hand, in instances where the aforementioned novel pH-dependent IL-8 antibody shows a higher rate of human IL-8 elimination, this suggests that the binding affinity and/or dissociation rate of H89/L118 at acidic pH has room for improvement.

[Example 8] Production and Evaluation of the pH-Dependent IL-8-Binding Antibody H553/L118

(8-1) Production of Novel H553/L118 Having pH-Dependent IL-8 Binding Ability Here, the inventors aimed to generate antibodies that have an even weaker human IL-8-binding affinity under acidic pH conditions and/or a greater dissociation rate than those of H89/L118.

Amino acid modifications, mainly involving histidine, were introduced using H89/L118 as a base, to produce the modified antibodies shown in Table 10 by a method similar to that of Example 5. Furthermore, the human IL-8-binding affinity for these antibodies was determined by a method similar to that of Example 5-2.

Part of the results is shown in Table 10. The H553/L118 having H553-IgG1 (SEQ ID NO:46) as the heavy chain and L118-k0MT as the light chain, and the H496/L118 having H496-IgG1 (SEQ ID NO:57) as the heavy chain and L118-k0MT as the light chain were shown to have further increased pH dependency than H89/L118.

TABLE 10

| Antibody Name | pH | kon (1/Ms) | koff (1/s) | KD (M) | kon Ratio (pH 7.4/pH 5.85) | koff Ratio (pH 5.8/pH 7.4) | KD Ratio pH 5.9/pH 7.4) |
|---|---|---|---|---|---|---|---|
| H89/L118 | pH 7.4 | 9.45E+05 | 1.14E−44 | 1.21E−10 | 7.7 | 34.2 | 263.0 |
| | pH 5.8 | 1.23E+05 | 3.90E−03 | 3.18E−08 | | | |
| H496/L118 | pH 7.4 | 1.29E+05 | 5.03E−05 | 3.91E−11 | 7.2 | 108.6 | 785.0 |
| | pH 5.8 | 1.78E+05 | 5.47E−03 | 3.07E−08 | | | |
| H553/L118 | pH 7.4 | 1.16E+06 | 1.13E−04 | 9.76E−11 | 1.9 | 270.7 | 509.3 |
| | pH 5.8 | 6.14E+05 | 3.05E−02 | 4.97E−08 | | | |

In the obtained H553/L118, two amino acid modifications, Y55H and R57P, were introduced into the heavy chain of H89/L118. On the other hand, H496/L118, in which only R57P was introduced into the heavy chain of H89/L118, has an enhanced binding affinity for human IL-8 at neutral pH but a hardly changed human IL-8-binding affinity at acidic pH, in comparison to H89/L118. More specifically, the R57P modification introduced into H89/L118 is a modification that enhances the human IL-8-binding affinity only at neutral pH without changing the binding affinity at acidic pH. Furthermore, H553/L118 produced by introducing the Y55H modification into the heavy chain of H496/L118 has a maintained or slightly enhanced binding affinity at neutral pH, but on the other hand, a decreased binding affinity at acidic pH in comparison to those of H89/L118. That is, introducing a combination of the two amino acid modifications, Y55H and R57P, into H89/L118 enabled further enhancement of the property of decreasing the binding affinity at acidic pH, while maintaining or slightly enhancing the binding affinity at neutral pH.

(8-2) Mouse PK Assay Using H553/L118

Figure 17:
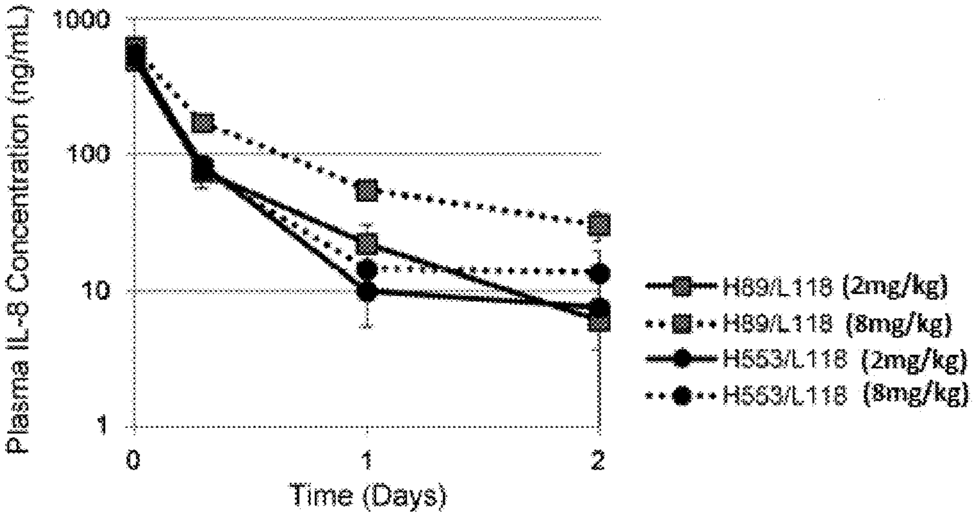
FIG. 17 shows a time course of human IL-8 concentration in the plasma of mice when H89/L118 and H553/L118 were each administered to the mice at 2 mg/kg or 8 mg/kg in combination with human IL-8.

Evaluation of the rate of human IL-8 elimination in mice using H553/L118 was carried out by a method similar to that of Example 7-2. The resulting data on the human IL-8 concentration in plasma is shown in FIG. 17, and the values of human IL-8 clearance (CL) from mouse plasma are shown in Table 11.

TABLE 11

| | Human IL-8 CL (mL/d/kg) | | | |
|---|---|---|---|---|
| Antibody Name | H89/L118 | H89/L118 | H553/L118 | H553/L118 |
| Antibody Dose | 2 mg/kg | 8 mg/kg | 2 mg/kg | 8 mg/kg |
| #1 | 181.2 | 93.0 | 250 | 256.6 |
| #2 | 237 | 101.6 | 245 | 248.4 |
| #3 | 247 | 114.5 | 249 | 244.1 |
| Average (N = 3) | 221.8 | 103.0 | 248 | 249.7 |
| Standard Deviation | 35.6 | 10.8 | 3 | 6.4 |

As a result, large differences were not observed between H553/L118 and H89/L118 when the groups administered with 2 mg/kg antibody were compared; however, it was confirmed that H553/L118 accelerates the elimination of human IL-8 by 2.5 fold or so in comparison to H89/L118 when the groups administered with 8 mg/kg antibody were compared. From another viewpoint, H553/L118 did not show difference in the rate of human IL-8 elimination between 2 mg/kg and 8 mg/kg, and a reduction of the antigen elimination rate due to increase of the antibody dose as with H89/L118 was not observed.

Without particular limitation, one reason why such results were obtained may be discussed as follows. H533/L118 showed an equivalent rate of human IL-8 elimination when the antibody was administered at 2 mg/kg and at 8 mg/kg. This indicates that the proportion of free IL-8 in the endosome achieves a level close to 100% even under the conditions of 8 mg/kg-administration, since the IL-8 binding by H553/L118 at acidic pH is sufficiently weak. In other words, this suggests that while H89/L118 can achieve a maximum human IL-8 elimination effect at a dose of about 2 mg/kg, its effects may be weakened at a high dose of around 8 mg/kg. On the other hand, H553/L118 can achieve a maximum effect of eliminating human IL-8 even at a high dose of about 8 mg/kg.

(8-3) Stability Evaluation Using H553/L118

H553/L118 was shown to be an antibody that can accelerate the elimination of human IL-8 more remarkably than H89/L118 in mice. However, in order for this antibody to sustain this inhibitory effect on human IL-8 for a long period of time in vivo, it is also important that the IL-8-neutralizing activity is stably kept (stability in IL-8-neutralizing activity of this antibody) during the period when the administered antibody is present in vivo (for example, in plasma). Accordingly, the stability of these antibodies in mouse plasma was evaluated by the following method.

Mouse plasma was collected from the blood of C57BL/6J (Charles River) by a method known to those skilled in the art. 200 μL of 200 mM PBS (Sigma, P4417) was added to 800 μL of mouse plasma to give 1 mL. Furthermore, sodium azide was added at a final concentration of 0.1% as an antiseptic. Then, each antibody (Hr9, H89/L118, and H553/L118) was added to the above-mentioned mouse plasma to a final concentration of 0.2 mg/mL. At this point, a portion of the sample was collected as the initial sample. The remaining sample was stored at 40° C. One week and two weeks after storage, a portion of each sample was collected, and they were used as the one-week-stored sample and the two-week-stored sample. All samples were frozen at −80° C. and stored until each analysis was performed.

Next, anti-IL-8 antibodies contained in mouse plasma were evaluated for their human IL-8-neutralizing activity as follows: CXCR1 and CXCR2 are known receptors for human IL-8. The PathHunter(registered trademark) CHO-K1 CXCR2 β-Arrestin cell line (DiscoveRx Co., Cat. #93-0202C2) expresses human CXCR2, and is a cell line artificially produced so as to emit chemiluminescence when human IL-8-mediated signals are transmitted. While it is not particularly limited, the human IL-8-neutralizing activity possessed by an anti-human IL-8 antibody can be evaluated using this cell. First, when human IL-8 is added to the culture solution of the cells, a certain amount of chemiluminescence is exhibited in a manner dependent on the concentration of the added human IL-8. When human IL-8 and an anti-human IL-8 antibody are added together to the culture solution, human IL-8 signal transduction may be blocked upon binding of the anti-human IL-8 antibody to human IL-8. As a result, chemiluminescence caused by addition of human IL-8 will be inhibited by the anti-human IL-8 antibody, and the chemiluminescence will be weaker than when the antibody is not added, or there will be no chemiluminescence at all. Therefore, as the human IL-8 neutralizing activity possessed by the antibody becomes stronger, the degree of chemiluminescence becomes weaker; and as the human IL-8 neutralizing activity possessed by the antibody becomes weaker, the degree of chemiluminescence becomes stronger.

This is the same for an antibody that has been added to mouse plasma and stored for a certain period of time. If the neutralizing activity of the antibody does not change due to storage in mouse plasma, the degree of the above-mentioned chemiluminescence before and after storage should not change. On the other hand, in the case of an antibody whose neutralizing activity decreases due to storage in mouse plasma, the degree of chemiluminescence by use of a stored antibody will increase as compared to that before storage.

Then, the above-mentioned cell line was used to examine whether the neutralizing activity of an antibody stored in mouse plasma was maintained. First, the cell line was suspended in the AssayComplete™ Cell Plating 0 Reagent, and then seeded into a 384-well plate at 5000 cells/well. One day after starting of the cell culture, an experiment was performed below for determining the concentration of human IL-8 to be added. Serially diluted human IL-8 solutions, which contain final human IL-8 concentrations from 45 nM (400 ng/mL) to 0.098 nM (0.1 ng/mL), were added to the cell culture solution. Next, a detection reagent was added according to the protocol of the product, and the relative chemiluminescence level was detected using a chemiluminescence detector. From this result, reactivity of the cells towards human IL-8 was confirmed, and the human IL-8 concentration suitable for confirming the neutralizing activity of anti-human IL-8 antibodies was determined. Here, the human IL-8 concentration was set to 2 nM.

Next, the aforementioned anti-human IL-8 antibody-added mouse plasma was used to evaluate the neutralizing activities of the antibodies contained therein. Human IL-8 at the concentration determined above and the aforementioned anti-human IL-8 antibody-containing mouse plasma were added to the cell culture. The amount of mouse plasma to be added was determined so as to contain stepwise concentrations of the anti-human IL-8 antibody in the range of 2 μg/mL (13.3 nM) to 0.016 μg/mL (0.1 nM). Next, detection reagents were added according to the product protocol, and the relative chemiluminescence levels were detected using a chemiluminescence detector.

Here, relative values for the relative chemiluminescence levels at each antibody concentration were calculated by defining the average relative chemiluminescence level in wells without addition of human IL-8 and antibody as 0%, and by defining the average relative chemiluminescence level in wells that have been added with only human IL-8 but no antibody as 100%.

Figure 2:
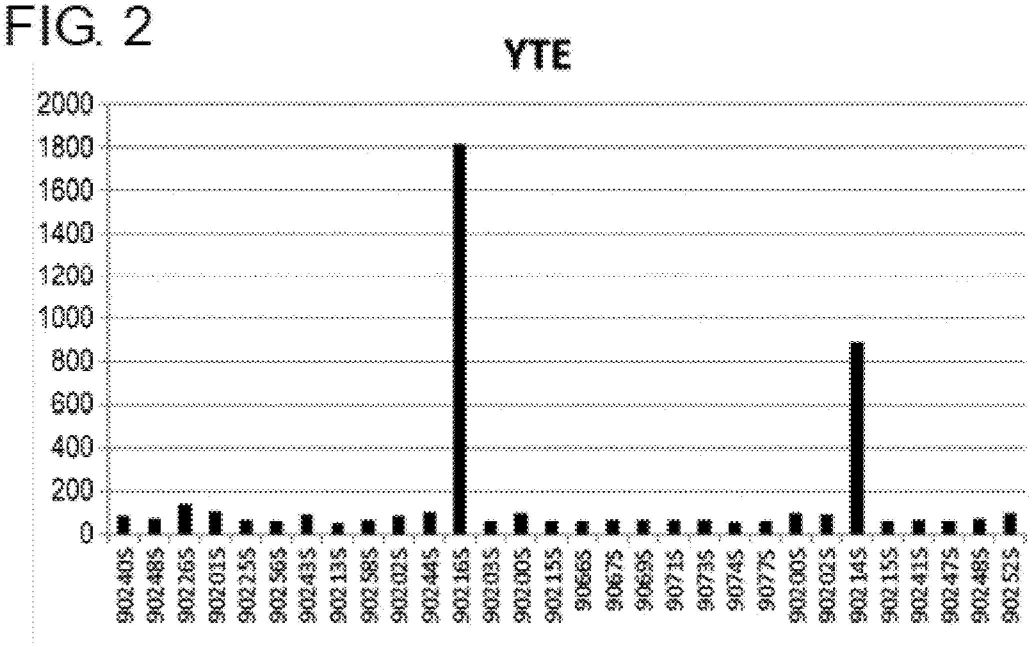
FIG. 2 shows the degree of binding of Fv4-YTE to rheumatoid factor in the sera of RA patients.
Figure 3:
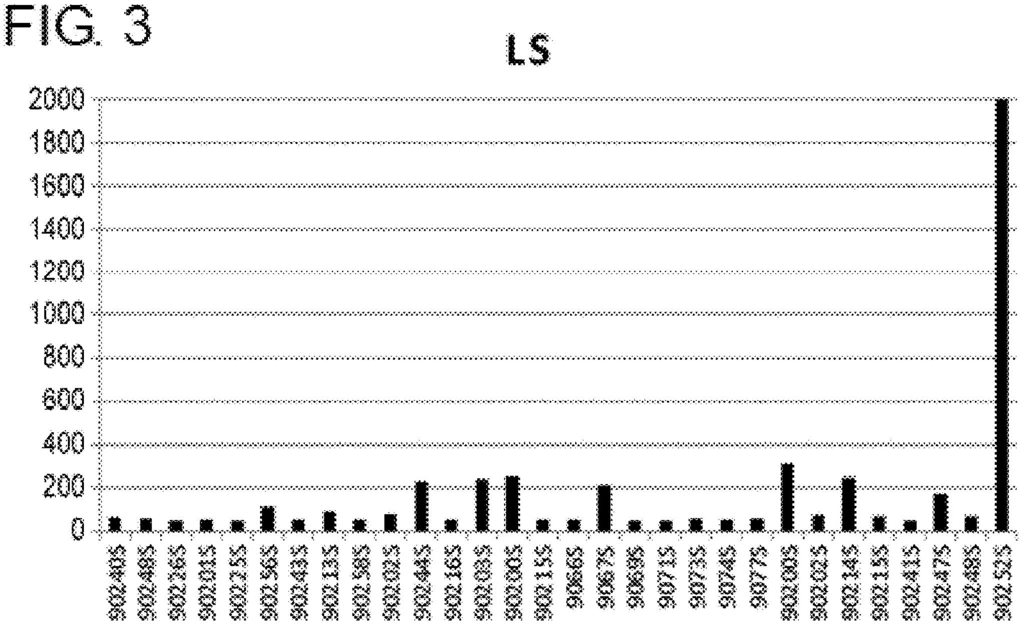
FIG. 3 shows the degree of binding of Fv4-LS to rheumatoid factor in the sera of RA patients.
Figure 4:
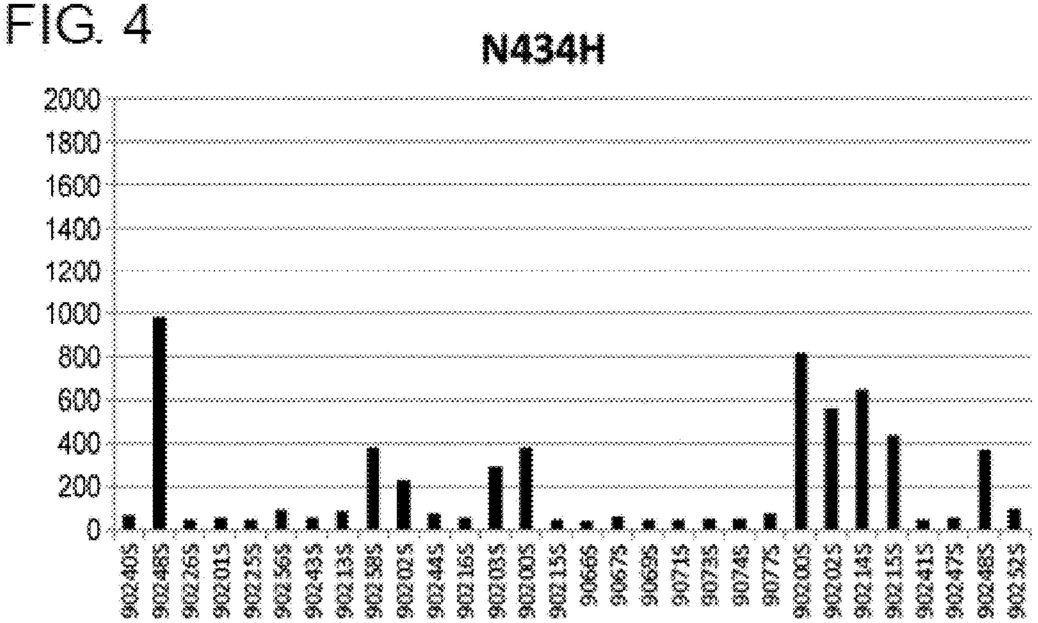
FIG. 4 shows the degree of binding of Fv4-N434H to rheumatoid factor in the sera of RA patients.
Figure 5:
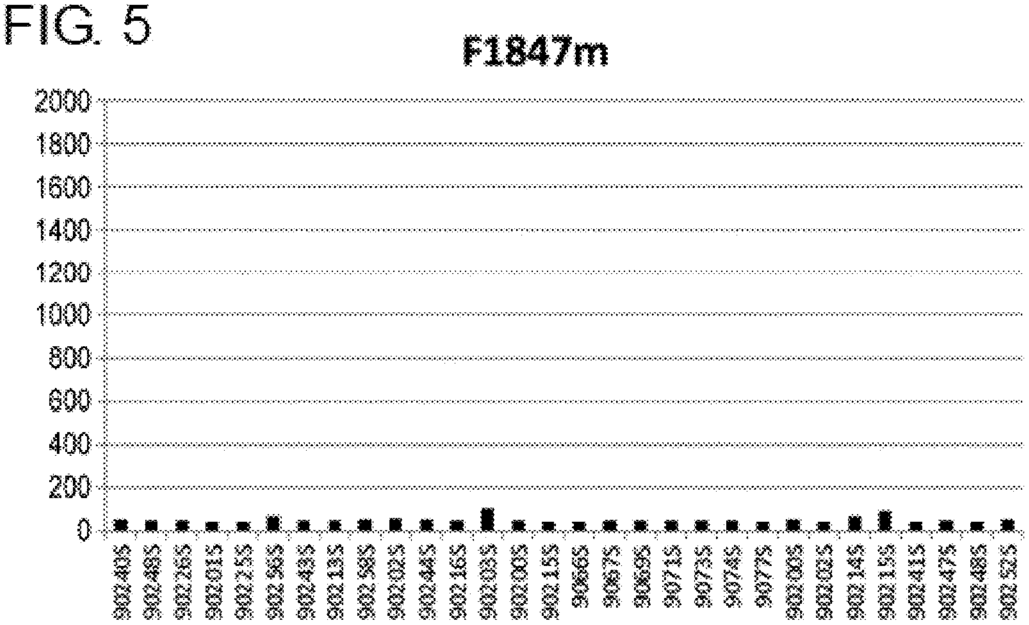
FIG. 5 shows the degree of binding of Fv4-F1847m to rheumatoid factor in the sera of RA patients.
Figure 6:
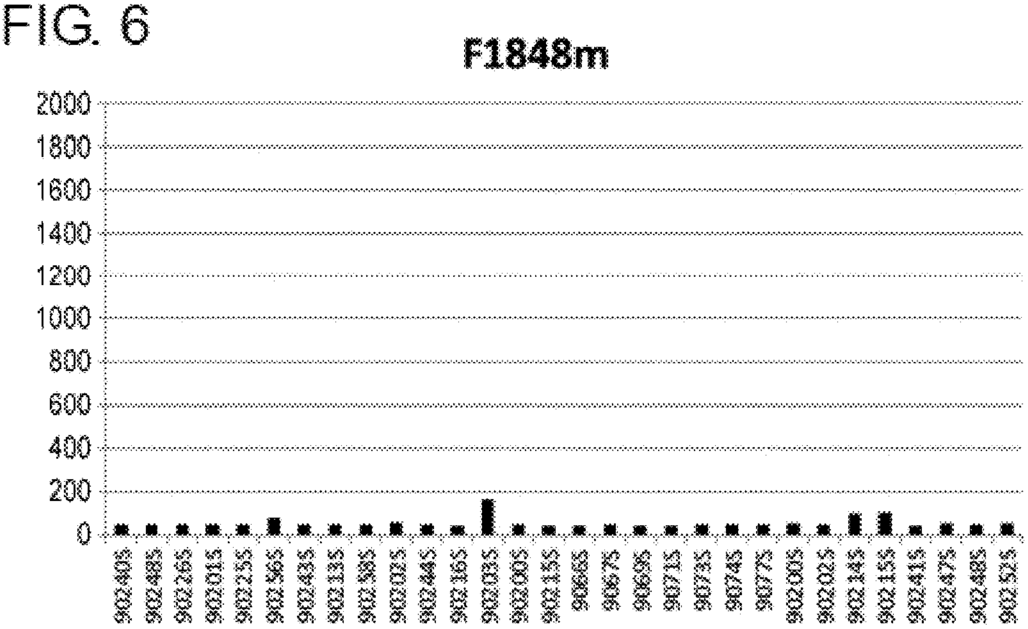
FIG. 6 shows the degree of binding of Fv4-F1848m to rheumatoid factor in the sera of RA patients.
Figure 7:
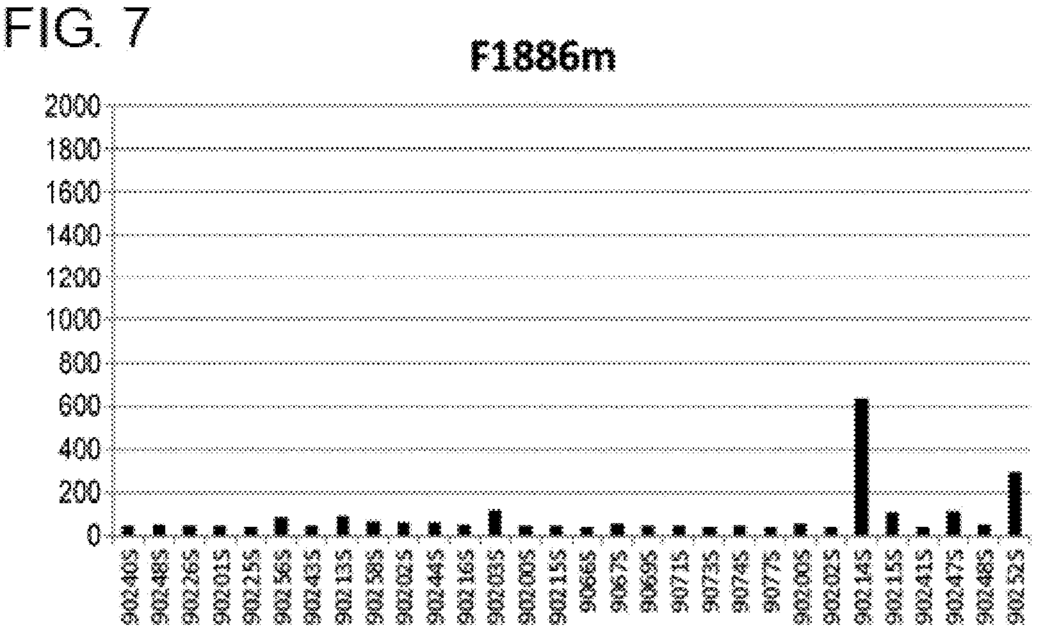
FIG. 7 shows the degree of binding of Fv4-F1886m to rheumatoid factor in the sera of RA patients.
Figure 8:
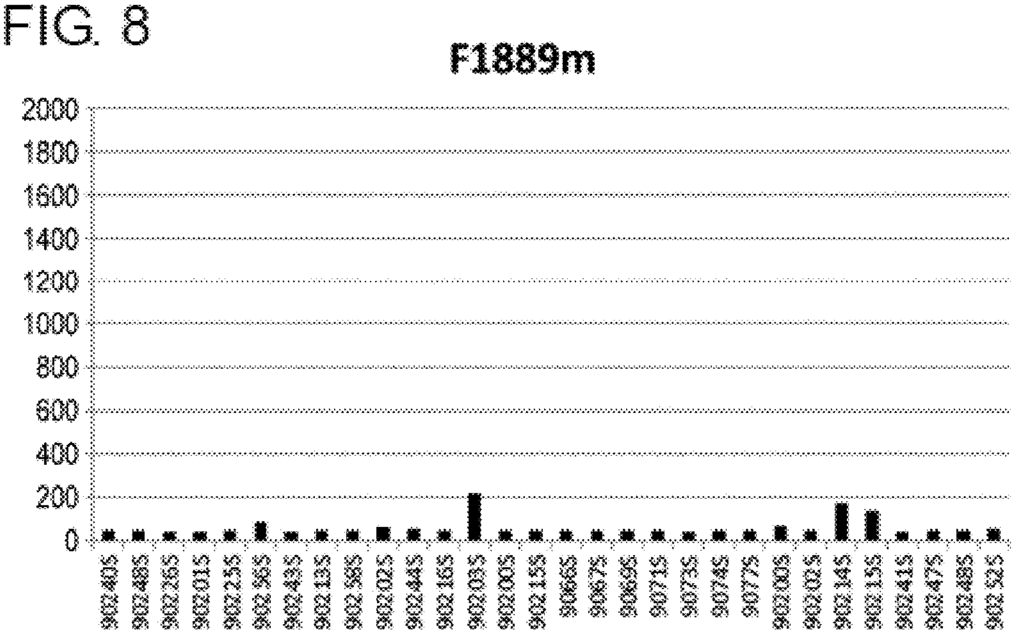
FIG. 8 shows the degree of binding of Fv4-F1889m to rheumatoid factor in the sera of RA patients.
Figure 9:
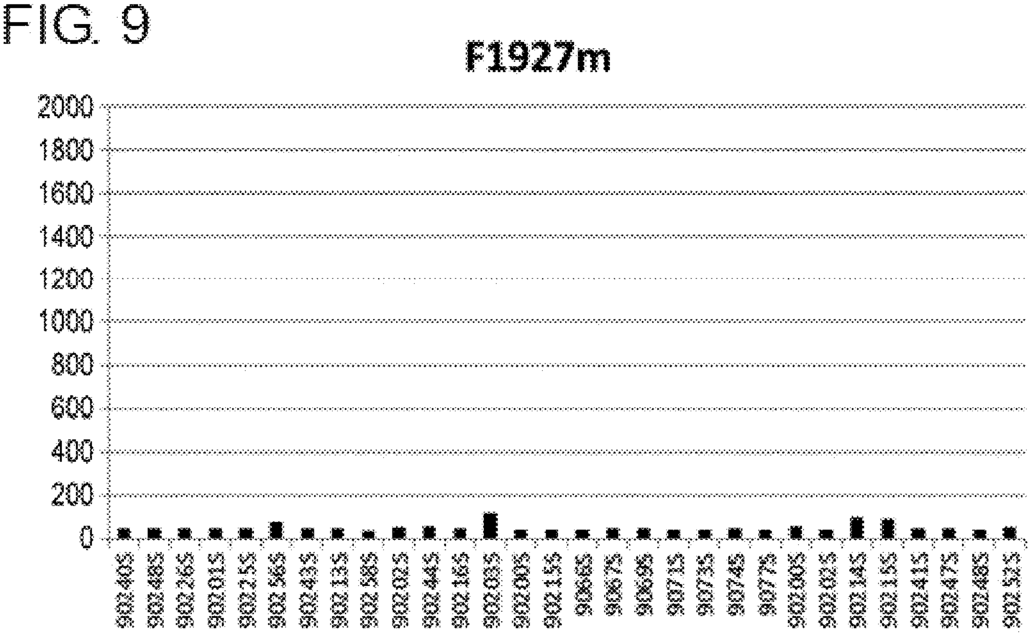
FIG. 9 shows the degree of binding of Fv4-F1927m to rheumatoid factor in the sera of RA patients.
Figure 10:
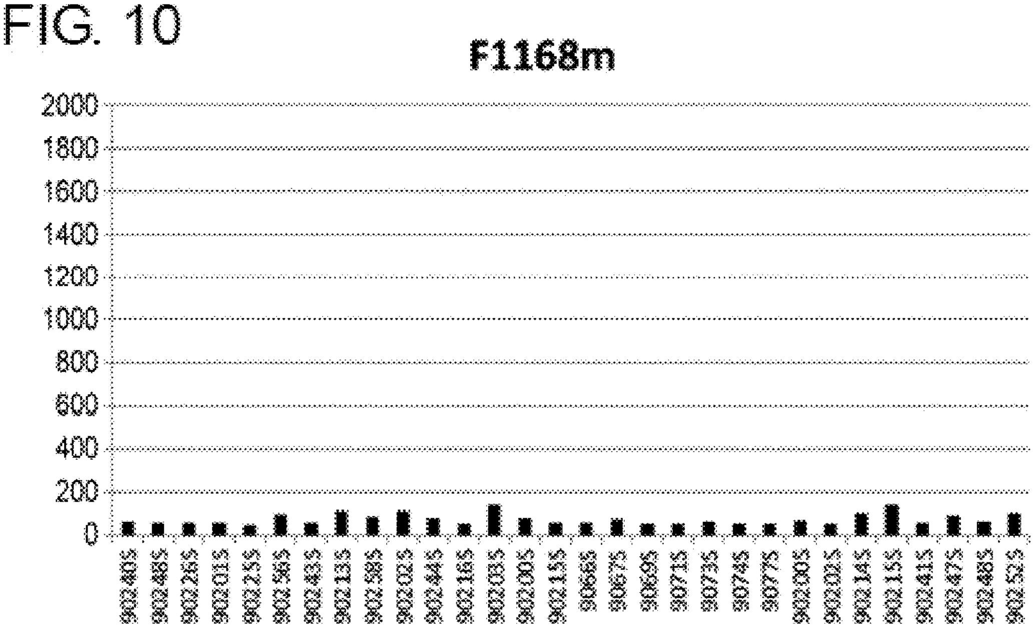
FIG. 10 shows the degree of binding of Fv4-F1168m to rheumatoid factor in the sera of RA patients.
Figures 1, 18:
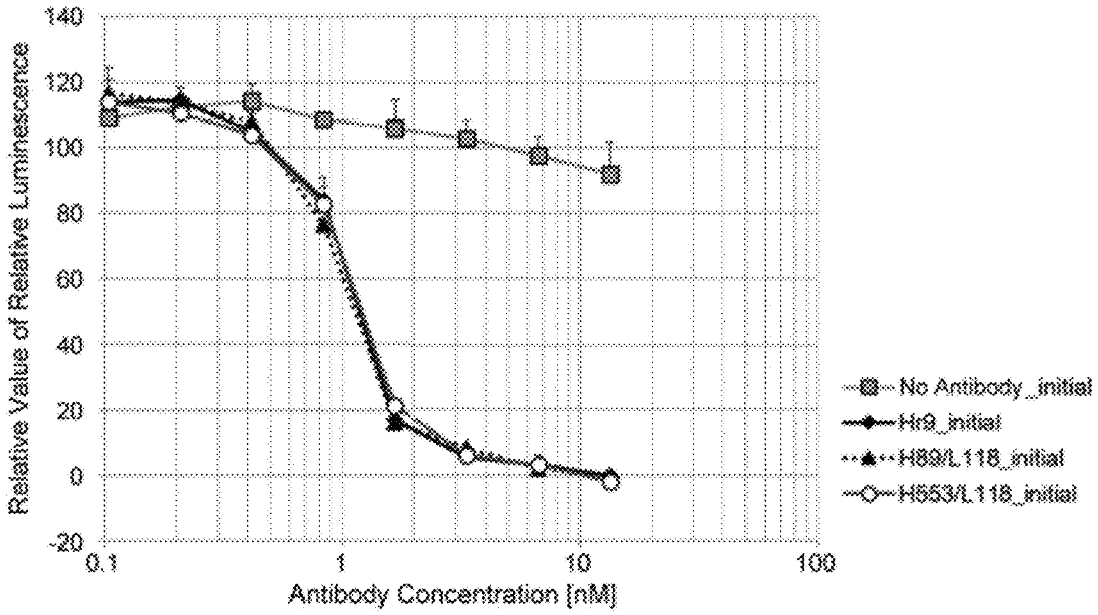
Figures 2, 18:
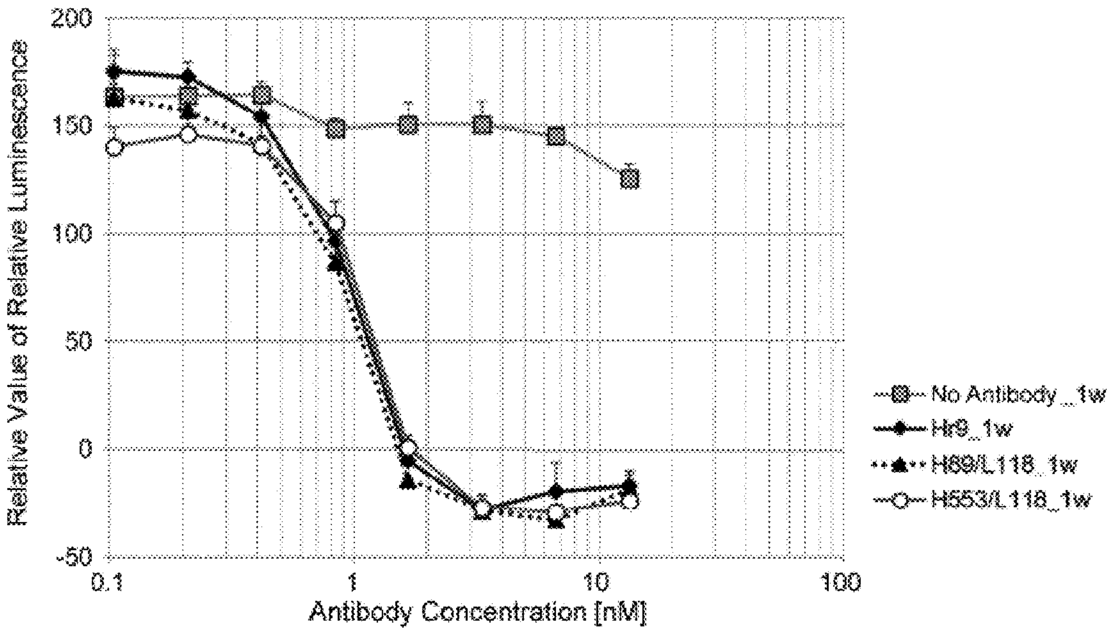
Figures 3, 18:
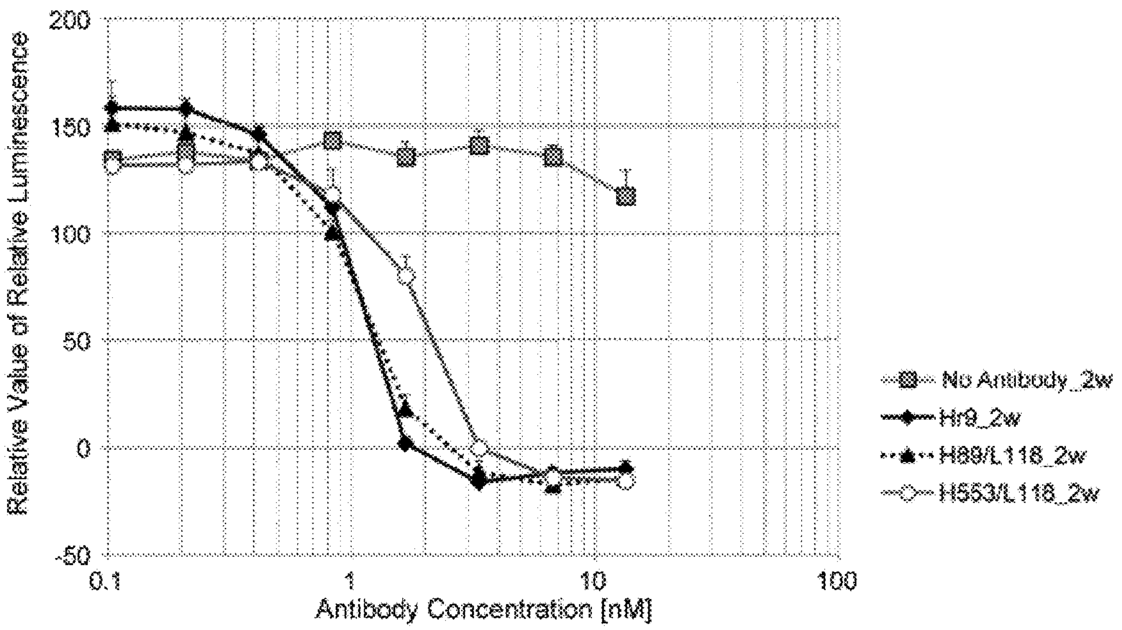

The results of human IL-8 inhibition assay using human CXCR2-expressing cells are shown in FIG. 18-1, which shows results from the initial sample (without preservative treatment in mouse plasma), FIG. 18-2, which shows results for the samples stored at 40° C. for one week, and FIG. 18-3, which shows results for the samples stored at 40° C. for two weeks.

As a result, differences in the human IL-8-neutralizing activity before and after storage in mouse plasma were not observed for Hr9 and H89/L118. On the other hand, H553/L118 showed decrease in the human IL-8-neutralizing activity after two-week storage. Therefore, the human IL-8-neutralizing activity of H553/L118 readily decreases in mouse plasma as compared to that of Hr9 and H89/L118, and H553/L118 was shown to be an antibody having unstable properties in terms of the IL-8 neutralizing activity.

[Example 9] Production of Antibodies with Reduced Predicted Immunogenicity Score Using an in Silico System

(9-1) Predicted Immunogenicity Score of Various IL-8-Binding Antibodies

Generation of anti-drug antibodies (ADA) influences the efficacy and pharmacokinetics of therapeutic antibodies, and brings about serious side effects in some cases; and therefore, clinical utility and drug efficacy of therapeutic antibodies may be limited by the generation of ADA. The immunogenicity of therapeutic antibodies is known to be affected by many factors, and in particular, there are many reports describing the importance of effector T cell epitopes possessed by the therapeutic antibodies.

In silico tools for predicting T cell epitopes such as Epibase (Lonza), iTope/TCED (Antitope), and EpiMatrix (EpiVax) have been developed. Using these in silico tools, T cell epitopes in each of the amino acid sequences can be predicted (Expert Opin. Biol. Ther. 2007 March; 7(3):405-418), and the potential immunogenicity of therapeutic antibodies can be evaluated.

Here, EpiMatrix was used to calculate the immunogenicity scores of each of the anti-IL-8 antibodies. EpiMatrix is a system for predicting the immunogenicity of a protein of interest by automatically designing sequences of peptide fragments by sectioning the amino acid sequence of the protein to be predicted for its immunogenicity by nine amino acids, and then calculating their ability to bind eight major MHC Class II alleles (DRB1*0101, DRB1*0301, DRB1*0401, DRB1*0701, DRB1*0801, DRB1*1101, DRB1*1301, and DRB1*1501) (Clin. Immunol. 2009 May; 131(2):189-201).

The immunogenicity scores of the heavy chains and light chains of each IL-8 antibody, which were calculated as described above, are shown in the “EpiMatrix Score” column of Table 12. Furthermore, regarding the EpiMatrix Scores, immunogenicity scores corrected for the Tregitope content are shown in the “tReg Adjusted Epx Score” column. Tregitope is a peptide fragment sequence present in large amounts mainly in native antibody sequences, and is a sequence considered to inhibit immunogenicity by activating regulatory T cells (Tregs).

Furthermore, regarding these scores, the sum of the scores for the heavy and light chains is shown in the “Total” column.

TABLE 12

| Antibody Name | Heavy Chain EpiMatrix Score | Heavy Chain tReg Adjusted Epx Score | Light Chain EpiMatrix Score | Light Chain tReg Adjusted Epx Score | Total EpiMatrix Score | Total tReg Adjusted Epx Score |
|---|---|---|---|---|---|---|
| hWS-4 | 62.44 | 12.18 | 22.64 | −23.89 | 85.08 | −11.71 |
| Hr9 | 56.52 | 6.27 | 22.64 | −23.89 | 79.16 | −17.62 |
| H89/L118 | 57.99 | 7.74 | 7.16 | −39.36 | 65.15 | −31.62 |
| H496/L118 | 54.13 | 3.87 | 7.16 | −39.36 | 61.29 | −35.49 |
| H553/L118 | 47.88 | −2.37 | 7.16 | −39.36 | 55.04 | −41.73 |

According to these results, both the “EpiMatrix Score” and the “tReg Adjusted Epx Score” showed that the immunogenicity scores of H89/L118, H496/L118, and H553/L118 were decreased as compared to that of hWS-4, which is a known humanized anti-human IL-8 antibody.

Figure 19:
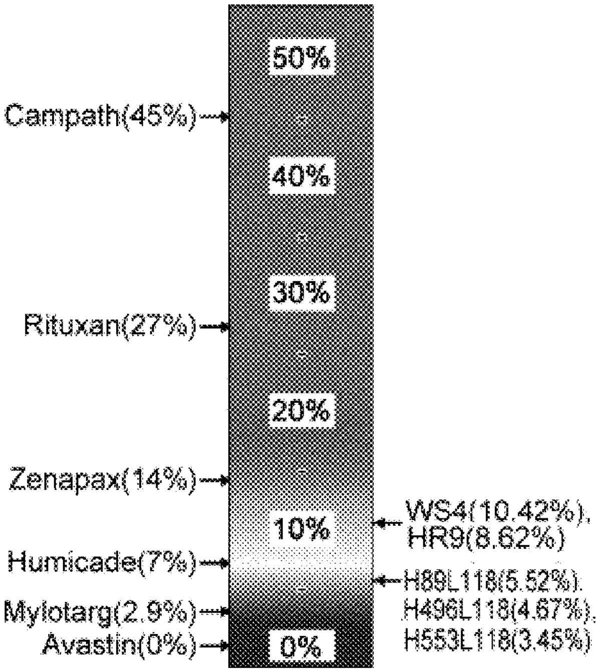
FIG. 19 shows the frequency of ADA occurrence predicted by EpiMatrix for each anti-IL-8 antibody (hWS4, Hr9, H89/L118, H496/L118, and H553/L118) and other existing antibody pharmaceuticals.

Furthermore, with EpiMatrix, it is feasible to compare the frequency of ADA development predicted for the antibody molecule as a whole by considering the heavy-chain and light-chain scores with the actual frequency of ADA development caused by various commercially available antibodies. Results of performing such analysis are shown in FIG. 19. Due to system limitations, the notations used in FIG. 19 are “WS4” for hWS-4, “HR9” for Hr9, “H89L118” for H89/L118, “H496L118” for H496/L118, and “H553L118” for H553/L118.

As shown in FIG. 19, the frequency of ADA development in humans caused by various commercially available antibodies is known to be 45% for Campath (Alemtuzumab), 27% for Rituxan (Rituximab), and 14% for Zenapax (Daclizumab). On the other hand, while the frequency of ADA development predicted from the amino acid sequence was 10.42% for hWS-4 which is a known humanized anti-human IL-8 antibody, the frequency of H89/L118 (5.52%), H496/L118 (4.67%), or H553/L118 (3.45%) newly identified this time were significantly lower in comparison to that of hWS-4.

(9-2) Production of Modified Antibodies with Lowered Predicted Immunogenicity Scores As described above, the immunogenicity scores of H89/L118, H496/L118, and H553/L118 were lower in comparison to that of hWS-4; however, as is apparent from Table 12, the immunogenicity scores for the heavy chain are higher than those for the light chains, which suggests that there is still room for improvement in the amino acid sequences of the heavy chain in particular from the viewpoint of immunogenicity. Then, a search was conducted in the heavy chain variable region of H496 for amino acid modifications that can decrease the immunogenicity score. As a result of diligent search, three variants, H496v1 in which alanine at position 52c according to Kabat numbering was substituted with aspartic acid, H496v2 in which glutamine at position 81 was substituted with threonine, and H496v3 in which serine at position 82b was substituted with aspartic acid were found. Furthermore, H1004 in which all three of these modifications were introduced was produced.

The results of immunogenicity scores calculated by a method similar to that of Example 9-1 are shown in Table 13.

TABLE 13

| Antibody Name | Heavy Chain EpiMatrix Score | Heavy Chain tReg Adjusted Epx Score | Light Chain EpiMatrix Score | Light Chain tReg Adjusted Epx Score | Total EpiMatrix Score | Total tReg Adjusted Epx Score |
|---|---|---|---|---|---|---|
| H496/L118 | 54.13 | 3.87 | 7.16 | −39.36 | 61.29 | −35.49 |
| H496v1/L118 | 32.17 | −18.08 | 7.16 | −39.36 | 39.33 | −57.44 |
| H496v2/L118 | 45.26 | −5.00 | 7.16 | −39.36 | 52.42 | −44.36 |
| H496v3/L118 | 38.27 | −11.98 | 7.16 | −39.36 | 45.43 | −51.34 |
| H1004/L118 | 10.79 | −39.47 | 7.16 | −39.36 | 17.95 | −78.83 |
| H1004/L395 | 10.79 | −39.47 | 7.79 | −38.74 | 18.58 | −78.21 |

The three heavy chains, H496v1, H496v2, and H496v3, all of which contain a single modification, showed decreased immunogenicity scores in comparison to that of H496. Furthermore, H1004, in which a combination of three modifications was introduced, achieved a remarkable improvement of the immunogenicity score.

Here, in addition to L118, L395 was identified as the light chain appropriate for combination with H1004. Therefore, in the calculation of immunogenicity scores, both the L118 combination and the L395 combination were used. As indicated in Table 13, H1004/L118 and H1004/L395, which are combinations of heavy and light chains, also showed very low immunogenicity scores.

Figure 20:
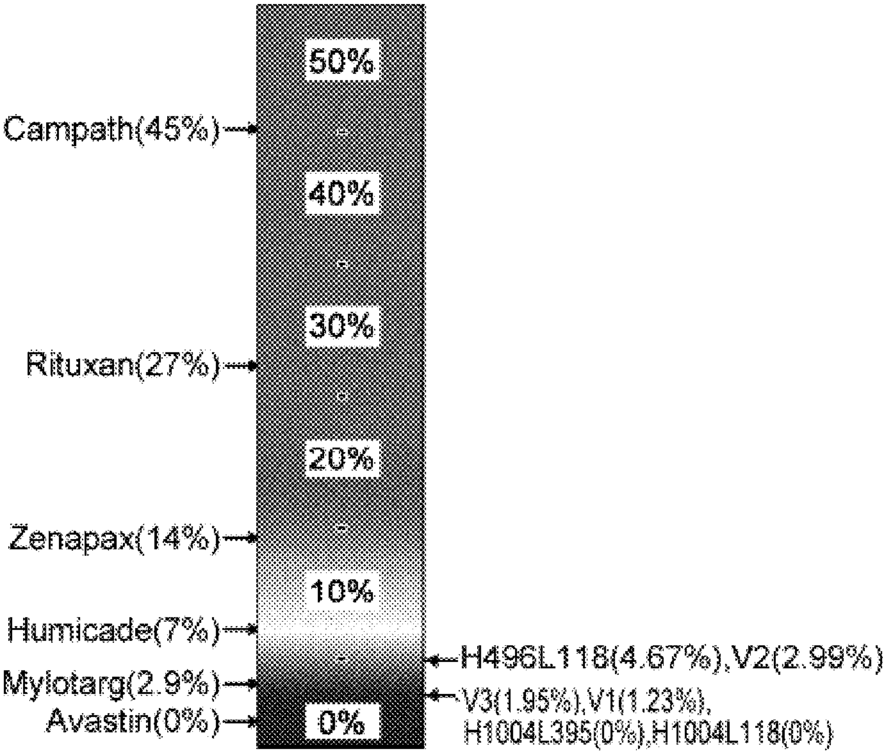
FIG. 20 shows the frequency of ADA occurrence predicted by EpiMatrix for each anti-IL-8 antibody (H496/L118, H496v1/L118, H496v2/L118, H496v3/L118, H1004/L118, and H1004/L395) and other existing antibody pharmaceuticals.

Next, the frequency of ADA development for these was predicted in a manner similar to Example 9-1. The results are shown in FIG. 20. The notations used in FIG. 20 are “V1” for H496v1/L118, “V2” for H496v2/L118, “V3” for H496v3/L118, “H1004L118” for H1004/L118, and “H1004L395” for H1004/L395.

Surprisingly, H1004/L118 and H1004/L395, which have remarkably lowered immunogenicity scores, also showed improvement in the predicted values for the frequency of ADA development, and showed a predicted value of 0%.

(9-3) Measurement of the IL-8-Binding Affinity of H1004/L395

H1004/L395 which is an antibody having H1004-IgG1m (SEQ ID NO:47) as the heavy chain and L395-k0MT (SEQ ID NO:38) as the light chain was produced. The binding affinity of H1004/L395 for human IL-8 was measured as described below using BIACORE T200 (GE Healthcare).

The following two running buffers were used, and measurements were carried out at the respective temperatures:

0.05% tween20, 40 mM ACES, 150 mM NaCl, pH 7.4, 40° C.

0.05% tween20, 40 mM ACES, 150 mM NaCl, pH 5.8, 37° C.

An appropriate amount of Protein A/G (PIERCE) was immobilized onto the Sensor chip CM4 (GE Healthcare) by the amine coupling method and the antibodies of interest were captured. Next, a diluted human IL-8 solution or a running buffer (used as a reference solution) was injected to allow interaction of the antibodies captured onto the sensor chip with human IL-8. For the running buffer, either one of the above-mentioned solutions was used, and the respective buffers were also used to dilute human IL-8. To regenerate the sensor chip, 25 mM NaOH and 10 mM glycine-HCl (pH 1.5) were used. KD (M) of each antibody for human IL-8 was calculated based on the association rate constant kon (1/Ms) and dissociation rate constant koff (l/s) which are kinetic parameters calculated from sensorgrams obtained by the measurements. The BIACORE T200 Evaluation Software (GE Healthcare) was used to calculate each parameter.

The measurement results are shown in Table 14. In comparison to H89/L118, H1004/L395, with lowered immunogenicity score, had an equivalent KD for human IL-8 at neutral pH, but increased KD and koff at acidic pH; and it was shown to have the property of dissociating readily from IL-8 in the endosome.

TABLE 14-2-continued

| | Heavy Chain |
|---|---|
| H1046 | D31E/A52cD/G54Y/Y55H/T56H/R57P/Q81T/S82bD/Y97H |
| H1047 | S30D/D31K/A52cD/R57P/Q81T/S82bD/Y97H |
| H1048 | D31E/A52cD/R57P/Q81T/S82bD/Y97H |
| H1049 | S30D/D31K/A52cD/G54Y/Y55H/R57P/Q81T/S82bD/Y97H |
| H1050 | D31E/A52cD/G54Y/Y55H/R57P/Q81T/S82bD/Y97H |

TABLE 14-3

| | |
|---|---|
| L395 | N50K/L54H/Q89K |
| L442 | S31E/N50K/L54H/Q89K |

Further, a total of 36 types of antibodies were produced by combining the 18 types of heavy chains and two types of light chains described above. Various evaluations were performed on these antibodies as indicated below.

The human IL-8-binding affinities under neutral and acidic pH conditions were measured in a manner similar to the method of Example 9-3. Among the obtained results, KD at pH 7.4, and KD and koff at pH 5.8 are shown in Table 15.

Next, stability in terms of IL-8 binding upon storage of the antibodies in PBS was evaluated by the method indicated below.

TABLE 14

| Antibody Name | pH | kon (1/Ms) | koff (1/s) | KD (M) | kon Ratio (pH 7.4/pH 5.8) | koff Radio (pH 5.8/pH 7.4) | KD Ratio (pH 5.8/pH 7.4) |
|---|---|---|---|---|---|---|---|
| H89/L118 | pH 7.4 | 7.51E+05 | 1.29E−04 | 1.72E−10 | 5.8 | 46.7 | 283.7 |
| | pH 5.8 | 1.29E+05 | 6.28E−03 | 4.88E−08 | | | |
| H1004/L395 | pH 7.4 | 1.02E+06 | 1.55E−04 | 1.51E−10 | 3.3 | 218.1 | 728.5 |
| | pH 5.8 | 3.06E+05 | 3.38E−02 | 1.10E−07 | | | |

[Example 10] Production and Evaluation of the pH-Dependent IL-8-Binding Antibody H1009/L395

(10-1) Production of various pH-dependent IL-8-binding antibodies

H1004/L395, which has pH-dependent IL-8 binding ability and also a lowered immunogenicity score was obtained by the evaluation shown in Example 9. Subsequently, a dedicated investigation was carried out to produce variants that have these favorable properties as well as stability in mouse plasma.

The following modified antibodies were produced based on H1004/L395 by introducing various modifications.

TABLE 14-2

| | Heavy Chain |
|---|---|
| H1004 | A52cD/R57P/Q81T/S82bD/Y97H |
| H0932 | A52cD/G54H/Y55H/R57P/Q81T/S82bD/Y97H |
| H1000 | D31E/A52cD/G54H/Y55H/R57P/Q81T/S82bD/Y97H |
| H1009 | A52cD/G54Y/Y55H/R57P/Q81T/S82bD/Y97H |
| H1022 | A52cD/G54H/Y55H/T56H/R57P/Q81T/S82bD/Y97H |
| H1023 | A52cD/T56S/R57P/Q81T/S82bD/Y97H |
| H1028 | A52cD/G54Y/Y55H/T56H/R57P/Q81T/S82bD/Y97H |
| H1029 | S30D/D31K/A52cD/G54H/Y55H/R57P/Q81T/S82bD/Y97H |
| H1031 | S30D/D31K/A52cD/G54H/Y55H/T56H/R57P/Q81T/S82bD/Y97H |
| H1032 | S30D/D31K/A52cD/T56H/R57P/Q81T/S82bD/Y97H |
| H1037 | S30D/D31K/A52cD/G54Y/Y55H/T56H/R57P/Q81T/S82bD/Y97H |
| H1040 | D31E/A52cD/G54H/Y55H/T56H/R57P/Q81T/S82bD/Y97H |
| H1041 | D31E/A52cD/T56H/R57P/Q81T/S82bD/Y97H |

The respective antibodies were dialyzed overnight against DPBS (Sigma-Aldrich), and then the concentration of each of the antibodies was adjusted to 0.1 mg/mL. At this point, some of the antibody samples were collected as initial samples. The remaining samples were stored at 50° C. for one week, and then collected as samples for the thermal acceleration test.

Next, BIACORE measurement of the IL-8-binding affinity was carried out as follows using the initial samples and samples for the thermal acceleration test.

The levels of human IL-8 binding to the modified antibodies were analyzed using BIACORE T200 (GE Healthcare). Measurements were carried out at 40° C. by using 0.05% tween20, 40 mM ACES, and 150 mM NaCl at pH 7.4 as the running buffer.

An appropriate amount of Protein A/G (PIERCE) was immobilized onto the Sensor chip CM4 (GE Healthcare) by the amine coupling method and the antibodies of interest was captured. Next, a diluted human IL-8 solution or a running buffer (used as a reference solution) was injected to allow interaction of the antibodies captured onto the sensor chip with human IL-8. The running buffer was also used to dilute human IL-8. To regenerate the sensor chip, 25 mM NaOH and 10 mM glycine-HCl (pH 1.5) were used. The measured binding level of human IL-8 and the amount of antibodies captured at that binding level were extracted using the BIACORE T200 Evaluation Software (GE Healthcare).

The amount of human IL-8-binding per 1000 RU of the amount of antibody captured was calculated for the initial samples and the samples for the thermal acceleration test. Furthermore, the ratio of the human IL-8-binding level for the initial samples to that for samples of the thermal acceleration test was calculated.

The resulting ratios of IL-8-binding level of the initial samples to that for samples of the thermal acceleration test are shown in Table 15 as well.

TABLE 15

| Antibody | pH 7.4 KD | pH 5.8 KD | pH 5.8 koff | Ratio of IL-8 Binding Amount (Thermal Acceleration/Initial) |
|---|---|---|---|---|
| H0089/L0118 | 1.7E−10 | 4.9E−08 | 6.3E−03 | 0.61 |
| H0932/L0395 | 1.6E−10 | 1.1E−07 | 5.7E−02 | 0.56 |
| H0932/L0442 | 2.1E−10 | 7.9E−08 | 2.2E−02 | 0.56 |
| H1000/L0395 | 1.4E−10 | 8.9E−08 | 2.0E−02 | 0.57 |
| H1000/L0442 | 2.0E−10 | 7.1E−08 | 1.7E−02 | 0.57 |
| H1004/L0395 | 1.5E−10 | 1.1E−07 | 3.4E−02 | 0.58 |
| H1004/L0442 | 2.2E−10 | 7.7E−08 | 2.0E−02 | 0.59 |
| H1009/L0395 | 7.1E−11 | 8.7E−08 | 1.0E−02 | 0.64 |
| H1009/L0442 | 1.1E−10 | 6.3E−08 | 6.0E−03 | 0.64 |
| H1022/L0395 | 2.7E−10 | 2.9E−07 | 1.2E+01 | 0.47 |
| H1022/L0442 | 3.6E−10 | 1.8E−07 | 2.0E−02 | 0.46 |
| H1023/L0395 | 7.6E−11 | 9.2E−08 | 1.8E−02 | 0.54 |
| H1023/L0442 | 1.2E−10 | 7.1E−08 | 1.7E−02 | 0.55 |
| H1028/L0395 | 1.8E−10 | 2.1E−07 | 1.0E+01 | 0.55 |
| H1028/L0442 | 2.4E−10 | 1.4E−07 | 1.3E−01 | 0.56 |
| H1029/L0395 | 8.6E−11 | 5.5E−08 | 8.0E−03 | 0.59 |
| H1029/L0442 | 1.4E−10 | 4.8E−08 | 8.5E−03 | 0.58 |
| H1031/L0395 | 1.5E−10 | 9.9E−08 | 4.6E−02 | 0.48 |
| H1031/L0442 | 2.1E−10 | 8.9E−08 | 3.9E−02 | 0.47 |
| H1032/L0395 | 4.2E−11 | 5.0E−08 | 4.1E−03 | 0.61 |
| H1032/L0442 | 7.8E−11 | 4.3E−08 | 5.9E−03 | 0.61 |
| H1037/L0395 | 9.4E−11 | 7.0E−08 | 1.5E−02 | 0.55 |
| H1037/L0442 | 1.3E−10 | 6.1E−08 | 1.5E−02 | 0.57 |
| H1040/L0395 | 2.6E−10 | 2.4E−07 | 4.6E−02 | 0.44 |
| H1040/L0442 | 3.4E−10 | 1.4E−07 | 2.1E−01 | 0.49 |
| H1041/L0395 | 8.0E−11 | 7.1E−08 | 1.3E−02 | 0.55 |
| H1041/L0442 | 1.2E−10 | 6.1E−08 | 1.5E−02 | 0.56 |
| H1046/L0395 | 1.8E−10 | 1.6E−07 | 1.2E−02 | 0.56 |
| H1046/L0442 | 2.3E−10 | 1.1E−07 | 1.2E−02 | 0.55 |
| H1047/L0395 | 9.5E−11 | 4.7E−08 | 6.0E−03 | 0.65 |
| H1047/L0442 | 1.5E−10 | 4.7E−08 | 4.6E−03 | 0.64 |
| H1048/L0395 | 1.5E−10 | 9.0E−08 | 6.4E−03 | 0.59 |
| H1048/L0442 | 2.1E−10 | 6.7E−08 | 1.5E−02 | 0.59 |
| H1049/L0395 | 2.5E−11 | 3.8E−08 | 4.0E−03 | 0.65 |
| H1049/L0442 | 5.3E−11 | 3.3E−08 | 4.5E−03 | 0.65 |
| H1050/L0395 | 6.6E−11 | 7.7E−08 | 5.0E−03 | 0.64 |
| H1050/L0442 | 9.9E−11 | 5.4E−08 | 7.6E−03 | 0.64 |

By the above-mentioned examination, H1009/L395 which is an antibody having H1009-IgG1m (SEQ ID NO:48) as the heavy chain and L395-k0MT as the light chain was obtained.

As shown in Table 15, in comparison to H89/L118, H1009/L395 had a slightly enhanced human IL-8-binding affinity at neutral pH, but on the other hand, a decreased binding affinity at acidic pH, that is, pH-dependence had been further strengthened. Furthermore, when exposed to severe conditions such as at 50° C. in PBS, H1009/L395 had a slightly improved stability in IL-8 binding when compared to that of H89/L118.

Accordingly, H1009/L395 was selected as an antibody whose neutralizing activity in mouse plasma may be stably maintained, while keeping its pH-dependent IL-8 binding ability.

(10-2) Stability evaluation of H1009/L395

Next, in a manner similar to the method of Example 8-3, it was evaluated whether the IL-8 neutralizing activity of H1009/L395 is stably maintained in mouse plasma. Here, H1009/L395-F1886s which will be described in detail later in Example 15 was used. This antibody has the same variable region as that of H1009/L395, and a constant region having modifications that enhance FcRn binding under acidic pH conditions and modifications for reducing its binding towards FcγR(s) in comparison to those of the native human IgG1. The variable region of H1009/L395, especially the region around HVR, is responsible for human IL-8-binding and IL-8-neutralizing activity of this antibody, and modifications introduced into the constant region are considered not to affect these properties.

Evaluation of the stability in mouse plasma was performed as follows. 150 μL of 200 mM phosphate buffer (pH 6.7) was added to 585 μL of mouse plasma. In addition, sodium azide was added as an antiseptic at a final concentration of 0.1%. Each antibody (Hr9, H89/L118, or H1009/L395-F1886s) was added to the above-mentioned mouse plasma at a final concentration of 0.4 mg/mL. At this point, a portion of the sample was collected as the initial sample. The remaining sample was stored at 40° C. One week and two weeks after the start of storage, a portion of each sample was collected, and they were used as the sample stored for one week and the sample stored for two weeks. All samples were frozen at −80° C. and stored until each analysis was performed.

Measurement of the human IL-8-neutralizing activity was carried out using human CXCR2-expressing cells by a method similar to that of Example 8-3. However, the concentration of human IL-8 used to confirm the neutralizing activity of an anti-human IL-8 antibody this time was 1.2 nM.

Figures 1, 21:
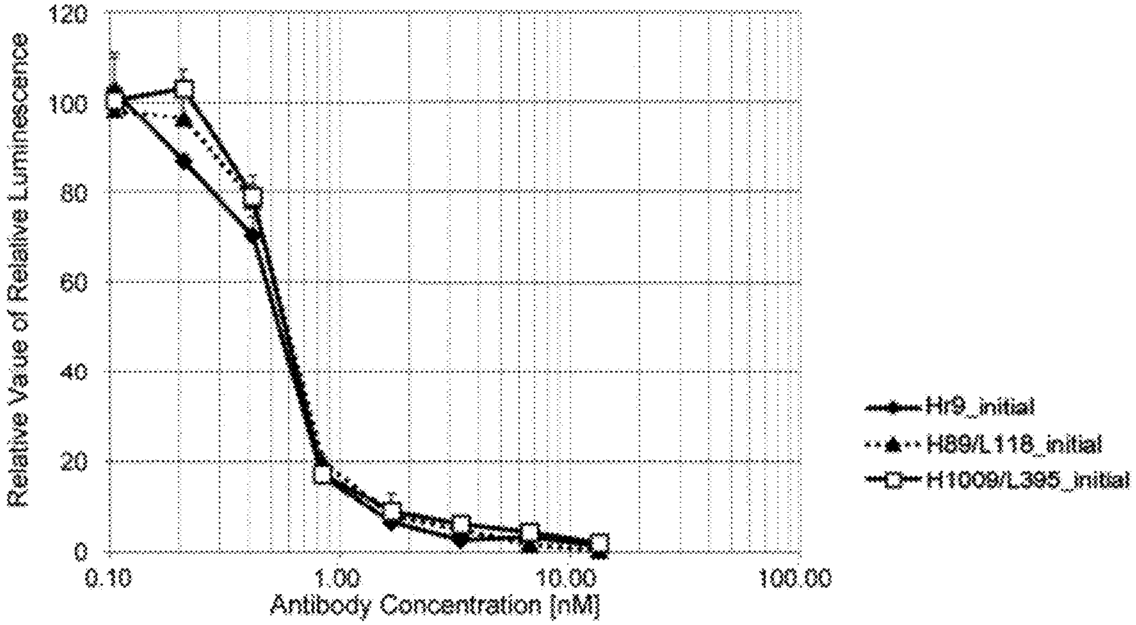
Figures 2, 21:
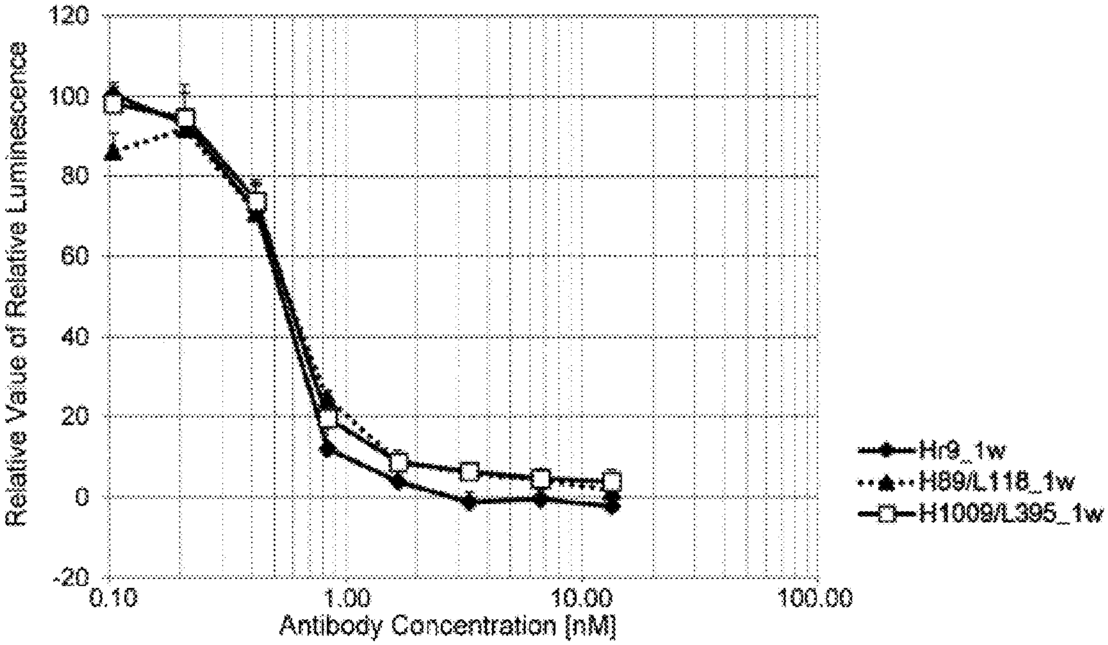
Figures 3, 21:
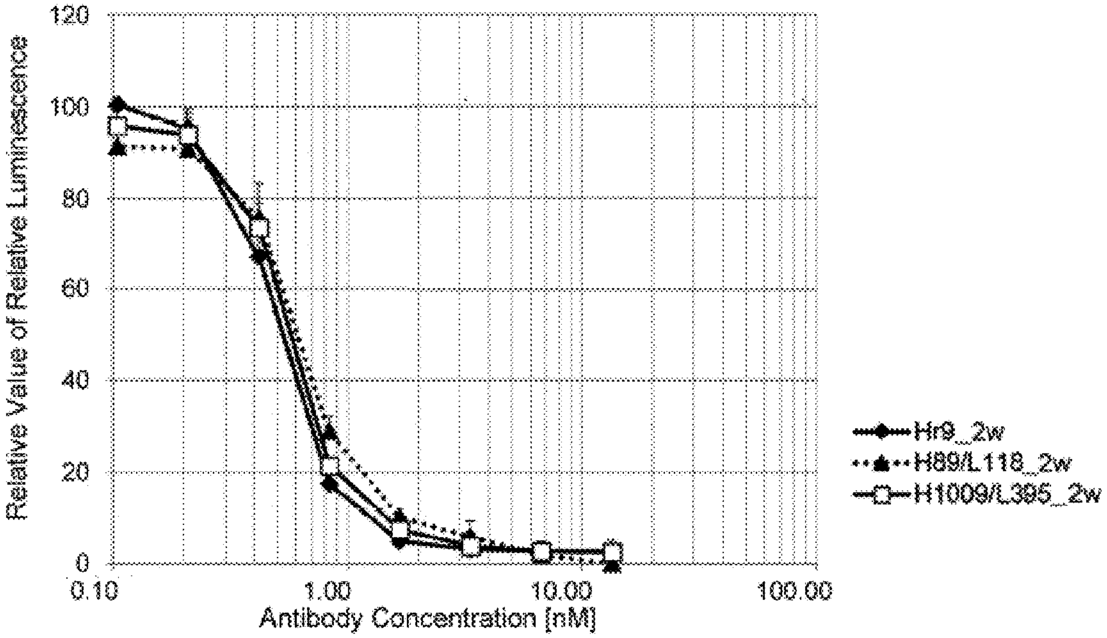

The results of human IL-8 inhibition assay obtained using the above-mentioned antibodies with human CXCR2-expressing cells are shown in FIG. 21-1, which shows results for the initial sample (without storage treatment in mouse plasma), FIG. 21-2, which shows results for the samples stored at 40° C. for one week, and FIG. 21-3, which shows results for the samples stored at 40° C. for two weeks.

As a result, surprisingly, the human IL-8-neutralizing activity was maintained in H1009/L395-F1886s even after it was stored in mouse plasma at 40° C. for two weeks, and the IL-8-neutralizing activity was more stably maintained than in the case of H553/L118.

(10-3) Mouse PK assay using H1009/L395

The rate of human IL-8 elimination by H1009/L395 in mice was evaluated by the following method. H1009/L395, H553/L118, and H998/L63 were used as the antibodies. Administration to mice and blood collection, and measurement of the human IL-8 concentration in mouse plasma were carried out by the method shown in Example 7.

Figure 22:
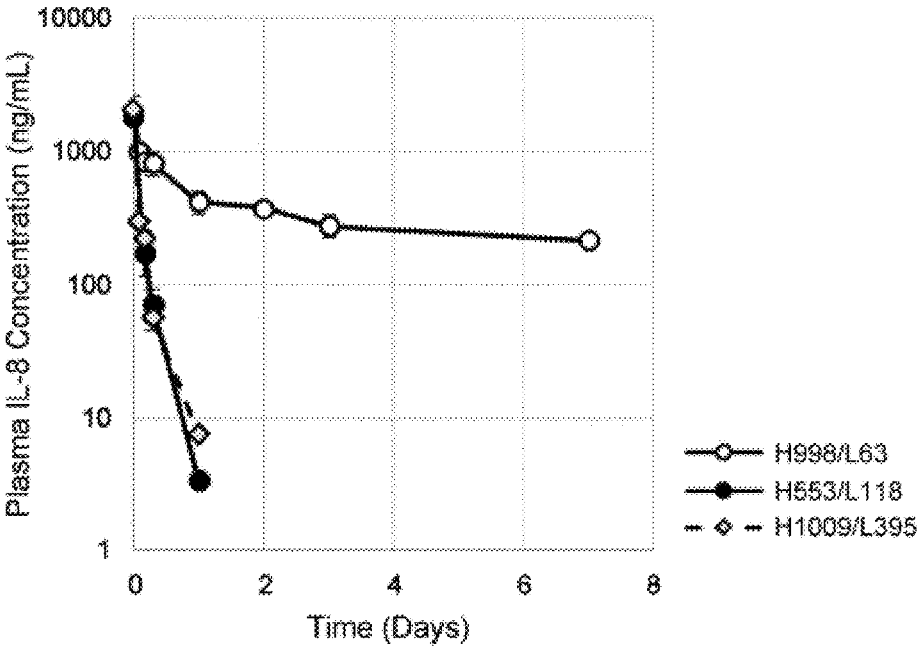
FIG. 22 shows a time course of human IL-8 concentration in the plasma of mice when H1009/L395, H553/L118, and H998/L63 were each administered to the mice in combination with human IL-8.

The resulting data on the concentration of human IL-8 in plasma are shown in FIG. 22, and the values of human IL-8 clearance (CL) from mouse plasma are shown in Table 16.

TABLE 16

| | Human IL-8 CL (mL/d/kg) | | |
|---|---|---|---|
| Antibody Name | H998/L63 | H553/L118 | H1009/L395 |
| #1 | 21.4 | 773.2 | 705.0 |
| #2 | 27.5 | 497.6 | 777.3 |
| #3 | 24.7 | 879.8 | 737.7 |
| Average (N = 3) | 24.5 | 716.9 | 740.0 |
| Standard Deviation | 3.0 | 197.2 | 36.2 |

As a result, the rate of human IL-8 elimination in mice when H1009/L395 was administered at 2 mg/kg was equivalent to that of H553/L118, and it was shown that H1009/L395 achieves nearly 100% free IL-8 in the endosome. The value of clearance (CL) which quantitatively represents the rate of human IL-8 elimination from mouse plasma was shown to be approximately 30-fold higher than that of H998/L63.

Without being particularly limited, the effect of increasing the rate of human IL-8 elimination can be understood as follows. Generally, in a living body where antigens are maintained at nearly constant concentrations, production rates and elimination rates of antigens will also be maintained at nearly constant values. When antibodies are administered under such conditions, even in cases where the antigen production rates are not affected, the rates of antigen elimination may change due to the complex formation of antigen with antibodies. Generally, since the antigen-elimination rate is greater than the antibody-elimination rate, in such cases, the elimination rate of antigens that have formed complexes with antibodies decreases. When the antigen elimination rate decreases, the antigen concentration in plasma increases, but the degree of increase in this case may also be defined by the ratio of the elimination rate when the antigen is present alone to the elimination rate when the antigen forms a complex. That is, in comparison to the elimination rate when the antigen is present alone, if the elimination rate when a complex is formed is decreased to one tenth, the antigen concentration in the plasma of the antibody-administered organism may increase up to approximately ten times that before antibody administration. Here, clearance (CL) may be used as the elimination rate. More specifically, increase of the antigen concentration (antigen accumulation) that takes place after antibody administration to an organism may be defined by the antigen CL under each of the conditions before antibody administration and after antibody administration.

Here, the presence of an approximately 30-fold difference in CL of human IL-8 when H998/L63 and H1009/L395 were administered suggests that there may be an approximately 30-fold difference between the levels of increase in the human IL-8 concentration in plasma when these antibodies are administered to humans. Furthermore, generation of a 30-fold difference in the human IL-8 concentration in plasma indicates that there will also be approximately a 30-fold difference in the amount of antibodies necessary for completely blocking the biological activity of human IL-8 under the respective conditions. That is, in comparison to H998/L63, H1009/L395 can block the biological activity of IL-8 in plasma at approximately 1/30 of the amount, which is a very small amount of antibody. Furthermore, when H1009/L395 and H998/L63 are individually administered to humans at the same dose, H1009/L395 will be able to block the biological activity of IL-8 for a longer period of time with greater strength. To block the biological activity of IL-8 for a long period of time, it is necessary that the IL-8-neutralizing activity is stably maintained. As shown in Example 10, experiments using mouse plasma have elucidated that H1009/L395 can maintain its human IL-8-neutralizing activity for a long period of time. H1009/L395 which includes these noteworthy properties was also shown to be an antibody that has superior effects from the viewpoint of the efficacy in neutralizing IL-8 in vivo.

[Example 11] Evaluation of Extracellular Matrix-Binding Using the pH-Dependent IL-8-Binding Antibody H1009/L395

The excellent 30-fold greater effect of H1009/L395 in eliminating human IL-8 as shown in Example 10 was a surprising effect. It is known that the rate of antigen elimination when a pH-dependent antigen-binding antibody is administered depends on the rate of uptake of the antibody-antigen complex into cells. That is, if the rate of the pH-dependent antibody uptake into cells increases when a complex with an antigen is formed in comparison to when the complex is not formed, the antigen-eliminating effect of the pH-dependent antibody can be increased. Known methods for increasing the rate of uptake of an antibody into cells include the method of conferring the FcRn-binding ability under neutral pH conditions to an antibody (WO 2011/122011), the method for enhancing the binding ability of an antibody towards FcγR(s) (WO 2013/047752), and the method that uses promotion of the formation of complexes containing a polyvalent antibody and a polyvalent antigen (WO 2013/081143).

However, the above-mentioned technique is not used in the constant regions of H1009/L395. Furthermore, while IL-8 is known to form a homodimer, human IL-8 bound by H1009/L395 has been found to exist in the form of a monomer because H1009/L395 recognizes the homodimer-forming surface of human IL-8. Therefore, these antibodies will not form polyvalent complexes.

More specifically, while the above-mentioned technique is not used for H1009/L395, H1009/L395 showed a 30-fold greater human IL-8-eliminating effect.

Without intending to be bound by theory, a possible factor that may bring about the aforementioned properties of pH-dependent IL-8-binding antibodies represented by H1009/L395 is presented below.

Human IL-8 is a protein that has a high isoelectric point (pI), and the theoretical isoelectric point calculated by a known method is approximately 10. That is, under neutral pH conditions, human IL-8 is a protein whose charge is shifted towards the positive side. pH-dependent IL-8-binding antibodies represented by H1009/L395 are also proteins whose charge is shifted towards the positive side, and the theoretical isoelectric point of H1009/L395 is approximately 9. That is, the isoelectric point of a complex produced by binding of H1009/L395, a protein that has a high isoelectric point and is originally rich in positive charges, to human IL-8 which has a high isoelectric point will be higher than that of H1009/L395 alone.

Increasing the isoelectric point of an antibody, which includes increasing the number of positive charges and/or decreasing the number of negative charges on the antibody, can be considered to increase non-specific uptake of the antibody-antigen complex into cells. There is also a possibility that the isoelectric point of complex formed between an anti-IL-8 antibody and human IL-8 which has a high isoelectric point is higher compared to that of the anti-IL-8 antibody alone, and the complex may be taken up more readily into cells.

As described earlier, binding to the extracellular matrix is also a factor that may influence uptake into cells. Then, it was examined whether there is a difference in extracellular matrix binding between an antibody alone and a complex with a human IL-8-antibody.

(11-1) Evaluation of the Amount of Antibody Binding to the Extracellular Matrix by the ECL (Electrochemiluminescence) Method Extracellular matrix (the BD Matrigel Basement Membrane Matrix/manufactured by BD) was diluted to 2 mg/mL using TBS (Takara, T903). The diluted extracellular matrix was dispensed into the MULTI-ARRAY 96 well Plate, High bind, Bare (manufactured by Meso Scale Discovery: MSD) at 5 μL per well, and immobilized overnight at 4° C. Then, blocking was performed using 20 mM ACES buffer (pH 7.4) containing 150 mM NaCl, 0.05% Tween20, 0.5% BSA, and 0.01% $NaN_3$.

The antibodies to be evaluated were prepared as follows. The antibody samples to be added alone were prepared by diluting each antibody to 9 μg/mL using Buffer-1 shown below, and then further diluting them using Buffer-2 to a final concentration of 3 μg/mL. Buffer-1: 20 mM ACES buffer containing 150 mM NaCl, 0.05% Tween20, and 0.01% $NaN_3$, at pH 7.4 Buffer-2: 20 mM ACES buffer containing 150 mM NaCl, 0.05% Tween20, 0.1% BSA, and 0.01% $NaN_3$, at pH 7.4

On the other hand, the antibody-human IL-8 complex samples to be added were prepared by adding human IL-8 at ten times the molar concentration of the antibody to an antibody sample, then diluting each antibody using Buffer-I so that the antibody concentration became 9 μg/mL, respectively, and then further diluting each of them using Buffer-2 to a final antibody concentration of 3 μg/mL. At this point, the human IL-8 concentration was approximately 0.6 μg/mL. This was shaken at room temperature for one hour for complex formation.

Next, solutions of the antibody alone or the complex were added to the plate from which the blocking solution had been removed, and this was shaken at room temperature for one hour. Then, after removal of the antibody-alone solution or the complex solution, Buffer-1 containing 0.25% Glutaraldehyde was added. Then, after the plate was allowed to stand for 10 minutes, it was washed with DPBS (manufactured by Wako Pure Chemical Industries) containing 0.05% Tween20. An antibody for ECL detection was prepared by sulfo-tagging the goat anti-human IgG (gamma) (manufactured by Zymed Laboratories) using the Sulfo-Tag NHS Ester (manufactured by MSD). The antibody for ECL detection was diluted with Buffer-2 to be 1 μg/mL, added to the plate, and then shaken in the dark at room temperature for one hour. The antibody for ECL detection was removed, a solution produced by 2-fold dilution of the MSD Read Buffer T (4×) (manufactured by MSD) using ultrapure water was added, and then the amount of luminescence was measured by SECTOR Imager 2400 (manufactured by MSD).

Figure 23:
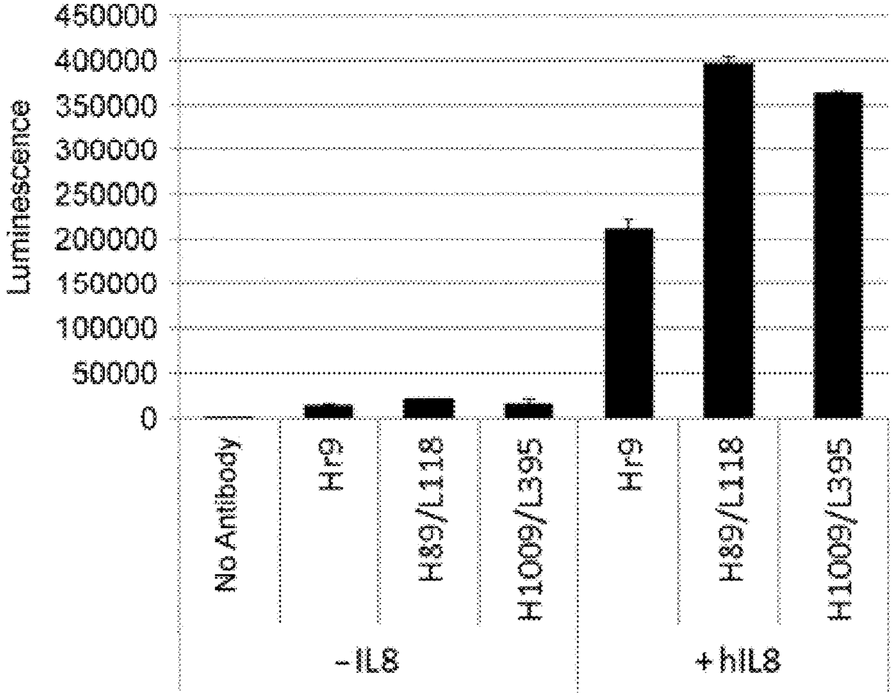
FIG. 23 shows the amount of binding of Hr9, H89/L118, or H1009/L395 to extracellular matrix when added alone or in combination with human IL-8 to extracellular matrix.

The results are shown in FIG. 23. Interestingly, it was found that all of the anti-IL-8 antibodies such as H1009/L395 hardly showed any binding to the extracellular matrix as the antibody alone (−IL8), but bound to the extracellular matrix upon complex formation with human IL-8 (+hIL8).

As described above, the property of anti-IL-8 antibodies to acquire binding ability to the extracellular matrix by binding to human IL-8 has not been elucidated from prior art information. Furthermore, without being limited, combining such properties with pH-dependent IL-8-binding antibodies can increase the rate of IL-8 elimination more efficiently.

[Example 12] Mouse PK Assay Using Non-FcRn-Binding Antibodies

The following method was used to confirm whether a complex between human IL-8 and a pH-dependent IL-8-binding antibody is formed and uptake of that complex into cells increases in mice in vivo.

First, a mutant comprising the variable region of H1009/L395 and an Fc region deficient in binding affinity to various Fc receptors was produced. Specifically, as modifications for deleting the binding ability towards human FcRn under acidic pH conditions, the heavy chain H1009-IgG1 was subjected to substitution of alanine for isoleucine at position 253 and aspartic acid for serine at position 254, according to EU numbering. Furthermore, as modifications for deleting the binding to mouse FcγR(s), leucine at position 235 was substituted with arginine, glycine at position 236 was substituted with arginine, and serine at position 239 was substituted with lysine. H1009-F1942m (SEQ ID NO:49) was produced as a heavy chain containing four of these modifications. Furthermore, H1009/L395-F1942m having H1009-F1942m as the heavy chain and L395-k0MT as the light chain was produced.

Since an antibody that has this Fe region is deficient in the FcRn binding affinity under acidic pH conditions, it is not transferred from the endosome into plasma. Therefore, such antibody is quickly eliminated from plasma in a living body as compared to antibody that has native Fc region. In this case, after the antibody that has native Fc region is taken up into cells, only a portion of them that is not salvaged by FcRn is degraded after being transferred to the lysosome, but in the case of antibody having Fc region that does not have FcRn-binding affinity, all of the antibody taken up into the cells are degraded in lysosomes. More specifically, in the case of antibody that has such modified Fc region, the rate of elimination of the administered antibody from plasma may be equivalent to the rate of incorporation into cells. That is, the rate of intracellular uptake of the antibody whose FcRn-binding affinity has been deleted can also be confirmed by measuring the rate of elimination of these antibodies from plasma.

Then, whether intracellular uptake of the complex formed between H1009/L395-F1942m and human IL-8 increases as compared to the uptake of H1009/L395-F1942m was tested. Specifically, whether the rate of elimination of the antibody from plasma will change when the antibody is administered alone and when the antibody is administered upon formation of a complex with human IL-8 was tested.

The respective biokinetics of the anti-human IL-8 antibody was evaluated in cases when the anti-human IL-8 antibody was administered alone to human FcRn transgenic mice (B6.mFcRn−/−.hFcRn Tg line 32+/+ mouse; Jackson Laboratories; Methods Mol. Biol. (2010) 602:93-104) and when human IL-8 and the anti-human IL-8 antibody were administered simultaneously to the human FcRn transgenic mice. The anti-human IL-8 antibody solution (200 μg/mL), and a mixed solution of human IL-8 (10 μg/mL) and the anti-human IL-8 antibody (200 μg/mL) were individually administered once at 10 mL/kg to the tail vein. In this case, since the anti-human IL-8 antibody was present in sufficient excess over human IL-8, almost all of human IL-8 was considered to be bound to the antibody. Blood was collected five minutes, two hours, seven hours, one day, and two days after the administration. The collected blood was immediately centrifuged at 4° C. and 15,000 rpm for 15 minutes to obtain plasma. The separated plasma was stored in a freezer set to −20° C. or below until measurements were taken.

The anti-human IL-8 antibody concentration in mouse plasma was measured by an electrochemiluminescence method. First, to the Streptavidin Gold Multi-ARRAY Plate (Meso Scale Discovery) which had been blocked overnight at room temperature using a PBS-Tween solution containing 5% BSA (w/v), an Anti-Human Kappa Light Chain Goat IgG Biotin (IBL) was allowed to react at room temperature for one hour to produce an anti-human antibody-immobilized plate. Samples for calibration curve containing the anti-human IL-8 antibody at concentrations of 3.20, 1.60, 0.800, 0.400, 0.200, 0.100, and 0.0500 μg/mL in plasma and samples for mouse plasma measurement diluted 100-fold or higher were prepared. Each sample was mixed with human IL-8, and then dispensed at 50 μL per well into the anti-human antibody-immobilized plate, and then stirred at room temperature for one hour. Human IL-8 was adjusted to a final concentration of 333 ng/mL.

Then, an anti-human IL-8 antibody (prepared in-house) having a mouse IgG constant region was added to the plate, and was allowed to react at room temperature for one hour. Furthermore, the Anti-Mouse IgG (BECKMAN COULTER) ruthenium-labeled with the SULFO-TAG NHS Ester (Meso Scale Discovery) was added to the plate, and this was allowed to react for one hour. Then, immediately after the Read Buffer T(×1) (Meso Scale Discovery) was dispensed into the plate, measurement was carried out using SECTOR Imager 2400 (Meso Scale Discovery). The anti-human IL-8 antibody concentration was calculated based on the response in the calibration curve using the analytical software, the SOFTmax PRO (Molecular Devices).

Figure 24:
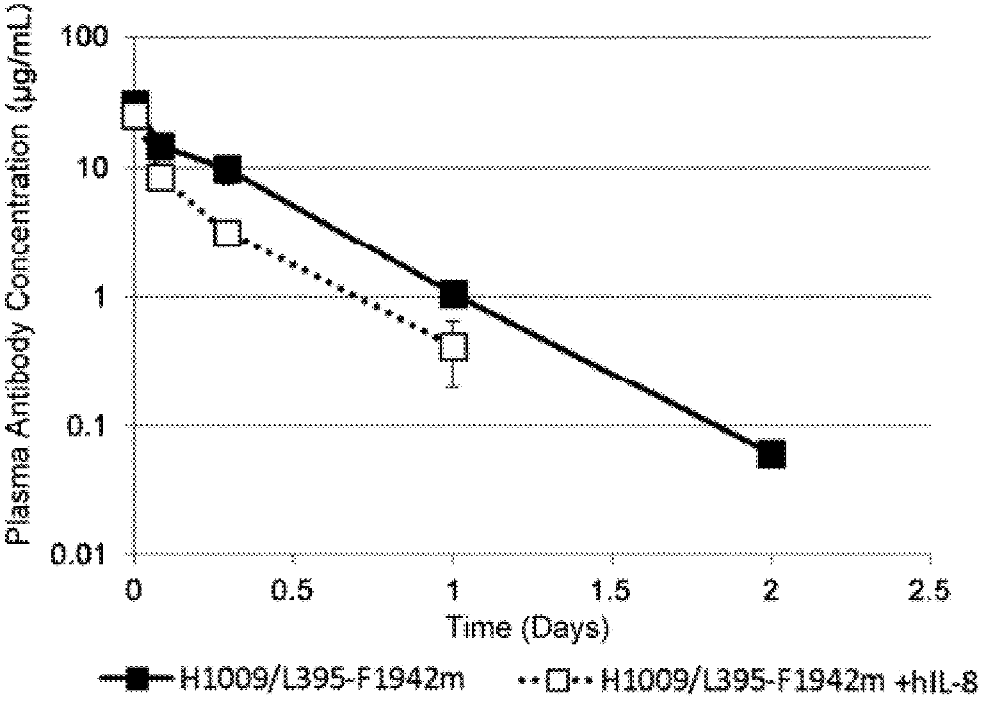
FIG. 24 shows a time course of antibody concentration in the plasma of human FcRn transgenic mice when an antibody having the variable region of H1009/L395 and an Fc domain (F1942m) that does not bind to FcRn was administered alone or in combination with human IL-8.

Antibody concentrations in mouse plasma obtained as a result are shown in FIG. 24, and the antibody clearance under the respective conditions are shown in Table 17.

TABLE 17

| Antibody Name | IL8 μg/kg | CL mL/d/kg |
|---|---|---|
| H1009/L395-F1942m | — | 134 |
| H1009/L395-F1942m | 100 | 291 |

The rate of intracellular uptake of the complex of H1009/L395-F1942m and human IL-8 was shown to be increased by at least 2.2 fold compared to the uptake rate of H1009/L395-F1942m. Here, it is noted as "at least 2.2-fold" because of the following reason which is included as one of the possibilities that the value may actually be 5-fold, 10-fold, or 30-fold. As the rate of elimination of human IL-8 from mouse plasma is very rapid compared to the rate of elimination of H1009/L395-F1942m, the proportion of H1009/L395-F1942m bound by human IL-8 in plasma quickly decreases after administration. More specifically, even when administered simultaneously with human IL-8, not all H1009/L395-F1942m present in the plasma are in the human IL-8-bound form, and in fact, at approximately seven hours after administration, most of them already exist in the free form antibody. Since the uptake rate is evaluated under such conditions, even if the rate of intracellular uptake of the complex of H1009/L395-F1942m and human IL-8 has been actually increased five-fold, ten-fold, or 30-fold in comparison to the uptake rate of H1009/L395-F1942m, the results in this experiment system are reflected only partially; therefore, the effect may possibly be presented as an increase of 2.2-fold or so. Accordingly, from these obtained results, whereas the intracellular uptake rate of the complex of H1009/L395 and IL-8 was shown to be increased compared to the actual intracellular uptake rate of H1009/L395 in vivo, this effect is not limited to the obtained value of 2.2-fold increase.

Without being particularly limited, the following interpretation may be made from the findings obtained so far. When H1009/L395, which is a pH-dependent IL-8-binding antibody, forms a complex with human IL-8, that complex has a higher isoelectric point and is shifted more towards a positive charge than when the antibody alone exists. At the same time, the binding of the complex to the extracellular matrix is more increased than the binding of the antibody alone. Properties such as elevation of isoelectric point and enhancement of the extracellular matrix binding can be considered as factors that promote uptake into cells in vivo. Furthermore, from mouse experiments, the rate of intracellular uptake of the complex of H1009/L395 and human IL-8 was also shown to be increased 2.2-fold or greater compared to the uptake rate of H1009/L395. From the above, the theoretical explanation as well as the in vitro properties and in vivo phenomena consistently support the hypothesis that H1009/L395 and human IL-8 form a complex to promote uptake of the complex into cells, and leads to a remarkable increase in the elimination of human IL-8.

Several antibodies against IL-8 have been reported to date, but there has been no report so far on the increase of binding to the extracellular matrix upon complex formation with IL-8 and the increase in uptake of the complexes into cells.

Furthermore, based on the finding that an increase in the intracellular uptake of the anti-IL-8 antibodies is observed when the antibodies form complexes with IL-8, one may consider that the anti-IL-8 antibodies that have formed complexes with IL-8 in plasma are quickly taken up into cells, while the free antibodies which have not formed complexes with IL-8 tend to be retained in plasma without being taken up into cells. In this case, when the anti-IL-8 antibody is pH-dependent, the anti-IL-8 antibody which has been taken up into the cells releases the IL-8 molecule in the cells and then returns to the outside of the cells, and then it can bind to another IL-8 molecule; and therefore, increase in the intracellular uptake upon complex formation may have a further effect of eliminating IL-8 more strongly. That is, selecting anti-IL-8 antibodies with increased binding to the extracellular matrix or anti-IL-8 antibodies with increased uptake into cells is also another aspect of the present disclosure.

Figure 25:
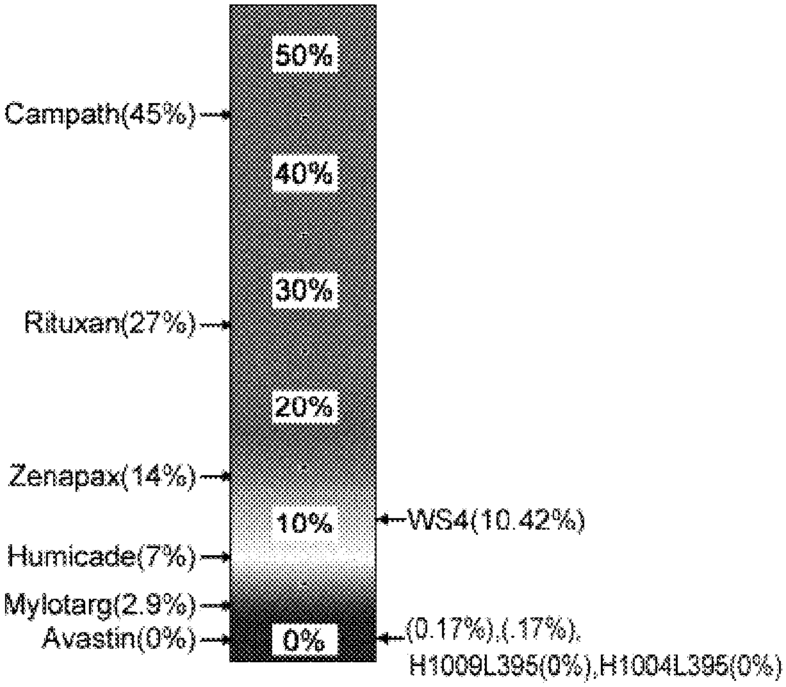
FIG. 25 shows the frequency of ADA occurrence predicted by EpiMatrix for H1009/L395 and H1004/L395, and for other existing antibody pharmaceuticals.

[Example 13] Immunogenicity Prediction of the pH-Dependent IL-8-Binding Antibody H1009/L395 Using an in Silico System Next, the immunogenicity score and frequency of ADA development were predicted for H1009/L395 by a method similar to that of Example 9-1. The results are shown in Table 18 and FIG. 25. In FIG. 25, H1009/L395 is noted as "H1009L395".

TABLE 18

| | Heavy Chain | | Light Chain | | Total | |
|---|---|---|---|---|---|---|
| Antibody Name | EpiMatrix Score | tReg Adjusted Epx Score | EpiMatrix Score | tReg Adjusted Epx Score | EpiMatrix Score | tReg Adjusted Epx Score |
| hWS-4 | 62.44 | 12.18 | 22.64 | −23.89 | 85.08 | −11.71 |
| H1004/L395 | 10.79 | −39.47 | 7.79 | −38.74 | 18.58 | −78.21 |
| H1009/L395 | 9.62 | −40.64 | 7.79 | −38.74 | 17.41 | −79.38 |

The results in Table 18 show that H1009/L395 has the same level of low immunogenicity scores as H1004/L395. Furthermore, the frequency of ADA development predicted for H1009/L395 from the results in FIG. 25 was 0%, and this was also similar to that of H1004/L395.

Accordingly, the predicted immunogenicity was greatly decreased for H1009/L395 in comparison to the known anti-human IL-8 antibody hWS-4. Therefore, H1009/L395 is considered to have very low immunogenicity in humans, and to be able to safely maintain the anti-IL-8-neutralizing activity for a long period of time.

[Example 14] Cynomolgus Monkey PK Assay Using an H89/L118 Variant with Enhanced FcRn-Binding Ability Under Acidic pH Conditions As described in the Examples above, among the cases where the antibodies have native IgG1 as their constant region, the pH-dependent IL-8-binding antibody H1009/L395 is an antibody that has superior properties. However, such antibodies can also be used as antibodies containing amino acid substitutions in the constant region, for example, those containing an Fc region with enhanced FcRn binding at acidic pH, as exemplified in Example 5. Therefore, H89/L118 was used to confirm that the Fc region with enhanced FcRn binding at acidic pH can also function in a pH-dependent IL-8-binding antibody.

(14-1) Production of an H89/L118 Fc Region-Modified Antibody with Enhanced FcRn Binding at Acidic pH Various modifications for enhancing FcRn binding as described in Example 5-1 were introduced into the Fc region of H89/L118. Specifically, the following variants were produced by introducing the modifications used in F1847m, F1848m, F1886m, F1889m, F1927m, and F1168m into the Fc region of H89-IgG1:

- H89/L118-IgG1 having H89-IgG1m (SEQ ID NO:50) as the heavy chain and L118-K0MT as the light chain;
- H89/L118-F1168m having H89-F1168m (SEQ ID NO:51) as the heavy chain and L118-K0MT as the light chain;
- H89/L118-F1847m having H89-F1847m (SEQ ID NO:52) as the heavy chain and L118-K0MT as the light chain;
- H89/L118-F1848m having H89-F1848m (SEQ ID NO:53) as the heavy chain and L118-K0MT as the light chain;
- H89/L118-F1886m having H89-F1886m (SEQ ID NO:54) as the heavy chain and L118-K0MT as the light chain;
- H89/L118-F1889m having H89-F1889m (SEQ ID NO:55) as the heavy chain and L118-K0MT as the light chain;
- H89/L118-F1927m having H89-F1927m (SEQ ID NO:56) as the heavy chain and L118-K0MT as the light chain.

Cynomolgus monkey PK assays using these antibodies were carried out by the method shown below.

H89/L118-F22, which is described later in the Examples, was also produced in the same manner (having H89-F22 (SEQ ID NO: 106) as the heavy chain and L118-K0MT as the light chain).

(14-2) Cynomolgus Monkey PK Assay of Novel Fc Region Variant-Containing Antibodies After administration of anti-human IL-8 antibodies to cynomolgus monkeys, biokinetics of the anti-human IL-8 antibodies was evaluated. An anti-human IL-8 antibody solution was intravenously administered once at 2 mg/kg. Blood was collected five minutes, four hours, one day, two days, three days, seven days, ten days, 14 days, 21 days, 28 days, 35 days, 42 days, 49 days, and 56 days after administration. The collected blood was immediately centrifuged at 4° C. and 15,000 rpm for ten minutes to obtain plasma. The separated plasma was stored in a freezer set to −60° C. or below until measurements were taken.

The anti-human IL-8 antibody concentration in cynomolgus monkey plasma was measured by an electrochemiluminescence method. First, the Anti-hKappa Capture Ab (Antibody Solutions) was dispensed into a MULTI-ARRAY 96-well Plate (Meso Scale Discovery), and was stirred at room temperature for one hour. Then, a PBS-Tween solution containing 5% BSA (w/v) was used for blocking at room temperature for two hours to prepare an anti-human antibody-immobilized plate. Samples for calibration curve containing an anti-human IL-8 antibody at concentrations of 40.0, 13.3, 4.44, 1.48, 0.494, 0.165, and 0.0549 μg/mL in plasma and samples for cynomolgus monkey plasma measurement diluted 500-fold or more were prepared, 50 μL of the solutions were dispensed into each well of the anti-human antibody-immobilized plate, and the solutions were stirred at room temperature for one hour. Then, the Anti-hKappa Reporter Ab, Biotin conjugate (Antibody Solutions) was added to the aforementioned plate, and allowed to react at room temperature for one hour. After further adding the SULFO-TAG Labeled Streptavidin (Meso Scale Discovery) and allowing to react at room temperature for one hour, the Read Buffer T(×1) (Meso Scale Discovery) was dispensed into the plate, and measurements were taken immediately using SECTOR Imager 2400 (Meso Scale Discovery). The anti-human IL-8 antibody concentration was calculated based on the response in the calibration curve using the analytical software, the SOFTmax PRO (Molecular Devices).

Figure 26:
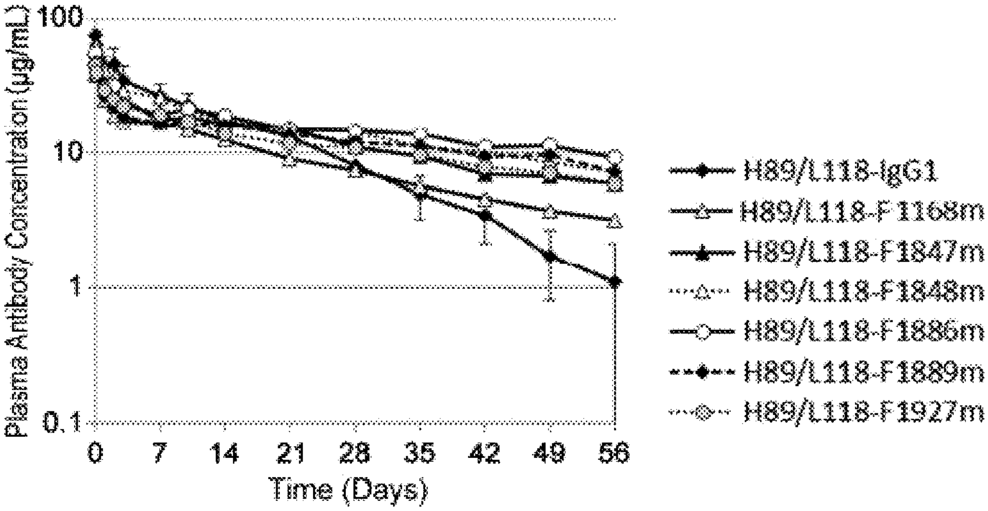
FIG. 26 shows a time course of the concentration of each anti-human IL-8 antibody in the plasma of cynomolgus monkeys when H89/L118-IgG1, which comprises the variable region of H89/L118 and the Fe domain of native human IgG1, and antibodies comprising various Fe region variants with increased FcRn binding (H89/L118-F1168m, H89/L118-F1847m, H89/L118-F1848m, H89/L118-F1886m, H89/L118-F1889m, and H89/L118-F1927m), were each administered to the cynomolgus monkeys.

The results obtained for the half-life (t½) and clearance (CL) of each of the antibodies are shown in Table 19, and changes in the antibody concentration in cynomolgus monkey plasma are shown in FIG. 26.

TABLE 19

| Antibody Name | t½ day | CL mL/d/kg |
|---|---|---|
| H89/L118-IgG1 | 11.9 | 2.95 |
| H89/L118-F1168m | 24.1 | 3.21 |
| H89/L118-F1847m | 27.9 | 2.09 |
| H89/L118-F1848m | 25.3 | 1.74 |
| H89/L118-F1886m | 45.1 | 1.34 |
| H89/L118-F1889m | 39.5 | 1.75 |
| H89/L118-F1927m | 30.3 | 2.13 |

The above results confirmed that all of the Fc region variants show improved retention in plasma in comparison to the antibody that has a native IgG1 Fc region. In particular, H89/L118-F1886m showed the most desirable blood kinetics.

[Example 15] Fc Region with Lowered Binding Ability Towards FcγRs

The Fc region of a native human IgG1 is known to bind to Fcγ receptor(s) (hereinafter, referred to as FcγR(s)) on various cells of the immune system, and exhibit effector functions such as ADCC and ADCP on target cells.

On the other hand, IL-8 is a soluble cytokine, and anti-IL-8 antibodies used as pharmaceuticals are mainly expected to show pharmacological actions by neutralizing the functions of IL-8 at sites where IL-8 is present in excess. Such sites where IL-8 is present in excess are not particularly limited, and for example, may be inflamed sites. It is known that generally at such inflamed sites, various immune cells gather and are activated. Transmitting unintended activation signals to these immune cells via Fc receptors and inducing activities such as ADCC and ADCP in unintended cells are not always favorable. Therefore, without being particularly limited, from a safety point of view, it may be preferable that anti-IL-8 antibodies administered in vivo have low binding ability to FcγR(s).

(15-1) Production of Modified Antibodies with Lowered Binding Towards FcγRs

Amino acid modifications were further introduced into the Fc region of H1009/L395-F1886m with the objective of reducing the binding ability towards various human and cynomolgus monkey FcγRs. Specifically, H1009-F1886s (SEQ ID NO:37) was produced by subjecting the H1009-F1886m heavy chain to each of the following substitutions: R for L at position 235, R for G at position 236, and K for S at position 239, according to EU numbering. Similarly, H1009-F1974m (SEQ ID NO:36) was produced by subjecting H1009-F1886m to substitution of R for L at position 235 and R for G at position 236, according to EU numbering, and substituting the region from position 327 to position 331 according to EU numbering with that of the native human IgG4 sequence. H1009/L395-F1886s and H1009/L395-F1974m were produced as antibodies having these heavy chains, and L395-k0MT as the light chain.

(15-2) Confirmation of the Binding to Various Human FcγRs

Next, the binding of the produced H1009/L395-F1886s or H1009/L395-F1974m to the soluble forms of FcγRIa or FcγRIIIa in human and cynomolgus monkey were confirmed by the following method.

Assays were performed for the binding of the produced H1009/L395-F1886s and the H1009/L395-F1974m to the soluble forms of FcγRIa and FcγRIIIa in human and cynomolgus monkey using BIACORE T200 (GE Healthcare). Soluble FcγRIa and FcγRIIIa in both human and cynomolgus monkey were produced in the form of His-tagged molecules by methods known to those of ordinary skill in the art. An appropriate amount of rProtein L (BioVision) was immobilized onto the Sensor chip CM4 (GE Healthcare) by the amine coupling method and an antibody was captured. Next, soluble FcγRIa or FcγRIIIa was injected with a running buffer (used as a reference solution), and was made to interact with the antibodies captured onto the sensor chip. HBS-EP+ (GE Healthcare) was used as the running buffer, and HBS-EP+ was also used to dilute the soluble FcγRIa or FcγRIIIa. To regenerate the sensor chip, 10 mM glycine-HCl at pH 1.5 was used. All measurements were carried out at 20° C.

Figure 27:
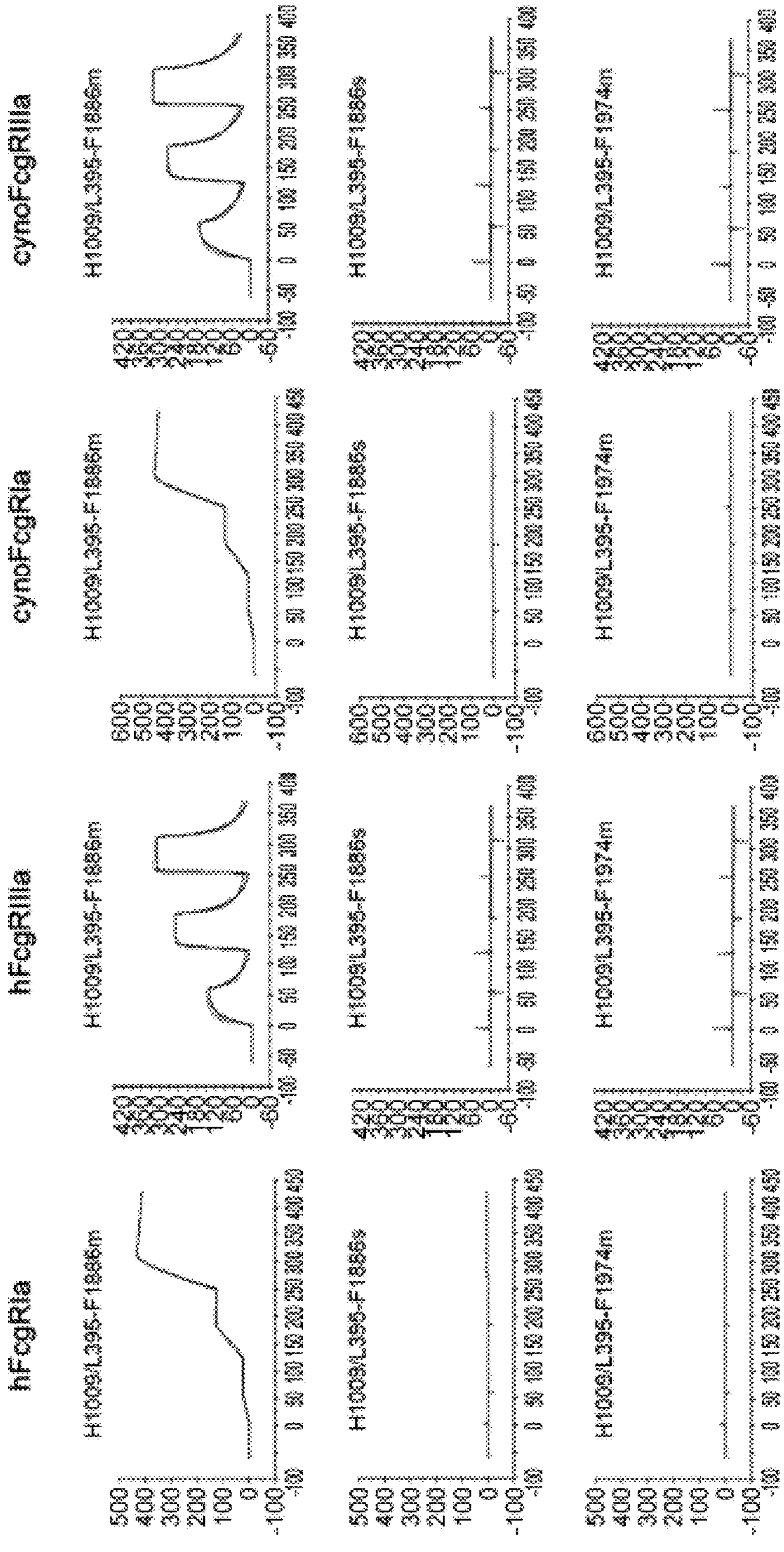
FIG. 27 shows the binding activity of antibodies to various FcγR, where the antibodies comprise the variable region of H1009/L395 and their Fc domains are variants (F1886m, F1886s, and F1974m).

The results are shown in FIG. 27. Here, the notations used for human FcγRIa, human FcγRIIIa, cynomolgus monkey FcγRIa, and cynomolgus monkey FcγRIIIa are in the same order: hFcγRIa, hFcγRIIIa, cynoFcγRIa, and cynoFcγRIIIa, respectively. H1009/L395-F1886m was shown to bind to all FcγRs, but on the other hand, the newly-produced H1009/L395-F1886s and H1009/L395-F1974m were confirmed not to bind to any of the FcγRs.

(15-3) Mouse IL-8 Elimination Assay of Fc Variants

Next, for the produced H1009/L395-F1886s and H1009/L395-F1974m, the rate of human IL-8 elimination and the retention in plasma of the antibodies in mice were confirmed by the following experiment. Here, three doses of H1009/L395-F1886s, 2 mg/kg, 5 mg/kg, and 10 mg/kg, were used for the evaluation so that the effects of increasing the antibody dosage can also be evaluated for H1009/L395-F1886s.

After simultaneous administration of human IL-8 and an anti-human IL-8 antibody to human FcRn transgenic mice (B6.mFcRn−/−.hFcRn Tg line 32+/+ mouse; Jackson Laboratories; Methods Mol. Biol. (2010) 602:93-104), the biokinetics of human IL-8 was evaluated. A mixed solution of human IL-8 (10 μg/mL) and an anti-human IL-8 antibody (200 μg/mL, 500 μg/mL, or 1000 μg/mL) was administered once at 10 mL/kg through the tail vein. In this case, since the anti-human IL-8 antibody was present in sufficient excess over human IL-8, almost all of human IL-8 was considered to be bound to the antibody. Blood was collected five minutes, two hours, four hours, seven hours, one day, two days, three days, seven days, 14 days, 21 days, and 28 days after the administration. The collected blood was immediately centrifuged at 4° C. and 15,000 rpm for 15 minutes to obtain plasma. The separated plasma was stored in a freezer set to −20° C. or below until measurements were taken.

Figure 28:
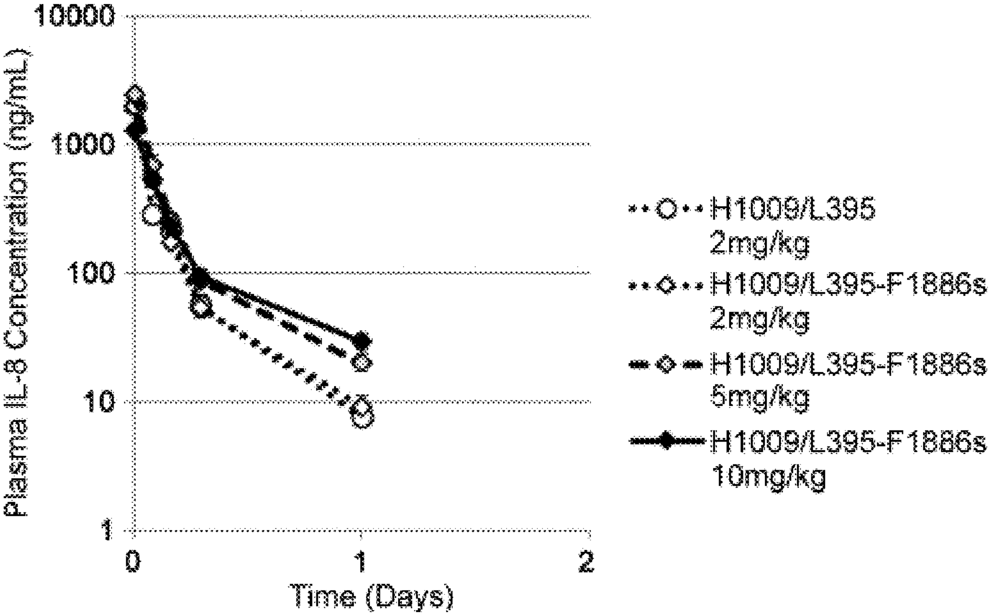
FIG. 28 shows a time course of human IL-8 concentration in the plasma of human FcRn transgenic mice when anti-IL-8 antibodies were administered to the mice in combination with human IL-8. The anti-IL-8 antibodies are: H1009/L395-IgG1 (2 mg/kg), which comprises the variable region of H1009/L395 and the Fe domain of native human IgG1; and H1009/L395-F1886s (2, 5, or 10 mg/kg), which comprises the variable region of H1009/L395 and a modified Fc domain.

The human IL-8 concentration in mouse plasma was measured by a method similar to that of Example 7. The resulting data on the human IL-8 concentration in plasma is shown in FIG. 28, and the values of human IL-8 clearance (CL) from mouse plasma are shown in Table 20.

First, H1009/L395 having the Fc region of a native IgG1 and H1009/L395-F1886s having the modified Fc region were shown to have equivalent human IL-8-eliminating effects when the 2 mg/kg-administered groups were compared.

Next, when the dosage of the H1009/L395-F1886s antibody was changed, significant difference in the human IL-8 clearance values was not observed between 2 mg/kg and 10 mg/kg while there was a slight difference in the plasma IL-8 concentration one day after administration. This strongly suggests that antibodies comprising the variable region of H1009/L395 showed sufficient IL-8-eliminating effects even when the antibodies were administered at high doses.

TABLE 20

| Antibody Name | Dose | Human IL-8 CL (mL/d/kg) |
|---|---|---|
| H1009/L395 | 2 mg/kg | 740 |
| H1009/L395-F1886s | 2 mg/kg | 628 |
| H1009/L395-F1886s | 5 mg/kg | 458 |
| H1009/L395-F1886s | 10 mg/kg | 560 |

(15-4) Cynomolgus Monkey PK Assay of Fc Region Variants

Next, plasma retention of antibodies in cynomolgus monkeys was verified by the following method using H1009/L395-F1886s or H1009/L395-F1974m.

Biokinetics of an anti-human IL-8 antibody were evaluated after the anti-human IL-8 antibody was administered alone or human IL-8 and the anti-human IL-8 antibody were simultaneously administered to cynomolgus monkeys. An anti-human IL-8 antibody solution (2 mg/mL) or a mixed solution of human IL-8 (100 μg/kg) and an anti-human IL-8 antibody (2 mg/kg) was intravenously administered once at 1 mL/kg. Blood was collected five minutes, four hours, one day, two days, three days, seven days, ten days, 14 days, 21 days, 28 days, 35 days, 42 days, 49 days, and 56 days after administration. The collected blood was immediately centrifuged at 4° C. and 15,000 rpm for ten minutes to obtain plasma. The separated plasma was stored in a freezer set to −60° C. or below until measurements were taken.

Figure 29:
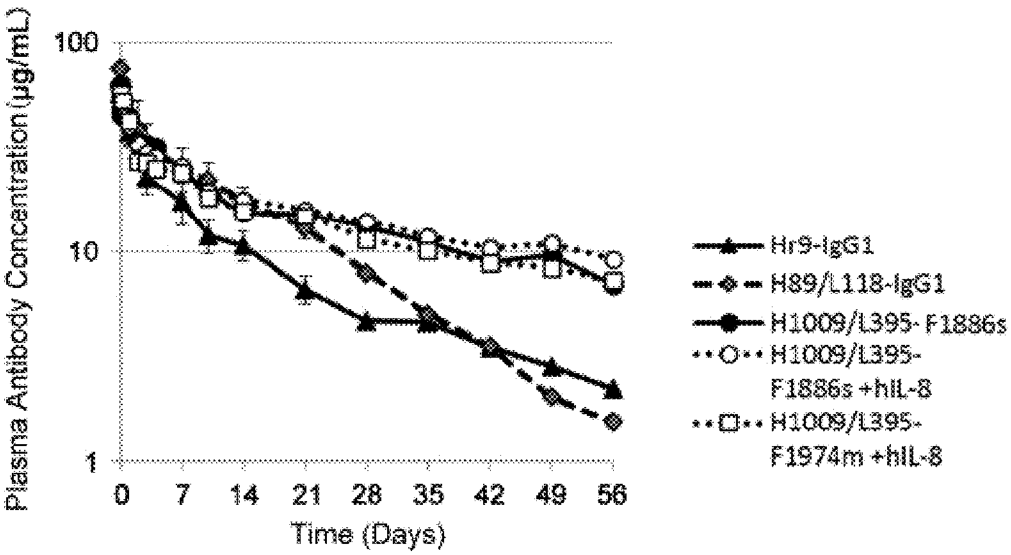
FIG. 29 shows a time course of antibody concentration in the plasma of cynomolgus monkeys when Hr9-IgG1 or H89/L118-IgG1, which comprises the Fc region of native human IgG1, or H1009/L395-F1886s or H1009/L395-F1974m, which comprises a modified Fc region, was administered to the cynomolgus monkeys.

The anti-human IL-8 antibody concentration in cynomolgus monkey plasma was measured by the method of Example 14. The resulting data on the anti-human IL-8 antibody concentration in plasma is shown in FIG. 29, and the values for the half-life ($t_1$12) and clearance (CL) of the anti-human IL-8 antibody from cynomolgus monkey plasma are shown in Table 21.

First, in comparison to Hr9 and H89/L118 which have the Fe region of a native human IgG1, H1009/L395-F1886s which has an Fe region with improved functions was shown to have significantly prolonged plasma retention.

Furthermore, when H1009/L395-F1886s was administered simultaneously with human IL-8, the change in plasma concentration was equivalent to that when the antibody was administered alone. Without being particularly limited, the following discussion is possible from this finding. As described above, intracellular uptake of the complex of H1009/L395 and human IL-8 has been shown to be increased compared to the uptake of H1009/L395 alone. Generally, high-molecular-weight proteins are thought to be incorporated non-specifically or in a receptor-dependent manner into cells, then transferred to the lysosome and degraded by various degrading enzymes present in the lysosome. Therefore, if the rate of uptake of the protein into cells increases, the plasma retention of that protein is likely to worsen as well. However, in the case of an antibody, it has the property of being returned to the plasma by FcRn in the endosome; and therefore, as long as the salvaging by FcRn functions sufficiently, plasma retention may not be affected even if the rate of intracellular uptake is accelerated. Here, even when H1009/L395-F1886s was administered simultaneously with human IL-8 to cynomolgus monkeys, plasma retention was not affected. This indicates the possibility that while the rate of antibody uptake into cells is increased for H1009/L395-F1886s, the antibody is sufficiently salvaged by FcRn such that it can return to the plasma.

Furthermore, another Fc variant H1009/L395-F1974m also showed equivalent plasma retention to that of H1009/L395-F1886s. While these Fc variants have been introduced with different modifications that decrease the binding ability to various FcγRs as describe above, they have been shown not to affect the plasma retention of the antibodies themselves. From the above, plasma retention of both H1009/L395-F1886s and H1009/L395-F1974m in cynomolgus monkeys was shown to be remarkably prolonged and extremely satisfactory in comparison to that of antibodies that have the native IgG1 Fc region.

TABLE 21

| | t½ day | CL mL/d/kg |
|---|---|---|
| Hr9 | 20.26 | 3.72 |
| H89/L118 | 11.88 | 2.95 |
| H1009/L395-F1886s | 35.75 | 1.64 |
| H1009/L395-F1886s + hIL-8 | 72.24 | 1.11 |
| H1009/L395-F1974m + hIL-8 | 43.78 | 1.60 |

As shown in the Examples described above, H1009/L395 is an antibody which was substantialized for the first time as an antibody that can markedly increase the rate of elimination of human IL-8 in vivo by having a pH-dependent IL-8 binding ability as well as the characteristic of being rapidly incorporated into cells when complexed with IL-8. Furthermore, since the IL-8-binding affinity of H1009/L395 under a neutral pH condition is also increased as compared to the known hWS-4 antibody, H1009/L395 can neutralize human IL-8 more strongly under a neutral pH condition such as in the plasma. In addition, it is an antibody that has superior stability under the conditions in the plasma, and whose IL-8-neutralizing activity is not reduced even after administration in vivo. Moreover, H1009/L395, which was constructed based on Hr9 whose quantity of production has been considerably improved as compared to hWS-4, is an antibody that is suitable for manufacture from the viewpoint of production quantity. Furthermore, in in silico immunogenicity prediction, H1009/L395 exhibited very low immunogenicity score, which was considerably lower as compared to the known hWS-4 antibody and some existing antibodies available on the market. Specifically, H1009/L395 is expected to be an antibody that can be used safely for a long period since ADA is less likely to be produced in human. Thus, H1009/L395 is an antibody that has been improved from various viewpoints as compared to known anti-human IL-8 antibodies, and is very useful as a pharmaceutical agent.

H1009/L395 having the Fc region of a native IgG is sufficiently useful as described above; however, H1009/L395 variants comprising a functionally improved Fc region can also be appropriately used as antibodies whose usefulness has been improved. Specifically, its effect can be sustained for a longer term by increasing FcRn binding under acid pH conditions and improving retention in the plasma. Furthermore, variants comprising an Fc region into which modifications have been introduced to reduce the FcγR binding ability avoid unexpected activation of cells of the immune system, development of cytotoxic activity, and such in the body of the administered organism, and can be used as highly safe antibody pharmaceuticals. Such Fc particularly preferably includes, but is not limited to, F1886s and F1974m described herein. Antibody pharmaceuticals comprising other modified Fc regions are also be used as an embodiment of the present invention as long as they have similar functions.

Consequently, the antibodies of the present disclosure including H1009/L395-F1886s and H1009/L395-F1974m can retain a state that allows strong inhibition of the biological activity of human IL-8 safely and for a long period of time. The antibodies have achieved a level that is unattainable with existing anti-IL-8 antibodies, and are expected to be useful as extremely high-quality anti-IL-8 antibody pharmaceuticals.

[Example 16] Measurement of the Concentration of IL-8 in the Cystic Fluid of Endometriosis Patients The concentration of IL-8 in the cystic fluid of endometriosis patients was determined to assess the involvement of IL-8 in endometriosis. As sample, the cystic fluid was collected from post-surgical tissues of endometriosis patients who underwent operation at Jichi Medical University, and after a first anonymization, the samples underwent a second anonymization in Chugai Pharmaceutical Co., Ltd. The concentration of IL-8 in the cystic fluid was measured by an electrochemiluminescence method. First, after labeling with biotin, an anti-human IL-8 antibody (Hycult Biotech) was aliquoted in MSD GOLD 96-Well Streptavidin SECTOR Plate (Meso Scale Discovery) that had been blocked for two hours using a PBS-Tween solution containing 5% (w/v) BSA, and shaken for one hour at room temperature in the dark to prepare an anti-human IL-8 antibody-immobilized plate. Standard curve samples containing human IL-8 (prepared in house with reference to NP_000575.1) at a concentration in cystic fluid of 900, 300, 100, 33.3, 11.1, 3.70, or 1.23 μg/ml and human cystic fluid measurement samples diluted 5-fold or more were prepared and aliquoted in 25 μl volumes into each well of the anti-human IL-8 antibody-immobilized plate, followed by stirring for one hour at room temperature in the dark. Then, after reacting SULFO-TAG Labeled anti-human IL-8 antibody (prepared in house) for one hour at room temperature in the dark, Read Buffer T (×1) (Meso Scale Discovery) was aliquoted and immediately measurement was carried out using SECTOR Imager 2400 (Meso Scale Discovery). The concentration of human IL-8 was calculated based on the standard curve responses using the analysis software SOFT Max PRO (Molecular Devices).

Figure 30:
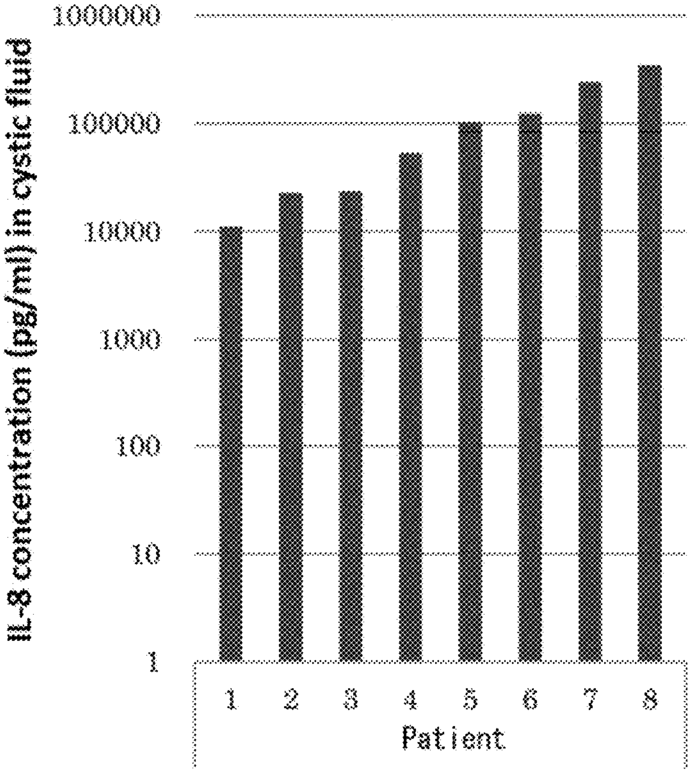
FIG. 30 is a graph showing the concentration of IL-8 in the cystic fluid of endometriosis patients.

As seen in FIG. 30, the result showed that the concentration of IL-8 in the cystic fluid of endometriosis patients was 10000 μg/ml or greater and thus was considerably high. This suggests the importance of IL-8 in endometriosis.

[Example 17] Preparation of a Monkey Model of Surgically-Induced Endometriosis and Assessment of Pathological Conditions A model of surgically-induced endometriosis was prepared and assessment was carried out to examine the drug efficacy of anti-IL-8 antibodies against endometriosis. The pathological model was prepared as follows.

Female cynomolgus monkeys of 8 to 14 years of age with regular sexual cycle (provided by the Tsukuba Primate Research Center at the National Institutes of Biomedical Innovation, Health and Nutrition) were laparotomized under anesthesia during the period corresponding to the luteal phase. The uterine corpus was removed by dissecting in a V shape. Then, the uterine corpus was cut into 5 to 10 mm cubes while leaving the smooth muscle layer of the uterus, and one and two pieces were transplanted onto the right abdominal wall and left abdominal wall (cranial and caudal sides), respectively, in such a manner that the endometrium part is in contact with the peritoneum by suturing with an absorbable suture and formed the transplant. After excision, the uterus was sutured with absorbable suture. Then, the remaining endometrial tissues were finely cut and suspended in 5 ml of 2 ng/ml Hepatocyte Growth Factor solution (R&D systems), and this was seeded in the peritoneal cavity for transplantation, followed by closure of the abdomen. Anesthesia was performed using balanced anesthesia of ketamine/xylazine (mixed at an adequate ratio of about 2:1); however, anesthesia was maintained with isoflurane depending on the maintenance period of anesthesia. The body temperature was maintained and controlled during surgery using a heating pad and the condition was monitored electrocardiographically. The antagonist Antisedan (at roughly the same amount as that of xylazine) and antibiotic cephradine were administered at the time of awakening after surgery. The pain reliever Zalban was administered for two days after surgery, and the monkeys were observed regularly every day to confirm the absence of post-surgical abnormalities. In laparoscopic observation, anesthesia and post-surgical monitoring were also performed in the same way.

Laparoscopic observation was carried out four months, nine months (3 months after administration), and 12 months (6 months after administration) following the surgical induction of endometriosis described above, and the pathological conditions of endometriosis were assessed as follows.

The abdomen was incised in the median line under anesthesia, and laparoscopic observation was performed by inserting a trocar and then introducing a laparoscope. The laparoscope was connected to a video system (KARL STORZ) and a monitor. The monitor was used for intraperitoneal observation, and the video system was used for recording. Then, the peritoneal cavity was filled with carbon dioxide gas using Intra-abdominal Insufflation Unit (OLYMPUS) to expand the abdomen, and graduated bars and forceps were inserted from the ventral portion. The size of the lesion was measured using the graduated bar or graduated forceps.

The sizes (width, height, and depth) of nodular lesions formed by suturing the endometrial tissues were measured and the volumes were calculated based on: width (mm)×height (mm)×depth (mm). The lesions and adhesion formed by seeding endometrial tissues after fine cutting were assessed for the site, area, and depth of adhesion and the size of lesion by laparoscopic observation based on modified r-AFS score modified for monkeys from the r-AFS score for clinical use. As shown in FIG. 31, the modified r-AFS score has the following two modifications for monkeys:

1. The item on adhesion to the vesicouterine pouch was added, because in the monkey model, the frequency of adhesion to the urinary bladder is higher than in humans. The method for assessing adhesion to the urinary bladder was the same scoring as that used for adhesion to the Douglas' pouch.
2. Since monkey's body and organ sizes are smaller than those of humans, the criteria of lesion size scoring were altered to: <3 mm, 3-10 mm, and >10 mm.

The laparoscopic assessments were finalized on a later date by confirming the videos of laparoscopic observations recorded using the video system.

Based on the results of laparoscopic observation four months after induction, the individuals that met the criteria were selected and grouped. The criteria for the selection are as follows:

1. Engraftment of endometrial transplant confirmed on the laparoscopic observation four months after induction.
2. Menstrual bleeding confirmed three or more times during the period after induction and before administration.

The grouping was performed in two separate times. After randomization based on the mean volume of nodular lesions and the number of measurable lesions in each individual, eventually, six individuals were assigned to vehicle group and seven individuals were assigned to the antibody H1009/L395-F1974m-administered group. To confirm that there is no deviation between the groups, the Kraskal-Wallis test was performed using the data for all of the finally assigned individuals. The assessed items were the volume of the nodular lesion (for each lesion), the body weight, the size r-AFS score, and the adhesion r-AFS score.

TABLE 22

| Group | Dose | Administration method | Animal ID |
|---|---|---|---|
| Vehicle group | — | s.c., q4w | #101, #102, #103, #110, #115, #120 |
| H1009/L395-F1974m group | 10 mg/kg | i.v., q4w | #105, #106, #112, #117, #119, #121, #123 |

Administration was performed, starting from six months after induction, every four weeks for six months, for six times. H1009/L395-F1974m was administered by intravenous injection at 10 mg/kg in the antibody administration group, while His Buffer (20 mM His-Asp, 150 mM Arg-Asp (pH6.0)) was administered subcutaneously in the vehicle group. To assess the pathological condition of endometriosis, laparoscopic observation was performed every three months after the start of administration, namely three and six months after the initial administration.

After the final laparoscopic observation six months following the start of administration, the monkeys were euthanized by exsanguination after supplemental anesthesia. Autopsy was carried out to collect pelvic organs (right and left ovaries, right and left oviducts, right and left mesosalpinges, right and left fimbriae of fallopian tubes, right and left broad ligaments of the uterus, uterus, vagina, Douglas' pouch, and vesicouterine pouch) including the transplant sites. The collected tissues were fixed with 10% neutral buffered formalin, and thin slices of paraffin-embedded tissue samples were stained with hematoxylin and eosin (HE). The tissues and lesions induced by suturing were also cut to collect the accumulated cystic fluid if any.

Figure 32:
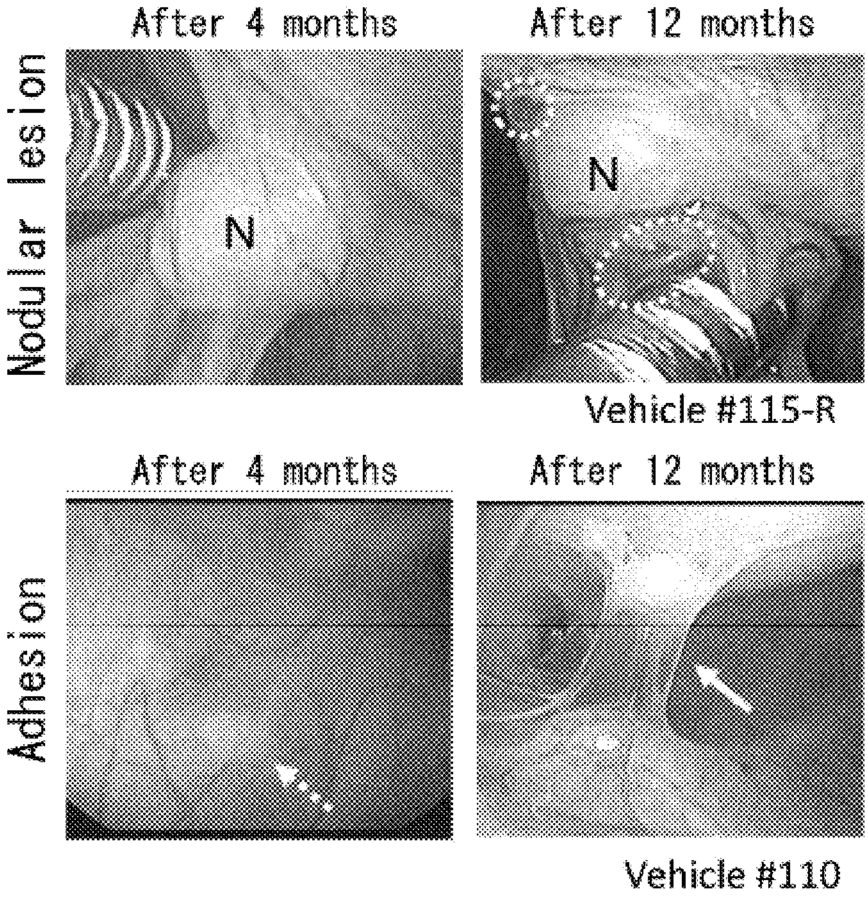
FIG. 32 is photographs showing the formation of nodular lesions and adhesion 4 months after induction and 12 months after induction (6 months after administration).
Figure 33:
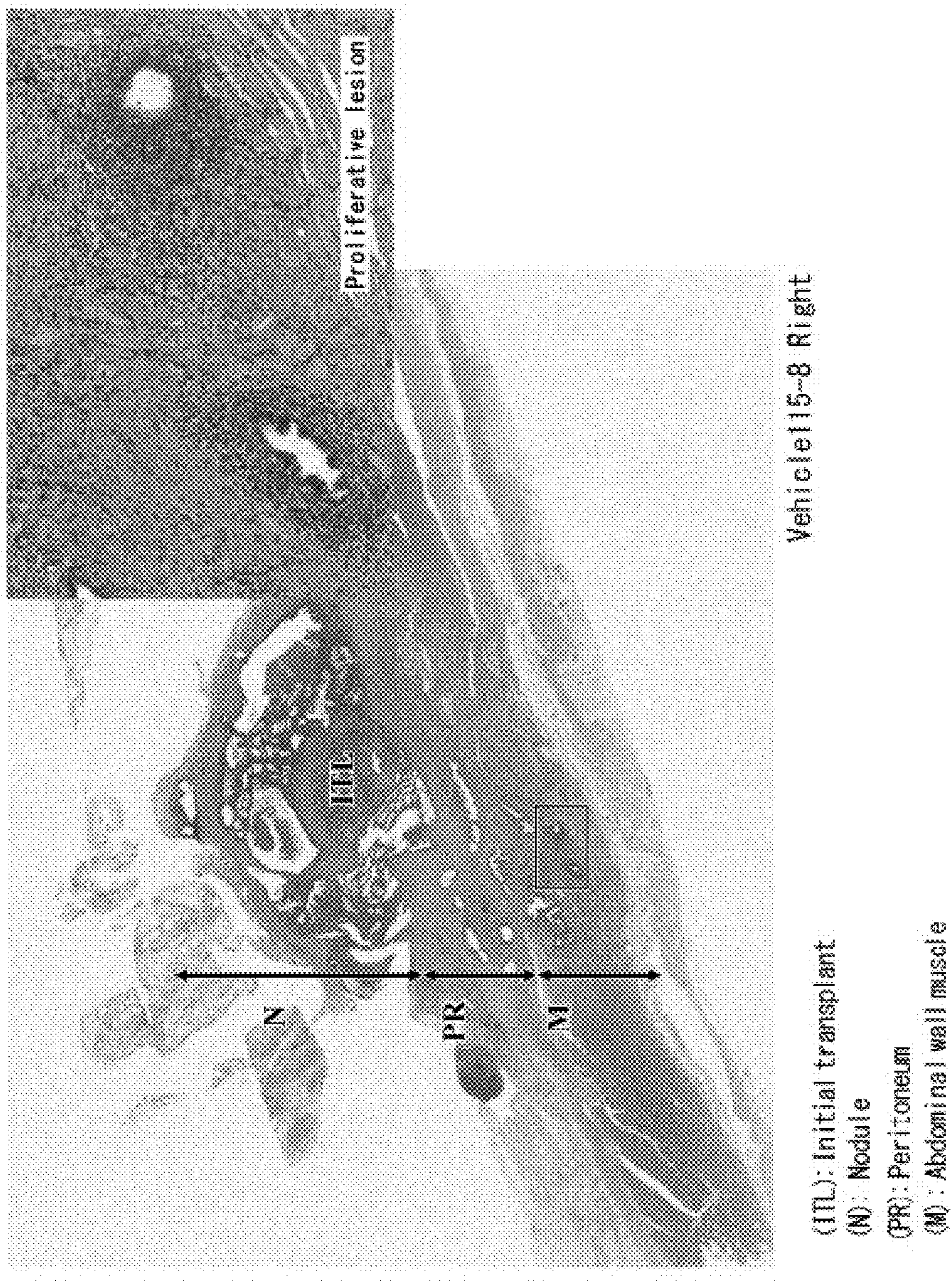
FIG. 33 is a photograph showing the formation of endometriosis-like proliferative endometrial epithelium and stroma 12 months after induction (6 months after administration).

The result of laparoscopic observation of the vehicle control group showed formation of nodular lesions formed by suturing of endometrial tissues four months after induction, and further formation of nodular lesions and adjacent black cysts 12 months after induction (six months after administration). Moreover, formation of adhesion was observed in the Douglas' pouch and urinary bladder due to fine cutting and seeding of endometrial tissues (FIG. 32). Furthermore, as shown in FIG. 33, HE staining of tissue samples of the vehicle group collected at the time of autopsy 12 months after induction showed that proliferative endometrial epithelia were densely formed adjacent to the transplanted endometrial tissues (initial transplant) up to the muscle layer of the abdominal wall. The areas surrounding the endometrial epithelia were constituted with multiple layers of stromal cells and interstitium rich in collagenous fibers, and thus the formation of a structure similar to the structure of human endometriosis tissues was observed. These results demonstrate that the model serves as a useful endometriosis model (12$^{th}$ World Congress on Endometriosis, 2014, P-221). Similarly, there are also reports on a method using baboons as surgically induced endometriosis model (Fertil Steril. 2013; 99(3):783-789, Fertil Steril. 2013; 100(4):1144-50).

Figures 1, 34:
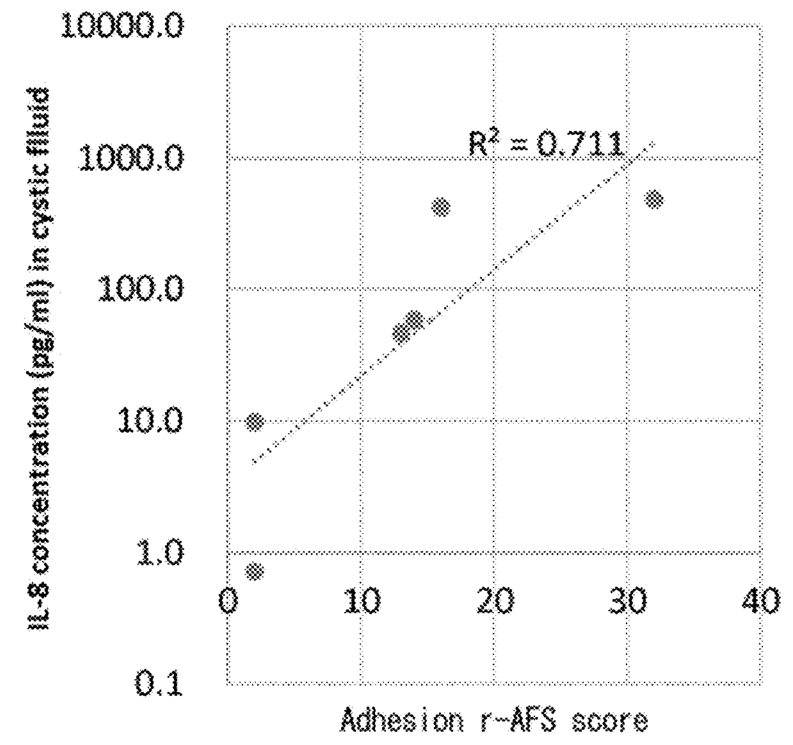
Figures 2, 34:
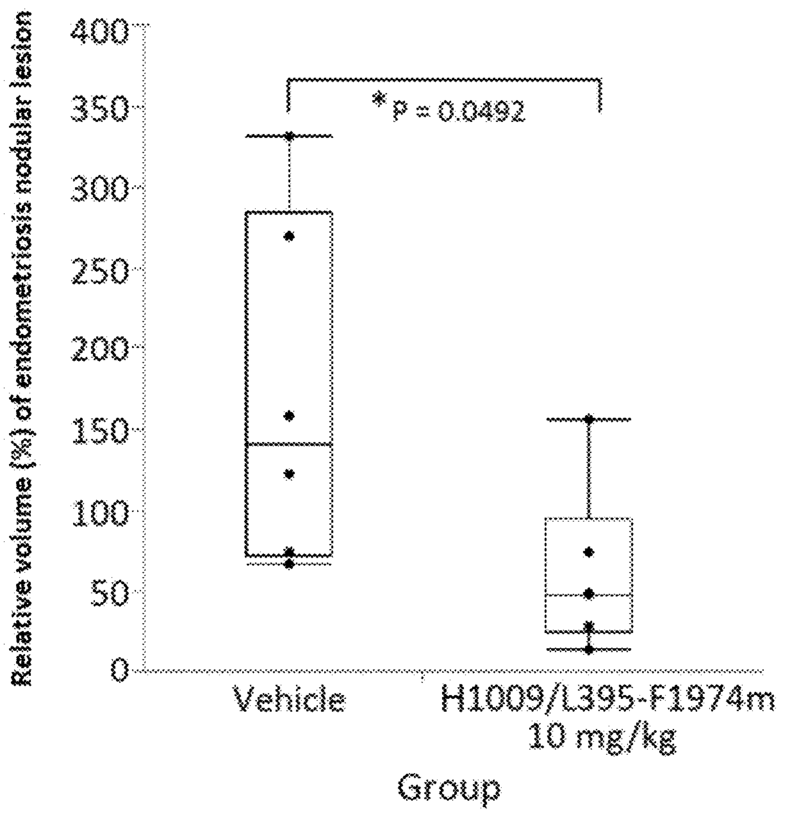

Furthermore, autopsy was performed after the final laparoscopic observation 12 months after induction (six months after administration). The accumulated cystic fluid was collected, and the concentration of IL-8 in the cystic fluid of the vehicle group was measured by an electrochemiluminescence method. First, a solution of antibody H1009/L395-F1974m was aliquoted into MULTI-ARRAY 96-well Plate (Meso Scale Discovery), and the plate was allowed to stand at 4° C. overnight to prepare an antibody H1009/L395-F1974m-immobilized plate. Standard curve samples of monkey IL-8 (prepared in house with reference to XM_005555087.1) at a concentration of 269, 108, 43.0, 17.2, 6.89, 2.75, or 1.10 μg/ml in buffer and monkey cystic fluid measurement samples diluted 50-fold or more were prepared and aliquoted into each well of the antibody H1009/L395-F1974m-immobilized plate, followed by stirring for two hours at room temperature in the dark. Then, rabbit anti-IL-8 antibody (Hycult Biotech) was reacted for one hour at room temperature in the dark. Then, after reacting SULFO-TAG labeled anti-rabbit antibody (Meso Scale Discovery) for one hour at room temperature in the dark, Read Buffer T (×1) (Meso Scale Discovery) was aliquoted and measurement was carried out immediately using SECTOR Imager 2400 (Meso Scale Discovery). The concentration of monkey IL-8 was calculated based on the standard curve responses using the analysis software SOFT Max PRO (Molecular Devices). As seen in Table 23, the result showed that the concentration of IL-8 is markedly high in the cystic fluid of surgically induced endometriosis monkey models similarly to that in the cystic fluid of human endometriosis patients. This finding supports that the monkey model is highly extrapolatable to human endometriosis. Further, the concentration of IL-8 in the cystic fluid of each individual was assessed for its correlation with the adhesion r-AFS score. Interestingly, as shown in FIG. 34-1, the concentration of IL-8 in the cystic fluid tended to correlate with the adhesion r-AFS score. When several cystic fluid IL-8 concentrations were measured in an individual, the highest value was used as the representative value. This result suggested that IL-8 is involved in adhesion in endometriosis.

TABLE 23

| | Concentration of IL-8 in cystic fluid (ng/mL) | | |
|---|---|---|---|
| #101 | 46.4 | | |
| #102 | 0.726 | | |
| #103 | 9.83 | | |
| #110 | 58.3 | | |
| #115 | 476 | 28.8 | 25.0 |
| #120 | 417 | | |

Drug efficacy assessment was performed by laparoscopic observation six months after initiation of administration in the antibody H1009/L395-F1974m administration group and vehicle group. Upon analysis, individuals whose menstrual bleeding was found less than three times during the six-month period of administration were excluded from the analysis. Of the individuals in this examination, an individual from the antibody H1009/L395-F1974m administration group #117 (10 mg/kg group) fell thereunder and thus was excluded from the analysis. In the antibody H1009/L395-F1974m administration group, anti-antibody detection was carried out by a method known to those skilled in the art. Anti-antibodies were detected and the API blood trough concentration was found to be reduced in two individuals out of six. The analysis described below was carried out by including the anti-antibody-positive individuals.

First, the volumes of each of the nodular lesions formed by suturing endometrial tissues were calculated and were classified based on their sizes and changes over time, as shown in Table 24 below. Lesions which could not be assessed over time, such as because of adhesion, were not included in the analysis.

TABLE 24

| Type | |
|---|---|
| A: Proliferative, ≥500 mm$^3$ | Significant growth to 500 mm$^3$ or larger after 6 months of adminstration |
| B: Proliferative, <500 mm$^3$ | Less than 500 mm$^3$ after 6 months of adminstration, and tendency to grow after administration as compared to before admnistration |
| C: No change | No significant change albeit increases/decreases during the administration period |
| D: Decreased | Tendancy to decrease after adminstration as compared to before administration |

As seen in Table 25, the result showed that in the vehicle group, the frequency of types A and B, which show proliferation, was as high as 54% (7/13 lesions), and type D, which shows a decrease, was as low as 15% (2/13 lesions), while in the antibody H1009/L395-F1974m administration group, the frequency of type D which shows a decrease was as high as 58% (7/12 lesions). Thus, administration of the antibody H1009/L395-F1974m was shown to have the effect of reducing nodular lesions.

TABLE 25

| group | A: proliferative, ≥500 mm3 | B: proliferative, <500 mm$^3$ | C: no change | D: decreased |
|---|---|---|---|---|
| Vehicle | 8% (1/13) | 46% (6/13) | 31% (4/13) | 15% (2/13) |
| H1009/ L395-F1974m 10 mg/kg | 0% (0/12) | 8% (1/12) | 33% (4/12) | 58% (7/12) |

Moreover, the relative volume of nodular lesions was calculated for each individual by the calculational procedure below to assess the drug efficacy of antibody H1009/L395-F1974m against nodular lesions (relative volume of nodular lesions (%)=sum of volumes of selected lesions at six months from initiation of administration/sum of volumes of selected lesions at two months before initiation of administration)×100). The result is shown in FIG. 34-2. The relative volume of nodular lesions was 141% (67-331) (median value (minimum value–maximum value)) for the vehicle group and 49% (15-156) for the antibody H1009/L395-F1974m administration group. Nodular lesions were significantly reduced by administration of antibody H1009/L395-F1974m as compared to the vehicle group (P=0.0492). Parametric t-test (significance level: P<0.05) was used in the statistical analysis. The result showed an effect of suppressing the volume increase of nodular lesions by anti-IL-8 antibodies.

Figures 1, 35:
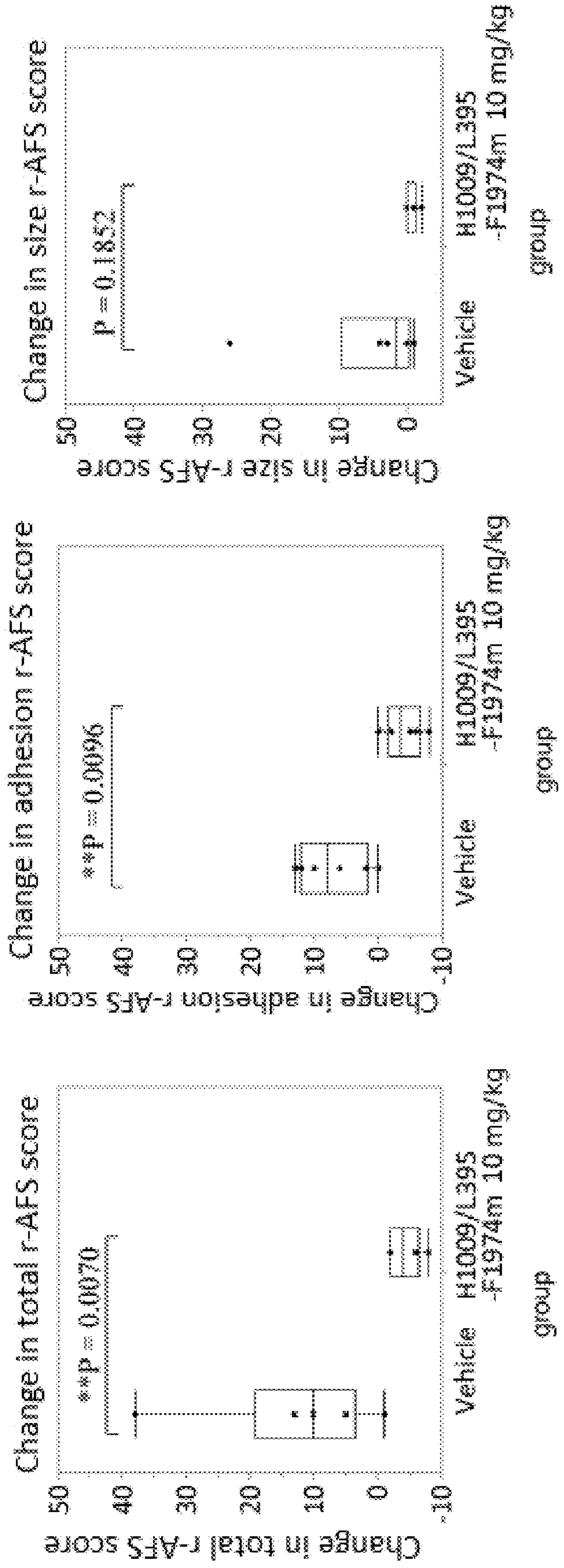
Figures 2, 35:
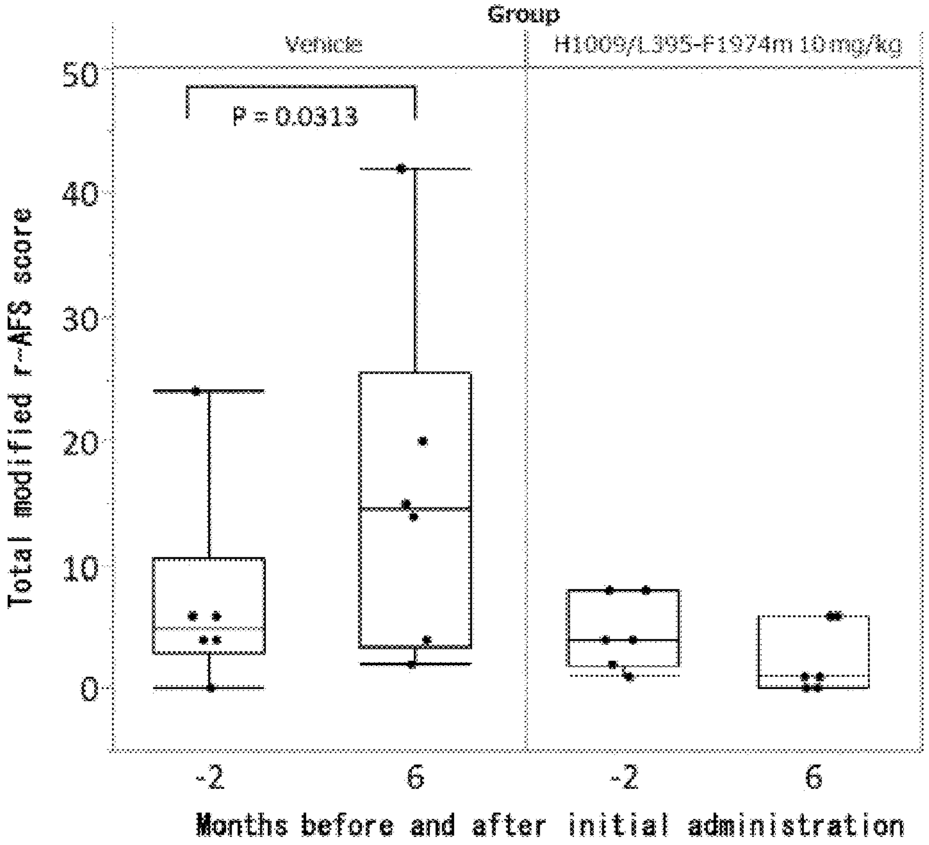

Next, lesions formed by fine cutting and seeding of endometrial tissues and adhesion were assessed based on the "modified r-AFS score" to examine the drug efficacy in the antibody H1009/L395-F1974m administration group (N=6) and the vehicle group (N=6). The "change of modified r-AFS score" was calculated by the procedure described below to see the change before and after antibody administration in each individual. The result is shown in FIG. 35-1.

Change of total r-AFS score=total r-AFS score (after administration)−total r-AFS score (before administration)

Change of adhesion r-AFS score=adhesion r-AFS score (after administration)−adhesion r-AFS score (before administration)

Change of size r-AFS score=size r-AFS score (after administration)−size r-AFS score (before administration)

The "change of total r-AFS score" and the "change of adhesion score" of the antibody H1009/L395-F1974m administration group were clearly decreased as compared to the vehicle group (p=0.0070, p=0.0096). The "change of size r-AFS score" also tended to decrease in the antibody H1009/L395-F1974m group as compared to the vehicle group. Statistical analysis was performed by non-parametric Steel test (significance level: 5% for a two-sided test) using statistical analysis software (SAS Institute). The results that the "change of adhesion score" was significantly decreased by administration of antibody H1009/L395-F1974m and that, as shown in FIG. 34-1 above, there was a tendency of correlation between the concentration of IL-8 in the cystic fluid and the "adhesion r-AFS score" demonstrate that IL-8 is closely involved in adhesion in endometriosis and that anti-IL-8 antibodies are useful in improving adhesion in endometriosis.

FIG. 35-1 shows the "change of modified r-AFS score" as assessed based on images recorded during laparoscopic surgery. FIG. 35-2 shows the "total modified r-AFS score" based on scores recorded by the practitioner during laparoscopic surgery. The scores two months before the initial administration were used as the scores before administration. Changes in the "total modified r-AFS score" before and after administration were statistically analyzed for each group by Wilcoxon's signed-rank-sum test carried out on corresponding pairs. The result (significance level: P<0.05) showed that the score after administration was significantly increased in the vehicle group (P=0.0313) but the score did not change in the antibody H1009/L395-F1974m administration group (P=0.875). Since the "total modified r-AFS score" represents the pathological malignancy of endometriosis, this result showed the effect by anti-IL-8 antibodies of suppressing pathological exacerbation of endometriosis.

Figure 36:
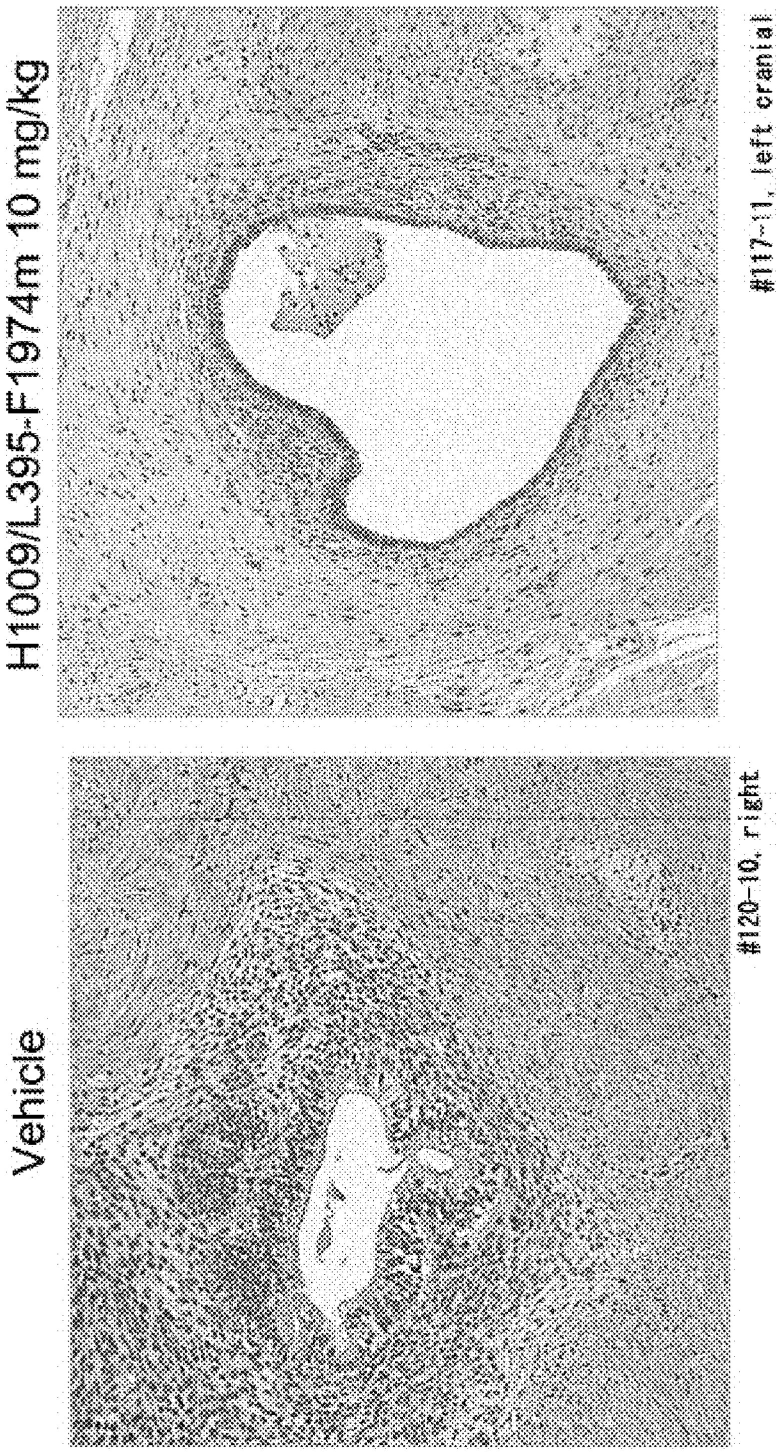
FIG. 36 shows histopathological images of the site of transplantation in the vehicle group and the antibody H1009/L395-F1974m-administration group 12 months after induction (6 months after administration). Atrophy of proliferative epithelium and stromal cells, and reduction of interstitium were observed in the antibody H1009/L395-F1974m-administration group as compared to the vehicle group.

After final laparoscopic observation, the grafts and the grafted sites collected at the time of autopsy were HE-stained and observed histopathologically under a light microscope. As a result, atrophic changes of proliferative epithelia and stromal cells as well as reduction of the interstitium whose major component is collagenous fibers was observed in the antibody H1009/L395-F1974m administration group as compared to the vehicle group, as seen in FIG. 36, and the effect was particularly strong in anti-antibody-negative individuals whose API blood concentration was maintained (Table 26). Although type D lesions (#102-L2 and #115-R) which showed a tendency for reduction in the volume of nodular lesions were observed in the vehicle group, the pathological result on the nodular lesions did not show atrophy or interstitial reduction so that the lesions were maintained. Although the group administered with antibody H1009/L395-F1974m included individuals of type B which showed a tendency for increase in the volume of nodular lesions, the pathological result on nodular lesions showed an atrophic change of the stroma and an interstitial reduction in #106-L1, demonstrating improvement of the pathological condition. Furthermore, hemosiderin was observed in 56% (9/16) of the vehicle group but in only 24% (4/17) of the antibody administration group, suggesting that infiltration of macrophages or monocytes was suppressed by antibody administration. Moreover, muscle tissue regeneration, which was not seen in the vehicle group, was observed in the antibody administration group, and this data suggested that the lesions that had invaded up to the muscle layer had regressed and were replaced with muscular tissues. When the presence of deep lesions was assessed based on the presence of endometriosis gland ducts that have invaded up to the muscle layer of abdominal wall, there was not much difference between the vehicle group and the antibody H1009/L395-F1974m administration group that included anti-antibody-positive individuals; however, when the anti-antibody-positive individuals were excluded, the frequency was as low as 1/11 lesions in the antibody H1009/L395-F1974m administration group as compared to 5/18 lesions in the vehicle group. Thus, the antibody was also suggested to have an effect of suppressing the formation of deep lesions.

TABLE 26

Result of pathological analysis of nodular lesions
Data of monkeys with regular menstrual cycles during treatment

| Article | | Vehicle | | | | | | | | | | | | | | | | | |
|---|---|---|---|---|---|---|---|---|---|---|---|---|---|---|---|---|---|---|---|
| Animal No. | | 110 | | | 101 | | | 103 | | | 115 | | | 120 | | | 102 | | |
| Slide No. | | 11 | 13 | 15 | 13 | 18 | 11 | 8 | 11 | 13 | 8 | 10 | 13 | 9 | 10 | 12 | 9 | 13 | 15 |
| Findings | site | R | L1 | L2 | R | L1 | L2 | R | L1 | L2 | R | L1 | L2 | R | L1 | L2 | R | L1 | L2 |
| Atrophy of endometrial epithelium | P | – | – | – | NA | – | – | NA | – | – | – | – | – | – | – | NL | – | – | – |
| Atrophy/decrease, stromal cell | P | – | – | – | NA | – | – | NA | – | – | – | – | – | – | – | NL | – | – | – |
| Decreased insterstitium | P | – | – | – | NA | – | – | NA | – | – | – | – | – | – | – | NL | – | – | – |
| Atrophy of endometrial epithellum | F | – | – | – | NA | NL | NL | NA | + | + | – | – | – | NL | – | – | – | – | – |
| Decreased Insterstitium | F | – | – | – | NA | NL | NL | NA | – | – | – | – | – | NL | – | – | – | – | – |
| Hemsiderin deposition | P and/or F | + | + | + | NA | + | + | NA | – | – | + | + | + | – | + | – | – | – | – |
| Granulation tissue | P and/or F | – | – | – | NA | – | – | NA | – | – | – | – | + | – | – | – | – | – | – |
| Deep lesion | Muscle | – | + | – | – | – | – | – | + | + | + | – | + | – | – | – | – | – | – |

| Article | | H1009/L395-F1974m 10 mg/kg | | | | | | | | | | | | | | | | | |
|---|---|---|---|---|---|---|---|---|---|---|---|---|---|---|---|---|---|---|---|
| Low exposure | | | | | | | | | | | | | | | + | | | ++ | |
| Animal No. | | 112 | | | 105 | | | 106 | | | 121 | | | 119 | | | 123 | | |
| Slide No. | | 8 | 9 | 30 | 8 | 18 | 13 | 8 | 13 | | 8 | 10 | 13 | 50 | 11 | 50 | 8 | 51 | 54 |
| Findings | site | R | L1 | L2 | R | L1 | L2 | R | L1 | L2 | R | L1 | L2 | R | L1 | L2 | R | L1 | L2 |
| Atrophy of endometrial epithelium | P | – | + | + | – | – | – | + | – | NA | NL | NL | + | + | – | + | – | – | – |
| Atrophy/decrease, stromal cell | P | – | + | + | + | + | + | + | + | NA | NL | NL | + | ± | ± | + | ± | ± | – |
| Decreased insterstitium | P | + | + | + | + | + | + | + | + | NA | NL | NL | + | ± | – | + | ± | ± | – |
| Atrophy of endometrial epithellum | F | + | NL | NL | – | + | + | NL | + | NA | + | NL | + | – | – | + | + | + | – |
| Decreased Insterstitium | F | + | NL | NL | + | + | ± | NL | + | NA | + | NL | + | ± | ± | + | ± | ± | – |
| Hemsiderin deposition | P and/or F | – | – | – | + | – | – | – | – | NA | – | – | – | – | – | + | – | + | + |
| Granulation tissue | P and/or F | + | – | – | – | – | + | + | + | NA | – | – | + | + | + | + | + | + | |
| Deep lesion | Muscle | – | – | – | – | – | – | – | + | NA | – | – | – | + | – | – | + | + | |

Site
R: right transplantation tissue
L1: left cranial transplantation tissue
L2: left caudal transplantation tissue
P: Proliferation lesion
F: Fibrotic lesion
NL: no lesion
NA: not applicable
Low exposure
+: BLQ ≤ minimum trough of API < minimum trough In ADA-negative monkeys
++: Minimum trough of API <BLQ (0.100 μg/mL)
Sections used in drug efficacy assessment: when two or more samples were prepared from a single graft, a section was used on which the total number of gland ducts was the greatest.
When sections contained the same number of gland ducts, a section on which gland ducts were broadly observed was chosen: when sections had no gland ducts, a section which allowed broad tissue observation was chosen.
Deep lesion: The case where an endometriosis lesion was observed on the abdominal wall at the transplantation site was taken as a finding.
Muscle: Abdominal wall muscle at the transplantation site
Grading
Atrophy of endometrial epithelium
+: Epithelial atrophy was observed
–: Epithelial atrophy was not observed
Decreased interstitium
–: Insterstitial decrease was not observed
+: Insterstitial decrease was observed
±: Elements from both were found
Granulation tissue
–: None TABLE 26-continued

| Result of pathological analysis of nodular lesions<br>Data of monkeys with regular menstrual cycles during treatment |
| --- |

+: Granulation tissues were observed
Hemosiderin deposition
+: Deposition of brown-black granules was observed
−: Deposition of brown-black granules was not observed
Atrophy/decrease, stromal cell
−: Atrophy or reduction of stromal cells was not observed
+: Atrophy or reduction of stromal cells was observed
±: Elements from both were found
Deep lesion:
+: An endometriosis lesion was observed on the abdominal wall muscle at the transplantation site
−: No endometriosis lesion was observed on the abdominal wall muscle at the transplantation site Furthermore, antibody H89/L118-F22, which is the antibody before modification into antibody H1009/L395-F1974m, was also assessed for its drug efficacy in the same manner using the surgically-induced monkey model. Atrophy of proliferative epithelia and stromal cells as well as reduction of the interstitium whose major component is collagenous fibers were also observed in the antibody H89/L118-F22 administration group.

These results showed that anti-IL-8 antibodies have drug efficacy in reducing the volume of endometriosis lesions, ameliorating adhesion, inducing atrophic change of epithelia and stromal cells, reducing infiltration of immune cells, and ameliorating fibrosis, demonstrating that anti-IL-8 antibodies are useful as therapeutic agents for endometriosis. Based on the results described above, those skilled in the art will naturally appreciate that IL-8 signal inhibitors are useful as therapeutic or preventive agents for endometriosis.

[Example 18] Drug Efficacy of Anti-IL-8 Antibody Against Adenomyosis

Figure 37:
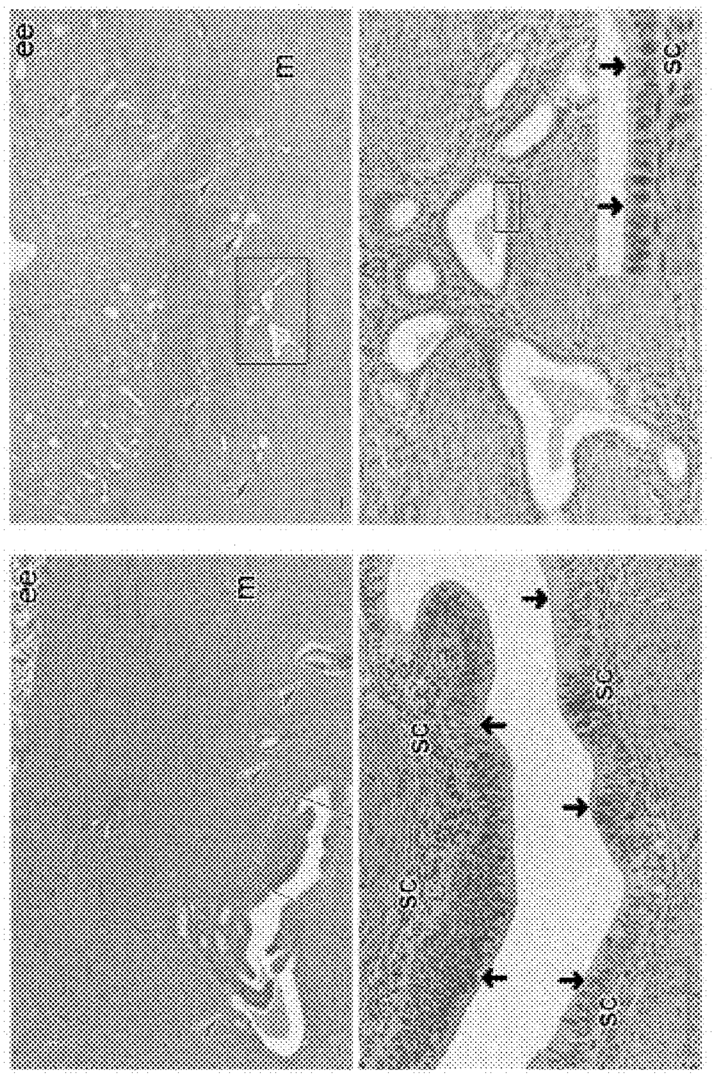
FIG. 37 is a set of photographs showing endometrial tissues in the vehicle group and the antibody H1009/L395-F1974m-administration group of monkeys with concurrent adenomyosis. Atrophy of endometrial epithelium, and atrophy and reduction of stromal cells were observed in the antibody H1009/L395-F1974m-administration group as compared to the vehicle group.

After the final laparoscopic observation six months after the start of antibody administration in surgically-induced endometriosis monkey models, the uteri collected during autopsy were fixed with 10% neutral buffered formalin and HE-stained for observation. Endometrial tissues analogous to those of adenomyosis were strongly seen in the uterus in one case of the vehicle group as well as in one case of the antibody administration group. The endometrial tissues observed in these two cynomolgus monkeys exhibited pathological features of adenomyosis seen in human uteri, with endometrial glands and surrounding endometrial stroma in the myometrium. Thus, the monkeys were considered as being a human adenomyosis complication model, and the endometrial tissues in the myometria of these single cases were compared. As shown in FIG. 37, in the antibody H1009/L395-F1974m administration group, atrophy of endometrial epithelia in the adenomyosis lesions as well as reduction and atrophy of stromal cells were observed as compared to the vehicle group. This finding showed that anti-IL-8 antibodies also have a suppressing effect on adenomyosis. Based on the results described above, those skilled in the art will naturally appreciate that IL-8 signal inhibitors are useful as therapeutic or preventive agents for adenomyosis.

[Example 19] Analysis of CXCR1 and CXCR2 Expression in Endometriosis Tissues

CXCR1 and CXCR2 are known as human IL-8 receptors. In order to examine the cells that IL-8 acts on in endometriosis lesions, paraffin-embedded blocks of surgically-excised human endometriosis tissues were stained immunohistochemically using a mouse anti-human CXCR1 monoclonal antibody (R&D Systems, Catalog No: 42705) and a mouse anti-human CXCR2 monoclonal antibody (Abcam, Catalog No: 19). Thin slices of the tissues were prepared from these paraffin blocks, and incubated with the antibodies against CXCR1 and CXCR2 as the primary antibody. Then, goat anti-mouse IgG antibody (Dako) conjugated with polymer-HRP was reacted as the secondary antibody, and visualization was carried out using diaminobenzidine (Wako Pure Chemical Industries). The result showed that CXCR1 and CXCR2 were negative in stromal cells, as seen in Table 27. Meanwhile, both CXCR1 and CXCR2 were positive in neutrophils that infiltrated into tissues as well as in macrophages and mononuclear cells with hemosiderin deposits, and their expression was also found to be weakly positive to positive in the epithelial cells. Furthermore, both CXCR1 and CXCR2 were observed to be weakly positive in vascular endothelial cells. These findings suggest the possibility that IL-8 has a direct pharmacological effect on endometriosis epithelial cells as well as a pharmacological effect via infiltrating immune cells such as neutrophils and macrophages.

TABLE 27

| | CXCR1 (IL-8 RA) | | | CXCR2 (IL-8RB) | | |
| --- | --- | --- | --- | --- | --- | --- |
| | No. 1 | No. 2 | No. 3 | No. 1 | No. 2 | No. 3 |
| Endometrial epithelium with the stromal cell | ± | ± | − | − | ± | − |
| Endometrial epithelium without the stromal cell | + | + | + | + | + | + |
| Stromal cell | − | − | − | − | − | − |
| Neutrophilis | + | + | + | + | + | + |
| Hemosiderin-laden macrophage | + | + | + | + | + | + |
| Mononuclear cell* | + | + | + | + | + | + |
| Vascular endothelial cell | ± | ± | ± | ± | ± | ± |

*Macrophage-like cell
NA: No application
−: Negative,
+: Positive,
±: Partly positive

Figure 38:
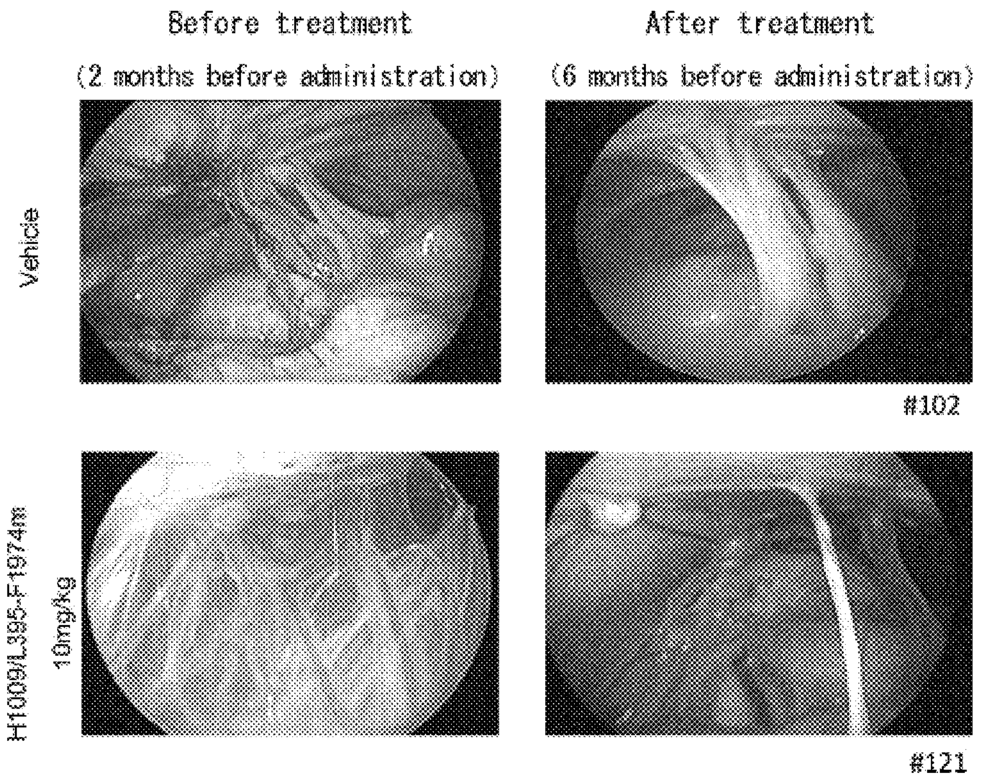
FIG. 38 is a set of photographs concerning post-surgical adhesion, showing representative abdominal cavities in the vehicle group and the antibody H1009/L395-F1974m-administration group of the monkey endometriosis model.

[Example 20] Drug Efficacy of Anti-IL-8 Antibody Against Adhesion after Surgery In the above-described surgically-induced endometriosis cynomolgus monkey models, adhesion to the area surrounding the incision site in the abdominal wall, which was different from adhesion from endometriosis that occurred after laparotomy for induction, was observed in all of the individuals upon laparoscopic observation four months after induction (two months before antibody administration). In order to examine the drug efficacy of anti-IL-8 antibody against adhesion after surgery, the numbers of the individuals were anonymized and the adhesion to the area surrounding the incision site on the abdominal wall was assessed by comparing the results of laparoscopic observations two months before administration with photographs from the final laparoscopic observations six months after initiation of administration. Specifically, adhesion to the area surrounding the incision site on the abdominal wall was compared before and after administration and evaluated by five evaluators on a three-point scale: (1) Improved, (2) Stable, and (3) Progressed. Ratings with a consensus among three or more of the five evaluators were adopted; otherwise (2) Stable was used. Evaluations were carried out on six monkeys in the vehicle group as well as seven monkeys in the antibody H1009/L395-F1974m administration group. FIG. 38 shows representative photographs of the peritoneal cavities in the vehicle group and the antibody H1009/L395-F1974m administration group. As shown in Table 28, of the six monkeys in the vehicle group, five were "Stable" and one was "Progressed", whereas in the antibody H1009/L395-F1974m administration group, out of the seven monkeys, six were "Improved" although one was "Progressed". The monkey with "Progressed" was an individual in which the blood concentration of antibody H1009/L395-F1974m had decreased due to anti-antibody production. The findings described above suggested that anti-IL-8 antibodies are useful as post-surgical adhesion-ameliorating therapeutic agents or preventive agents. Based on the results described above, those skilled in the art will naturally appreciate that IL-8 signal inhibitors are useful as therapeutic or preventive agents for adhesion.

TABLE 28

| Group | Improved | Stable | Progressed |
|---|---|---|---|
| Vehicle | 0/6 | 5/6 | 1/6 |
| H1009/L395-F1974m 10 mg/kg | 6/7 | 0/7 | 1/7 |

[Example 21] Isolation of Neutrophils and Assessment of Neutrophil Migration Due to IL-8

IL-8 has a chemotactic activity on neutrophils. It has been considered that IL-8 produced by damaged tissues promotes the migration of neutrophils adhered to vascular endothelial cells toward the tissues and induces inflammation associated with neutrophil infiltration. As shown in Table 27, infiltration of neutrophils, macrophages, and mononuclear cells was also observed in endometriosis lesion sites and both CXCR1 expression and CXCR2 expression were positive in these immune cells. Furthermore, expression was also weakly positive to positive in epithelial cells, suggesting the possibility that IL-8 has a direct pharmacological effect on endometriosis epithelial cells as well as a pharmacological effect via infiltrating immune cells such as neutrophils and macrophages. In this context, the present inventors assessed, as a first step, the migratory ability of neutrophils toward IL-8. Neutrophils were collected from the peripheral blood of healthy individuals and isolation and purification were performed as described below.

Heparin-treated whole blood was combined with a ⅕ volume of HetaSep (STEMCELL Technologies). The supernatant containing nucleated cells was collected according to the product's protocol and then ACK solution (GIBCO) was added thereto to induce hemolysis. After hemolysis, the cells were suspended in 0.1% BSA/PBS to determine the cell count. Following cell count measurement, the cell count was adjusted and neutrophils were isolated using EasySep (registered trademark) Human Neutrophil Enrichment Kit (STEMCELL technologies) and EasySep (registered trademark) Magnet (STEMCELL technologies) according to the product's protocol. After isolation, the neutrophils were assessed by FACS using anti-CD66b antibody and anti-CD45RA antibody to confirm their purity.

Figure 39:
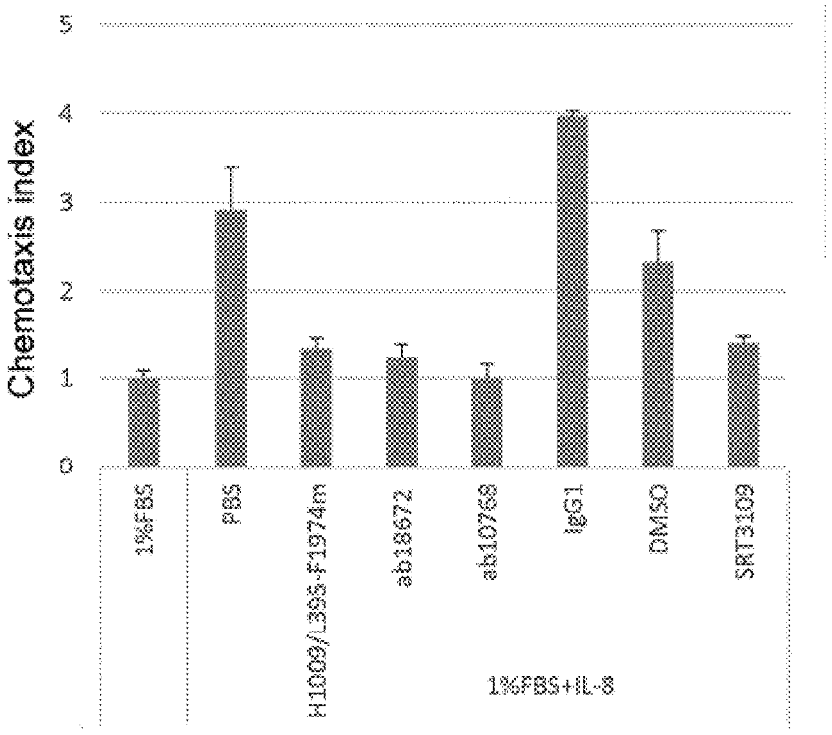
FIG. 39 shows an assessment result for the relative migration ability of neutrophils in the respective wells supplemented with various reagents, relative to the migration ability of neutrophils in a well without IL-8.

The isolated neutrophils were assessed for their migratory ability using Migration Plate for CytoSelect (registered trademark) 96-Well Cell Migration Assay (Cell Biolabs, Catalog No: CBA-104). The bottom layer below the membrane was a feeder tray to which was added 1% FBS or 1% FBS+IL-8 (100 ng/ml) and 150 μl of an RPMI-1640 medium (SIGMA) supplemented with various antibodies, chemical compounds, or control solvents. The subjects of evaluation were as follows: as antibodies, 10 μg/ml each of: H1009/L395-F1974m, the anti-IL-8-neutralizing antibodies Anti-IL-8 antibody [807] (abcam, Catalog No: ab18672) and Anti-IL-8 antibody [6217] (abcam, Catalog No: ab10768), and IgG1 (Sigma, Catalog No: 15154) as the negative control; as chemical compounds, 10 μM of the CXCR2 inhibitor SRT3109 (Shanghai Haoyuan Chemexpress, Catalog No: HY-15462); and as control media, PBS and DMSO. The top layer above the membrane was a membrane chamber, and neutrophils suspended in a serum-free RPMI-1640 medium were seeded at 50000 cells/well in the chamber. After two hours of incubation, the number of viable cells (neutrophils) that had migrated to the bottom-layer feeder tray was detected based on the amount of relative chemiluminescence using CellTiter-Glo (registered trademark) Luminescent Cell Viability Assay (Promega). The average relative chemiluminescence amount of a well with no IL-8 addition was taken as 1 to calculate relative values of the relative chemiluminescence amounts upon addition of various reagents. The result is shown in FIG. 39.

The result showed the promotion of neutrophil migration by IL-8 and inhibition of neutrophil migration by the various anti-IL-8-neutralizing antibodies and CXCR2 inhibitors. The result described above convincingly supported the point that not only IL-8 inhibitors but also a wide range of IL-8 signal inhibitors such as CXCR1 inhibitors and CXCR2 inhibitors which are known to be involved in IL-8 signal inhibition, suppress neutrophil migration. Thus, the result also convincingly suggested that IL-8 signal inhibitors suppress the infiltration of neutrophils in endometriosis as well as in lesions where the IL-8 concentration is high. Therefore, by generalizing and extending these results, those skilled in the art will sufficiently appreciate that IL-8 signal inhibitors are capable of preventing endometriosis as well as inflammatory diseases where the IL-8 concentration is known to be high.

Next, endometriosis cells were examined to assess how neutrophils that infiltrated endometriosis lesions act. Endometriosis cells were obtained by the following procedure. Human endometriosis tissues excised by surgery were finely cut in a DMEM/F-12, HEPES (GIBCO) medium containing 0.5 mg/ml collagenase and 0.1 mg/ml DNase 1, and the cells were collected after incubation at 37° C. The cell suspension was passed through a 100-μm cell strainer, and then Lysing Buffer (BD Biosciences) was added thereto to induce hemolysis. After hemolysis, the cells were seeded, and the passaged cells were frozen in liquid nitrogen and stored as endometriosis cells. Culture was carried out using DMEM/F-12, HEPES supplemented with 10% FBS, 2.5 μg/ml amphotericin B, 100 U/ml penicillin, and 100 µg/ml streptomycin. The frozen stored cells were initiated before use in the experiments.

[Example 22] Neutrophils' Action on Endometriosis Cells

The neutrophil culture supernatant was added to the endometriosis cells obtained by the method described above and the reactivity of endometriosis cells was assessed. In order to prepare the neutrophil culture supernatant, isolated neutrophils were suspended in an RPMI-1640 medium containing 1% FBS and seeded at $3.0\times10^6$ cells/well in a 6-well plate. The culture supernatant was collected after one day of culture. Endometriosis cells were seeded at 10000 cells/well in a 96-well plate, and the collected neutrophil culture supernatant was added thereto in such a way that it accounts for half of the volume of the medium. Likewise, to the control group (also referred to as "Ctrl" in the present Examples), an RPMI-1640 medium containing 1% FBS was added in such a way that it accounts for half of the volume of the medium. Eight hours later, the medium was removed and RNAs were purified using the RNeasy 96 Kit (QIAGEN) according to the product's protocol. cDNAs were synthesized from the purified RNAs using SuperScript (registered trademark) VILO (registered trademark) MasterMix (Invitrogen) and the expression level of aromatase mRNA was compared by real-time PCR. The probes used were Taqman probe Hs00903411_ml (Thermo Fisher) for aromatase and Human GAPD (GAPDH) Endogenous Control (Applied Biosystems, Catalog No: 4326317E) for GAPDH assay.

Figure 40:
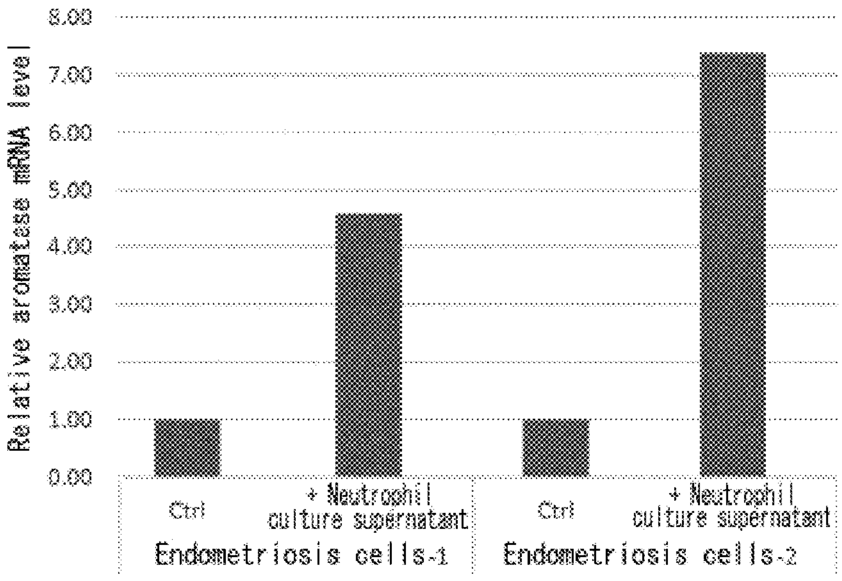
FIG. 40 shows a result of analyzing the expression level of aromatase when a culture supernatant of neutrophils was added to endometriosis cells.

The relative expression level of aromatase, when Ctrl is taken as 1 after normalization of the expression level of aromatase with that of GAPDH, is shown in FIG. 40. The expression level of aromatase was demonstrated to be increased in endometriosis cells to which the neutrophil culture supernatant was added.

Aromatase is an estrogen synthetase and estrogen is known to promote the proliferation of endometriosis epithelial cells. Aromatase expression was enhanced in endometriosis cells by addition of the neutrophil culture supernatant, and this finding suggests that neutrophil infiltration into endometriosis lesions increases aromatase expression level in endometriosis cells, which enhances the proliferation of endometriosis epithelial cells. Thus, it is speculated that by suppressing neutrophil infiltration into endometriosis lesions using an IL-8 signal inhibitor, the proliferation of endometriosis epithelial cells is suppressed. The speculation described above is also supported by the finding that proliferative epithelial cells were atrophied in the antibody H1009/L395-F1974m administration group of surgically induced endometriosis monkey models.

[Example 23] Analysis of Chemokines and Cytokines Produced by Neutrophils

Next, what kinds of chemokines, cytokines, and growth factors are produced in neutrophils was analyzed in the presence or absence of IL-8 or in the presence of an anti-IL-8 antibody. Isolated neutrophils were suspended in an RPMI-1640 medium containing 1% FBS and seeded at $1.5\times10^6$ cells/well into a 6-well plate. IL-8 was added or not added thereto, or IL-8 and various antibodies were added thereto, and the neutrophils were cultured for one day. Antibodies H1009/L395-F1974m, anti-IL-8 antibody [807] (ab18672), and IgG1 were each added at a final concentration of 10 µg/ml, and IL-8 was added at a final concentration of 100 ng/ml. After one day, the cell culture solution was collected, and the concentrations of the various cytokines, chemokines, and growth factors in the cell culture solution were determined using Cytokine Human Magnetic 30-Plex Panel for the Luminex (registered trademark) platform (Thermo Fisher) according to the product's protocol.

Figure 41:
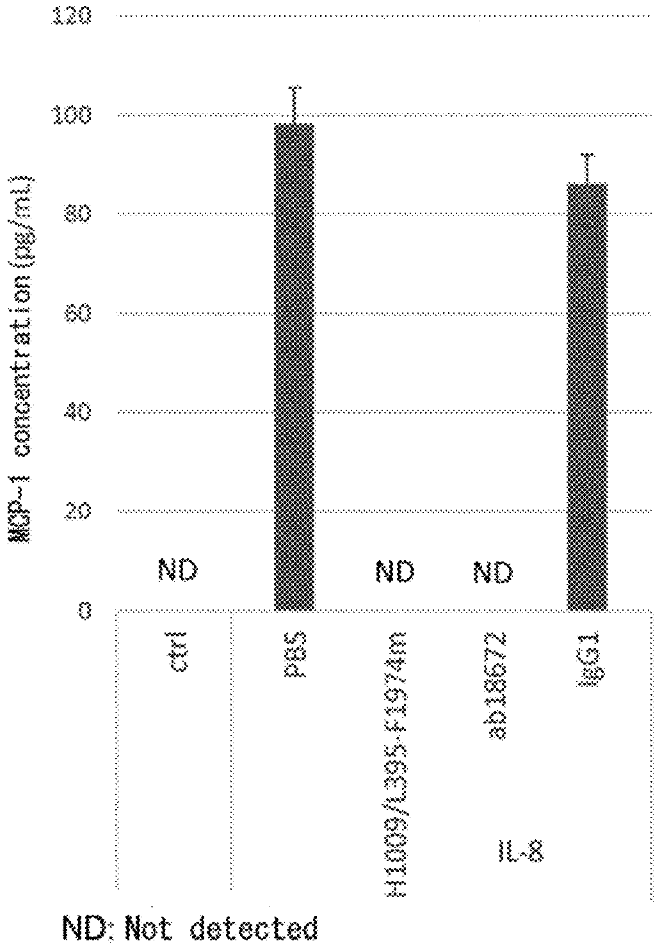
FIG. 41 shows a result of analyzing the concentration of MCP-1 in the culture fluid of neutrophils when IL-8 and an anti-IL-8 antibody were added.

As shown in FIG. 41, the result showed that the concentration of MCP-1 (monocyte chemoattractant protein 1) in the cell culture solution was strongly elevated by addition of IL-8 and the elevation was suppressed by anti-IL-8-neutralizing antibodies.

MCP-1 is also referred to as CCL2 and has chemotactic activity on monocytes. MCP-1 is considered to promote the migration and infiltration of monocytes into local inflammatory sites. As shown in Table 26, hemosiderin was reduced in the antibody H1009/L395-F1974m administration group in the nodular lesions of surgically-induced endometriosis monkey models, and this finding suggested that the infiltration of macrophages or monocytes was suppressed by antibody administration. Since MCP-1 which has a chemotactic activity on monocytes was produced by IL-8 stimulation of neutrophils, the above result suggested the possibility that in response to IL-8, neutrophils infiltrate into endometriosis lesions and produce MCP-1, which leads to migration and infiltration of monocytes and macrophages into the lesion sites.

Furthermore, MCP-1 is known to act on fibroblasts and promote collagen production (J Biol Chem. 1996 Jul. 26; 271(30):17779-84), and there are many reports describing that MCP-1 enhances tissue fibrosis in vivo (J Immunol. 1994 Nov. 15, 153(10):4733-41; Am J Physiol Lung Cell Mol Physiol. 2004 May, 286(5):L1038-44; J Invest Dermatol. 2003 September; 121(3):510-6). This suggested the possibility that in response to IL-8, neutrophils infiltrate into endometriosis lesion sites and further produce MCP-1, thereby enhancing fibrosis of the endometriosis lesion sites in addition to enhancing migration and infiltration of monocytes and macrophages. The result described above suggested that fibrosis in endometriosis lesion sites is ameliorated by suppressing infiltration of neutrophils using IL-8 signal inhibitors. Indeed, as shown in FIG. 36 and Table 26, a decrease of the interstitium whose major component is collagenous fibers was observed in the nodular lesion sites of surgically-induced endometriosis monkey models in the antibody H1009/L395-F1974m administration group, thus demonstrating drug efficacy in ameliorating fibrosis. The result described above convincingly supports that IL-8 signal inhibitors are useful against fibrosis in endometriosis. By generalizing and extending these results, those skilled in the art will sufficiently appreciate that IL-8 signal inhibitors can treat or prevent fibrosis in endometriosis as well as in various fibrotic diseases.

[Example 24] Preparation of a Post-Surgical Adhesion-Induced Monkey Model and Assessment of Pathological Conditions (24-1) Preparation of a Post-Surgical Adhesion-Induced Monkey Model To prepare a post-surgical adhesion-induced model, female cynomolgus monkeys 9 to 16 years of age (provided by the Tsukuba Primate Research Center at the National Institutes of Biomedical Innovation, Health and Nutrition) were treated under anesthesia as follows. Anesthesia was performed using balanced anesthesia of ketamine/xylazine (mixed at an adequate ratio of about 2:1) and isoflurane. An incision of 5 to 6 cm was made in the median line of the abdominal wall. After opening the abdomen, a 1-cm incision was made on the uterine corpus and sutured with 4 stitches using a single suture. Then, the whole uterus was brushed five times with gauze. Next, a 1-cm incision was made to the right abdominal wall peritoneal part at 2 cm from the incised median line of the abdominal wall and sutured by running suture with 4 stitches using an absorbable suture. After suture, the sutured part was brushed five times with gauze. Likewise, the peritoneum of left abdominal wall was incised, sutured, and brushed with gauze. Finally, the median line of abdominal wall was sutured by running suture with 10 to 11 stitches. The entire steps were completed in one hour or less. The antagonist Antisedan (in roughly the same amount as that of xylazine) and the antibiotic cephradine were administered at the time of awakening after surgery. Then, the pain reliever Zalban was administered for two days after surgery, and the monkeys were observed regularly every day to confirm the absence of post-surgical abnormalities. At laparoscopic observation, anesthesia and post-surgical monitoring were also performed in the same way.

(24-2) Drug Efficacy Assessment of Anti-IL-8 Antibodies in Post-Surgical Adhesion-Induced Models Animals in the anti-IL-8 antibody administration group were intravenously administered with the anti-IL-8 antibody H1009/L395-F1974m at 10 mg/kg one hour or less after the surgery to induce post-surgical adhesion described above. The control group was untreated. 24 to 35 days after administration of the anti-IL-8 antibody, laparoscopy was performed to observe the adhesion formed due to incision, suture, and blushing with gauze. The abdomen was incised in the median line under anesthesia, and laparoscopic observation was performed by inserting a trocar and then introducing a laparoscope. The laparoscope was connected to a video system (KARL STORZ) and a monitor. The video system was used for recording, and the monitor was used for intraperitoneal observation. The size of the adhesion was measured using a graduated bar or graduated forceps. The presence, range, and location of adhesion were assessed during laparoscopic observation. The result is shown in Table 29. The result of laparoscopic observation showed that adhesion was seen over the entire incision site in the two monkeys of the untreated group. Although adhesion was found in individual No. 206 in the anti-IL-8 antibody administration group, no adhesion was found in the right and left abdominal wall peritoneum or at the uterine incision site in individual No. 201. Thus, the adhesion-preventive effect of anti-IL-8 antibodies was demonstrated. This result shows that anti-IL-8 antibodies are useful as adhesion-preventive agents. Those skilled in the art will naturally appreciate that anti-IL-8 antibodies may exert a stronger adhesion formation-preventive effect by appropriately altering the timing of administration or such. In addition, based on the result described above, those skilled in the art will naturally appreciate that IL-8 signal inhibitors are useful as adhesion-preventing agents.

TABLE 29

| | | Incision site | | | |
|---|---|---|---|---|---|
| | | Abdominal wall | | | |
| | | Median line | Peritoneum (R) | Peritoneum (L) | Uterus |
| Untreated | #202 | ○ | ○ | ○ | ○ |
| | #204 | ○ | ○ | ○ | ○ |
| Anti-IL-8 antibody | #201 | ○ | x | x | x |
| | #206 | ○ | ○ | ○ | ○ |

○ = Adhesion found
x = No adhesion

[Example 25] Functional Analysis of IL-8 in Macrophages Differentiated from Monocytes and Assessment of Anti-IL-8 Antibodies for their Drug Efficacy Monocytes (All Cells, Catalog No: PB011-P-F-2) separated as a CD14-positive fraction from the peripheral blood of healthy persons were purchased and stored at −80° C. When used in experiments, the cells were thawed and used as described below. The cells were thawed at 37° C. in a water bath, and a medium containing DNase I (STEMCELL Technologies, Catalog No: 07900) and 10% FBS was added thereto. Following centrifugation in a high-speed centrifuge, the supernatant was removed. After repeating this step, the cells were suspended in an adequate volume of medium to determine the cell count. The monocytes were cultured for in vitro differentiation into macrophages and analyzed for changes in the expression of connecting tissue growth factor (CTGF) between presence and absence of IL-8. CTGF is a factor that promotes fibrosis. The monocytes were suspended in an RPMI-1640 medium (SIGMA) containing 10% FBS and 25 ng/ml GM-CSF (SIGMA) and seeded in a culture plate. The cells were cultured for seven days while changing half of the culture supernatant every two or three days. After seven days, the culture supernatant was removed and 100 ng/ml IL-8 and various antibodies were added to an RPMI-1640 medium containing 10% FBS, 20 ng/mL IFN-γ (SIGMA), and 10 μg/ml LPS (Wako Pure Chemical Industries), and cells were cultured therein for three days.

The antibodies assessed were: antibody H1009/L395-F1974m, anti-IL-8 antibody [807](abcam, Catalog No: ab18672), anti-IL-8 antibody [6217] (abcam, Catalog No: ab10768), anti-IL-8 antibody (Becton Dickinson, Catalog No: BD554726), and anti-IL-8 antibody (Becton Dickinson, Catalog No: BD555717); they were used at a concentration of 10 μg/ml. As a negative control, IgG1 (SIGMA, Catalog No: 15154) was used at a concentration of 10 μg/ml.

Following culture for three days, the cells were collected and RNAs were purified using the RNeasy Mini Kit (QIAGEN) according to the product's protocol. cDNAs were synthesized from the purified RNAs using SuperScript VILO MasterMix (Thermo Fisher), and the expression level of CTGF mRNA was estimated by real-time PCR. The probes used were Taqman probe Hs00170014_ml (Thermo Fisher) for CTGF and Eukaryotic 18S rRNA Endogenous Control (Thermo Fisher, Catalog NO: E4319413E) for 18SrRNA assay.

Figure 42:
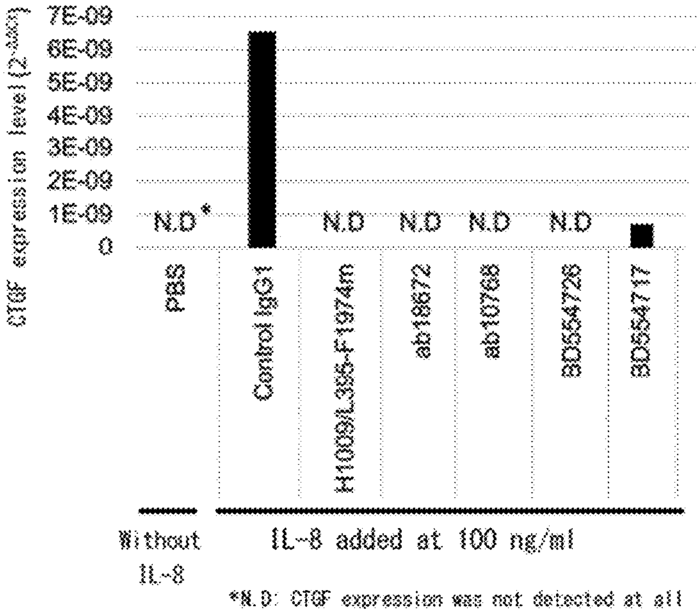
FIG. 42 shows a result of analyzing the expression of CTGF in macrophages when IL-8 and an anti-IL-8 antibody were added.

The expression level of CTGF was normalized with with 18S rRNA. The normalized value is shown in FIG. 42. Under the condition of no IL-8 addition, CTGF expression was not observed in macrophages differentiated from monocytes. Meanwhile, under the condition of IL-8 addition, CTGF expression was increased in the differentiated macrophages. This result shows that IL-8 has a function of inducing an elevation of CTGF expression in macrophages differentiated from monocytes. Further, when an anti-IL-8 antibody was added simultaneously with IL-8, the elevation of CTGF expression was not observed. The elevation of CTGF expression by IL-8 was shown to be suppressed by various anti-IL-8 antibodies. Based on the result described above, those skilled in the art will naturally appreciate that IL-8 is a factor involved in the progression of fibrosis and that IL-8 signal inhibitors such as anti-IL-8 antibodies are useful as therapeutic or preventive agents for fibrotic diseases.

[Reference 1] Construction of Expression Vectors for IgG Antibodies with Amino Acid Substitutions H chain expression vectors and L chain expression vectors of interest were constructed by inserting into an animal cell expression vector a plasmid fragment containing a variant prepared using the QuikChange Site-Directed Mutagenesis Kit (Stratagene) by the method described in the attached instructions. The nucleotide sequences of the prepared expression vectors were determined by a method known to those skilled in the art.

[Reference Example 2] Expression and Purification of IgG Antibodies

Antibody expression was carried out by the method described below. The human embryonic kidney cancer-derived HEK293H cell line (Invitrogen) was suspended in a DMEM medium (Invitrogen) containing 10% Fetal Bovine Serum (Invitrogen) and plated in 10 ml per dish of dishes for adherent cells (10 cm in diameter, CORNING) at a cell density of $5\times10^5$ to $6\times10^5$ cells/ml. After incubation in a $CO_2$ incubator (37° C., 5% $CO_2$) for one day and night, the medium was removed by aspiration, and 6.9 ml of a CHO-S-SFM-II (Invitrogen) medium was added thereto. The prepared plasmids were introduced into the cells by a lipofection method. The resulting culture supernatant was collected, centrifuged (about 2000 g, for 5 minutes, at room temperature) to remove cells, and passed through a 0.22-μm filter MILLEX®-GV (Millipore) for sterilization to obtain the culture supernatant. The obtained culture supernatant was purified using rProtein A Sepharose™ Fast Flow (Amersham Biosciences) by a method known to those skilled in the art. The concentration of the purified antibody was determined from the absorbance at 280 nm measured using a spectrophotometer. The antibody concentrations were calculated from the determined values using extinction coefficient determined by the method described in Protein Science 1995, 4: 2411-2423.

INDUSTRIAL APPLICABILITY

The present invention demonstrated that anti-IL-8 antibodies and such are useful as therapeutic and/or preventive agents for endometriosis and the like. The present invention is useful in reducing the volume of endometriosis lesions, ameliorating adhesion, inducing atrophic changes in epithelia and stromal cells, reducing the infiltration of immune cells, ameliorating fibrosis, and others.

The invention claimed is:

1. A method of inhibiting IL-8, which comprises administering an anti-IL-8 antibody that binds to human IL-8 to a subject in need thereof, wherein the subject suffers from an IL-8-related disease selected from the group consisting of chronic obstructive pulmonary disease (COPD), cystic fibrosis, psoriasis, hepatic fibrosis, renal fibrosis, and pulmonary fibrosis, and wherein the anti-IL-8 antibody comprises:

(a) the amino acid sequence of SEQ ID NO: 23 as HVR-H1, (b) the amino acid sequence of SEQ ID NO: 29 as HVR-H2, (c) the amino acid sequence of SEQ ID NO: 30 as HVR-H3, (d) the amino acid sequence of SEQ ID NO: 26 as HVR-L1, (e) the amino acid sequence of SEQ ID NO: 31 as HVR-L2, and (f) the amino acid sequence of SEQ ID NO: 32 as HVR-L3.

2. The method of claim 1, wherein the anti-IL-8 antibody comprises a heavy chain variable region comprising the amino acid sequence of SEQ ID NO: 34 and a light chain variable region comprising the amino acid sequence of SEQ ID NO: 35.

3. The method of claim 2, wherein the anti-IL-8 antibody comprises a heavy chain comprising the amino acid sequence of SEQ ID NO: 36 and a light chain comprising the amino acid sequence of SEQ ID NO: 38.

4. The method of claim 2, wherein the anti-IL-8 antibody comprises a heavy chain comprising the amino acid sequence of SEQ ID NO: 37 and a light chain comprising the amino acid sequence of SEQ ID NO: 38.

5. The method of claim 1, wherein the disease is COPD.

6. The method of claim 1, wherein the disease is cystic fibrosis.

7. The method of claim 1, wherein the disease is psoriasis.

8. The method of claim 1, wherein the disease is hepatic fibrosis.

9. The method of claim 1, wherein the disease is renal fibrosis.

10. The method of claim 1, wherein the disease is pulmonary fibrosis.

11. The method of claim 2, wherein the disease is COPD.

12. The method of claim 2, wherein the disease is cystic fibrosis.

13. The method of claim 2, wherein the disease is psoriasis.

14. The method of claim 2, wherein the disease is hepatic fibrosis.

15. The method of claim 2, wherein the disease is renal fibrosis.

16. The method of claim 2, wherein the disease is pulmonary fibrosis.

* * * * *

SEQUENCE LISTING

```
Sequence total quantity: 110
SEQ ID NO: 1            moltype = AA  length = 214
FEATURE                 Location/Qualifiers
REGION                  1..214
                        note = An artificially synthesized sequence
source                  1..214
                        mol_type = protein
                        organism = synthetic construct
SEQUENCE: 1
DIQMTQSPSS LSASVGDRVT ITCRASQDIS SYLNWYQQKP GKAPKLLIYY TSRLHSGVPS  60
RFSGSGSGTD FTFTISSLQP EDIATYYCQQ GNTLPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 2            moltype = AA  length = 447
FEATURE                 Location/Qualifiers
REGION                  1..447
                        note = An artificially synthesized sequence
source                  1..447
                        mol_type = protein
                        organism = synthetic construct
SEQUENCE: 2
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                      447

SEQ ID NO: 3            moltype = AA  length = 447
FEATURE                 Location/Qualifiers
REGION                  1..447
                        note = An artificially synthesized sequence
source                  1..447
                        mol_type = protein
                        organism = synthetic construct
```

```
SEQUENCE: 3
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLYITREPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                      447

SEQ ID NO: 4            moltype = AA  length = 447
FEATURE                 Location/Qualifiers
REGION                  1..447
                        note = An artificially synthesized sequence
source                  1..447
                        mol_type = protein
                        organism = synthetic construct
SEQUENCE: 4
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHSHYTQ KSLSLSP                                      447

SEQ ID NO: 5            moltype = AA  length = 447
FEATURE                 Location/Qualifiers
REGION                  1..447
                        note = An artificially synthesized sequence
source                  1..447
                        mol_type = protein
                        organism = synthetic construct
SEQUENCE: 5
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHHHYTQ KSLSLSP                                      447

SEQ ID NO: 6            moltype = AA  length = 447
FEATURE                 Location/Qualifiers
REGION                  1..447
                        note = An artificially synthesized sequence
source                  1..447
                        mol_type = protein
                        organism = synthetic construct
SEQUENCE: 6
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHAHTTR KELSLSP                                      447

SEQ ID NO: 7            moltype = AA  length = 447
FEATURE                 Location/Qualifiers
REGION                  1..447
                        note = An artificially synthesized sequence
source                  1..447
                        mol_type = protein
                        organism = synthetic construct
SEQUENCE: 7
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHAHVTR KELSLSP                                      447

SEQ ID NO: 8            moltype = AA  length = 447
```

-continued

```
FEATURE                Location/Qualifiers
REGION                 1..447
                       note = An artificially synthesized sequence
source                 1..447
                       mol_type = protein
                       organism = synthetic construct
SEQUENCE: 8
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHAHTTR KELSLSP                                    447

SEQ ID NO: 9           moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 9
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHAHVTR KELSLSP                                    447

SEQ ID NO: 10          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 10
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHAHYTR KELSLSP                                    447

SEQ ID NO: 11          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 11
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHAHYTR KELSLSP                                    447

SEQ ID NO: 12          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 12
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
```

```
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSP                                     447

SEQ ID NO: 13          moltype = AA  length = 218
FEATURE                Location/Qualifiers
REGION                 1..218
                       note = An artificially synthesized sequence
source                 1..218
                       mol_type = protein
                       organism = synthetic construct
SEQUENCE: 13
DIQMTQSPSS LSASVGDRVT ITCQASENIY SSLAWYQQKP GQAPRLLIYY ASNLASGVPS  60
RFSGSGSGTD FTLTISSLQP EDVATYYCQS YYFISSTDFN AFGQGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 14          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 14
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHSHYTQ KSLSLSP                                     447

SEQ ID NO: 15          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 15
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHAHYTQ KSLSLSP                                     447

SEQ ID NO: 16          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 16
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHAHTTR KELSLSP                                     447

SEQ ID NO: 17          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 17
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
```

```
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHAHVTR KELSLSP                                      447

SEQ ID NO: 18          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 18
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHAHTTR KELSLSP                                      447

SEQ ID NO: 19          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 19
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHAHVTR KELSLSP                                      447

SEQ ID NO: 20          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 20
QVTLKESGGR LVKPTETLTL TCTVSGFSLS SFNMDWVRQP PGKGLEWIGA VSTGGSAYYA  60
KWAKGRFTIS KDTSKNQVVL TITNMDPVDT ATYFCARVDS SGWGYFDLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVL HEALHAHYTR KELSLSP                                      447

SEQ ID NO: 21          moltype = AA  length = 447
FEATURE                Location/Qualifiers
REGION                 1..447
                       note = An artificially synthesized sequence
source                 1..447
                       mol_type = protein
                       organism = synthetic construct
SEQUENCE: 21
QVQLQESGPG LVKPSETLSL TCAVSGHSIS HDHAWSWVRQ PPGEGLEWIG FISYSGITNY  60
NPSLQGRVTI SRDNSKNTLY LQMNSLRAED TAVYYCARSL ARTTAMDYWG EGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHYHVTR KELSLSP                                      447

SEQ ID NO: 22          moltype = AA  length = 77
FEATURE                Location/Qualifiers
source                 1..77
                       mol_type = protein
```

```
                      organism = Homo sapiens
SEQUENCE: 22
AVLPRSAKEL RCQCIKTYSK PFHPKFIKEL RVIESGPHCA NTEIIVKLSD GRELCLDPKE  60
NWVQRVVEKF LKRAENS                                                  77

SEQ ID NO: 23         moltype = AA  length = 5
FEATURE               Location/Qualifiers
REGION                1..5
                      note = An artificially synthesized sequence
source                1..5
                      mol_type = protein
                      organism = synthetic construct
SEQUENCE: 23
DYYLS                                                               5

SEQ ID NO: 24         moltype = AA  length = 19
FEATURE               Location/Qualifiers
REGION                1..19
                      note = An artificially synthesized sequence
source                1..19
                      mol_type = protein
                      organism = synthetic construct
SEQUENCE: 24
LIRNKANGYT REYSASVKG                                                19

SEQ ID NO: 25         moltype = AA  length = 11
FEATURE               Location/Qualifiers
REGION                1..11
                      note = An artificially synthesized sequence
source                1..11
                      mol_type = protein
                      organism = synthetic construct
SEQUENCE: 25
ENYRYDVELA Y                                                        11

SEQ ID NO: 26         moltype = AA  length = 11
FEATURE               Location/Qualifiers
REGION                1..11
                      note = An artificially synthesized sequence
source                1..11
                      mol_type = protein
                      organism = synthetic construct
SEQUENCE: 26
RASEIIYSYL A                                                        11

SEQ ID NO: 27         moltype = AA  length = 7
FEATURE               Location/Qualifiers
REGION                1..7
                      note = An artificially synthesized sequence
source                1..7
                      mol_type = protein
                      organism = synthetic construct
SEQUENCE: 27
NAKTLAD                                                             7

SEQ ID NO: 28         moltype = AA  length = 9
FEATURE               Location/Qualifiers
REGION                1..9
                      note = An artificially synthesized sequence
source                1..9
                      mol_type = protein
                      organism = synthetic construct
SEQUENCE: 28
QHHFGFPRT                                                           9

SEQ ID NO: 29         moltype = AA  length = 19
FEATURE               Location/Qualifiers
REGION                1..19
                      note = An artificially synthesized sequence
source                1..19
                      mol_type = protein
                      organism = synthetic construct
SEQUENCE: 29
LIRNKDNYHT PEYSASVKG                                                19

SEQ ID NO: 30         moltype = AA  length = 11
FEATURE               Location/Qualifiers
REGION                1..11
                      note = An artificially synthesized sequence
```

```
source                  1..11
                        mol_type = protein
                        organism = synthetic construct
SEQUENCE: 30
ENHRYDVELA Y                                                       11

SEQ ID NO: 31           moltype = AA  length = 7
FEATURE                 Location/Qualifiers
REGION                  1..7
                        note = An artificially synthesized sequence
source                  1..7
                        mol_type = protein
                        organism = synthetic construct
SEQUENCE: 31
KAKTHAD                                                            7

SEQ ID NO: 32           moltype = AA  length = 9
FEATURE                 Location/Qualifiers
REGION                  1..9
                        note = An artificially synthesized sequence
source                  1..9
                        mol_type = protein
                        organism = synthetic construct
SEQUENCE: 32
KHHFGFPRT                                                          9

SEQ ID NO: 33           moltype = AA  length = 122
FEATURE                 Location/Qualifiers
REGION                  1..122
                        note = An artificially synthesized sequence
source                  1..122
                        mol_type = protein
                        organism = synthetic construct
SEQUENCE: 33
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENYRYDVELA YWGQGTLVTV  120
SS                                                                 122

SEQ ID NO: 34           moltype = AA  length = 122
FEATURE                 Location/Qualifiers
REGION                  1..122
                        note = An artificially synthesized sequence
source                  1..122
                        mol_type = protein
                        organism = synthetic construct
SEQUENCE: 34
QVQLVESGGG LVQPGGSLRL SCAASGFTFS DYYLSWVRQA PGKGLEWVGL IRNKDNYHTP  60
EYSASVKGRF TISRDDSKNS LYLTMSDLKT EDTAVYYCAR ENHRYDVELA YWGQGTLVTV  120
SS                                                                 122

SEQ ID NO: 35           moltype = AA  length = 107
FEATURE                 Location/Qualifiers
REGION                  1..107
                        note = An artificially synthesized sequence
source                  1..107
                        mol_type = protein
                        organism = synthetic construct
SEQUENCE: 35
DIQMTQSPSS LSASVGDRVT ITCRASEIIY SYLAWYQQKP GKAPKLLIYK AKTHADGVPS  60
RFSGSGSGTD FTFTISSLQP EDIATYYCKH HFGFPRTFGQ GTKVEIK                107

SEQ ID NO: 36           moltype = AA  length = 450
FEATURE                 Location/Qualifiers
REGION                  1..450
                        note = An artificially synthesized sequence
source                  1..450
                        mol_type = protein
                        organism = synthetic construct
SEQUENCE: 36
QVQLVESGGG LVQPGGSLRL SCAASGFTFS DYYLSWVRQA PGKGLEWVGL IRNKDNYHTP  60
EYSASVKGRF TISRDDSKNS LYLTMSDLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELR  240
RGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KGLPSSIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVLHEALHAH TTRKELSLSP                                   450

SEQ ID NO: 37           moltype = AA  length = 450
```

```
FEATURE                Location/Qualifiers
REGION                 1..450
                       note = An artificially synthesized sequence
source                 1..450
                       mol_type = protein
                       organism = synthetic construct
SEQUENCE: 37
QVQLVESGGG LVQPGGSLRL SCAASGFTFS DYYLSWVRQA PGKGLEWVGL IRNKDNYHTP  60
EYSASVKGRF TISRDDSKNS LYLTMSDLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELR  240
RGPKVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVLHEALHAH TTRKELSLSP                                   450

SEQ ID NO: 38          moltype = AA  length = 214
FEATURE                Location/Qualifiers
REGION                 1..214
                       note = An artificially synthesized sequence
source                 1..214
                       mol_type = protein
                       organism = synthetic construct
SEQUENCE: 38
DIQMTQSPSS LSASVGDRVT ITCRASEIIY SYLAWYQQKP GKAPKLLIYK AKTHADGVPS  60
RFSGSGSGTD FTFTISSLQP EDIATYYCKH HFGFPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 39          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 39
EVQLLESGGG LVQPGGSLRL SCAASGFTFS DYYLSWVRQA PGKGLEWVGL IRNKANGYTR  60
EYSASVKGRF TISREDSKNT LYLQMSSLKT EDLAVYYCAR ENYRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP                                   450

SEQ ID NO: 40          moltype = AA  length = 214
FEATURE                Location/Qualifiers
REGION                 1..214
                       note = An artificially synthesized sequence
source                 1..214
                       mol_type = protein
                       organism = synthetic construct
SEQUENCE: 40
DIQMTQSPSS LSASVGDRVT ITCRASEIIY SYLAWYQQKP GKAPKLLIYN AKTLADGVPS  60
RFSGSGSGTD FTFTISSLQP EDIATYYCQH HFGFPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 41          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 41
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENYRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP                                   450

SEQ ID NO: 42          moltype = AA  length = 450
FEATURE                Location/Qualifiers
REGION                 1..450
```

```
                         note = An artificially synthesized sequence
source                   1..450
                         mol_type = protein
                         organism = synthetic construct
SEQUENCE: 42
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP                                  450

SEQ ID NO: 43            moltype = AA  length = 214
FEATURE                  Location/Qualifiers
REGION                   1..214
                         note = An artificially synthesized sequence
source                   1..214
                         mol_type = protein
                         organism = synthetic construct
SEQUENCE: 43
DIQMTQSPSS LSASVGDRVT ITCRASEIIY SYLAWYQQKP GKAPKLLIYH AKTHADGVPS  60
RFSGSGSGTD FTFTISSLQP EDIATYYCQH HFGFPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 44            moltype = AA  length = 214
FEATURE                  Location/Qualifiers
REGION                   1..214
                         note = An artificially synthesized sequence
source                   1..214
                         mol_type = protein
                         organism = synthetic construct
SEQUENCE: 44
DIQMTQSPSS LSASVGDRVT ITCRASEIIY SYLAWYQQKP GKAPKLLIYH AKTHADGVPS  60
RFSGSGSGTD FTFTISSLQP EDIATYYCKH HFGFPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 45            moltype = AA  length = 450
FEATURE                  Location/Qualifiers
REGION                   1..450
                         note = An artificially synthesized sequence
source                   1..450
                         mol_type = protein
                         organism = synthetic construct
SEQUENCE: 45
QVQLVESGGG LVQPGGSLRL SCAASGFTFS DYYLSWVRQA PGKGLEWVGL IRNKANGYLR  60
EYSASVKGRF TISRDDSKNS LYLTMSSLKT EDTAVYYCAR ENYRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP                                  450

SEQ ID NO: 46            moltype = AA  length = 450
FEATURE                  Location/Qualifiers
REGION                   1..450
                         note = An artificially synthesized sequence
source                   1..450
                         mol_type = protein
                         organism = synthetic construct
SEQUENCE: 46
QVQLVESGGG LVQPGGSLRL SCAASGFTFS DYYLSWVRQA PGKGLEWVGL IRNKANGHTP  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP                                  450

SEQ ID NO: 47            moltype = AA  length = 450
FEATURE                  Location/Qualifiers
REGION                   1..450
                         note = An artificially synthesized sequence
source                   1..450
```

```
                        mol_type = protein
                        organism = synthetic construct
SEQUENCE: 47
QVQLVESGGG LVQPGGSLRL SCAASGFTFS DYYLSWVRQA PGKGLEWVGL IRNKDNGYTP  60
EYSASVKGRF TISRDDSKNS LYLTMSDLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP                                  450

SEQ ID NO: 48           moltype = AA  length = 450
FEATURE                 Location/Qualifiers
REGION                  1..450
                        note = An artificially synthesized sequence
source                  1..450
                        mol_type = protein
                        organism = synthetic construct
SEQUENCE: 48
QVQLVESGGG LVQPGGSLRL SCAASGFTFS DYYLSWVRQA PGKGLEWVGL IRNKDNYHTP  60
EYSASVKGRF TISRDDSKNS LYLTMSDLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP                                  450

SEQ ID NO: 49           moltype = AA  length = 450
FEATURE                 Location/Qualifiers
REGION                  1..450
                        note = An artificially synthesized sequence
source                  1..450
                        mol_type = protein
                        organism = synthetic construct
SEQUENCE: 49
QVQLVESGGG LVQPGGSLRL SCAASGFTFS DYYLSWVRQA PGKGLEWVGL IRNKDNYHTP  60
EYSASVKGRF TISRDDSKNS LYLTMSDLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELR  240
RGPKVFLFPP KPKDTLMADR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP                                  450

SEQ ID NO: 50           moltype = AA  length = 450
FEATURE                 Location/Qualifiers
REGION                  1..450
                        note = An artificially synthesized sequence
source                  1..450
                        mol_type = protein
                        organism = synthetic construct
SEQUENCE: 50
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP                                  450

SEQ ID NO: 51           moltype = AA  length = 450
FEATURE                 Location/Qualifiers
REGION                  1..450
                        note = An artificially synthesized sequence
source                  1..450
                        mol_type = protein
                        organism = synthetic construct
SEQUENCE: 51
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHAH YTRKELSLSP                                  450
```

```
SEQ ID NO: 52          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 52
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHAH TTRKELSLSP                                 450

SEQ ID NO: 53          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 53
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHAH VTRKELSLSP                                 450

SEQ ID NO: 54          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 54
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVLHEALHAH TTRKELSLSP                                 450

SEQ ID NO: 55          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 55
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVLHEALHAH VTRKELSLSP                                 450

SEQ ID NO: 56          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 56
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
```

```
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVLHEALHAH YTRKELSLSP                                    450

SEQ ID NO: 57          moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 57
QVQLVESGGG LVQPGGSLRL SCAASGFTFS DYYLSWVRQA PGKGLEWVGL IRNKANGYTP  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP                                    450

SEQ ID NO: 58          moltype = AA  length = 5
FEATURE                Location/Qualifiers
REGION                 1..5
                       note = An artificially synthesized sequence
source                 1..5
                       mol_type = protein
                       organism = synthetic construct
SEQUENCE: 58
SYGML                                                               5

SEQ ID NO: 59          moltype = AA  length = 17
FEATURE                Location/Qualifiers
REGION                 1..17
                       note = An artificially synthesized sequence
source                 1..17
                       mol_type = protein
                       organism = synthetic construct
SEQUENCE: 59
DISYDGSNKY YADSVKG                                                  17

SEQ ID NO: 60          moltype = AA  length = 8
FEATURE                Location/Qualifiers
REGION                 1..8
                       note = An artificially synthesized sequence
source                 1..8
                       mol_type = protein
                       organism = synthetic construct
SEQUENCE: 60
DRIAVADY                                                            8

SEQ ID NO: 61          moltype = AA  length = 12
FEATURE                Location/Qualifiers
REGION                 1..12
                       note = An artificially synthesized sequence
source                 1..12
                       mol_type = protein
                       organism = synthetic construct
SEQUENCE: 61
RASQSVSSSY LA                                                       12

SEQ ID NO: 62          moltype = AA  length = 7
FEATURE                Location/Qualifiers
REGION                 1..7
                       note = An artificially synthesized sequence
source                 1..7
                       mol_type = protein
                       organism = synthetic construct
SEQUENCE: 62
GASSRAT                                                             7

SEQ ID NO: 63          moltype = AA  length = 8
FEATURE                Location/Qualifiers
REGION                 1..8
                       note = An artificially synthesized sequence
source                 1..8
```

```
                        mol_type = protein
                        organism = synthetic construct
SEQUENCE: 63
QQYGSSFT                                                8

SEQ ID NO: 64           moltype = AA  length = 5
FEATURE                 Location/Qualifiers
REGION                  1..5
                        note = An artificially synthesized sequence
source                  1..5
                        mol_type = protein
                        organism = synthetic construct
SEQUENCE: 64
NYGMH                                                   5

SEQ ID NO: 65           moltype = AA  length = 17
FEATURE                 Location/Qualifiers
REGION                  1..17
                        note = An artificially synthesized sequence
source                  1..17
                        mol_type = protein
                        organism = synthetic construct
SEQUENCE: 65
VIYFEGSNKY NADSVKG                                      17

SEQ ID NO: 66           moltype = AA  length = 9
FEATURE                 Location/Qualifiers
REGION                  1..9
                        note = An artificially synthesized sequence
source                  1..9
                        mol_type = protein
                        organism = synthetic construct
SEQUENCE: 66
SPYGDYLDY                                               9

SEQ ID NO: 67           moltype = AA  length = 12
FEATURE                 Location/Qualifiers
REGION                  1..12
                        note = An artificially synthesized sequence
source                  1..12
                        mol_type = protein
                        organism = synthetic construct
SEQUENCE: 67
RASQTIDYNY LH                                           12

SEQ ID NO: 68           moltype = AA  length = 7
FEATURE                 Location/Qualifiers
REGION                  1..7
                        note = An artificially synthesized sequence
source                  1..7
                        mol_type = protein
                        organism = synthetic construct
SEQUENCE: 68
GTFIRAT                                                 7

SEQ ID NO: 69           moltype = AA  length = 9
FEATURE                 Location/Qualifiers
REGION                  1..9
                        note = An artificially synthesized sequence
source                  1..9
                        mol_type = protein
                        organism = synthetic construct
SEQUENCE: 69
QQFGRSPLT                                               9

SEQ ID NO: 70           moltype = AA  length = 5
FEATURE                 Location/Qualifiers
REGION                  1..5
                        note = An artificially synthesized sequence
source                  1..5
                        mol_type = protein
                        organism = synthetic construct
SEQUENCE: 70
SYGML                                                   5

SEQ ID NO: 71           moltype = AA  length = 17
FEATURE                 Location/Qualifiers
REGION                  1..17
                        note = An artificially synthesized sequence
```

```
source                 1..17
                       mol_type = protein
                       organism = synthetic construct
SEQUENCE: 71
DISYDGSNKY YADSVKG                                                  17

SEQ ID NO: 72          moltype = AA  length = 8
FEATURE                Location/Qualifiers
REGION                 1..8
                       note = An artificially synthesized sequence
source                 1..8
                       mol_type = protein
                       organism = synthetic construct
SEQUENCE: 72
DRIAVADY                                                            8

SEQ ID NO: 73          moltype = AA  length = 12
FEATURE                Location/Qualifiers
REGION                 1..12
                       note = An artificially synthesized sequence
source                 1..12
                       mol_type = protein
                       organism = synthetic construct
SEQUENCE: 73
RASQSVSSSF LA                                                       12

SEQ ID NO: 74          moltype = AA  length = 7
FEATURE                Location/Qualifiers
REGION                 1..7
                       note = An artificially synthesized sequence
source                 1..7
                       mol_type = protein
                       organism = synthetic construct
SEQUENCE: 74
GASSRAT                                                             7

SEQ ID NO: 75          moltype = AA  length = 8
FEATURE                Location/Qualifiers
REGION                 1..8
                       note = An artificially synthesized sequence
source                 1..8
                       mol_type = protein
                       organism = synthetic construct
SEQUENCE: 75
QQYDSSFT                                                            8

SEQ ID NO: 76          moltype = AA  length = 5
FEATURE                Location/Qualifiers
REGION                 1..5
                       note = An artificially synthesized sequence
source                 1..5
                       mol_type = protein
                       organism = synthetic construct
SEQUENCE: 76
GYYWT                                                               5

SEQ ID NO: 77          moltype = AA  length = 16
FEATURE                Location/Qualifiers
REGION                 1..16
                       note = An artificially synthesized sequence
source                 1..16
                       mol_type = protein
                       organism = synthetic construct
SEQUENCE: 77
EVIHHGSTNY SPSLKS                                                   16

SEQ ID NO: 78          moltype = AA  length = 9
FEATURE                Location/Qualifiers
REGION                 1..9
                       note = An artificially synthesized sequence
source                 1..9
                       mol_type = protein
                       organism = synthetic construct
SEQUENCE: 78
GGAAAALDS                                                           9

SEQ ID NO: 79          moltype = AA  length = 17
FEATURE                Location/Qualifiers
REGION                 1..17
```

```
                        note = An artificially synthesized sequence
source                  1..17
                        mol_type = protein
                        organism = synthetic construct
SEQUENCE: 79
KSSQSVLFSS NNRKYLA                                               17

SEQ ID NO: 80           moltype = AA  length = 7
FEATURE                 Location/Qualifiers
REGION                  1..7
                        note = An artificially synthesized sequence
source                  1..7
                        mol_type = protein
                        organism = synthetic construct
SEQUENCE: 80
WASTRES                                                          7

SEQ ID NO: 81           moltype = AA  length = 9
FEATURE                 Location/Qualifiers
REGION                  1..9
                        note = An artificially synthesized sequence
source                  1..9
                        mol_type = protein
                        organism = synthetic construct
SEQUENCE: 81
QQYYSTPFT                                                        9

SEQ ID NO: 82           moltype = AA  length = 5
FEATURE                 Location/Qualifiers
source                  1..5
                        mol_type = protein
                        organism = Mus musculus
SEQUENCE: 82
SYWMH                                                            5

SEQ ID NO: 83           moltype = AA  length = 17
FEATURE                 Location/Qualifiers
source                  1..17
                        mol_type = protein
                        organism = Mus musculus
SEQUENCE: 83
EIDPSDSNTN YNQKFKG                                               17

SEQ ID NO: 84           moltype = AA  length = 7
FEATURE                 Location/Qualifiers
source                  1..7
                        mol_type = protein
                        organism = Mus musculus
SEQUENCE: 84
ELLHAVY                                                          7

SEQ ID NO: 85           moltype = AA  length = 11
FEATURE                 Location/Qualifiers
source                  1..11
                        mol_type = protein
                        organism = Mus musculus
SEQUENCE: 85
TASQDIHKYI S                                                     11

SEQ ID NO: 86           moltype = AA  length = 6
FEATURE                 Location/Qualifiers
source                  1..6
                        mol_type = protein
                        organism = Mus musculus
SEQUENCE: 86
TSTLQP                                                           6

SEQ ID NO: 87           moltype = AA  length = 8
FEATURE                 Location/Qualifiers
source                  1..8
                        mol_type = protein
                        organism = Mus musculus
SEQUENCE: 87
LQYDNLWT                                                         8

SEQ ID NO: 88           moltype = AA  length = 5
FEATURE                 Location/Qualifiers
source                  1..5
                        mol_type = protein
```

```
                       organism = Mus musculus
SEQUENCE: 88
NYWIV                                                           5

SEQ ID NO: 89          moltype = AA  length = 17
FEATURE                Location/Qualifiers
source                 1..17
                       mol_type = protein
                       organism = Mus musculus
SEQUENCE: 89
DLYSGGGYTF YSENFKG                                              17

SEQ ID NO: 90          moltype = AA  length = 10
FEATURE                Location/Qualifiers
source                 1..10
                       mol_type = protein
                       organism = Mus musculus
SEQUENCE: 90
SGYDRTWFAH                                                      10

SEQ ID NO: 91          moltype = AA  length = 11
FEATURE                Location/Qualifiers
source                 1..11
                       mol_type = protein
                       organism = Mus musculus
SEQUENCE: 91
QASQDIESYL S                                                    11

SEQ ID NO: 92          moltype = AA  length = 7
FEATURE                Location/Qualifiers
source                 1..7
                       mol_type = protein
                       organism = Mus musculus
SEQUENCE: 92
YATRLAD                                                         7

SEQ ID NO: 93          moltype = AA  length = 9
FEATURE                Location/Qualifiers
source                 1..9
                       mol_type = protein
                       organism = Mus musculus
SEQUENCE: 93
LQHGESPPT                                                       9

SEQ ID NO: 94          moltype = AA  length = 5
FEATURE                Location/Qualifiers
source                 1..5
                       mol_type = protein
                       organism = Homo sapiens
SEQUENCE: 94
HYGMY                                                           5

SEQ ID NO: 95          moltype = AA  length = 17
FEATURE                Location/Qualifiers
source                 1..17
                       mol_type = protein
                       organism = Homo sapiens
SEQUENCE: 95
VIWYDGSYEY NADSVKG                                              17

SEQ ID NO: 96          moltype = AA  length = 8
FEATURE                Location/Qualifiers
source                 1..8
                       mol_type = protein
                       organism = Homo sapiens
SEQUENCE: 96
DRVGLFDY                                                        8

SEQ ID NO: 97          moltype = AA  length = 12
FEATURE                Location/Qualifiers
source                 1..12
                       mol_type = protein
                       organism = Homo sapiens
SEQUENCE: 97
RASQSISSSY LA                                                   12

SEQ ID NO: 98          moltype = AA  length = 7
FEATURE                Location/Qualifiers
source                 1..7
```

```
                       mol_type = protein
                       organism = Homo sapiens
SEQUENCE: 98
GPSSRAT                                                                   7

SEQ ID NO: 99          moltype = AA  length = 8
FEATURE                Location/Qualifiers
source                 1..8
                       mol_type = protein
                       organism = Homo sapiens
SEQUENCE: 99
QQYAGSLT                                                                  8

SEQ ID NO: 100         moltype = AA  length = 330
FEATURE                Location/Qualifiers
source                 1..330
                       mol_type = protein
                       organism = Homo sapiens
SEQUENCE: 100
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 101         moltype = AA  length = 326
FEATURE                Location/Qualifiers
source                 1..326
                       mol_type = protein
                       organism = Homo sapiens
SEQUENCE: 101
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                      326

SEQ ID NO: 102         moltype = AA  length = 377
FEATURE                Location/Qualifiers
source                 1..377
                       mol_type = protein
                       organism = Homo sapiens
SEQUENCE: 102
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                377

SEQ ID NO: 103         moltype = AA  length = 327
FEATURE                Location/Qualifiers
source                 1..327
                       mol_type = protein
                       organism = Homo sapiens
SEQUENCE: 103
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 104         moltype = AA  length = 107
FEATURE                Location/Qualifiers
source                 1..107
                       mol_type = protein
                       organism = Homo sapiens
SEQUENCE: 104
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 105         moltype = AA  length = 105
FEATURE                Location/Qualifiers
source                 1..105
                       mol_type = protein
```

-continued

```
                       organism = Homo sapiens
SEQUENCE: 105
QPKAAPSVTL FPPSSEELQA NKATLVCLIS DFYPGAVTVA WKADSSPVKA GVETTTPSKQ  60
SNNKYAASSY LSLTPEQWKS HRSYSCQVTH EGSTVEKTVA PTECS                 105

SEQ ID NO: 106         moltype = AA  length = 450
FEATURE                Location/Qualifiers
REGION                 1..450
                       note = An artificially synthesized sequence
source                 1..450
                       mol_type = protein
                       organism = synthetic construct
SEQUENCE: 106
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVLHEALHSH YTQKSLSLSP                                 450

SEQ ID NO: 107         moltype = AA  length = 7
FEATURE                Location/Qualifiers
REGION                 1..7
                       note = An artificially synthesized sequence
source                 1..7
                       mol_type = protein
                       organism = synthetic construct
SEQUENCE: 107
HAKTHAD                                                          7

SEQ ID NO: 108         moltype = AA  length = 122
FEATURE                Location/Qualifiers
REGION                 1..122
                       note = An artificially synthesized sequence
source                 1..122
                       mol_type = protein
                       organism = synthetic construct
SEQUENCE: 108
QVQLVESGGG LVQPGGSLRL SCAASGFTFS DYYLSWVRQA PGKGLEWVGL IRNKANGYTR  60
EYSASVKGRF TISRDDSKNS LYLQMSSLKT EDTAVYYCAR ENHRYDVELA YWGQGTLVTV  120
SS                                                               122

SEQ ID NO: 109         moltype = AA  length = 107
FEATURE                Location/Qualifiers
REGION                 1..107
                       note = An artificially synthesized sequence
source                 1..107
                       mol_type = protein
                       organism = synthetic construct
SEQUENCE: 109
DIQMTQSPSS LSASVGDRVT ITCRASEIIY SYLAWYQQKP GKAPKLLIYH AKTHADGVPS  60
RFSGSGSGTD FTFTISSLQP EDIATYYCKH HFGFPRTFGQ GTKVEIK              107

SEQ ID NO: 110         moltype = AA  length = 214
FEATURE                Location/Qualifiers
REGION                 1..214
                       note = An artificially synthesized sequence
source                 1..214
                       mol_type = protein
                       organism = synthetic construct
SEQUENCE: 110
DIQMTQSPSS LSASVGDSVT ITCQASTDIS SHLNWYQQKP GKAPELLIYY GSHLLSGVPS  60
RFSGSGSGTD FTFTISSLEA EDAATYYCGQ GNRLPYTFGQ GTKVEIERTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```